US009315581B2

(12) United States Patent
Hudson et al.

(10) Patent No.: US 9,315,581 B2
(45) Date of Patent: Apr. 19, 2016

(54) IMMUNO-CONJUGATES AND METHODS FOR PRODUCING THEM

(75) Inventors: Peter J. Hudson, Blackburn (AU); Debra Tamvakis, Camberwell (AU); Michael P. Wheatcroft, Southbank (AU); Fabio Turatti, Docklands (AU)

(73) Assignee: A VIPEP PTY LIMITED, Parkville, Victoria (AU)

( * ) Notice: Subject to any disclaimer, the term of this patent is extended or adjusted under 35 U.S.C. 154(b) by 317 days.

(21) Appl. No.: 13/383,836

(22) PCT Filed: Dec. 23, 2010

(86) PCT No.: PCT/AU2010/001737
§ 371 (c)(1), (2), (4) Date: Mar. 16, 2012

(87) PCT Pub. No.: WO2011/075786
PCT Pub. Date: Jun. 30, 2011

(65) Prior Publication Data

US 2012/0171115 A1 Jul. 5, 2012

Related U.S. Application Data

(60) Provisional application No. 61/289,497, filed on Dec. 23, 2009.

(51) Int. Cl.

*A61K 51/10* (2006.01)
*C07K 16/30* (2006.01)
*A61K 47/48* (2006.01)
*A61K 49/00* (2006.01)
*C07K 16/32* (2006.01)

(52) U.S. Cl.

CPC ........... *C07K 16/30* (2013.01); *A61K 47/48215* (2013.01); *A61K 49/0002* (2013.01); *C07K 16/3092* (2013.01); *C07K 16/32* (2013.01); *C07K 2317/21* (2013.01); *C07K 2317/565* (2013.01); *C07K 2317/567* (2013.01); *C07K 2317/622* (2013.01); *C07K 2317/624* (2013.01); *C07K 2317/626* (2013.01); *C07K 2319/21* (2013.01)

(58) Field of Classification Search

CPC .............. A61K 51/1093; A61K 51/10; A61K 2039/505; C07K 2319/31; C07K 2317/505; C07K 2317/56; C07K 2317/565; C07K 2317/567; C07K 2317/624
USPC ............. 424/9.6, 133.1; 435/69.6; 530/387.1, 530/387.3
See application file for complete search history.

(56) References Cited

U.S. PATENT DOCUMENTS

2010/0004429 A1 1/2010 Kai et al.

FOREIGN PATENT DOCUMENTS

| | | | |
|---|---|---|---|
| WO | 0350531 | A2 | 6/2003 |
| WO | WO 2004/003019 | * | 6/2004 |
| WO | 2006008096 | A1 | 1/2006 |
| WO | WO 2006/116076 | | 11/2006 |
| WO | WO 2008/052187 | | 5/2008 |
| WO | 2009012268 | A1 | 1/2009 |
| WO | WO 2009/012256 | | 1/2009 |
| WO | WO 2009/099728 | | 8/2009 |
| WO | 2010141902 | A2 | 12/2010 |

OTHER PUBLICATIONS

WIPO Written Opinion (PCT/AU2010/001737; mailed Feb. 23, 2011).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Ward et al. (Nature 341:544-546 (1989)).*
Webber, K.O. et al. Preparation and Characterization of a Disulfide-Stabilized Fv Fragment of the Anti-TAC Antibody: Comparison with its Single-Chain Analog. Molecular Immunology. 1995, vol. 2 (4), pp. 249-258.
International Search Report issued in International Patent Application No. PCT/AU2010/001737.
Saerens et al., "Disulfide Bond Introduction for General Stabilization of Immunoglobulin Heavy-Chain Variable Domains"; Journal of Molecular Biology; Mar. 21, 2008; pp. 478-488; vol. 377, No. 2; Elsevier Ltd.
Junutula et al. "Rapid identification of reactive cysteine residues for site-specific labelling of antibody-Fabs", Journal of Immunological Methods, Available online Jan. 14, 2008; pp. 2-13; Genentech Inc., San Francisco, California.
Sirk et al. "Site-Specific, Thiol-Mediated Conjugation of Fluorescent Probes to Cysteine-Modified Diabodies Targeting CD20 or HER2", Bioconjugate Chem 2008; Published on Web Nov. 18, 2008; pp. 2-9; vol. 19; American Chemical Society.
Voynov et al. "Design and Application of Antibody Cysteine Variants", Published on Web Jan. 21, 2010; BioConjugate Chem 2010; pp. 385-392; vol. 21; American Chemical Society.

* cited by examiner

*Primary Examiner* — Lynn Bristol
(74) *Attorney, Agent, or Firm* — Perkins Coie LLP

(57) ABSTRACT

The present invention provides an isolated protein comprising an immunoglobulin variable region comprising at least two cysteine residues positioned within framework region (FR) 2 and/or at least two cysteine residues positioned within framework region (FR3), wherein if at least two of the cysteine residues in FR2 and/or FR3 are not conjugated to a compound then an intra-framework disulphide bond is capable of forming between the cysteine residues. Preferably the protein comprises an immunoglobulin heavy chain variable region ($V_H$) and an immunoglobulin light chain variable region ($V_L$), wherein at least one of the variable regions comprises the two cysteine residues. The present invention also provides conjugates of the protein and another compound.

29 Claims, 47 Drawing Sheets

IMMUNO-CONJUGATES AND METHODS FOR PRODUCING THEM

CROSS-REFERENCE TO RELATED APPLICATION

This application is a 371 application of PCT/AU2010/001737 which claims priority from U.S. Patent Application No. 61/289,497 entitled "Immuno-conjugates and methods for producing them 2" filed on 23 Dec. 2009, the contents of each of which is herein incorporated by reference in its entirety.

FIELD OF INVENTION

The present invention relates to proteins comprising immunoglobulin variable regions modified to facilitate conjugation of a compound thereto or having a compound conjugated thereto.

BACKGROUND OF THE INVENTION

The highly specific binding nature of immunoglobulins, e.g., antibodies and antibody-like molecules (e.g., camelid immunoglobulin or immunoglobulin new antigen receptors (IgNARs) from cartilaginous fish) or proteins comprising antigen binding domains thereof makes them particularly suitable for delivering molecules to specific targets in a subject. For example, immunoglobulins or proteins comprising antigen binding domains thereof can be conjugated to cytotoxic or cytostatic compounds e.g., drugs, to kill or inhibit growth of cells, such as tumour cells (Lambert, 2005). Such a conjugate facilitates targeted delivery of the cytotoxic or cytostatic compounds to cells expressing the antigen to which the immunoglobulin or fragment binds, rather than non-specifically throughout a subject. Such conjugates can permit use of compounds that are generally toxic to a subject by ensuring the delivery of toxic levels of the compound to the site at which it is required rather than systemically within a subject. Furthermore, conjugation of antibodies or proteins comprising antigen binding domains thereof to detectable compounds, such as fluorophores or radioisotopes facilitates detection of target molecules within a subject, for example to facilitate detection of diseased cells such as cancer cells, e.g., using in vivo, imaging-based methods.

Conventional means of linking a compound to an antibody or a protein comprising antigen binding domain generally leads to a heterogeneous mixture of molecules where the compounds are attached at a number of sites on the antibody. For example, compounds have typically been conjugated to an antibody or protein comprising antigen binding domains thereof through the often-numerous lysine residues in the antibody or antigen binding domain, generating a heterogeneous antibody-compound conjugate mixture. Depending on reaction conditions used, the heterogeneous mixture typically contains a distribution of conjugates with from 0 to about 8, or more, attached compounds. In addition, within each subgroup of conjugates with a particular integer ratio of compounds to antibody or protein there is a potentially heterogeneous mixture where the compound is attached at various sites on the antibody or protein. Analytical and preparative methods are inadequate to separate and characterize the various conjugate species within the heterogeneous mixture resulting from a conjugation reaction.

Furthermore, non-specific conjugation of a compound to an antibody or protein comprising an antigen binding domain thereof may reduce or completely prevent binding of the antibody/protein to an antigen, for example, if the compound is conjugated to a region required for antigen binding. This risk is increased in proteins that comprise antigen binding domains that are far smaller than an intact antibody in which there may be few residues suitable for conjugation that are not important for antigen binding. For example, proteins comprising little more than antigen binding domains of an antibody have few sites to which a compound can be conjugated without reducing or preventing antigen binding.

Carbohydrate(s) on the Fc region of an antibody is a natural site for attaching compounds. Generally, the carbohydrate is modified by periodate oxidation to generate reactive aldehydes, which can then be used to attach reactive amine containing compounds by Schiff base formation. As the aldehydes can react with amine groups, reactions are carried out at low pH so that lysine residues in the antibody or antigen binding domain are protonated and unreactive. Hydrazide groups are most suitable for attachment to the aldehydes generated since they are reactive at low pH to form a hydrazone linkage. The linkage can then be further stabilised by reduction with sodium cyanoborohydride to form a hydrazine linkage (Rodwell et al, 1986). Disadvantages of this approach include the harsh conditions required for linkage which can damage and aggregate some antibody molecules. For example, methionine residues present in some antibody variable regions may be particularly susceptible to oxidation by periodate which can lead to loss of antigen binding avidity. Histidine and/or tryptophan residues are also susceptible to oxidation. Furthermore, many proteins comprising antigen binding domains of an antibody do not necessarily comprise a Fc region, meaning that they cannot be conjugated to a compound using the foregoing process.

Cysteine thiols are reactive at neutral pH, unlike most amines which are protonated and less nucleophilic near pH 7. Since free thiol groups are relatively reactive, proteins with cysteine residues often exist in their oxidized form as disulfide-linked oligomers or have internally bridged disulfide groups. Extracellular proteins generally do not have free thiols (Garman, 1997). Cysteine residues have been introduced into proteins by genetic engineering techniques to form covalent attachments to ligands or to form new intramolecular disulfide bonds. However, inserting or substituting cysteine thiol groups into a protein is potentially problematic, particularly in the case of those which are relatively accessible for reaction or oxidation, i.e., positioned at sites useful for conjugation of a compound. This is because, in concentrated solutions of the protein, whether in the periplasm of *Escherichia coli*, culture supernatants, or partially or completely purified protein, cysteine residues on the surface of the protein can pair and oxidize to form intermolecular disulfides, and hence protein aggregates. Such protein aggregation often leads to poor yields of isolated protein that is in a useful form, e.g., having a desired biological activity. Furthermore, the protein oxidatively can form an intramolecular disulfide bond between the newly engineered cysteine and an existing cysteine residue, which can render the protein inactive or non-specific by misfolding or loss of tertiary structure. Each of the foregoing problems are exacerbated in antibodies and proteins comprising antigen binding domains thereof which generally comprise several cysteine residues that bond with one another to ensure correct folding and stability and, as a consequence antigen binding activity.

It will be clear to the skilled artisan from the foregoing that there is a need in the art for proteins comprising antigen binding domains of immunoglobulins that are modified so as to permit simple conjugation of a compound thereto. Preferred proteins will facilitate recombinant production in a variety of systems, preferably without resulting in considerably levels of multimeric aggregates linked by intermolecular bonds.

SUMMARY OF INVENTION

In work leading up to the present invention, the inventors sought to identify sites within a variable region of an immunoglobulin, e.g., an antibody that permit conjugation of a compound thereto without preventing binding of the variable region to an antigen. As exemplified herein, the inventors have determined that numerous sites within framework region 2 (FR2) and/or framework region 3 (FR3) of a variable region that are accessible for conjugation, and are sufficiently removed from the antigen binding site of the variable region that a compound conjugated thereto is unlikely to interfere with or prevent antigen binding. These sites are conserved in both heavy chain variable regions ($V_H$) and light chain variable regions ($V_L$). Based on this determination, the inventors produced various proteins comprising mutated variable regions in which two cysteine residues are inserted into FR2 and/or FR3. These cysteine residues are positioned such that a disulfide bond can also form between them if they are not conjugated to a compound. During recombinant production and/or purification, the cysteine residues are linked by a disulphide bond thereby reducing or preventing those residues bonding with other cysteine residues either within the same protein or in another protein. This reduces the likelihood of production of linked multimers and/or an aberrantly folded variable region, and permits production and/or isolation of functional protein. Following isolation, the cysteine residues are reduced or otherwise broken permitting conjugation of a compound to the protein. The inventors have also demonstrated that conjugation of numerous compounds to these proteins, including bulky compounds such as polyethylene glycol (PEG) does not prevent binding of the variable region to an antigen.

In one example, the present invention provides an isolated protein comprising an immunoglobulin variable region comprising:

(i) at least two cysteine residues positioned within framework region (FR) 2, wherein if at least two of the cysteine residues in FR2 are not conjugated to a compound then a disulphide bond is capable of forming between the cysteine residues in FR2; and/or (ii) at least two cysteine residues positioned within a region comprising FR3 and complementarity determining region (CDR) 2, wherein if at least two of the cysteine residues in the region are not conjugated to a compound then a disulphide bond is capable of forming between the cysteine residues in the region.

In an alternative or additional example, the present invention provides an isolated protein comprising an immunoglobulin variable region comprising:

(i) at least two cysteine residues positioned within framework region (FR) 2, wherein if at least two of the cysteine residues in FR2 are not conjugated to a compound then a disulphide bond is capable of forming between the cysteine residues in FR2; and/or (ii) at least two cysteine residues positioned within FR3, wherein if at least two of the cysteine residues in FR3 are not conjugated to a compound then a disulphide bond is capable of forming between the cysteine residues in FR3.

In an alternative or additional example, the present invention provides an isolated protein comprising an immunoglobulin heavy chain variable region ($V_H$) and an immunoglobulin light chain variable region ($V_L$), wherein at least one of the variable regions comprises:

(i) at least two cysteine residues positioned within framework region (FR) 2, wherein if at least two of the cysteine residues in FR2 are not conjugated to a compound then a disulphide bond is capable of forming between the cysteine residues in FR2; and/or (ii) at least two cysteine residues positioned within a region comprising FR3 and complementarity determining region (CDR) 2, wherein if at least two of the cysteine residues in the region are not conjugated to a compound then a disulphide bond is capable of forming between the cysteine residues in the region.

In an alternative or additional example, the present invention provides an isolated protein comprising an immunoglobulin heavy chain variable region ($V_H$) and an immunoglobulin light chain variable region ($V_L$), wherein at least one of the variable regions comprises:

(i) at least two cysteine residues positioned within framework region (FR) 2, wherein if at least two of the cysteine residues in FR2 are not conjugated to a compound then a disulphide bond is capable of forming between the cysteine residues in FR2; and/or (ii) at least two cysteine residues positioned within FR3, wherein if at least two of the cysteine residues in FR3 are not conjugated to a compound then a disulphide bond is capable of forming between the cysteine residues in FR3.

Preferably, the cysteine residues in FR3 are additional to the conserved cysteine residue in FR3, e.g., are additional to a cysteine residue at position 88 of a $V_L$ according to the Kabat numbering system or position 92 of a $V_H$ according to the Kabat numbering system. Preferably, the cysteine residues do not form a disulphide bond with the conserved cysteine residue.

Preferably, the protein comprises at least one of $V_L$ and at least one of $V_H$ in a single polypeptide chain.

Preferably, the cysteine residues are positioned such that the disulphide bond is present under non-reducing conditions.

Preferably, the cysteine residues are positioned such that a compound can be conjugated to at least one of the residues if they are not linked by a disulphide bond.

Preferably, wherein the cysteine residues within FR2 are positioned between CDR1 and CDR2, and/or the cysteine residues FR3 are positioned between CDR2 and CDR3.

In one example, the cysteine residues are positioned within one or more loop regions of FR2 and/or FR3.

In an alternative or additional example, the cysteine residues are within a $V_H$. For example, the cysteine residues within FR2 are positioned between residues 36 to 49 numbered according to the Kabat numbering system, and/or the cysteine residues within FR3 are positioned between residues 66 to 94 according to the Kabat numbering system. Preferably, the cysteine residues within FR2 are positioned between residues 39 to 45 numbered according to the Kabat numbering system, and/or the cysteine residues in FR3 are positioned between residues 68 to 86 numbered according to the Kabat numbering system.

In one example, the cysteine residues within FR2 are positioned between residues 39 to 45 numbered according to the Kabat numbering system, and/or the cysteine residues within FR3 are positioned between residues 68 to 81 numbered according to the Kabat numbering system. In one example, the cysteine residues within FR3 are positioned between residues 82C to 86 numbered according to the Kabat numbering system. In one example, the cysteine residues are positioned within FR3 between residues 68 to 81 numbered according to the Kabat numbering system.

Exemplary positions of the cysteine residues are:

(i) positions 39 and 43 of FR2 numbered according to the Kabat numbering system;

(ii) positions 39 and 45 of FR2 numbered according to the Kabat numbering system;

(iii) positions 70 and 79 of FR3 numbered according to the Kabat numbering system; and/or (iv) positions 72 and 75 of FR3 numbered according to the Kabat numbering system.

In one example, the cysteine residues within the region comprising CDR2 and FR3 are positioned between residues 59 to 86 numbered according to the Kabat numbering system. For example, the cysteine residues within the region are positioned between residues 59 to 63 and/or 65 to 68 and/or 82C to 86 numbered according to the Kabat numbering system.

In an alternative or additional example, the cysteine residues are within a $V_L$. Preferably, the cysteine residues within FR2 are positioned between residues 35 to 49 numbered according to the Kabat numbering system, and/or the cysteine residues positioned within FR3 are positioned between residues 57 to 88 numbered according to the Kabat numbering system. In one example, the cysteine residues within FR2 are positioned between residues 38 to 44 numbered according to the Kabat numbering system, and/or the cysteine residues within FR3 are positioned between residues 63 to 82 numbered according to the Kabat numbering system.

In one example, the cysteine residues within FR3 are positioned between residues 63 to 74 numbered according to the Kabat numbering system In one example, the cysteine residues within FR3 are positioned between residues 78 to 82 numbered according to the Kabat numbering system.

In one example, the cysteine residues are positioned within FR3 between residues 63 to 74 numbered according to the Kabat numbering system.

Exemplary positions for cysteine resides are:

(i) positions 38 and 42 of FR2 numbered according to the Kabat numbering system;

(ii) positions 38 and 44 of FR2 numbered according to the Kabat numbering system; and/or (iii) positions 65 and 72 of FR3 numbered according to the Kabat numbering system.

In one example, the cysteine residues within the region comprising CDR2 and FR3 are positioned between residues 54 to 82 numbered according to the Kabat numbering system. In an additional or alternative example, the cysteine residues within the region are positioned between residues 54 to 58 and/or 60 to 63 and/or 78 to 82 numbered according to the Kabat numbering system.

The present invention clearly contemplates modifying additional residues within the variable region or protein comprising same. For example, the invention additionally contemplates substituting residues positioned between cysteine residues or even replacing cysteine residues naturally occurring within CDRs.

In one example, a protein as described herein specifically binds to human epidermal growth factor HER2, tumor associated glycoprotein TAG72, MUC1 or prostate specific membrane antigen (PSMA). Other proteins bind to a plurality of antigens, e.g. the previously listed antigens, by virtue of cross-reactivity or the protein being multi-specific.

In one example, the protein comprises a $V_H$ and a $V_L$ comprising sequences at least about 80% identical to a $V_H$ and a $V_L$ sequence set forth in any one or more of SEQ ID NOs: 59, 61, 63 or 65, modified to include the two or more cysteine residues positioned within FR2 and/or FR3.

In one example, the protein comprises a sequence at least about 80% identical to a sequence set forth in any one or more of SEQ ID NO: 101, 103, 105, 107, 109, 111, 113, 115, 117, 119, 121, 123, 125, 127, 129, 131, 133, 135, 137, 139, 141, 143, 145, 147 or 149, optionally comprising a N-terminal serine residue.

The present invention also provides an isolated protein comprising a Fv comprising at least one protein of the invention in which at least one $V_L$ binds to at least one $V_H$ to form an antigen binding site.

One form of the protein comprises the $V_L$ and the $V_H$ which form the antigen binding site being in a single polypeptide chain. For example, the protein is:

(i) a single chain Fv fragment (scFv);

(ii) a dimeric scFv (di-scFv); or (iii) at least one of (i) and/or (ii) linked to a Fc or a heavy chain constant domain ($C_H$) 2 and/or $C_H$3.

Alternatively, the protein comprises the $V_L$ and the $V_H$ which form the antigen binding site being in different polypeptide chains. In one example, each polypeptide chain in the protein comprises a $V_L$ and a $V_H$. Preferably, such a protein is:

(i) a diabody;

(ii) a triabody; or (iii) a tetrabody.

In this specification the term Avibody or Avibodies includes any form of Avibody™ products which include any diabody (diabodies), triabody (triabodies) and tetrabody (tetrabodies), such as those described in WO98/044001 and/or WO94/007921.

In another example, the protein of the present invention is an immunoglobulin, preferably an antibody. Exemplary forms of immunoglobulins are described herein and are to be taken to apply mutatis mutandis to the present example of the invention.

In some examples of the invention, the protein of the invention comprises the cysteine residues being linked by a disulphide bond. Alternatively, the protein of the invention comprises a compound conjugated to at least one of the cysteine residues, wherein conjugation of the compound does not prevent binding of the protein to an antigen. Exemplary compounds include a compound selected from the group consisting of a radioisotope, a detectable label, a therapeutic compound, a colloid, a toxin, a nucleic acid, a peptide, a protein, a compound that increases the half life of the protein in a subject and mixtures thereof. The skilled artisan will appreciate that the term protein encompasses proteins comprising one or more immunoglobulin variable regions, for example, an antibody or fragment thereof including an Fv containing protein such as is described herein.

In one example, a protein of the present invention further comprises at least two cysteine residues positioned within framework region (FR) 1, wherein if at least two of the cysteine residues are not conjugated to a compound a disulphide bond is capable of forming between the cysteine residues in FR1. Exemplary variable region containing proteins comprising cysteine residues in FR1 that are adaptable to the present invention are disclosed in co-pending International Application No. PCT/AU2010/000847, the entire contents of which are incorporated by reference.

In one example, the cysteine residues are positioned such that the disulphide bond is present under non-reducing conditions.

In one example, the cysteine residues in FR1 are positioned between residue 2 numbered according to the Kabat numbering system and CDR1.

In one example, the cysteine residues are positioned within one or more loop regions of FR1.

In an alternative or additional example, the cysteine residues are within the $V_H$ and are positioned between residues 2 to 30 numbered according to the Kabat numbering system. Preferably, the cysteine residues are positioned between residues 7-20 and/or residues 24-30 numbered according to the Kabat numbering system, and more preferably positioned between residues 7-20. In a further example, the residues are positioned between residues 6-16 numbered according to the Kabat numbering system. In a further example, the residues are positioned between residues 7-16 numbered according to the Kabat numbering system.

In an alternative or additional example, the cysteine residues are within the $V_L$ and are positioned between residues 2 to 22 numbered according to the Kabat numbering system. Preferably, the cysteine residues are positioned between residues 7-20 numbered according to the Kabat numbering system. In a further example, the residues are positioned between residues 7-19 numbered according to the Kabat numbering system. In a further example, the residues are positioned between residues 7-17 numbered according to the Kabat numbering system.

In an exemplified form of the invention the cysteine residues are additional to a conserved cysteine residue in the $V_H$ and/or $V_L$. The skilled artisan will be aware that the conserved cysteine residue is at residue 23 in the $V_L$ and/or residue 22 in the $V_H$ numbered according to the Kabat numbering system in at least a majority of naturally occurring antibodies.

In one preferred form of the invention the cysteine residues are positioned N-terminal to the conserved cysteine residue. Preferably, the cysteine residues are positioned at one or more of the following:

(i) residue 8 and residue 11 of a $\kappa V_L$ numbered according to the Kabat numbering system;

(ii) residue 14 and residue 17 of a $\kappa V_L$ numbered according to the Kabat numbering system;

(iii) residue 7 and residue 11 of a $\lambda V_L$ numbered according to the Kabat numbering system;

(iv) residue 14 and residue 17 of a $\lambda V_L$ numbered according to the Kabat numbering system;

(v) residue 8 and residue 12 of a $\lambda V_L$ numbered according to the Kabat numbering system;

(vi) residue 7 and residue 10 of a $V_H$ numbered according to the Kabat numbering system; and/or (vii) residue 13 and residue 16 of a $V_H$ numbered according to the Kabat numbering system.

In another preferred example of the invention, the cysteine residues are positioned at one or more of the following:

(i) residue 13 and residue 19 of a $\kappa V_L$ numbered according to the Kabat numbering system;

(ii) residue 13 and residue 19 of a $\lambda V_L$ numbered according to the Kabat numbering system;

(iii) residue 6 and residue 9 of a $V_H$ numbered according to the Kabat numbering system; and/or (iv) residue 12 and residue 18 of a $V_H$ numbered according to the Kabat numbering system.

The protein described herein according to any example can comprise one or more and preferably less than 10 or 5 or 4 or 3 or 2 substitutions, preferably conservative amino acid substitutions or deletions or insertions. Exemplary changes to the recited sequence include deleting a N-terminal serine or substituting the serine for another amino acid residue (preferably a conservative amino acid substitution) and/or deleting or substituting a C terminal lysine and/or arginine.

The inventors have also modified proteins comprising variable regions to include a serine or threonine residue at the N-terminus. This residue permits site-specific conjugation of a compound thereto. By combining the N-terminal serine/threonine mutation with the cysteine mutations discussed above, the inventors have produced proteins to which they can site-specifically conjugate at least two different compounds.

Accordingly, an example of the invention provides a protein of the invention additionally comprises at least one N-terminal threonine or serine residue. The serine or threonine residue may be added to the N-terminus of the protein (i.e., is additional to the sequence of the protein). Preferably, the serine or threonine residue replaces a naturally occurring amino acid residue at the N-terminus of the protein, i.e., is the result of a substitutional mutation. Optionally, the threonine or serine residue is linked to a compound such as a compound described above, wherein conjugation of the compound does not prevent binding of the protein to an antigen.

In one example, a protein of the invention comprises a first compound conjugated to at least one of the cysteine residues and a second compound conjugated to the threonine or serine residue, wherein the second compound is different to the first compound.

In one example a protein as described herein according to any example is conjugated to polyethylene glycol (PEG). In one example, the PEG is monodispersed PEG. In one example, the monodispersed PEG has no more than 48 ethylene glycol units, such as about 24 ethylene glycol units.

Examples of proteins of the invention comprise a sequence 80% or 90% or 95% or 96% or 97% or 98% or 99% or 100% identical to the sequence set forth in any one of SEQ ID NOs: 59, 61, 63 or 65, modified to include the two or more positioned within FR2 and/or FR3. Suitable sites for modification are described herein and are to be taken to apply mutatis mutandis to this example of the invention. For example, the protein comprises a sequence at least about 80% or 90% or 95% or 96% or 97% or 98% or 99% or 100% identical to the sequence set forth in SEQ ID NO: 83, 85, 87 or 89, optionally comprising a N-terminal serine residue.

In one example, the protein TAG72 and comprises a $V_H$ and a $V_L$ comprising sequences at least about 80% identical to a sequence set forth in SEQ ID NO: 101, 103, 105, 107, 109, 111, 113, 115, 117 or 119.

In another example, the protein binds to Her2 and comprises a $V_H$ and a $V_L$ comprising sequences at least about 80% identical to a sequence set forth in one or more of SEQ ID NO: 127, 129, 141, 143, 145, 147 or 149.

In another example, the protein binds to MUC1 and comprises a $V_H$ and a $V_L$ comprising sequences at least about 80% identical to a sequence set forth in one or more of SEQ ID NO: 131, 133, 135, 137 or 139.

In one example, a protein of the invention is human, humanized, deimmunized or chimeric.

The present invention also provides a composition comprising a protein of the invention and a pharmaceutically acceptable carrier.

The present invention also encompasses an isolated nucleic acid encoding a protein of the invention. Exemplary nucleic acids include those having a sequence at least about 80% or 90% or 95% or 96% or 97% or 98% or 99% or 100% identical to the sequence set forth in any one or more of SEQ ID NOs: 58, 60, 62 or 64 altered to include codons encoding at least two cysteine residues in FR2 and/or FR3 of the encoded protein, optionally including a N-terminal serine or threonine residue. In one example, a nucleic acid of the invention comprises a sequence at least about 80% or 90% or 95% or 96% or 97% or 98% or 99% or 100% identical to the sequence set forth in any one or more of SEQ ID NO: 82, 84, 86 or 88. The skilled artisan will be aware that due to the degeneracy of codon usage, numerous nucleotide sequences can encode a protein of the invention. All such nucleotide sequences are encompassed by the present invention. For example, a codon optimized nucleic acid can be produced to facilitate expression in a specific cell type or organism.

A nucleic acid of the invention can be operably linked to a promoter to thereby produce an expression construct. Such an expression construct or the nucleic acid is preferably included in a vector, preferably a vector replicable in a cell, e.g., a plasmid or phagemid or cosmid or artificial chromosome.

The present invention also provides an isolated cell comprising an exogenous nucleic acid or expression construct of the invention, preferably wherein the cell expresses a protein of the invention. Exemplary cells include, but are not limited to, bacterial cells, yeast cells, mammalian cells or insect cells.

The nucleic acids and/or expression constructs and/or cells provided by the invention also provide a basis for methods for producing proteins of the invention. Accordingly, the present invention also provides a method for producing a protein of the invention, the method comprising maintaining an expression construct of the invention under conditions sufficient for the encoded protein to be produced. For example, the method comprises culturing a cell of the invention under conditions sufficient the encoded for the protein to be produced. In one example, the method additionally comprises isolating the protein. The method can additionally comprise testing the protein, e.g., for binding activity or affinity. The method can additionally comprise formulating the protein into a pharmaceutical composition.

The present invention also provides a method for producing a conjugate comprising a protein of the invention, the method comprising:

(i) obtaining a protein of the invention comprising at least two cysteine residues positioned within FR2 and/or FR3; and
(ii) conjugating a compound to at least one of the cysteine residues to thereby produce the conjugate.

In one example, the cysteine residues in the protein obtained at (i) are linked by a disulphide bond and the method additionally comprises reducing or otherwise breaking the disulphide bond prior to linking the compound to the cysteine residue(s). Preferably, reducing or otherwise breaking the disulphide bond generates a free thiol group in the protein and the compound has a thiol reactive group. By reacting the compound with the thiol reactive group, the conjugate is produced.

In one example, the compound is conjugated to the protein using a maleimide. For example, the protein is contacted with a compound comprising a maleimide functional group such that conjugation occurs.

In a further example of the invention, the protein additionally comprises at least one N-terminal serine or threonine residue and the method additionally comprises conjugating a compound to the serine or threonine residue. Preferably, the compound conjugated to the serine or threonine residue is different to the compound conjugated to the cysteine residue(s).

The present invention provides an alternative method for producing a conjugate comprising a protein of the invention, the method comprising:

(i) obtaining a protein of the invention comprising a N-terminal threonine or serine residue; and
(ii) conjugating a compound to at least one serine or threonine residue at the N-terminus of the protein to thereby produce the conjugate.

Optionally, a method of the invention for producing a conjugate additionally comprises isolating the conjugate and/or formulating the conjugate into a pharmaceutical composition.

It will be apparent to the skilled artisan based on the foregoing that the inventors have produced reagents that are useful in a variety of applications, including, delivery of a toxic compound or a radioisotope to a diseased cell, tissue or organ (e.g., a cancer) and/or in vivo imaging and/or for increasing the stability of a protein.

Accordingly, the present invention also provides for use of a protein or a composition of the invention in medicine. For example, the present invention provides for use of a protein of the invention in the manufacture of a medicament for treating or preventing a condition. The present invention also provides a method of treating or preventing a condition in a subject, the method comprising administering a protein or composition of the invention to a subject in need thereof. Exemplary conditions are described herein and are to be taken to apply mutatis mutandis to the present example of the invention. Furthermore exemplary conjugated forms of a protein of the invention are described herein and shall be taken to apply mutatis mutandis to the present example of the invention.

The present invention additionally provides a method for delivering a compound to a cell, the method comprising contacting the cell with a protein of the invention that is conjugated to the compound or a composition comprising same. In one example, the cell is contacted by administering the protein or composition to a subject.

The present invention also provides imaging methods, such as a method for localising or detecting an antigen in a subject, said method comprising:

(i) administering to a subject a protein of the invention for a time and under conditions sufficient for the protein to bind to the antigen, wherein the protein is conjugated to a detectable label; and
(ii) localising or detecting the detectable label in vivo.

The skilled artisan will recognise that the foregoing method is useful for localising or detecting cells, groups of cells such as tumours, tissues and organs or parts thereof expressing the antigen. Exemplary antigens are described throughout this specification and are to be taken to apply mutatis mutandis to the present example of the invention.

The present invention also provides a method for diagnosing or prognosing a condition in a subject, the method comprising contacting a sample from the subject with a protein or composition of the invention for a time and under conditions sufficient for the protein to bind to an antigen and form a complex and detecting the complex, wherein detection of the complex is diagnostic or prognostic of the condition. Preferably, the protein is conjugated to a detectable label and detection of the label is indicative of the complex.

In one example, the method comprises determining the level of the complex, wherein an enhanced or reduced level of said complex compared to a control sample is diagnostic or prognostic of the condition.

The present invention additionally provides a library comprising a plurality of proteins of the invention. In one example, the proteins are displayed on the surface of a particle (e.g., a phage or a ribosome) or a cell. Clearly, the present invention also provides a library of nucleic acids encoding said library comprising a plurality of proteins of the invention.

The present invention additionally provides a method for isolating a protein of the invention, the method comprising contacting a library of the invention with an antigen for a time and under conditions sufficient for (or such that) a protein binds to the antigen and isolating the protein.

The present invention additionally provides a method for producing a library comprising a plurality of proteins of the invention, the method comprising:

(i) obtaining or producing nucleic acids encoding a plurality of proteins comprising an immunoglobulin variable region, wherein the variable regions comprising at least two cysteine residues positioned within FR2 and/or FR3 and, optionally a N-terminal threonine or serine residue;

(ii) producing a library of expression constructs comprising the following operably linked nucleic acids:

a) a promoter;

b) a nucleic acid obtained or produced at (i); and c) a nucleic acid encoding a polypeptide that facilitates display of the variable region containing protein in/on the cells or particles; and (iii) expressing proteins encoded by the expression constructs such that they are displayed in/on the cells or particles.

Suitable sites for positioning the cysteine residues and/or threonine or serine residue are described herein and are to be taken to apply mutatis mutandis to the present example of invention.

In one example, the amino acids in the CDRs of the protein are random or semi-random or are derived from a human antibody.

In one example, the method additionally comprises isolating nucleic acid encoding the protein. Such a nucleic acid can be introduced into an expression construct. Optionally, the protein can be expressed.

KEY TO SEQUENCE LISTING

Figure 1A:
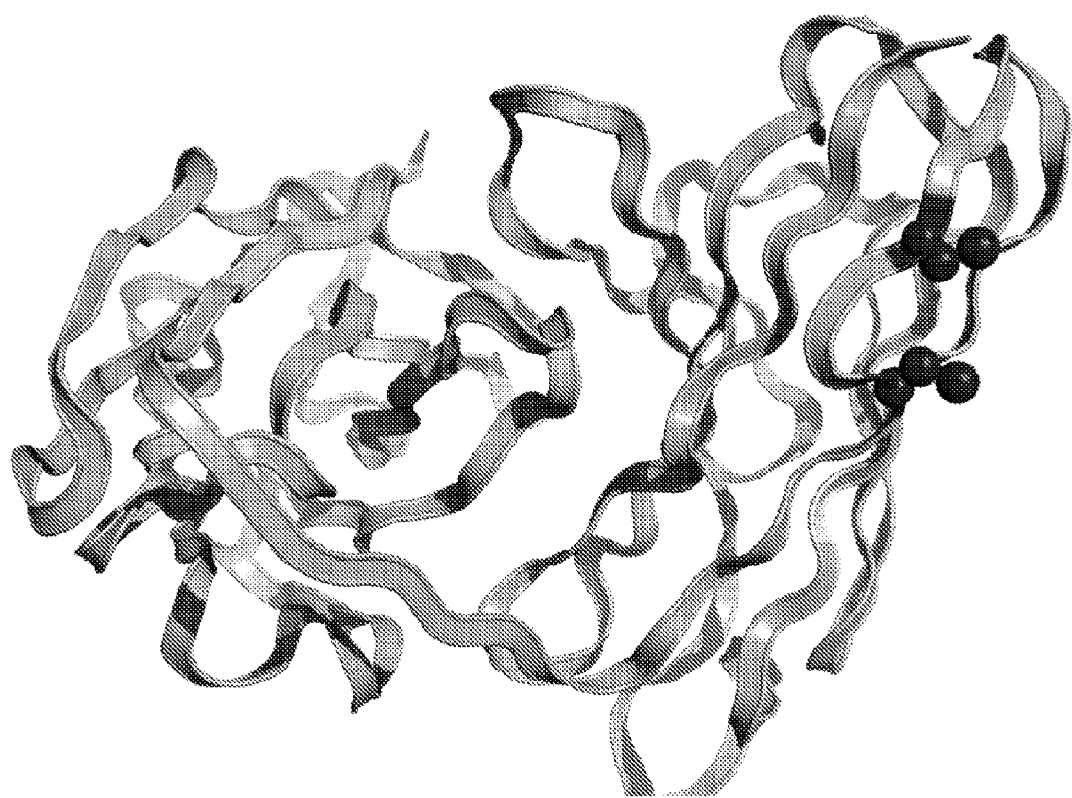
FIG. 1A is a diagrammatic representation showing a molecular model generated for AVP04-50 in which the amino acids in $V_L$ framework 1 at Kabat residues 8 and 11 (black space fill) have been converted to cysteines (in silico).

SEQ ID NO: 1—amino acid sequence of FR2 of a human antibody heavy chain;

SEQ ID NO: 2—amino acid sequence of FR2 of a human antibody heavy chain;

SEQ ID NO: 3—amino acid sequence of FR2 of a human antibody heavy chain;

SEQ ID NO: 4—amino acid sequence of FR2 of a human antibody heavy chain;

SEQ ID NO: 5—amino acid sequence of FR2 of a human antibody heavy chain;

SEQ ID NO: 6—amino acid sequence of FR2 of a human antibody heavy chain;

SEQ ID NO: 7—amino acid sequence of FR2 of a human antibody heavy chain;

SEQ ID NO: 8—amino acid sequence of FR2 of a human antibody heavy chain;

SEQ ID NO: 9—amino acid sequence of FR2 of a human antibody κ light chain;

SEQ ID NO: 10—amino acid sequence of FR2 of a human antibody κ light chain;

SEQ ID NO: 11—amino acid sequence of FR2 of a human antibody κ light chain;

SEQ ID NO: 12—amino acid sequence of FR2 of a human antibody κ light chain;

SEQ ID NO: 13—amino acid sequence of FR2 of a human antibody κ light chain;

SEQ ID NO: 14—amino acid sequence of FR2 of a human antibody κ light chain;

SEQ ID NO: 15—amino acid sequence of FR2 of a human antibody κ light chain;

SEQ ID NO: 16—amino acid sequence of FR2 of a human antibody κ light chain;

SEQ ID NO: 17—amino acid sequence of FR2 of a human antibody λ light chain;

SEQ ID NO: 18—amino acid sequence of FR2 of a human antibody λ light chain;

SEQ ID NO: 19—amino acid sequence of FR2 of a human antibody λ light chain;

SEQ ID NO: 20—amino acid sequence of FR2 of a human antibody λ light chain;

SEQ ID NO: 21—amino acid sequence of FR2 of a human antibody λ light chain;

SEQ ID NO: 22—amino acid sequence of FR3 of a human antibody heavy chain;

SEQ ID NO: 23—amino acid sequence of FR3 of a human antibody heavy chain;

SEQ ID NO: 24—amino acid sequence of FR3 of a human antibody heavy chain;

SEQ ID NO: 25—amino acid sequence of FR3 of a human antibody heavy chain;

SEQ ID NO: 26—amino acid sequence of FR3 of a human antibody heavy chain;

SEQ ID NO: 27—amino acid sequence of FR3 of a human antibody heavy chain;

SEQ ID NO: 28—amino acid sequence of FR3 of a human antibody heavy chain;

SEQ ID NO: 29—amino acid sequence of FR3 of a human antibody heavy chain;

SEQ ID NO: 30—amino acid sequence of FR3 of a human antibody heavy chain;

SEQ ID NO: 31—amino acid sequence of FR3 of a human antibody heavy chain;

SEQ ID NO: 32—amino acid sequence of FR3 of a human antibody heavy chain;

SEQ ID NO: 33—amino acid sequence of FR3 of a human antibody heavy chain;

SEQ ID NO: 34—amino acid sequence of FR3 of a human antibody heavy chain;

SEQ ID NO: 35—amino acid sequence of FR3 of a human antibody heavy chain;

SEQ ID NO: 36—amino acid sequence of FR3 of a human antibody heavy chain;

SEQ ID NO: 37—amino acid sequence of FR3 of a human antibody heavy chain;

SEQ ID NO: 38—amino acid sequence of FR3 of a human antibody heavy chain;

SEQ ID NO: 39—amino acid sequence of FR3 of a human antibody heavy chain;

SEQ ID NO: 40—amino acid sequence of FR3 of a human antibody heavy chain;

SEQ ID NO: 41—amino acid sequence of FR3 of a human antibody κ light chain;

SEQ ID NO: 42—amino acid sequence of FR3 of a human antibody κ light chain;

SEQ ID NO: 43—amino acid sequence of FR3 of a human antibody κ light chain;

SEQ ID NO: 44—amino acid sequence of FR3 of a human antibody κ light chain;

SEQ ID NO: 45—amino acid sequence of FR3 of a human antibody κ light chain;

SEQ ID NO: 46—amino acid sequence of FR3 of a human antibody κ light chain;

SEQ ID NO: 47—amino acid sequence of FR3 of a human antibody κ light chain;

SEQ ID NO: 48—amino acid sequence of FR3 of a human antibody κ light chain;

SEQ ID NO: 49—amino acid sequence of FR3 of a human antibody λ light chain;

SEQ ID NO: 50—amino acid sequence of FR3 of a human antibody λ light chain;

SEQ ID NO: 51—amino acid sequence of FR3 of a human antibody λ light chain;

SEQ ID NO: 52—amino acid sequence of FR3 of a human antibody λ light chain;

SEQ ID NO: 53—amino acid sequence of FR3 of a human antibody λ light chain;

SEQ ID NO: 54—amino acid sequence of FR3 of a human antibody λ light chain;

SEQ ID NO: 55—amino acid sequence of FR3 of a human antibody λ light chain;

SEQ ID NO: 56—amino acid sequence of FR3 of a human antibody λ light chain;

SEQ ID NO: 57—amino acid sequence of a linker;

SEQ ID NO: 58—nucleotide sequence encoding AVP04-07 anti-TAG72 diabody;

SEQ ID NO: 59—amino acid sequence of AVP04-07 anti-TAG72 diabody;

SEQ ID NO: 60—nucleotide sequence encoding AVP07-17 anti-Her2 diabody;

SEQ ID NO: 61—amino acid sequence of AVP07-17 anti-Her2 diabody;

SEQ ID NO: 62—nucleotide sequence encoding AVP02-60 anti-MucI diabody;

SEQ ID NO: 63—amino acid sequence of AVP02-60 anti-MucI diabody;

SEQ ID NO: 64—nucleotide sequence encoding a modified AVP07-17 anti-HER2 diabody replacing CDR3H Cysteine residues Cys104 (Kabat numbering H100) and Cys109 (H100E) with Alanines and comprising a N-terminal serine designated AVP07-86;

SEQ ID NO: 65—amino acid sequence of modified AVP07-17 anti-HER2 diabody replacing CDR3H Cysteine residues Cys104 (Kabat numbering H100) and Cys109 (H100E) with Alanines and comprising a N-terminal serine designated AVP07-86;

SEQ ID NO: 66—nucleotide sequence of mutagenic primer for substituting the N-terminal Gln residue with a Ser residue in AVP04-07;

SEQ ID NO: 67—nucleotide sequence of mutagenic primer for substituting the N-terminal Gln residue with a Ser residue in AVP04-07;

SEQ ID NO: 68—nucleotide sequence of mutagenic primer for introducing cysteine residue substitutions at positions 38 and 42 in the $V_L$ FR2 of AVP04-07

SEQ ID NO: 69—nucleotide sequence of mutagenic primer for introducing cysteine residue substitutions at positions 38 and 42 in the $V_L$ FR2 of AVP04-07

SEQ ID NO: 70—nucleotide sequence of mutagenic primer for introducing cysteine residue substitutions at positions 38 and 44 in the $V_L$ FR2 of AVP04-07

SEQ ID NO: 71—nucleotide sequence of mutagenic primer for introducing cysteine residue substitutions at positions 38 and 44 in the $V_L$ FR2 of AVP04-07

SEQ ID NO: 72—nucleotide sequence of mutagenic primer for introducing cysteine residue substitutions at positions 78 and 82 in the $V_L$ FR3 of AVP04-07

SEQ ID NO: 73—nucleotide sequence of mutagenic primer for introducing cysteine residue substitutions at positions 78 and 82 in the $V_L$ FR3 of AVP04-07

SEQ ID NO: 74—nucleotide sequence of mutagenic primer for introducing cysteine residue substitutions at positions 39 and 43 in the $V_H$ FR2 of AVP04-07

SEQ ID NO: 75—nucleotide sequence of mutagenic primer for introducing cysteine residue substitutions at positions 39 and 43 in the $V_H$ FR2 of AVP04-07

SEQ ID NO: 76—nucleotide sequence of mutagenic primer for introducing cysteine residue substitutions at positions 39 and 45 in the $V_H$ FR2 of AVP04-07

SEQ ID NO: 77—nucleotide sequence of mutagenic primer for introducing cysteine residue substitutions at positions 39 and 45 in the $V_H$ FR2 of AVP04-07

SEQ ID NO: 78—nucleotide sequence of mutagenic primer for introducing cysteine residue substitutions at positions 82C and 86 in the $V_H$ FR3 of AVP04-07

SEQ ID NO: 79—nucleotide sequence of mutagenic primer for introducing cysteine residue substitutions at positions 82C and 86 in the $V_H$ FR3 of AVP04-07

SEQ ID NO: 80—nucleotide sequence of mutagenic primer for introducing cysteine residue substitutions at positions 70 and 79 in the $V_H$ FR3 of AVP04-07

SEQ ID NO: 81—nucleotide sequence of mutagenic primer for introducing cysteine residue substitutions at positions 70 and 79 in the $V_H$ FR3 of AVP04-07

SEQ ID NO: 82—nucleotide sequence of mutagenic primer for introducing cysteine residue substitutions at positions 72 and 75 in the $V_H$ FR3 of AVP04-07

SEQ ID NO: 83—nucleotide sequence of mutagenic primer for introducing cysteine residue substitutions at positions 72 and 75 in the $V_H$ FR3 of AVP04-07

SEQ ID NO: 84—nucleotide sequence of mutagenic primer for introducing cysteine residue substitutions at positions 65 and 72 in the $V_L$ FR3 of AVP04-07

SEQ ID NO: 85—nucleotide sequence of mutagenic primer for introducing cysteine residue substitutions at positions 65 and 72 in the $V_L$ FR3 of AVP04-07

SEQ ID NO: 86—nucleotide sequence of mutagenic primer for modification of linker residues of AVP04-79 for scFv expression SEQ ID NO: 87—nucleotide sequence of mutagenic primer for modification of linker residues of AVP04-79 for scFv expression SEQ ID NO: 88—nucleotide sequence of mutagenic primer for modification of linker residues of AVP04-79 for triabody expression.

SEQ ID NO: 89—nucleotide sequence of mutagenic primer for modification of linker residues of AVP04-79 for triabody expression.

SEQ ID NO: 90—nucleotide sequence of mutagenic primer for AVP07-17 anti-HER2 diabody replacing CDR3H Cysteine residues with alanines designated AVP07-86

SEQ ID NO: 91—nucleotide sequence of mutagenic primer for AVP07-17 anti-HER2 diabody replacing CDR3H Cysteine residues with alanines designated AVP07-86

SEQ ID NO: 92—nucleotide sequence of mutagenic primer for introducing cysteine residue substitutions at positions 38 and 42 in the $V_L$ FR2 of AVP02-60

SEQ ID NO: 93—nucleotide sequence of mutagenic primer for introducing cysteine residue substitutions at positions 38 and 42 in the $V_L$ FR2 of AVP02-60

SEQ ID NO: 94—nucleotide sequence of mutagenic primer for introducing cysteine residue substitutions at positions 39 and 43 in the $V_H$ FR2 of AVP02-60

SEQ ID NO: 95—nucleotide sequence of mutagenic primer for introducing cysteine residue substitutions at positions 39 and 43 in the $V_H$ FR2 of AVP02-60

SEQ ID NO: 96—nucleotide sequence of mutagenic primer for introducing cysteine residue substitutions at positions 38 and 42 in the $V_L$ FR2 of AVP07-86

SEQ ID NO: 97—nucleotide sequence of mutagenic primer for introducing cysteine residue substitutions at positions 38 and 42 in the $V_L$ FR2 of AVP07-86

SEQ ID NO: 98—nucleotide sequence of mutagenic primer for introducing cysteine residue substitutions at positions 39 and 43 in the $V_H$ FR2 of AVP07-86

SEQ ID NO: 99—nucleotide sequence of mutagenic primer for introducing cysteine residue substitutions at positions 39 and 43 in the $V_H$ FR2 of AVP07-86

SEQ ID NO: 100—nucleotide sequence of an anti-TAG72 diabody comprising cysteine replacement mutations in the $V_L$ FR2 Kabat positions 38 and 42 designated AVP04-79.

SEQ ID NO: 101—amino acid sequence of an anti-TAG72 diabody comprising cysteine replacement mutations in the $V_L$ FR2 Kabat positions 38 and 42 designated AVP04-79.

SEQ ID NO: 102—nucleotide sequence of an anti-TAG72 diabody comprising cysteine replacement mutations in the $V_L$ FR2 Kabat positions 38 and 44 is designated AVP04-80.

SEQ ID NO: 103—amino acid sequence of an anti-TAG72 diabody comprising cysteine replacement mutations in the $V_L$ FR2 Kabat positions 38 and 44 is designated AVP04-80.

SEQ ID NO: 104—nucleotide sequence of an anti-TAG72 diabody comprising cysteine replacement mutations in the $V_L$ FR3 Kabat positions 78 and 82 designated AVP04-83.

SEQ ID NO: 105—amino acid sequence of an anti-TAG72 diabody comprising cysteine replacement mutations in the $V_L$ FR3 Kabat positions 78 and 82 designated AVP04-83.

SEQ ID NO: 106—nucleotide sequence of an anti-TAG72 diabody comprising cysteine replacement mutations in the $V_H$ FR2 Kabat positions 39 and 43 designated AVP04-111.

SEQ ID NO: 107—amino acid sequence of an anti-TAG72 diabody comprising cysteine replacement mutations in the $V_H$ FR2 Kabat positions 39 and 43 designated AVP04-111.

SEQ ID NO: 108—nucleotide sequence of an anti-TAG72 diabody comprising cysteine replacement mutations in the $V_H$ FR2 Kabat positions 39 and 45 designated AVP04-112.

SEQ ID NO: 109—amino acid sequence of an anti-TAG72 diabody comprising cysteine replacement mutations in the $V_H$ FR2 Kabat positions 39 and 45 designated AVP04-112.

SEQ ID NO: 110—nucleotide sequence of an anti-TAG72 diabody comprising cysteine replacement mutations in the $V_H$ FR3 Kabat positions 82C and 86 designated AVP04-114.

SEQ ID NO: 111—amino acid sequence of an anti-TAG72 diabody comprising cysteine replacement mutations in the $V_H$ FR3 Kabat positions 82C and 86 designated AVP04-114.

SEQ ID NO: 112—nucleotide sequence of an anti-TAG72 diabody comprising cysteine replacement mutations in the $V_H$ FR3 Kabat positions 70 and 79 designated AVP04-120.

SEQ ID NO: 113—amino acid sequence of an anti-TAG72 diabody comprising cysteine replacement mutations in the $V_H$ FR3 Kabat positions 70 and 79 designated AVP04-120.

SEQ ID NO: 114—nucleotide sequence of an anti-TAG72 diabody comprising cysteine replacement mutations in the $V_H$ FR3 Kabat positions 72 and 75 designated AVP04-121.

SEQ ID NO: 115—amino acid sequence of an anti-TAG72 diabody comprising cysteine replacement mutations in the $V_H$ FR3 Kabat positions 72 and 75 designated AVP04-121.

SEQ ID NO: 116—nucleotide sequence of an anti-TAG72 diabody comprising cysteine replacement mutations in the $V_L$ FR3 Kabat positions 65 and 72 designated AVP04-123.

SEQ ID NO: 117—amino acid sequence of an anti-TAG72 diabody comprising cysteine replacement mutations in the $V_L$ FR3 Kabat positions 65 and 72 designated AVP04-123.

SEQ ID NO: 118—nucleotide sequence of an anti-TAG72 scFv comprising cysteine replacement mutations in the $V_L$ FR2 Kabat positions 38 and 42 designated AVP04-124.

SEQ ID NO: 119—amino acid sequence of an anti-TAG72 scFv comprising cysteine replacement mutations in the $V_L$ FR2 Kabat positions 38 and 42 designated AVP04-124.

SEQ ID NO: 120—nucleotide sequence of an anti-TAG72 triabody comprising cysteine replacement mutations in the $V_L$ FR2 Kabat positions 38 and 42 designated AVP04-125.

SEQ ID NO: 121—amino acid sequence of an anti-TAG72 triabody comprising cysteine replacement mutations in the $V_L$ FR2 Kabat positions 38 and 42 designated AVP04-125.

SEQ ID NO: 122—nucleotide sequence of an anti-MucI diabody comprising cysteine replacement mutations in the $V_L$ FR2 Kabat positions 38 and 42 designated AVP02-115.

SEQ ID NO: 123—amino acid sequence of an anti-MucI diabody comprising cysteine replacement mutations in the $V_L$ FR2 Kabat positions 38 and 42 designated AVP02-115.

SEQ ID NO: 124—nucleotide sequence of an anti-MucI diabody comprising cysteine replacement mutations in the $V_H$ FR2 Kabat positions 39 and 43 designated AVP02-116.

SEQ ID NO: 125—amino acid sequence of an anti-MucI diabody comprising cysteine replacement mutations in the $V_H$ FR2 Kabat positions 39 and 43 designated AVP02-116.

SEQ ID NO: 126—nucleotide sequence of an anti-Her2 diabody comprising cysteine replacement mutations in the $V_L$ FR2 Kabat positions 38 and 42 designated AVP07-117.

SEQ ID NO: 127—amino acid sequence of an anti-Her2 diabody comprising cysteine replacement mutations in the $V_L$ FR2 Kabat positions 38 and 42 designated AVP07-117.

SEQ ID NO: 128—nucleotide sequence of an anti-Her2 diabody comprising cysteine replacement mutations in the $V_H$ FR2 Kabat positions 39 and 43 designated AVP07-118.

SEQ ID NO: 129—amino acid sequence of an anti-Her2 diabody comprising cysteine replacement mutations in the $V_H$ FR2 Kabat positions 39 and 43 designated AVP07-118.

SEQ ID NO: 130—nucleotide sequence of an anti-MucI diabody comprising cysteine replacement mutations in the $V_L$ FR2 Kabat positions 38 and 44 designated AVP02-126.

SEQ ID NO: 131—amino acid sequence of an anti-MucI diabody comprising cysteine replacement mutations in the $V_L$ FR2 Kabat positions 38 and 44 designated AVP02-126.

SEQ ID NO: 132—nucleotide sequence of an anti-MucI diabody comprising cysteine replacement mutations in the $V_H$ FR2 Kabat positions 39 and 45 designated AVP02-127.

SEQ ID NO: 133—amino acid sequence of an anti-MucI diabody comprising cysteine replacement mutations in the $V_H$ FR2 Kabat positions 39 and 45 designated AVP02-127.

SEQ ID NO: 134—nucleotide sequence of an anti-MucI diabody comprising cysteine replacement mutations in the $V_L$ FR3 Kabat positions 65 and 72 designated AVP02-128.

SEQ ID NO: 135—amino acid sequence of an anti-MucI diabody comprising cysteine replacement mutations in the $V_L$ FR3 Kabat positions 65 and 72 designated AVP02-128.

SEQ ID NO: 136—nucleotide sequence of an anti-MucI diabody comprising cysteine replacement mutations in the $V_H$ FR3 Kabat positions 70 and 79 designated AVP02-129.

SEQ ID NO: 137—amino acid sequence of an anti-MucI diabody comprising cysteine replacement mutations in the $V_H$ FR3 Kabat positions 70 and 79 designated AVP02-129.

SEQ ID NO: 138—nucleotide sequence of an anti-MucI diabody comprising cysteine replacement mutations in the $V_H$ FR3 Kabat positions 72 and 75 designated AVP02-130.

SEQ ID NO: 139—amino acid sequence of an anti-MucI diabody comprising cysteine replacement mutations in the $V_H$ FR3 Kabat positions 72 and 75 designated AVP02-130.

SEQ ID NO: 140—nucleotide sequence of an anti-Her2 diabody comprising cysteine replacement mutations in the $V_L$ FR2 Kabat positions 38 and 44 designated AVP07-131.

SEQ ID NO: 141—amino acid sequence of an anti-Her2 diabody comprising cysteine replacement mutations in the $V_L$ FR2 Kabat positions 38 and 44 designated AVP07-131.

SEQ ID NO: 142—nucleotide sequence of an anti-Her2 diabody comprising cysteine replacement mutations in the $V_H$ FR2 Kabat positions 39 and 45 designated AVP07-132.

SEQ ID NO: 143—amino acid sequence of an anti-Her2 diabody comprising cysteine replacement mutations in the $V_H$ FR2 Kabat positions 39 and 45 designated AVP07-132.

SEQ ID NO: 144—nucleotide sequence of an anti-Her2 diabody comprising cysteine replacement mutations in the $V_L$ FR3 Kabat positions 65 and 72 designated AVP07-133.

SEQ ID NO: 145—amino acid sequence of an anti-Her2 diabody comprising cysteine replacement mutations in the $V_L$ FR3 Kabat positions 65 and 72 designated AVP07-133.

SEQ ID NO: 146—nucleotide sequence of an anti-Her2 diabody comprising cysteine replacement mutations in the $V_H$ FR3 Kabat positions 70 and 79 designated AVP07-134.

SEQ ID NO: 147—amino acid sequence of an anti-Her2 diabody comprising cysteine replacement mutations in the $V_H$ FR3 Kabat positions 70 and 79 designated AVP07-134.

SEQ ID NO: 148—nucleotide sequence of an anti-Her2 diabody comprising cysteine replacement mutations in the $V_H$ FR3 Kabat positions 72 and 75 designated AVP07-135.

SEQ ID NO: 149—amino acid sequence of an anti-Her2 diabody comprising cysteine replacement mutations in the $V_H$ FR3 Kabat positions 72 and 75 designated AVP07-135.

SEQ ID NO: 150—amino acid sequence of human HER2;

SEQ ID NO: 151—amino acid sequence of human PSMA;

SEQ ID NO: 152—amino acid sequence of an isoform of human MUC1;

SEQ ID NO: 153—amino acid sequence of an isoform of human MUC1 expressed in several forms of cancer;

SEQ ID NO: 154—nucleotide sequence of anti-HER2 diabody designated AVP04-50;

SEQ ID NO: 155—amino acid sequence of anti-HER2 diabody designated AVP04-50;

SEQ ID NO: 156—nucleotide sequence of anti-HER2 diabody designated AVP07-17; and SEQ ID NO: 157—amino acid sequence of anti-HER2 diabody designated AVP07-17.

DETAILED DESCRIPTION OF PREFERRED EMBODIMENTS

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

Any embodiment herein shall be taken to apply mutatis mutandis to any other embodiment unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, biochemistry and homology modeling).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in, for example, Kabat (1987 and/or 1991), Bork et al (1994) and/or Chothia and Lesk (1987 and 1989) or Al-Lazikani et al (1997).

The term "and/or", e.g., "X and/or Y" shall be understood to mean either "X and Y" or "X or Y" and shall be taken to provide explicit support for both meanings or for either meaning.

As used herein, the term "between" in the context of defining the positioning of an amino acid residue or nucleotide residue based on a specific position number (e.g., according to the Kabat numbering system) shall be taken to mean any residues located between the two recited residues and the two recited residues. For example, the term "between residues 38-42" shall be understood to include residues 38, 39, 40, 41 and 42.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

As used herein, the term "immunoglobulin" shall be taken to mean an antibody or any antibody-related protein. The skilled artisan will be aware that an antibody is generally considered to be a protein that comprises a variable region made up of a plurality of polypeptide chains, e.g., a light chain variable region ($V_L$) and a heavy chain variable region ($V_H$). An antibody also generally comprises constant domains, which can be arranged into a constant region or constant fragment or fragment crystallisable (Fc). Antibodies can bind specifically to one or a few closely related antigens. Generally, antibodies comprise a four-chain structure as their basic unit. Full-length antibodies comprise two heavy chains (~50-70 kD) covalently linked and two light chains (~23 kD each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is ~330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. Preferably, the antibody is a murine (mouse or rat) antibody or a primate (preferably human) antibody. The term "antibody" also encompasses humanized antibodies, primatized antibodies, human antibodies and chimeric antibodies. Proteins related to antibodies, and thus encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. As used herein, the term "immunoglobulin" does not encompass T cell receptors and other immunoglobulin-like domain containing proteins that are not capable of binding to an antigen, e.g., by virtue of an antigen binding site comprising a variable region. Furthermore, the term "immunoglobulin" does not encompass a protein comprising an immunoglobulin domain that does not comprise a FR2 and/or FR3, since the invention cannot be performed with such a protein.

As used herein, "variable region" refers to the portions of the light and heavy chains of an antibody or immunoglobulin as defined herein that includes amino acid sequences of CDRs; i.e., CDR1, CDR2, and CDR3, and FRs. In the case of IgNARs the term "variable region" does not require the presence of a CDR2. $V_H$ refers to the variable region of the heavy chain. $V_L$ refers to the variable region of the light chain. According to the methods used in this invention, the amino acid positions assigned to CDRs and FRs are defined according to Kabat (1987 and 1991). The skilled artisan will be readily able to use other numbering systems in the performance of this invention, e.g., the hypervariable loop numbering system of Chothia and Lesk (1987 and/or 1989 and/or Al-Lazikani et al 1997).

As used herein, the term "heavy chain variable region" or "$V_H$" shall be taken to mean a protein capable of binding to one or more antigens, preferably specifically binding to one or more antigens and at least comprising a FR2 and/or FR3.

Sequences of exemplary FR2 and/or FR3 from a heavy chain are provided herein (see, for example, SEQ ID NOs 1 to 8 or 22 to 40). Preferably, the heavy chain comprises three or four FRs (e.g., FR1, FR2, FR3 and optionally FR4) together with three CDRs. Preferably, a heavy chain comprises FRs and CDRs positioned as follows residues 1-30 (FR1), 31-25 (CDR1), 36-49 (FR2), 50-65 (CDR2), 66-94 (FR3), 95-102 (CDR3) and 103-113 (FR4), numbered according to the Kabat numbering system. In one example, the heavy chain is derived from an immunoglobulin comprising said heavy chain and a plurality of (preferably 3 or 4) constant domains or linked to a constant fragment (Fc).

As used herein, the term "light chain variable region" or "$V_L$" shall be taken to mean a protein capable of binding to one or more antigens, preferably specifically binding to one or more antigens and at least comprising a FR2 and/or FR3. Sequences of exemplary FR2 and/or FR3 from a light chain are provided herein (see, for example, SEQ ID NO's 9 to 21 or 41 to 56). Preferably, the light chain comprises three or four FRs (e.g., FR1, FR2, FR3 and optionally FR4) together with three CDRs. Preferably, a light chain comprises FRs and CDRs positioned as follows residues 1-23 (FR1), 24-34 (CDR1), 35-49 (FR2), 50-56 (CDR2), 57-88 (FR3), 89-97 (CDR3) and 98-107 (FR4), numbered according to the Kabat numbering system. In one example, the light chain is derived from an immunoglobulin comprising said light chain linked to one constant domain and/or not linked to a constant fragment (Fc).

In some examples of the invention the term "framework regions" will be understood to mean those variable region residues other than the CDR residues. Each variable region of a naturally-occurring immunoglobulin (e.g., antibody) typically has four FRs identified as FR1, FR2, FR3 and FR4. If the CDRs are defined according to Kabat, exemplary light chain FR (LCFR) residues are positioned at about residues 1-23 (LCFR1), 35-49 (LCFR2), 57-88 (LCFR3), and 98-107 (LCFR4). Note that λLCFR1 does not comprise residue 10, which is included in κLCFR1. Exemplary heavy chain FR (HCFR) residues are positioned at about residues 1-30 (HCFR1), 36-49 (HCFR2), 66-94 (HCFR3), and 103-113 (HCFR4).

For all immunoglobulin variable regions of the invention, "framework region 2" (FR2) is defined as the residues between CDR1 and CDR2. These residues have been numbered by at least two nomenclatures being 1) Kabat (1987 and/or 2001) and 2) Chothia and Lesk (1987, 1989 and Al-Lazikani et al 1997). The Chothia and Lesk numbering system was based on the well established Kabat system and attempted to correct the numbering of light chain CDR1 and heavy chain CDR1 sequence length variability in the immunoglobulin variable regions to better fit their actual position in the three-dimensional structure. The CDR-specific numbering adopted by Chothia and Lesk was later modified in 1989 but then reverted in 1997. There are subtle differences between these numbering systems when dealing with residues found within CDR loops. According to the Kabat numbering system, FR2 is positioned between residues 36 to 49 in a $V_H$ and 35 to 49 in a $V_L$.

For all immunoglobulin variable regions of the invention, "framework region 3" (FR3) is defined as the residues between CDR2 and CDR3. As with FR2 these residues have been numbered by at least two nomenclatures being 1) Kabat (1987 and/or 2001) and 2) Chothia and Lesk (1987, 1989 and Al-Lazikani et al 1997). According to the Kabat numbering system, FR3 is positioned between residues 66 to 94 in a $V_H$ and 57 to 88 in a $V_L$.

For all immunoglobulin variable regions of the invention, "framework region 1" (FR1) is defined as the residues between the natural N-terminal residue and the start of the complementarity determining region No. 1 (CDR1). As with FR2 and FR3, these residues have been numbered by at least two nomenclatures being 1) Kabat (1987 and/or 2001) and 2) Chothia and Lesk (1987, 1989 and Al-Lazikani et al 1997). As the skilled person will appreciate, within framework region 1, and thus prior to CDR1, a single highly-conserved cysteine residue (Cys) is generally present. Within both kappa and lambda variable light chains, this conserved cysteine is invariantly in Kabat position 23 and forms a disulphide bond with another highly conserved cysteine residue, invariantly in Kabat position 88, within the region defined as framework region 3, between CDR2 and CDR3. However, the present invention contemplates indels, generally man made indels of one, two or three amino acids, which may alter the position of the conserved cysteine relative to other amino acids of FR1.

The pairing of highly conserved cysteines is subtly different in variable heavy chains, occurring between conserved cysteines in invariant Kabat positions 22 (within FR1) and 92 (within FR3). However, this pairing is almost perfectly conserved in all immunoglobulins, suggesting this disulfide bond was probably already present at the beginning of Ig-loop diversification and was maintained under selective pressure. The almost perfect conservation of the disulfide bond further suggests that it contributes significantly to the stability of the Ig-loop.

As used herein, the term "complementarity determining regions" (syn. CDRs; i.e., CDR1, CDR2, and CDR3 or hypervariable region) refers to the amino acid residues of an immunoglobulin variable region the presence of which are necessary for antigen binding. Each variable region typically has three CDR regions identified as CDR1, CDR2 and CDR3. Each CDR may comprise amino acid residues from a "complementarity determining region" as defined by Kabat (1987 and/or 1991). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991).

The term "constant region" (syn. CR or fragment crystalizable or Fc) as used herein, refers to a portion of an immunoglobulin comprising at least one constant domain and which is generally (though not necessarily) glycosylated and which binds to one or more F receptors and/or components of the complement cascade (e.g., confers effector functions). The heavy chain constant region can be selected from any of the five isotypes: α, δ, ϵ, γ, or μ. Furthermore, heavy chains of various subclasses (such as the IgG subclasses of heavy chains) are responsible for different effector functions and thus, by choosing the desired heavy chain constant region, proteins with desired effector function can be produced. Preferred heavy chain constant regions are gamma 1 (IgG1), gamma 2 (IgG2) and gamma 3 (IgG3).

A "constant domain" is a domain in an immunoglobulin the sequence of which is highly similar in immunoglobulins/antibodies of the same type, e.g., IgG or IgM or IgE. A constant region of an immunoglobulin generally comprises a plurality of constant domains, e.g., the constant region of γ, α and δ heavy chains comprise three constant domains and the Fc of γ, α and δ heavy chains comprise two constant domains. A constant region of μ and ϵ heavy chains comprises four constant domains and the Fc region comprises two constant domains.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore an Fv of the invention (as well as any protein of the invention) may have multiple antigen binding sites which may or may not bind the same antigen. This term shall be understood to encompass fragments directly derived from an immunoglobulin as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain. A "Fab fragment" consists of a monovalent antigen-binding fragment of an immunoglobulin, and can be produced by digestion of a whole immunoglobulin with the enzyme papain, to yield a fragment consisting of an intact light chain and a portion of a heavy chain or can be produced using recombinant means. A "Fab' fragment" of an immunoglobulin can be obtained by treating a whole immunoglobulin with pepsin, followed by reduction, to yield a molecule consisting of an intact light chain and a portion of a heavy chain. Two Fab' fragments are obtained per immunoglobulin treated in this manner. A Fab' fragment can also be produced by recombinant means. A "F(ab')2 fragment" of an immunoglobulin consists of a dimer of two Fab' fragments held together by two disulfide bonds, and is obtained by treating a whole immunoglobulin molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an immunoglobulin in which the variable region of the light chain and the variable region of the heavy chain are covalently linked by a suitable, flexible polypeptide linker. A detailed discussion of exemplary Fv containing proteins falling within the scope of this term is provided herein below.

As used herein, the term "antigen binding site" shall be taken to mean a structure formed by a protein that is capable of specifically binding to an antigen. The antigen binding site need not be a series of contiguous amino acids, or even amino acids in a single polypeptide chain. For example, in a Fv produced from two different polypeptide chains the antigen binding site is made up of a series of regions of a $V_L$ and a $V_H$ that interact with the antigen and that are generally, however not always in the one or more of the CDRs in each variable region.

By "Kabat numbering system" is meant the numbering system to determining the position of FRs and CDRs in a variable region of an immunoglobulin as set out in Kabat (1987 and/or 1991).

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions. A non-covalent bond contemplated by the present invention is the interaction between a $V_H$ and a $V_L$, e.g., in some forms of diabody or a triabody or a tetrabody.

The term "polypeptide chain" will be understood to mean from the foregoing paragraph to mean a series of contiguous amino acids linked by peptide bonds.

The skilled artisan will be aware that a "disulphide bond" is a covalent bond formed by coupling of thiol groups. The bond is also called an SS-bond or disulfide bridge. In proteins, a disulphide bond generally occurs between the thiol groups of two cysteine residues to produce cysteine.

The skilled artisan will also be aware that the term "non-reducing conditions" includes conditions sufficient for oxidation of sulfhydryl (—SH) groups in a protein, e.g., permissive for disulphide bond formation.

As used herein, the term "antigen" shall be understood to mean any composition of matter against which an immunoglobulin response (e.g., an antibody response) can be raised. Exemplary antigens include proteins, peptides, polypeptides, carbohydrates, phosphate groups, phosphor-peptides or polypeptides, glycosylated peptides or peptides, etc.

As used herein, the term "specifically binds" shall be taken to mean a protein of the invention reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". Generally, but not necessarily, reference to binding means specific binding, and each term shall be understood to provide explicit support for the other term.

The term the terms "preventing", "prevent" or "prevention" in the context of binding of a protein of the invention to an antigen shall be taken to mean complete abrogation or complete inhibition of binding to the antigen.

Variable Region Containing Proteins

The present invention contemplates any protein that comprises an immunoglobulin variable region that specifically or selectively binds to one or more antigens and that is modified as described herein according to any embodiment. Preferred proteins comprise at least one $V_H$ and at least one $V_L$. Exemplary immunoglobulin variable regions are variable regions from antibodies and modified forms thereof (e.g., humanized antibodies) and heavy chain antibodies, such as, camelid immunoglobulin and IgNAR.

Immuno Globulin Variable Regions

Antibody Variable Regions

As will be apparent to the skilled artisan based on the description herein, the proteins of the invention can comprise one or more variable regions from an antibody modified to comprise at least two cysteine residues in FR2 and/or FR3 as described herein. The present invention also provides antibody molecules. Such antibodies may be produced by first producing an antibody against an antigen of interest and modifying that antibody (e.g., using recombinant means) or by modifying a previously produced antibody.

Methods for producing antibodies are known in the art. For example, methods for producing monoclonal antibodies, such as the hybridoma technique, are by Kohler and Milstein, (1975). In a hybridoma method, a mouse, hamster, or other appropriate host animal, is typically immunized with an immunogen or antigen or cell expressing same to elicit lymphocytes that produce or are capable of producing antibodies that will specifically bind to the immunogen or antigen. Lymphocytes or spleen cells from the immunized animals are then fused with an immortalized cell line using a suitable fusing agent, such as polyethylene glycol, to form a hybridoma cell (Goding, 1986). The resulting hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Other methods for producing antibodies are also contemplated by the present invention, e.g., using ABL-MYC technology described generically in detail in Largaespada (1990) or Weissinger et al. (1991).

Alternatively, the antibody, or sequence encoding same is generated from a previously produced cell expressing an antibody of interest, e.g., a hybridoma or transfectoma. Various sources of such hybridomas and/or transfectomas will be apparent to the skilled artisan and include, for example, American Type Culture Collection (ATCC) and/or European Collection of Cell Cultures (ECACC). Methods for isolating and/or modifying sequences encoding variable regions from antibodies will be apparent to the skilled artisan and/or described herein.

Following antibody production and/or isolation of a sequence encoding same, the antibody is modified to include cysteine residues in FR2 and/or FR3 as described herein at sites as described herein according to any embodiment. Generally, this involves isolating the nucleic acid encoding the antibody, modifying the sequence thereof to include codons encoding cysteine residues (i.e., TGT or TGC) at the requisite sites in a FR2 and/or FR3 as described herein encoding region and expressing the modified antibody.

Exemplary human antibody heavy chain FR2 sequences comprise a sequence selected from the group consisting of WVRQAPGKGLEWVS (SEQ ID NO: 1); WVRQAPGKGLEWVG (SEQ ID NO: 2); WVRQAPGQLEWMG (SEQ ID NO: 3); WVRQAPGKGLEWMG (SEQ ID NO: 4); WIRQPPGKGLEWIG (SEQ ID NO: 5); WIRQPPGKALEWLG (SEQ ID NO: 6); WVRQMPGKGLEWMG (SEQ ID NO: 7); and WIRQSPSRGLEWLG (SEQ ID NO: 8).

Exemplary human antibody κ light chain FR2 sequences comprise a sequence selected from the group consisting of WYQQKPGKAPKLLIY (SEQ ID NO: 9); WYQQKPGQAPRLLIY (SEQ ID NO: 10); WYQQKPGQPPKLLIY (SEQ ID NO: 11); WYLQKPGQSPQLLIY (SEQ ID NO: 12); WYQQKPCQAPRLLIY (SEQ ID NO: 13); WFQQKPGKAPKSLIY (SEQ ID NO: 14); WYQQKPAKAPKLFIY (SEQ ID NO: 15); and WYLQKPGQPPQLLIY (SEQ ID NO: 16).

Exemplary human antibody λ light chain FR2 sequences comprise a sequence selected from the group consisting of WYQQLPGTAPKLLIY (SEQ ID NO: 17); WYQQHPGKAPKLMIY (SEQ ID NO: 18); WYQQKPGQAPVLVIY (SEQ ID NO: 19); WYQQKPGQSPVLVIY (SEQ ID NO: 20); and WHQQQPEKGPRYLMY (SEQ ID NO: 21);

Exemplary human antibody heavy chain FR3 sequences comprise a sequence selected from the group consisting of (SEQ ID NO: 22)
RFTISRDNAKNSLYLQMNSLRAEDTAVYYCAR;

(SEQ ID NO: 23)
RFTISRDNSKNTLHLQMNSLRAEDTAVYYCKR;

(SEQ ID NO: 24)
RFTISRDDSKNTAYLQMNSLKTEDTAVYYCTR;

(SEQ ID NO: 25)
RVTISVDTSKNQFSLKLSSVTAADTAVYYCAR;

(SEQ ID NO: 26)
RLTISKDTSKNQVVLTMTNMDPVDTATYYCAR;

(SEQ ID NO: 27)
RFVFSLDTSVSTAYLQMSSLKAEDTAVYYCAR;

(SEQ ID NO: 28)
RVTISADKSISTAYLQWSSLKASDTAMYYCAR;

(SEQ ID NO: 29)
RVTITADKSTSTAYMELSSLRSEDTAVYYCAR;

(SEQ ID NO: 30)
RFTISRDNAKNSLYLQMNSLRAEDTALYYCAKD;

(SEQ ID NO: 31)
RVTITADESTSTAYMELSSLRSEDTAVYYCAR;

(SEQ ID NO: 32)
RVTMTRNTSISTAYMELSSLRSEDTAVYYCAR;

(SEQ ID NO: 33)
RFTISRDNSKNTLHLQMNSLRAEDTAVYYCKK;

(SEQ ID NO: 34)
RFTISRDNSKNSLYLQMNSLRTEDTALYYCAKD;

(SEQ ID NO: 35)
RFTISRDNSKNTLYLQMNSLRAEDTAVYYCAR;

(SEQ ID NO: 36)
RLTISKDTSKNQVVLTMTNMDPVDTATYYCARI;

(SEQ ID NO: 37)
RFVFSLDTSVSTAYLQICSLKAEDTAVYYCAR;

(SEQ ID NO: 38)
RITINPDTSKNQFSLQLNSVTPEDTAVYYCAR;

(SEQ ID NO: 39)
HVTISADKSISTAYLQWSSLKASDTAMYYCAR;
and (SEQ ID NO: 40)
RVTMTRDTSTSTAYMELSSLRSEDTAVYYCAR.

Exemplary human antibody κ light chain FR3 sequences comprise a sequence selected from the group consisting of GVPSRFSGSGSGTDFTLTISSLQPEDFATYYC (SEQ ID NO: 41); GVPSRFSGSGSGTDFTFTISSLQPEDIATYYC (SEQ ID NO: 42); GVPSRFSGSGSGTEFTLTISSLQPDDFATYYC (SEQ ID NO: 43); GIPARFSGSGSGTEFTLTISSLQSEDFAVYYC (SEQ ID NO: 44); GIPARFSGSGSGTDFTLTISSLEPEDFAVYYC (SEQ ID NO: 45); GIPDRFSGSGSGTDFTLTISRLEPEDFAVYYC (SEQ ID NO: 46); GVPDRFSGSGSGTDFTLTISSLQAEDVAVYYC (SEQ ID NO: 47); and GVPDRFSGSGSGTDFTLKISRVEAEDVGVYYC (SEQ ID NO: 48).

Exemplary human antibody λ light chain FR3 sequences comprise a sequence selected from the group consisting of (SEQ ID NO: 49)
GVPSRFSGSGSGTDFTLTISCLQSEDFATYYC;

-continued (SEQ ID NO: 50)
GVPSRFSGSGSGTEFTLTISSLQPEDFATYYC;

(SEQ ID NO: 51)
GIPARFSGSGPGTDFTLTISSLEPEDFAVYYC;

(SEQ ID NO: 52)
GVPSRFSGSGSGTDFTLTINSLEAEDAATYYC;

(SEQ ID NO: 53)
GIPARFSGSGSGTDFTLTISSLQPEDFAVYYC;

(SEQ ID NO: 54)
GVPSRFSGSGSGTDFTFTISSLEAEDAATYYC;

(SEQ ID NO: 55)
GIPPRFSGSGYGTDFTLTINNIESEDAAYYFC;
and (SEQ ID NO: 56)
GVPSRFSGSGSGTDFTLTISSLQPEDVATYYC.

The foregoing sequences are merely exemplary of sequences that may be used to perform the invention and are not an exhaustive list of such sequences. These examples are provided for the purposes of describing the invention and not limiting the invention. It is within the capability of the skilled artisan to determine the sequence of an additional FR2 and/or FR3 using known methods and/or based on the disclosure in, for example, Kabat (1987 and/or 2001).

The foregoing examples of FR2 and/or FR3 regions are readily modified to include two or more cysteine residues at positions as described herein in any example or embodiment.

The skilled artisan will be readily able to determine the sequence of nucleic acid encoding a FR2 and/or FR3 based on knowledge in the art and/or sequences set forth herein.

Chimeric, Deimmunized, Humanized and Human Antibodies

The proteins of the present invention may be derived from or may be humanized antibodies or human antibodies or variable regions derived therefrom. The term "humanized antibody" shall be understood to refer to a chimeric molecule, generally prepared using recombinant techniques, having an antigen binding site derived from an antibody from a non-human species and the remaining antibody structure of the molecule based upon the structure and/or sequence of a human antibody. The antigen-binding site preferably comprises CDRs from the non-human antibody grafted onto appropriate FRs in the variable regions of a human antibody and the remaining regions from a human antibody. Antigen binding sites may be wild type or modified by one or more amino acid substitutions. In some instances, framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable regions, in which all or substantially all of the CDR regions correspond to those of a non-human immunoglobulin and all or substantially all of the FR regions are those of a human immunoglobulin consensus sequence. Methods for humanizing non-human antibodies are known in the art. Humanization can be essentially performed following the method of U.S. Pat. No. 5,225,539, U.S. Pat. No. 6,054,297 or U.S. Pat. No. 5,585,089. Other methods for humanizing an antibody are not excluded. The skilled artisan will understand that a protein of the invention that is not a complete antibody can also be humanized, e.g., a variable domain can be humanized.

The term "human antibody" as used herein in connection with antibody molecules and binding proteins refers to antibodies having variable and, optionally, constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4 or 5 of the residues of the antibody, preferably e.g. in 1, 2, 3, 4 or 5 of the residues making up one or more of the CDRs of the antibody). These "human antibodies" do not actually need to be produced by a human, rather, they can be produced using recombinant means and/or isolated from a transgenic animal (e.g., a mouse) comprising nucleic acid encoding human antibody constant and/or variable regions. Human antibodies or fragments thereof can be produced using various techniques known in the art, including phage display libraries (e.g., as described in U.S. Pat. No. 6,300,064; U.S. Pat. No. 5,885,793; U.S. Pat. No. 6,204,023; U.S. Pat. No. 6,291,158; or U.S. Pat. No. 6,248,516), or using transgenic animals expressing human immunoglobulin genes (e.g., as described in WO2002/066630; Lonberg et al. (1994) or Jakobovits et al. (2007)).

In one example, a protein of the invention is a chimeric antibody or part thereof, e.g., a Fab fragment. The term "'chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity (U.S. Pat. No. 4,816,567). Typically chimeric antibodies utilize rodent or rabbit variable regions and human constant regions, in order to produce an antibody with predominantly human domains. For example, a chimeric antibody comprises a variable region from a mouse antibody modified according to the present invention any embodiment fused to a human constant domain and/or a human constant region. The production of such chimeric antibodies is known in the art, and may be achieved by standard means (as described, e.g., in U.S. Pat. No. 5,807,715; U.S. Pat. No. 4,816,567 and U.S. Pat. No. 4,816,397).

The present invention also contemplates a deimmunized protein. De-immunized proteins have one or more epitopes, e.g., B cell epitopes or T cell epitopes removed (i.e., mutated) to thereby reduce the likelihood that a subject will raise an immune response against the protein. Methods for producing deimmunized proteins are known in the art and described, for example, in WO00/34317, WO2004/108158 and WO2004/064724. For example, the method comprises performing an in silico analysis to predict an epitope in a protein and mutating one or more residues in the predicted epitope to thereby reduce its immunogenicity. The protein is then analyzed, e.g., in silico or in vitro or in vivo to ensure that it retains its ability to bind to an antigen. Preferable an epitope that occurs within a CDR is not mutated unless the mutation is unlikely to reduce antigen binding. Methods for predicting antigens are known in the art and described, for example, in Saha (2004). Exemplary epitopes in AVP04-07 occur at the following positions 35-41; 68-77; 84-90; 109-119; 122-128; 160-169; and 185-194 of SEQ ID NO: 59. Residues that may be mutated to potentially reduce immunogenicity include K38, T71, A72, K74, T87, T112, V113, S114, S115, G116, T125, Q163, Q164, P166, F188, T189, G190 or S191.

Heavy Chain Immunoglobulins

Heavy chain immunoglobulins differ structurally from many other forms of immunoglobulin (e.g., antibodies,), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This feature distinguishes heavy chain immunoglobulins from some conventional 4-chain antibodies, which comprise both $V_H$ and $V_L$ domains. This means that single domain binding fragments can be derived from heavy chain immunoglobulins, which are easy to express and are generally stable and soluble. Heavy chain immunoglobulins and variable regions domains thereof domains derived therefrom can also comprise long surface loops (particularly CDR3), which facilitate penetration of and binding to cavities often found in antigens such as enzymes and on the surface of proteins of viruses and agents causative of infectious diseases.

A general description of heavy chain immunoglobulins from camelids and the variable regions thereof and methods for their production and/or isolation and/or use is found inter alia in the following references WO94/04678, WO97/49805 and WO 97/49805; Riechmann and Muyldermans (1999) and Nguyen et al. (2001).

A general description of heavy chain immunoglobulins from cartilaginous fish and the variable regions thereof and methods for their production and/or isolation and/or use is found inter alia in WO2005/118629; Shao et al. (2007); and/or Dooley and Flajnik (2006).

Variable Region Containing Proteins

Diabodies, Triabodies, Tetrabodies

Exemplary preferred proteins comprising an immunoglobulin variable region are diabodies, triabodies, tetrabodies and higher order protein complexes such as those described in WO98/044001 and WO94/007921. In this specification the term "Avibody" or "Avibodies" includes any form of Avibody™ products which include any diabody (diabodies), triabody (triabodies) and tetrabody (tetrabodies), such as those described in WO98/044001 and/or WO94/007921.

As used herein, the term "diabody" shall be taken to mean a protein comprising two associated polypeptide chains, each polypeptide chain comprising the structure $V_L$-X-$V_H$ or $V_H$-X-$V_L$, wherein $V_L$ is an immunoglobulin light chain variable region, $V_H$ is an immunoglobulin heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain so as to form a bivalent diabody (i.e., comprising two Fvs of the same specificity) or the $V_L$ and $V_H$ can be different in each polypeptide chain so as to form a bispecific diabody (i.e., comprising two Fvs having different specificity).

As used herein, the term "triabody" shall be taken to mean a protein comprising three associated polypeptide chains, each polypeptide chain comprising the structure $V_L$-X-$V_H$ or $V_H$-X-$V_L$, wherein $V_L$ is an immunoglobulin light chain variable region, $V_H$ is an immunoglobulin heavy chain variable region, X is a linker comprising insufficient residues to permit the $V_H$ and $V_L$ in a single polypeptide chain to associate (or form an Fv) or is absent, and wherein the $V_H$ of one polypeptide chain is associated with the $V_L$ of another polypeptide chain to thereby form a trimeric protein (a triabody). For example, a $V_H$ of a first polypeptide chain is associated with the $V_L$ of a second polypeptide chain, the $V_H$ of the second polypeptide chain is associated with the $V_L$ of a third polypeptide chain and the $V_H$ of the third polypeptide is associated with the $V_L$ of the first polypeptide chain. The $V_L$ and $V_H$ associate so as to form an antigen binding site, i.e., a Fv capable of specifically binding to one or more antigens. The $V_L$ and $V_H$ can be the same in each polypeptide chain (i.e., to produce a monospecific triabody) or two of the $V_L$ and two of the $V_H$ can be the same and the third of each different in the third polypeptide chain to produce a bispecific protein or the $V_L$ and $V_H$ can be different in each polypeptide chain so as to form a trivalent protein.

As used herein, the term "tetrabody" shall be taken to mean a protein comprising four associated polypeptide chains, each polypeptide chain comprising the structure $V_L$-X-$V_H$ or $V_H$-X-$V_L$, wherein $V_L$ is an immunoglobulin light chain variable region, $V_H$ is an immunoglobulin heavy chain variable region, X is a linker comprising insufficient residues to permit the $V_H$ and $V_L$ in a single polypeptide chain to associate (or form an Fv) or is absent, and wherein the $V_H$ of one polypeptide chain is associated with the $V_L$ of another polypeptide chain to thereby form a tetrameric protein (a tetrabody). The $V_L$ and $V_H$ associate so as to form an antigen binding site, i.e., a Fv capable of specifically binding to one or more antigens. For example, the $V_H$ of a first polypeptide chain is associated with the $V_L$ of a second polypeptide chain, the $V_H$ of the second polypeptide chain is associated with the $V_L$ of a third polypeptide chain, the $V_H$ of the third polypeptide chain is associated with the $V_L$ of a fourth polypeptide chain and the $V_H$ of the fourth polypeptide chain is associated with the $V_L$ of the first polypeptide chain. The $V_L$ and $V_H$ can be the same in each polypeptide chain (i.e., to produce a monospecific tetrabody) or the $V_L$ and $V_H$ can be of one type in two polypeptide chains and a different type in the other two polypeptide chains to produce a bispecific tetrabody or the $V_L$ and $V_H$ can be different in each polypeptide chain so as to form a tetraspecific tetrabody.

The skilled artisan will be aware of diabodies, triabodies and/or tetrabodies and methods for their production. Generally, these proteins comprise a polypeptide chain in which a $V_H$ and a $V_L$ are linked directly or using a linker that is of insufficient length to permit the $V_H$ and $V_L$ to associate. The $V_H$ and $V_L$ can be positioned in any order, i.e., $V_L$-$V_H$ or $V_H$-$V_L$. The $V_H$ and $V_L$ are readily obtained, e.g., by isolating nucleic acid encoding these polypeptide chains from a cell expressing an immunoglobulin comprising one or more variable region(s) of interest (including an antibody or a chimeric antibody or a humanized antibody or a human antibody) or from a recombinant library expressing $V_H$ and $V_L$ polypeptide chains (e.g., a scFv library, e.g., as described in EP0239400 or U.S. Pat. No. 4,946,778). The $V_H$ and/or $V_L$ can then readily be modified to include the requisite cysteine residues as described herein according to any embodiment.

Proteins comprising $V_H$ and $V_L$ associate to form diabodies, triabodies and/or tetrabodies depending on the length of the linker (if present) and/or the order of the $V_H$ and $V_L$ domains. Preferably, the linker comprises 12 or fewer amino acids. For example, in the case of polypeptide chains having the following structure arranged in N to C order $V_H$-X-$V_L$, wherein X is a linker, a linker having 3-12 residues generally results in formation of diabodies, a linker having 1 or 2 residues or where a linker is absent generally results in formation of triabodies. In the case of polypeptide chains having the following structure arranged in N to C order $V_L$-X-$V_H$, wherein X is a linker, a linker having 3-12 residues generally results in formation of diabodies, a linker having 1 or 2 residues generally results in formation of diabodies, triabodies and tetrabodies and a polypeptide lacking a linker generally forms triabodies or tetrabodies.

Linkers for use in fusion proteins are known in the art. Linker sequence composition could affect the folding stability of a fusion protein. By indirect fusion of proteins through a linker not related to the fused proteins, the steric hindrance between the two proteins is avoided and the freedom degree for the linking is achieved.

It is often unfavorable to have a linker sequence with high propensity to adopt α-helix or β-strand structures, which could limit the flexibility of the protein and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

In one embodiment, the linker is a glycine rich linker. Preferably, the linker is a glycine linker that additionally comprises alanine and/or serine. Such linkers provide flexibility, enhance hydrophilicity and are relatively protease resistant, see, e.g., Kortt et a., 2001.

The conformational flexibility imparted by glycine may be important at the junction between C terminus of the protein and the N terminus of the linker. Accordingly, linkers that comprise glycine in the region adjacent to the C terminus of the protein are preferred. In this regard, this does not impart a requirement that the first amino acid residue of the linker need be a glycine.

Proline residues can be incorporated into the linker to prevent the formation of significant secondary structural elements by the linker. For example, a linker comprises the sequence $Gly_n$-Pro-$Gly_n$ where n is a number between about 1 and about 5.

Preferred linkers include a sequence selected from the group consisting of G; GG; GGG; GGGG; GGGGS (SEQ ID NO: 57); S; SG; SGG; and SGGG.

Diabodies and higher order multimers can also comprise proteins that are covalently linked, e.g., by virtue of a disulphide bond between the proteins, e.g., as described in WO2006/113665.

Multispecific diabodies and higher order multimers can be produced through the noncovalent association of two single chain fusion products comprising $V_H$ domain from one immunoglobulin connected by a short linker to the $V_L$ domain of another immunoglobulin, thereby forming two Fvs, each from a different immunoglobulin, see, for example, Hudson and Kortt (1999). Similarly, multispecific triabodies can be produced by noncovalent association of three single chain fusion proteins as follows:

(i) a first protein comprising a $V_H$ domain from a first immunoglobulin connected by a short linker to the $V_L$ domain of a second immunoglobulin;

(ii) a second protein comprising a $V_H$ domain from the second immunoglobulin connected by a short linker to the $V_L$ domain of a third immunoglobulin; and (iii) a third protein comprising a $V_H$ domain from the third immunoglobulin connected by a short linker to the $V_L$ domain of the first immunoglobulin.

The skilled artisan will readily be able to determine suitable modifications to the foregoing to produce bispecific triabodies, bispecific tetrabodies, trispecific tetrabodies and tetraspecific tetrabodies.

The present invention contemplates a diabody, triabody, tetrabody or higher order multimer against any antigen or combination thereof, and is not to be construed to be limited to those that bind to a specific antigen. Exemplary antigens are described herein for the purposes of illustration and not limitation.

Exemplary publications describing diabodies, triabodies and/or tetrabodies include WO94/07921; WO98/44001; Holliger et al (1993); Kortt et al (1997); Hudson and Kortt (1999); Le Gall et al (1999); Todorovska et al., (2001); Hollinger and Hudson (2005); and references cited therein.

Exemplary diabodies, triabodies and/or tetrabodies comprise a $V_H$ sequence set forth in amino acids 1-115 of SEQ ID NO: 59 or amino acids 1-129 of SEQ ID NO: 61 or amino acids 1-129 of SEQ ID NO: 63 or amino acids 1-129 of SEQ ID NO: 65, which are modified to include two or more cysteine residues in FR2 and/or FR3 as described herein, optionally with a N-terminal threonine/serine residue.

Exemplary diabodies, triabodies and/or tetrabodies comprise a $V_L$ sequence set forth in amino acids 121-239 of SEQ ID NO: 59 or amino acids 135-262 of SEQ ID NO: 61 or amino acids 126-237 of SEQ ID NO: 63 or amino acids 135-262 of SEQ ID NO: 65, which are modified to include two or more cysteine residues in FR2 and/or FR3, optionally with a N-terminal threonine/serine residue. For example, the $V_L$ comprises a sequence set forth in:

(i) amino acids 121-239 of SEQ ID NO: 101;
(ii) amino acids 121-239 of SEQ ID NO: 103;
(iii) amino acids 121-239 of SEQ ID NO: 105;
(iv) amino acids 121-239 of SEQ ID NO: 117;
(v) amino acids 136-254 of SEQ ID NO: 119;
(vi) amino acids 115-233 of SEQ ID NO: 121;
(vii) amino acids 126-237 of SEQ ID NO: 123;
(viii) amino acids 135-262 of SEQ ID NO: 127;
(ix) amino acids 126-237 of SEQ ID NO: 131;
(x) amino acids 126-237 of SEQ ID NO: 135;
(xi) amino acids 135-262 of SEQ ID NO: 141; and/or
(xii) amino acids 135-262 of SEQ ID NO: 145.

Exemplary diabodies, triabodies and/or tetrabodies comprise a $V_H$ sequence set forth in amino acids 1-115 of SEQ ID NO: 59 or amino acids 1-129 of SEQ ID NO: 61 or amino acids 1-120 of SEQ ID NO: 63 or amino acids 1-129 of SEQ ID NO: 65, which are modified to include two or more cysteine residues in FR2 and/or FR3 as described herein, optionally with a N-terminal threonine/serine residue. For example, the $V_H$ comprises a sequence set forth in:

(i) amino acids 1-115 of SEQ ID NO: 107;
(ii) amino acids 1-115 of SEQ ID NO: 109;
(iii) amino acids 1-115 of SEQ ID NO: 111;
(iv) amino acids 1-115 of SEQ ID NO: 113;
(v) amino acids 1-115 of SEQ ID NO: 115;
(vi) amino acids 1-120 of SEQ ID NO: 125;
(vii) amino acids 1-129 of SEQ ID NO: 129;
(viii) amino acids 1-120 of SEQ ID NO: 133;

(ix) amino acids 1-120 of SEQ ID NO: 137;

(x) amino acids 1-120 of SEQ ID NO: 139;

(xi) amino acids 1-129 of SEQ ID NO: 143;

(xii) amino acids 1-129 of SEQ ID NO: 147; and/or (xiii) amino acids 1-129 of SEQ ID NO: 149.

The $V_H$ and $V_L$ described in the foregoing paragraphs can be arranged in any order and linked by a suitable linker as described herein. For a diabody, the linker preferably comprises the sequence GGGGS (SEQ ID NO: 57). For a triabody or tetrabody, preferably there is no linker or a single glycine residue.

In one example, a diabody binds to TAG72 and comprises at least one polypeptide chain comprising (and preferably two polypeptide chains each comprising) a sequence set forth in SEQ ID NO: 59 which are modified to include two or more cysteine residues in FR2 and/or FR3, optionally with a N-terminal threonine/serine residue. For example, a diabody comprises at least one polypeptide chain comprising (and preferably two polypeptide chains each comprising) a sequence set forth in SEQ ID NO: 101, 103, 105, 107, 109, 111, 113, 115, 117 or 119.

In one example, a triabody binds to TAG72 and comprises at least one polypeptide chain comprising (and preferably two or three polypeptide chains each comprising) a sequence set forth in SEQ ID NO: 121.

In another example, a diabody binds to Her2 and comprises at least one polypeptide chain comprising (and preferably two polypeptide chains each comprising) a sequence set forth in SEQ ID NO: 61 or 64 which are modified to include two or more cysteine residues in FR2 and/or FR3 and optionally a N-terminal threonine/serine residue. For example, a diabody comprises at least one polypeptide chain comprising (and preferably two polypeptide chains each comprising) a sequence set forth in one or more of SEQ ID NO: 127, 129, 141, 143, 145, 147 or 149.

In another example, a diabody binds to MUC1 and comprises at least one polypeptide chain comprising (and preferably two polypeptide chains each comprising) a sequence set forth in SEQ ID NO: 63 which are modified to include two or more cysteine residues in FR1 and/or FR2 and, optionally a N-terminal threonine/serine residue. For example, a diabody comprises at least one polypeptide chain comprising (and preferably two polypeptide chains each comprising) a sequence set forth in one or more of SEQ ID NO: 131, 133, 135, 137 or 139.

Single Chain Fv (scFv) Fragments

The skilled artisan will be aware that scFvs comprise $V_H$ and $V_L$ regions in a single polypeptide chain. Preferably, the polypeptide chain further comprises a polypeptide linker between the $V_H$ and $V_L$ which enables the scFv to form the desired structure for antigen binding (i.e., for the $V_H$ and $V_L$ of the single polypeptide chain to associate with one another to form a Fv). This is distinct from a diabody or higher order multimer in which variable regions from different polypeptide chains associate or bind to one another. For example, the linker comprises in excess of 12 amino acid residues with $(Gly_4Ser)_3$ being one of the more favored linkers for a scFv.

Exemplary scFvs comprise a VH and a VL as described above in relation to diabodies, triabodies and tetrabodies. In one example, the scfv binds to TAG72. In one example, the scFv comprises a sequence set forth in SEQ ID NO: 119.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv (see, for example, Brinkmann et al., 1993).

Alternatively, or in addition, the present invention provides a dimeric scFv, i.e., a protein comprising two scFv molecules linked by a non-covalent or covalent linkage. Examples of such dimeric scFv include, for example, two scFvs linked to a leucine zipper domain (e.g., derived from Fos or Jun) whereby the leucine zipper domains associate to form the dimeric compound (see, for example, Kostelny 1992 or Kruif and Logtenberg, 1996). Alternatively, two scFvs are linked by a peptide linker of sufficient length to permit both scFvs to form and to bind to an antigen, e.g., as described in US20060263367. In a further example, each scFv is modified to include a cysteine residue, e.g., in the linker region or at a terminus, and the scFvs are linked by a disulfide bond, e.g., as described in Albrecht et al., (2004).

Modified forms of scFv are also contemplated by the present invention, e.g., scFv comprising a linker modified to permit glycosylation, e.g., as described in U.S. Pat. No. 623,322.

The skilled artisan will be readily able to produce a scFv or modified form thereof comprising a suitable modified $V_H$ and/or $V_L$ according to the present invention based on the disclosure herein. Exemplary sequences of $V_H$ and/or $V_L$ are described herein and are to be taken to apply mutatis mutandis to this embodiment of the invention.

For a review of scFv, see Plückthun (1994). Additional description of scFv is to be found in, for example, U.S. Pat. No. 5,260,203.

Minibodies

The skilled artisan will be aware that a minibody comprises the $V_H$ and $V_L$ domains of an immunoglobulin fused to the $C_H2$ and/or $C_H3$ domain of an immunoglobulin. Optionally, the minibody comprises a hinge region between the $V_H$ and a $V_L$, sometimes this conformation is referred to as a Flex Minibody (Hu et al., 1996). A minibody does not comprise a $C_H1$ or a CL. Preferably, the $V_H$ and $V_L$ domains are fused to the hinge region and the $C_H3$ domain of an immunoglobulin. Each of the regions may be derived from the same immunoglobulin. Alternatively, the $V_H$ and $V_L$ domains can be derived from one immunoglobulin and the hinge and $C_H2/C_H3$ from another, or the hinge and $C_H2/C_H3$ can also be derived from different immunoglobulins. The present invention also contemplates a multispecific minibody comprising a $V_H$ and $V_L$ from one immunoglobulin and a $V_H$ and a $V_L$ from another immunoglobulin. At least one of the variable regions of said minibody comprises cysteine residues in FR2 and/or FR3 as described herein.

The skilled artisan will be readily able to produce a minibody of the invention using methods known in the art together with the teaching provided herein.

Based on the foregoing, the skilled artisan will appreciate that minibodies are small versions of whole immunoglobulins encoded in a single protein chain which retain the antigen binding region, the $C_H3$ domain (or a $C_H2$ domain) to permit assembly into a bivalent molecule and the immunoglobulin hinge to accommodate dimerization by disulfide linkages.

Exemplary minibodies and methods for their production are described, for example, in WO94/09817.

Other Variable Region Containing Proteins

U.S. Pat. No. 5,731,168 describes molecules in which the interface between a pair of Fv is engineered to maximize the percentage of heterodimers which are recovered from recombinant cell culture to thereby produce bi-specific proteins. The preferred interface comprises at least a part of a $C_H3$ domain. In this method, one or more small amino acid side chains from the interface of the first protein are replaced with larger side chains {e.g., tyrosine or tryptophan). Compensatory "cavities" of identical or similar size to the large side chain(s) are created on the interface of the second protein by replacing large amino acid side chains with smaller ones (e.g., alanine or threonine).

Bispecific proteins comprising variable regions include cross-linked or "heteroconjugate" proteins. For example, one of the proteins in the heteroconjugate can be coupled to avidin, the other to biotin. Such proteins have, for example, been proposed to target immune system cells to unwanted cells (U.S. Pat. No. 4,676,980). Heteroconjugate proteins comprising variable regions may be made using any convenient cross-linking methods. Suitable cross-linking agents are known in the art, and are disclosed in U.S. Pat. No. 4,676,980, along with a number of cross-linking techniques.

Bispecific proteins comprising variable regions can also be prepared using chemical linkage. Brennan (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific protein.

Progress has facilitated the direct recovery of Fab'-SH fragments from *E. coli*, which can be chemically coupled to form bispecific proteins comprising variable regions. Shalaby (1992) describe the production of a fully humanized bispecific $F(ab')_2$ molecule. Each Fab' fragment was separately secreted from *E. coli* and subjected to directed chemical coupling in vitro to form the bispecific protein comprising variable regions. The bispecific protein thus formed was able to bind to cells expressing the relevant antigen and normal human T cells, as well as trigger the lytic activity of human cytotoxic lymphocytes against human breast tumor targets.

Additional variable region containing proteins include, for example, domain antibodies (dAbs) and fusions thereof (e.g., as described in U.S. Pat. No. 6,248,516), single chain Fab (e.g., Hust et al., 2007) or a $Fab_3$ (e.g., as described in EP19930302894).

Constant Domain Fusions

The present invention encompasses proteins comprising a variable region and a constant region (e.g., Fc) or a domain thereof, e.g., $C_H2$ and/or $C_H3$ domain. For example, the present invention provides a minibody (as discussed above) or a scFv-Fc fusion or a diabody-Fc fusion or a triabody-Fc fusion or a tetrabody-Fc fusion or a scFc-$C_H2$ fusion or a diabody-$C_H2$ fusion or a triabody-$C_H2$ fusion or a tetrabody-$C_H2$ fusion or a scFv-$C_H3$ fusion or a diabody-$C_H3$ fusion or a triabody-$C_H3$ fusion or a tetrabody-$C_H3$ fusion. Any of these proteins may comprise a linker, preferably an immunoglobulin hinge region, between the variable region and the constant region or constant domain.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. 1998).

As used herein, the term "$C_H2$ domain" includes the portion of a heavy chain immunoglobulin molecule that extends, e.g., from between about positions 231-340 according to the Kabat EU numbering system. Two N-linked branched carbohydrate chains are generally interposed between the two $CH_2$ domains of an intact native IgG molecule. In one embodiment, a protein of the invention comprises a $C_H2$ domain derived from an IgG1 molecule (e.g. a human IgG1 molecule). In another embodiment, a protein of the invention comprises a $C_H2$ domain derived from an IgG4 molecule (e.g., a human IgG4 molecule).

As used herein, the term "$C_H3$ domain" includes the portion of a heavy chain immunoglobulin molecule that extends approximately 110 residues from N-terminus of the $C_H2$ domain, e.g., from about position 341-446b (Kabat EU numbering system). The $C_H3$ domain typically forms the C-terminal portion of the immunoglobulin. In some immunoglobulins, however, additional domains may extend from $C_H3$ domain to form the C-terminal portion of the molecule (e.g. the $C_H4$ domain in the μ chain of IgM and the e chain of IgE). In one embodiment, a protein of the invention comprises a $C_H3$ domain derived from an IgG1 molecule (e.g., a human IgG1 molecule). In another embodiment, a protein of the invention comprises a $C_H3$ domain derived from an IgG4 molecule (e.g., a human IgG4 molecule).

Constant domain sequences useful for producing the proteins of the present invention may be obtained from a number of different sources. In preferred embodiments, the constant region domain or portion thereof of the protein is derived from a human immunoglobulin. It is understood, however, that the constant region domain or portion thereof may be derived from an immunoglobulin of another mammalian species, including for example, a rodent (e.g. a mouse, rat, rabbit, guinea pig) or non-human primate (e.g. chimpanzee, macaque) species. Moreover, the constant region domain or portion thereof may be derived from any immunoglobulin class, including IgM, IgG, IgD, IgA and IgE, and any immunoglobulin isotype, including IgG1, IgG2, IgG3 and IgG4. In a preferred example, the human isotype IgG1 is used.

A variety of constant region gene sequences (e.g. human constant region gene sequences) are available in the form of publicly accessible deposits or the sequence thereof is available from publicly available databases. Constant region domains can be selected having a particular effector function (or lacking a particular effector function) or with a particular modification to reduce immunogenicity.

As used herein, the term "effector function" refers to the functional ability of the Fc region or portion thereof (e.g., $C_H2$ domain) to bind proteins and/or cells of the immune system and mediate various biological effects. Effector functions may be antigen-dependent or antigen-independent. "Antigen-dependent effector function" refers to an effector function which is normally induced following the binding of an immunoglobulin to a corresponding antigen. Typical antigen-dependent effector functions include the ability to bind a complement protein (e.g. C1q). For example, binding of the C1 component of complement to the Fc region can activate the classical complement system leading to the opsonisation and lysis of cell pathogens, a process referred to as complement-dependent cytotoxicity (CDC). The activation of complement also stimulates the inflammatory response and may also be involved in autoimmune hypersensitivity. Other antigen-dependent effector functions are mediated by the binding of immunoglobulins, via their Fc region, to certain Fc receptors ("FcRs") on cells. There are a number of Fc receptors which are specific for different classes of immunoglobulin, including IgG (gamma receptors, or IgλRs), IgE (epsilon receptors, or IgϵRs), IgA (alpha receptors, or IgαRs) and IgM (mu receptors, or IgμRs). Binding of immunoglobulin to Fc receptors on cell surfaces triggers a number of important and diverse biological responses including endocytosis of immune complexes, engulfment and destruction of immunoglobulin-coated particles or microorganisms (also called antibody-dependent phagocytosis, or ADCP), clearance of immune complexes, lysis of antibody-coated target cells by killer cells (called antibody-dependent cell-mediated cytotoxicity, or ADCC), release of inflammatory mediators, regulation of immune system cell activation, placental transfer and control of immunoglobulin production.

As used herein, the term "antigen-independent effector function" refers to an effector function which may be induced by an immunoglobulin, regardless of whether it has bound its corresponding antigen. Typical antigen-independent effector functions include cellular transport, circulating half-life and clearance rates of immunoglobulins, and facilitation of purification. A structurally unique Fc receptor, the "neonatal Fc receptor" or "FcRn", also known as the salvage receptor, plays a critical role in regulating half-life and cellular transport. Other Fc receptors purified from microbial cells (e.g. Staphylococcal Protein A or G) are capable of binding to the Fc region with high affinity and can be used to facilitate the purification of the Fc-containing protein.

Constant region domains can be cloned, e.g., using the polymerase chain reaction and primers which are selected to amplify the domain of interest. The cloning of immunoglobulin sequences is described in for example, in U.S. Pat. No. 5,658,570.

The protein of the invention may comprise any number of constant region domains of different types.

The constant region domains or portions thereof making up the constant region of a protein may be derived from different immunoglobulin molecules. For example, a protein may comprise a $C_H2$ domain or portion thereof derived from an IgG1 molecule and a $C_H3$ region or portion thereof derived from an IgG3 molecule.

In another example of the invention, the protein of the invention comprises at least a region of an Fc sufficient to confer FcRn binding. For example, the portion of the Fc region that binds to FcRn comprises from about amino acids 282-438 of IgG1, according to Kabat numbering.

In one example, a protein of the invention comprises an altered synthetic constant region wherein or more constant region domains therein are partially or entirely deleted ("domain-deleted constant regions"). The present invention also encompasses modified Fc regions or parts there having altered, e.g., improved or reduced effector function. Many such modified Fc regions are known in the art and described, for example, in U.S. Pat. No. 7,217,797; U.S. Pat. No. 7,217,798; or WO2005/047327US20090041770 (having increased half-life) or US2005037000 (increased ADCC).

Mutations to Proteins

The present invention contemplates the use of mutant forms of a protein of the invention. For example, such a mutant polypeptide comprises one or more conservative amino acid substitutions compared to a sequence set forth herein. In some examples, the polypeptide comprises 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In a preferred example, a mutant protein has only, or not more than, one or two or three or four conservative amino acid changes when compared to a naturally occurring protein. Details of conservative amino acid changes are provided below. As the skilled person would be aware, such minor changes can reasonably be predicted not to alter the activity of the polypeptide when expressed in a recombinant cell Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

The present invention also contemplates one or more insertions or deletions compared to a sequence set forth herein. In some examples, the polypeptide comprises 10 or fewer, e.g., 9 or 8 or 7 or 6 or 5 or 4 or 3 or 2 insertions and/or deletions.

Positioning of Cysteine Residues

Figure 6A:
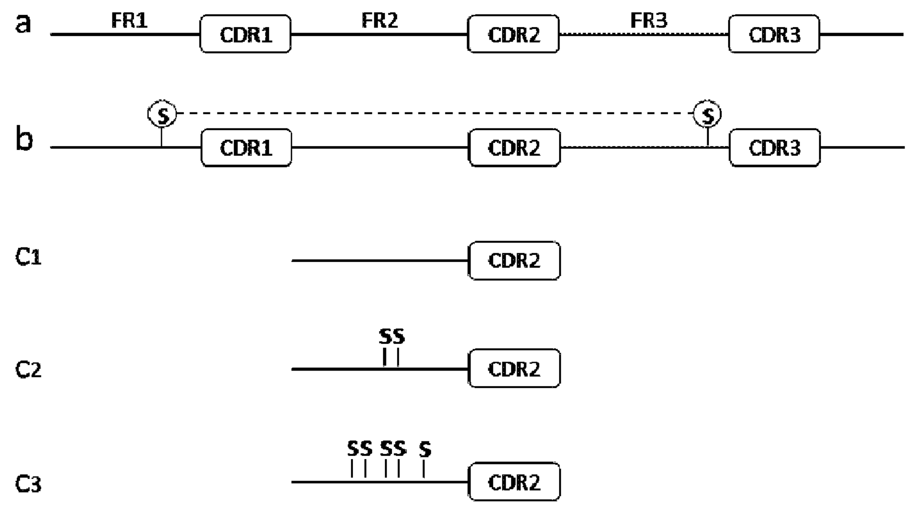
FIG. 6A is a diagrammatic representation of the positioning of cysteine residues in framework region FR2 according some examples of the invention. The circled "S" represents the conserved cysteine residue(s) present in most mammalian antibody variable (V)-domains whilst the uncircled "S" represents the cysteine residues of the invention in FR2.
Figure 6B:
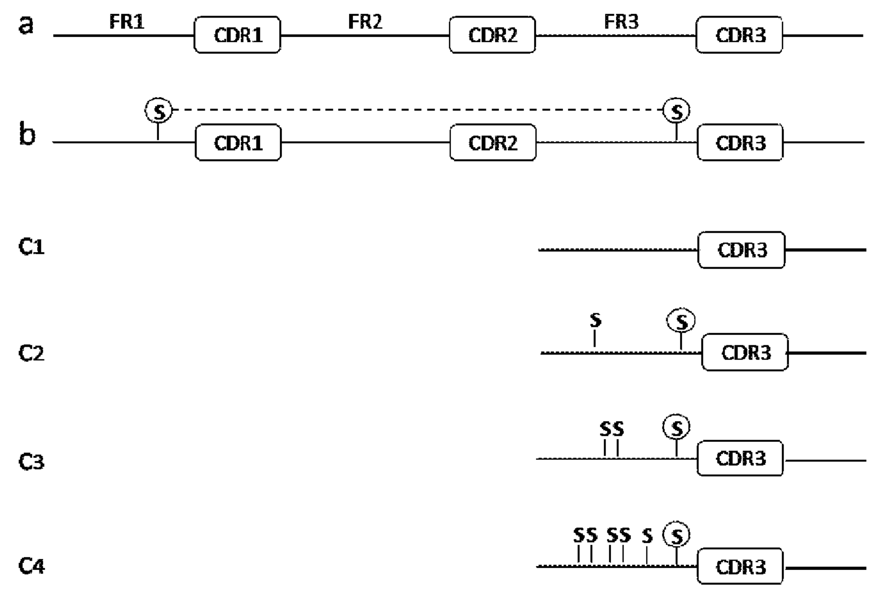
FIG. 6B is a diagrammatic representation showing some modifications and insertions of cysteine residues into FR3 according to some examples of the present invention. The circled "S" represents the conserved cysteine residue(s) present in most mammalian antibody V-domains whilst the uncircled "S" represents the cysteine residues of the invention. In one example, the situation depicted at C2 is not encompassed by the invention.

The present invention contemplates positioning of cysteine residues in FR2 and/or FR3 at any site as described herein in any embodiment or example. Exemplary cysteine residues contemplated by the present invention are depicted in FIGS. 6A and 6B.

In one example, the present invention provides an isolated protein comprising an immunoglobulin variable region comprising at least two cysteine residues positioned within framework region (FR) 1, wherein the cysteine residues are positioned such that at least one of the residues is capable of being conjugated to a compound and wherein if at least one of the cysteine residues is not conjugated to a compound a disulphide bond is capable of forming between the cysteine residues.

In another example, the present invention provides an isolated protein comprising an immunoglobulin variable region comprising at least two cysteine residues positioned within framework region (FR) 1, wherein the cysteine residues are positioned such that at least one of the residues is capable of being conjugated to a compound and wherein if at least two of the cysteine residues are not conjugated to a compound a disulphide bond is capable of forming between the cysteine residues.

In an alternative or additional example, the present invention provides an isolated protein comprising an immunoglobulin heavy chain variable region ($V_H$) and an immunoglobulin light chain variable region ($V_L$), wherein at least one of the variable regions comprises at least two cysteine residues positioned within framework region (FR) 1, wherein the cysteine residues are positioned such that at least one of the residues is capable of being conjugated to a compound and wherein if at least one of the cysteine residues is not conjugated to another compound a disulphide bond is capable of forming between the cysteine residues.

In an alternative or additional example, the present invention provides an isolated protein comprising an immunoglobulin heavy chain variable region ($V_H$) and an immunoglobulin light chain variable region ($V_L$), wherein at least one of the variable regions comprises at least two cysteine residues positioned within framework region (FR) 1, wherein the cysteine residues are positioned such that at least one of the residues is capable of being conjugated to a compound and wherein if at least two of the cysteine residues are not conjugated to another compound a disulphide bond is capable of forming between the cysteine residues.

In each of the above examples of the invention, it is preferable that at least two or the at least two cysteine residues are positioned such that they are capable of being conjugated to a compound.

In one example of the invention, the cysteine residues are positioned within a loop region of FR2 and/or FR3. As used herein, the term "loop region" shall be taken to mean a sequence of amino acids within FR2 or FR3 that provides flexibility for two regions and/or two amino acids of FR2 or FR3 to associate with or bind to one another (e.g., by virtue of a hydrogen bond), e.g., that provides sufficient flexibility for two amino acids in a beta sheet to associate with or bind to one another. A loop region of FR2 and/or FR3 is not part of the CDR1 or CDR3.

In another example, the cysteine residues in a FR2 and/or FR3 are positioned so as to permit formation of a disulfide bond between the residues.

By "positioned so as to permit formation of a disulphide bond" shall be understood to mean that two cysteine residues are positioned within a protein such that when the protein folds they are sufficiently close for a disulphide bond to be formed between the residues. For example, the distance between two carbon atoms in two cysteine residues may be within about 6-7 Å of one another or 2-9 Å of one another, such as about 6-7 Å of one another or 3.5-6.8 Å of one another, e.g., about 4 Å of one another. Methods for predicting the proximity of residues in a protein and/or predicting the likelihood of disulphide bond formation will be apparent to the skilled artisan and/or described herein.

Thus, in one example, a protein of the invention comprises at least two cysteine residues positioned within FR2 and/or FR3, wherein the cysteine residues are within about 2-9 Å of one another, preferably, within about 6-7 Å of one another.

In another example, the cysteine residues are positioned at residues in a protein at which their side chains will be exposed to solvent. Methods for determining solvent exposure or solvent accessible surface area are known in the art and include, for example, the Shrake-Rupley algorithm or the LCPO method.

Thus in another example, a protein of the invention comprises at least two cysteine residues positioned within FR2 and/or FR3, wherein the cysteine residues are positioned such that their side chains (preferably their thiol groups) are exposed to solvent.

By "exposed to solvent" shall be understood to mean that the side chains of the cysteine residues are on the surface of a protein when folded such that they are capable of being in contact with a solvent in which the protein is present or suspended. Preferably, at least one (or one or both) of the side chains are sufficiently exposed to solvent such that a compound can be conjugated thereto.

Preferably, the protein of the invention comprises at least two cysteine residues positioned at one or more of, preferably two or more of, preferably all of:

(i) positioned such that their side chains are angled towards one another;

(ii) positioned such that their side chain atoms are exposed to solvent; and/or (iii) positioned such that their Cα carbon atoms are about 6-7 Å of one another.

The proteins of the present invention (as described herein according to any one or more example of the invention) thus provide at least two cysteine residues positioned within FR2 and/or FR3 that can form a disulphide bond within FR2 and/or FR3 and which can alternatively be reduced for stoichiometric conjugation of compounds. These products of the invention have an advantage over other cysteine conjugation strategies that do not provide at least two cysteine residues positioned within framework regions ((FR1 and/or FR2 and/or FR3)) that can form a disulphide bond within frameworks region (FR1 and/or FR2 and/or FR3). These prior and ineffective strategies include single cysteine residues (Kim et al., 2008), C-terminal cysteine residues (Sirk et al., 2008) and single cysteine residues in intact antibodies (Junutula et al., 2008) all of which result in poor expression yield, variable conjugation and complications for large scale processing. Furthermore, antibodies that are conjugated on cysteine residues by partial reduction of interchain-disulfide bonds have variable stoichiometry (zero to eight drugs per antibody) and potentially yield >100 species (Junutula et al., 2008).

Methods for predicting loops and/or the position of residues within a folded protein will be apparent to the skilled artisan and include in silico methods. For example, structural features of a protein are determined using appropriate software available on the website of the National Center for Biotechnology Information (NCBI) at the National Institutes of Health, 8600 Rockville Pike, Bethesda Md. 20894 such as, for example, through the NCBI Molecules Modeling Database (MMDB) including three-dimensional biomolecular structures determined using X-ray crystallography and/or NMR spectroscopy. The NCBI conserved domain database (CDD) includes domains from the known Smart and Pham collections, with links to a 3D-structure viewer (Cn3D). The NCBI Conserved Domain Architecture Retrieval Tool (CDART) uses precalculated domain assignments to neighbor proteins by their domain architecture.

Additional methods for predicting protein or peptide secondary structure are known in the art and/or described, for example, in Moult, 1996; Chou et al., 1974; Chou et al., 1974; Chou et al., 1978; Chou et al., 1978; or Chou et al., 1979.

Additionally, computer programs are currently available to assist with predicting secondary structure of a protein or peptide. One such method of predicting secondary structure is based upon homology modeling. For example, two proteins that have a sequence identity of greater than 30%, or similarity greater than 40%, often have similar structural topologies. The recent growth of the protein structural database (PDB) has provided enhanced predictability of secondary structure, including the potential number of folds within the structure of a protein (Holm et al., 1999). For example, methods for determining the structure of a protein are described, for example, in US20020150906, or using a computer program or algorithm, such as, for example, MODELLER, (Sali and Blundell, 1993). These techniques rely upon aligning the sequence of a protein with the sequences of proteins that have a characterized structure. Such alignment algorithms are known in the art and are accessed through software packages such as, for example BLAST at NCBI. Structural information, i.e., three-dimensional structure, of a query protein is then be predicted based upon structural information corresponding to the sequence or subsequences aligned in the proteins or peptides that have previously been characterized. In this way it is possible to generate a library of three-dimensional structures of proteins corresponding to a FR2 and/or FR3 as described herein region of an immunoglobulin.

Additional methods of predicting secondary structure include, for example, "threading" (Jones, 1996), "profile analysis" (Bowie et al., 1991; Gribskov et al., 1990; Gribskov et al., 1989), and "evolutionary linkage". Conventional threading of protein sequence is used to predict the 3D structure scaffold of a protein. Typically, threading is a process of assigning the folding of the protein by threading (or comparing) its sequence to a library of potential structural templates (e.g., known structures of Fv or Fabs or FR2 and/or FR3 as described herein) by using a scoring function that incorporates the sequence as well as the local parameters such as secondary structure and solvent exposure (Rost et al. 1997; Xu and Xu 2000; and Panchenko et al. 2000). For example, the threading process starts from prediction of the secondary structure of the amino acid sequence and solvent accessibility for each residue of the query sequence. The resulting one-dimensional (1D) profile of the predicted structure is threaded into each member of a library of known 3D structures. The optimal threading for each sequence-structure pair is obtained using dynamic programming. The overall best sequence-structure pair constitutes the predicted 3D structure for the query sequence. Threading is made relatively simple in the present case because of the number of Fv and Fab fragments of immunoglobulins for which the secondary structure has been solved.

In the case of proteins comprising more than two cysteine residues, it is preferred that an even number of cysteine resides are included, e.g., 4 or 6 or 8 or 10 cysteine residues are included. For example, the cysteine residues are paired, i.e., combinations of two residues are arranged such that a disulphide bond can form between them.

Preferably, a protein of the invention does not comprise a free thiol in FR2 and/or FR3 under non-reducing conditions and/or does not comprise a cysteine residue that is not linked to another cysteine residue or to a compound under non-reducing conditions.

In an example of the invention, the cysteine residues are positioned such that an intra-framework disulphide bond can form between them when they are not conjugated to a compound. The term "intra-framework disulphide bond" shall be taken to mean that a disulphide bond is formed within a single framework region. For example, if two cysteine residues are positioned within FR2, an intrachain disulphide bond forms within FR2.

Protein Production

Mutagenesis

DNA encoding a protein comprising a variable region is isolated using standard methods in the art. For example, primers are designed to anneal to conserved regions within a variable region that flank the region of interest, and those primers are then used to amplify the intervening nucleic acid, e.g., by PCR. Suitable methods and/or primers are known in the art and/or described, for example, in Borrebaeck (ed), 1995 and/or Froyen et al., 1995. Suitable sources of template DNA for such amplification methods is derived from, for example, hybridomas, transfectomas and/or cells expressing proteins comprising a variable region, e.g., as described herein.

Following isolation, the DNA is modified to include cysteine residues at the requisite locations by any of a variety of methods known in the art. These methods include, but are not limited to, preparation by site-directed (or oligonucleotide-mediated) mutagenesis, PCR mutagenesis, and cassette mutagenesis of an earlier prepared DNA encoding the protein. Variants of recombinant proteins may be constructed also by restriction fragment manipulation or by overlap extension PCR with synthetic oligonucleotides. Mutagenic primers encode the cysteine codon replacement(s), for example include residues that make up a codon encoding cysteine (i.e., TGT or TGC). Standard mutagenesis techniques can be employed to generate DNA encoding such mutant DNA. General guidance can be found in Sambrook et al 1989; and/or Ausubel et al 1993.

Site-directed mutagenesis is one method for preparing substitution variants, i.e. mutant proteins. This technique is known in the art (see for example, Carter et al 1985; Ho et al 1989; and Kunkel 1987). Briefly, in carrying out site-directed mutagenesis of DNA, the starting DNA is altered by first hybridizing an oligonucleotide encoding the desired mutation (e.g., insertion of one or more cysteine encoding codons) to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations. Site-directed protocols and formats include commercially available kits, e.g. QuikChange® Multi Site-Directed Mutagenesis Kit (Stratagene, La Jolla, Calif.).

PCR mutagenesis is also suitable for making amino acid sequence variants of the starting protein. See Higuchi, 1990; Ito et al 1991; Bernhard et al 1994; and Vallette et al 1989. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al, 1985. The starting material is the plasmid (or other vector) comprising the starting protein DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, 2001; Zoller et al 1983; Zoller and Smith, 1982).

Recombinant Expression

In the case of a recombinant protein, nucleic acid encoding same is preferably placed into expression vectors, which are then transfected into host cells, preferably cells that can produce a disulphide bridge or bond, such as *E. coli* cells, yeast cells, insect cells, or mammalian cells, such as simian COS cells, Chinese Hamster Ovary (CHO) cells, or myeloma cells that do not otherwise produce immunoglobulin protein, to obtain the synthesis of proteins in the recombinant host cells. Review articles on recombinant expression in bacteria of DNA encoding the immunoglobulin include Skerra et al, (1993) and Plückthun, (1992). Molecular cloning techniques to achieve these ends are known in the art and described, for example in Ausubel or Sambrook. A wide variety of cloning and in vitro amplification methods are suitable for the construction of recombinant nucleic acids. Methods of producing recombinant immunoglobulins are also known in the art. See U.S. Pat. No. 4,816,567; U.S. Pat. No. 5,225,539, U.S. Pat. No. 6,054,297, U.S. Pat. No. 7,566,771 or U.S. Pat. No. 5,585,089.

Following isolation, the nucleic acid encoding a protein of the invention is preferably inserted into an expression construct or replicable vector for further cloning (amplification of the DNA) or for expression in a cell-free system or in cells. Preferably, the nucleic acid is operably linked to a promoter.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present invention. For example, a nucleic acid encoding a protein of the invention is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding protein of the present invention (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters include those active in prokaryotes (e.g., phoA promoter, β-lactamase and lactose promoter systems, alkaline phosphatase, a tryptophan (trp) promoter system, and hybrid promoters such as the tac promoter). These promoter are useful for expression in prokaryotes including eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Preferably, the host is *E. coli*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325), DH5α or DH10B are suitable.

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Typical promoters suitable for expression in insect cells include, but are not limited to, the OPEI2 promoter, the insect actin promoter isolated from *Bombyx muri*, the *Drosophila* sp. dsh promoter (Marsh et al 2000) and the inducible metallothionein promoter. Preferred insect cells for expression of recombinant proteins include an insect cell selected from the group comprising, BT1-TN-5B1-4 cells, and *Spodoptera frugiperda* cells (e.g., sf19 cells, sf21 cells). Suitable insects for the expression of the nucleic acid fragments include but are not limited to *Drosophila* sp. The use of *S. frugiperda* is also contemplated.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein of this invention may be cultured in a variety of media, depending on the cell type used. Commercially available media such as Ham's Fl0 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

A protein of the present invention is preferably isolated. By "isolated" is meant that the protein is substantially purified or is removed from its naturally-occurring environment, e.g., is in a heterologous environment. By "substantially purified" is meant the protein is substantially free of contaminating agents, e.g., at least about 70% or 75% or 80% or 85% or 90% or 95% or 96% or 97% or 98% or 99% free of contaminating agents.

Methods for purifying a protein of the invention are known in the art and/or described herein.

When using recombinant techniques, the protein of the invention can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Carter et al. (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, hydroxyl apatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the protein (if present at all). Protein A can be used to purify immunoglobulins that are based on human γ1, γ2, or γ4 heavy chains (Lindmark et al. 1983). Protein G is recommended for all mouse isotypes and for human γ3 (Guss et al. 1986). Otherwise affinity purification can be performed using the antigen or epitopic determinant to which a variable region in a protein of the invention binds or was raised. The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

The skilled artisan will also be aware that a protein of the invention can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. Preferably, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Following any preliminary purification step(s), the mixture comprising the protein of the invention and contaminants may be subjected to low pH hydrophobic interaction chromatography.

Protein Synthesis

A protein of the present invention is readily synthesized from its determined amino acid sequence using standard techniques, e.g., using BOC or FMOC chemistry. Synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, 1963, or the base-labile Nα-amino protected 9-fluorenylmethoxycarbonyl (Fmoc) amino acids described by Carpino and Han, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Conjugates

The present invention also provides conjugates of proteins described herein according to any embodiment. Examples of compounds to which a protein can be conjugated are the compound is selected from the group consisting of a radioisotope, a detectable label, a therapeutic compound, a colloid, a toxin, a nucleic acid, a peptide, a protein, a compound that increases the half life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid.

A toxin includes any agent that is detrimental to (e.g., kills) cells. For a description of these classes of drugs which are known in the art, and their mechanisms of action, see Goodman et al., Goodman and Gilman's The Pharmacological Basis of Therapeutics, 8th Ed., Macmillan Publishing Co., 1990. Additional techniques relevant to the preparation of immunoglobulin-immunotoxin conjugates are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232.

Suitable chemotherapeutic agents for forming immunoconjugates of the present invention include auristatins and maytansines, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-de-hydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

Examples of suitable angiogenesis inhibitors (anti-angiogenic agents) include, but are not limited to, urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one example, a protein as described herein according to any embodiment is conjugated or linked to another protein, including another protein of the invention or a protein comprising an immunoglobulin variable region, such as an immunoglobulin or a protein derived therefrom, e.g., as described herein. Other proteins are not excluded. Additional proteins will be apparent to the skilled artisan and include, for example, an immunomodulator or a half-life extending protein or a peptide or other protein that binds to serum albumin amongst others.

Exemplary immunomodulators include cytokines and chemokines. The term "cytokine" is a generic term for proteins or peptides released by one cell population which act on another cell as intercellular mediators. Examples of cytokines include lymphokines, monokines, growth factors and traditional polypeptide hormones. Included among the cytokines are growth hormones such as human growth hormone, N-methionyl human growth hormone, and bovine growth hormone; parathyroid hormone, thyroxine, insulin, proinsulin, relaxin, prorelaxin, glycoprotein hormones such as follicle stimulating hormone (FSH), thyroid stimulating hormone (TSH) and luteinizing hormone (LH), hepatic growth factor; prostaglandin, fibroblast growth factor, prolactin, placental lactogen, OB protein, tumor necrosis factor-α and -β; mullerian-inhibiting substance, gonadotropin-associated peptide, inhibin, activin, vascular endothelial growth factor, integrin, thrombopoietin (TPO), nerve growth factors such as NGF-B, platelet-growth factor, transforming growth factors (TGFs) such as TGF-α and TGF-β, insulin-like growth factor-I or -II, erythropoietin (EPO), osteoinductive factors, interferons such as interferon-α, -β, or -γ; colony stimulating factors (CSFs) such as macrophage-CSF (M-CSF), granulocyte-macrophage-CSF (GM-CSF); and granulocyte-CSF (G-CSF), interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21 and LIF.

Chemokines generally act as chemoattractants to recruit immune effector cells to the site of chemokine expression. Chemokines include, but are not limited to, RANTES, MCAF, MIP1-alpha or MIP1-Beta. The skilled artisan will recognize that certain cytokines are also known to have chemoattractant effects and could also be classified under the term chemokines.

Exemplary serum albumin binding peptides or protein are described in US20060228364 or US20080260757.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. Preferably, the radionuclide is a gamma, photon, or positron-emitting radionuclide with a half-life suitable to permit activity or detection after the elapsed time between administration and localization to the imaging site. The present invention also encompasses high energy radioactive nuclei (e.g., for therapeutic purposes), such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

In another embodiment, the protein is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The proteins of the present invention can be modified to contain additional nonproteinaceous moieties that are known in the art and readily available. Preferably, the moieties suitable for derivatization of the protein are water soluble polymers. Non-limiting examples of water soluble polymers include, but are not limited to, polyethylene glycol (PEG), polyvinyl alcohol (PVA), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol (PPG) homopolymers, prolypropylene oxide/ethylene oxide co-polymers, polyoxyethylated polyols (e.g., glycerol; POG), polyvinyl alcohol, and mixtures thereof. Polyethylene glycol propionaldehyde may have advantages in manufacturing due to its stability in water.

The polymer molecules are typically characterized as having for example from about 2 to about 1000, or from about 2 to about 300 repeating units.

For example water-soluble polymers, including but not limited to PEG, poly(ethylene oxide) (PEO), polyoxyethylene (POE), polyvinyl alcohols, hydroxyethyl celluloses, or dextrans, are commonly conjugated to proteins to increase stability or size, etc., of the protein.

PEG, PEO or POE refers to an oligomer or polymer of ethylene oxide. In the case of PEG, these oligomers or polymers are produced by, e.g., anionic ring opening polymerization of ethylene oxide initiated by nucleophilic attack of a hydroxide ion on the epoxide ring. One of the more useful forms of PEG for protein modification is monomethoxy PEG (mPEG).

Preferred PEGs are monodisperse or polydisperse, preferably monodisperse. The skilled artisan will be aware that PEG can be polydisperse or monodisperse. Polydisperse PEG comprises a mixture of PEGs having different molecular weights. In the case of polydisperse PEGs, reference to a specific molecular weight will be understood to refer to the number average molecular weight of PEGs in the mixture. The size distribution is characterized statistically by its weight average molecular weight (MW) and its number average molecular weight (Mn), the ratio of which is called the polydispersity index (Mw/Mn). MW and Mn are measured, in certain aspects, by mass spectroscopy. Most of the PEG-protein conjugates, particularly those conjugated to PEG larger than 1 KD, exhibit a range of molecular weights due to a polydisperse nature of the parent PEG molecule. For example, in case of mPEG2K (Sunbright ME-020HS, NOF), actual molecular masses are distributed over a range of 1.5~3.0 KD with a polydispersity index of 1.036.

Based on the foregoing, the skilled artisan will be aware that monodisperse PEG comprises a mixture of PEGs comprising substantially the same molecular weight. Monodisperse PEGs are commercially available, e.g., from Polypure AS, Norway.

The average or preferred molecular weight of the PEG will range from about 500 Da to about 200 kDa. For example, the molecular weight of the PEG is from about 1 to about 100 kDa, from about 1.5 to about 50 kDa, from about 1.5 to about 10 kDa, from about 1.5 kDa to about 5 kDa, from about 1.5 kDa to about 4 kDa, from about 1.5 to about 2 kDa.

Preferably, the PEG is monodisperse and has a molecular weight of about 500 Da. Preferably, the PEG has a molecular weight of about 1.5 kDa. Preferably, the PEG has a molecular weight of about 2 kDa.

Preferably, the PEG comprises a reactive group, such as a maleimide group. Preferably, the PEG is $PEG_{24}$-maleimide.

The physiologically acceptable polymer molecule is not limited to a particular structure and is, in various aspects, linear (e.g. alkoxy PEG or bifunctional PEG), branched or multi-armed (e.g. forked PEG or PEG attached to a polyol core), dentritic, or with degradable linkages. Moreover, the internal structure of the polymer molecule is organized in any number of different patterns and is selected from the group consisting of homopolymer, alternating copolymer, random copolymer, block copolymer, alternating tripolymer, random tripolymer, and block tripolymer.

The number of polymers attached to the protein may vary, and if more than one polymer is attached, they can be the same or different molecules. In general, the number and/or type of polymers used for derivatization can be determined based on considerations including, but not limited to, the particular properties or functions of the protein to be improved, whether the protein derivative will be used in a therapy under defined conditions, etc. Preferably, the polymer is PEG.

The skilled artisan will be aware that prior to conjugation to a protein a polymer (e.g., PEG) may need to be activated by preparing a derivative having a functional group at one or both termini.

Particularly preferred compounds for conjugation to the protein of the present invention are set out in Table 1.

TABLE 1

Preferred compounds for conjugation

| Group | Detail |
| --- | --- |
| Radioisotopes (either directly or indirectly) | $^{123}I$, $^{125}I$, $^{130}I$, $^{133}I$, $^{135}I$, $^{47}Sc$, $^{72}As$, $^{72}Sc$, $^{90}Y$, $^{88}Y$, $^{97}Ru$, $^{100}Pd$, $^{101m}Rh$, $^{101m}Rh$, $^{119}Sb$, $^{128}Ba$, $^{197}Hg$, $^{211}At$, $^{212}Bi$, $^{153}Sm$, $^{169}Eu$, $^{212}Pb$, $^{109}Pd$, $^{111}In$, $^{67}Gu$, $^{68}Gu$, $^{67}Cu$, $^{75}Br$, $^{76}Br$, $^{77}Br$, $^{99m}Tc$, $^{11}C$, $^{13}N$, $^{15}O$, $^{18}I$, $^{188}Rc$, $^{203}Pb$, $^{64}Cu$, $^{105}Rh$, $^{198}Au$, $^{199}Ag$ or $^{177}Lu$ |
| Half life extenders | Polyethylene glycol |
| | Glycerol |
| | Glucose |
| Fluorescent probes | Phycoerythrin (PE) |
| | Allophycocyanin (APC) |
| | Alexa Fluor 488 |
| | Cy5.5 |
| Biologies | Fluorescent proteins such as *Renilla* luciferase, GFP |
| | Immune modulators |
| | Toxins |
| | An Immunoglobulin |
| | Half life extenders such as albumin |
| Chemotherapeutics | Taxol |
| | 5-FU |
| | Doxorubicin |
| | Idarubicin |

In one example of the invention, a spacer moiety is included between the compound and the protein to which it is conjugated. The spacer moieties of the invention may be cleavable or non-cleavable. For example, the cleavable spacer moiety is a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety.

In another example, a decrease in pH causes cleavage of the spacer to thereby release of the compound into a target cell. A decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumor-associated enzymes. Examples of linking moieties that can be cleaved enzymatically include, but are not limited to, peptides and esters. Exemplary enzyme cleavable linking moieties include those that are sensitive to tumor-associated proteases such as Cathepsin B or plasmin. Cathepsin B cleavable sites include the dipeptide sequences valine-citrulline, phenylalanine-lysine and/or valine-alanine.

Conjugation Methods

Conjugation to Cysteine (Thiol)

Various methods are known in the art for conjugating a compound to a cysteine residue are known in the art and will be apparent to the skilled artisan. Reagents for such conjugation typically bear reactive functionality which may react (i) directly with a cysteine thiol of a cysteine to form the labeled protein, (ii) with a linker reagent to form a linker-label intermediate, or (iii) with a linker protein to form the labeled protein. In the case of a linker several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form compound-linker intermediate, via a covalent bond, followed by reaction with a cysteine group of a protein of the invention. As will be apparent to the skilled artisan from the foregoing, bifunctional linkers are useful in the present invention. For example, the bifunctional linker comprises a thiol modification group for covalent linkage to the cysteine residue(s) and at least one attachment moiety (e.g., a second thiol modification moiety) for covalent or non-covalent linkage to the compound.

A variety of proteins and compounds, (and linkers) can be used to prepare a conjugate of the invention. Cysteine thiol groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a compound or linker include, but are not limited to amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Preferred labelling reagents include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used.

Maytansine may, for example, be converted to May-$SSCH_3$, which can be reduced to the free thiol, May-SH, and reacted with a protein of the invention (Chari et al, 1992) to generate a maytansinoid-immunoconjugate with a disulfide linker. Maytansinoid conjugates with disulfide linkers have been reported (WO 04/016801; U.S. Pat. No. 6,884,874; and WO 03/068144). The disulfide linker SPP is constructed with linker reagent N-succinimidyl 4-(2-pyridylthio) pentanoate.

Another exemplary reactive functional group is N-hydroxysuccinimidyl ester (NHS) of a carboxyl group substituent of a compound, e.g. biotin or a fluorescent dye or a toxin or a protein. The NHS ester of the compound may be preformed, isolated, purified, and/or characterized, or it may be formed in situ and reacted with a nucleophilic group of the protein. Typically, the carboxyl form of the compound is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxy benzotriazole (HOBt), and N-hydroxysuccinimide to give the NHS ester of the compound. In some cases, the compound and the protein, may be coupled by in situ activation of the compound and reaction with the protein to form the conjugate in one step. Other activating and coupling reagents include TBTU (2-(1H-benzotriazo-1-yl)-1-1,3,3-tetramethyluronium hexafluorophosphate), TFFH (N,N',N',N'-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Additional conjugation methods include, for example, the use of maleimides, iodoacetimides or haloacetyl/alkyl halides, aziridine, acryloyl derivatives to react with the thiol of a cysteine to produce a thioester that is reactive with a compound (e.g., Schelte et al., 2000 (use of maleimides); Reddy et al., 1988 (use of maleimide derivatives); Ramseier and Chang, 1994 (use of iodacetamide); Eisen et al., 1953 (use of 2,4-dinitrobenzeneulfonic acid); Grossman et al., 1981 (use of aziridine); or Yem et al., 1992 (use of acryloyl derivatives). Disulphide exchange of a free thiol with an activated piridyldisulphide is also useful for producing a conjugate (King et al., 1978 and references cited therein, e.g., use of 5-thio-2-nitrobenzoic (TNB) acid). Preferably, a maleimide is used.

With respect to the use of radiolabeled conjugates, proteins of the invention may be directly labeled (such as through iodination) or may be labeled indirectly through the use of a chelating agent. As used herein, the phrases "indirect labeling" and "indirect labeling approach" both mean that a chelating agent is covalently attached to a protein and at least one radionuclide is associated with the chelating agent. Such chelating agents are typically referred to as bifunctional chelating agents as they bind both the protein and the radioisotope. Exemplary chelating agents comprise 1-isothiocycmatobenzyl-3-methyldiothelene triaminepentaacetic acid ("MX-DTPA",) and cyclohexyl diethylenetriamine pentaacetic acid ("CHX-DTPA") derivatives, or DOTA. Linker reagents such as DOTA-maleimide (4-maleimidobutyramidobenzyl-DOTA) can be prepared by the reaction of aminobenzyl-DOTA with A-maleimidobutyric acid (Fluka) activated with isopropylchloroformate (Aldrich), following the procedure of Axworthy et al, (2000). DOTA-maleimide reagents react with free cysteine amino acids of the proteins of the invention and provide a metal complexing ligand thereon (Lewis et al, 1998). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.).

Prior to linkage it is preferred that the protein of the invention is made reactive for conjugation with linker reagents by treatment with a reducing agent such as DTT (Cleland's reagent, dithiothreitol) or TCEP (tris(2-carboxyethyl)phosphine hydrochloride; Getz et al, 1999; Soltec Ventures, Beverly, Mass.). Disulfide bonds can be re-established between cysteine residues that are not required for linkage with dilute (200 nM) aqueous copper sulfate ($CuSO_4$) at room temperature. Other oxidants, i.e. oxidizing agents, and oxidizing conditions, which are known in the art may be used. Ambient air oxidation is also effective. This mild, partial reoxidation step forms intrachain disulfides efficiently with high fidelity.

Conjugation to Threonine/Serine

Methods are also known in the art for conjugating a compound to a threonine or serine residue. For example, Zhang and Tam (1996) described a method in which carbonyl precursors are derived from the 1,2-aminoalcohols of serine or threonine, which can be selectively and rapidly converted to aldehyde form by periodate oxidation. Reaction of the aldehyde with a 1,2-aminothiol of cysteine in a compound to be attached to a protein of the invention forms a stable thiazolidine product. This method is particularly useful for labelling proteins at N-terminal serine or threonine residues.

In one example of the invention, a spacer moiety is included between the compound and the protein to which it is conjugated. The spacer moieties of the invention may be cleavable or non-cleavable. For example, the cleavable spacer moiety is a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety.

In another example, a decrease in pH causes cleavage of the spacer to thereby release of the compound into a target cell. A decrease in pH is implicated in many physiological and pathological processes, such as endosome trafficking, tumour growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumor-associated enzymes. Examples of linking moieties that can be cleaved enzymatically include, but are not limited to, peptides and esters. Exemplary enzyme cleavable linking moieties include those that are sensitive to tumor-associated proteases such as Cathepsin B or plasmin. Cathepsin B cleavable sites include the dipeptide sequences valine-citrulline and phenylalanine-lysine.

PEGylation Methods

Various methods are known in the art for conjugating compounds, e.g., PEG, to a protein to which it is conjugated. The spacer moieties of the invention may be cleavable or non-cleavable. For example, the cleavable spacer moiety is a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety. In the case of PEG, the molecule can be activated to facilitate its binding to amines or imidazoles, a carboxylic group, a hydroxyl group or a sulfhydryl group.

In another example, a decrease in pH causes cleavage of the spacer to thereby release of the compound into a target cell. A decrease in pH is implicated in many physiological and pathological processes, such as endosome trafficking, tumour growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumor-associated enzymes. Examples of linking moieties that can be cleaved enzymatically include, but are not limited to, peptides and esters. Exemplary enzyme cleavable linking moieties include those that are sensitive to tumor-associated proteases such as Cathepsin B or plasmin. Cathepsin B cleavable sites include the dipeptide sequences valine-citrulline and phenylalanine-lysine.

For example, Abuchowski et al (1977) activated PEG using cyanuric chloride to produce a PEG dichlorotriazine derivative. This derivative can react with multiple functional nucleophilic functional groups, such as lysine, serine, tyrosine, cysteine and histidine. A modified form of this protocol produced PEG-chlorotriazine, which has lower reactivity and conjugates more selectively with lysine or cysteine residues (Mutsushima et al., 1980).

Two widely used forms of PEG used to conjugate to proteins are succinimidyl carbonate PEG (SC-PEG; Zalipsky et al., 1992) and benzotriazole carbonate PEG (BTC-PEG; U.S. Pat. No. 5,560,234). Both of these compounds react preferentially with lysine residues to form carbamate linkages, however are also known to react with hystidine and tyrosine. SC-PEG is slightly more resistant to hydrolysis than BTC-PEG.

Another PEG useful for conjugating to proteins is PEG-propionaldehyde (U.S. Pat. No. 5,252,714). An advantage of this chemistry is that under acidic conditions (about pH5) it is largely selective for N-terminal $\alpha$-amine thus avoiding potential problems with non-specific conjugation. A acetal derivative of PEG-propionaldehyde, i.e., PEG-acetalaldehyde provides an additional benefit in so far as it provides for longer storage than PEG-propionaldehyde (U.S. Pat. No. 5,990,237).

Active esters of PEG carboxylic acids are probably one of the most used acylating agents for protein conjugation. Active esters react with primary amines near physiological conditions to form stable amides. Activation of PEG-carboxylic acids to succinimidyl active esters is accomplished by reacting the PEG-carboxylic acid with N-hydroxysuccinimide (NHS or HOSu) and a carbodiimide. Exemplary carboxylic acid derivatives of PEG include carboxymethylated PEG (CM-PEG; Zalipsky et al., 1990), butanoic acid derivatives and propionic acid derivatives (U.S. Pat. No. 5,672,662). Changing the distance between the active ester and the PEG backbone by the addition of methylene units can dramatically influence reactivity towards water and amines (e.g., by reducing hydrolysis). Alternatively or in addition, hydrolysis can be reduced by introducing an $\alpha$-branching moiety to the carboxylic acid.

PEGylation of free cysteine residues in a protein is useful for site-specific conjugation (e.g., using a protein modified to include cysteine residues as described herein). Exemplary PEG derivatives for cysteine conjugation include PEG-maleimide, PEG-vinylsulfone, PEG-iodoacetamide and PEG-orthopyridyl disulfide. Exemplary methods for conjugating PEG to cysteine residues are described in Goodson and Katre (1990) and/or above. Exemplary methods for conjugation using PEG-vinylsulfone are described, for example, in Li et al. (2006).

U.S. Pat. No. 5,985,263 describes methods for conjugating PEG to the secondary amine group of histidine, which has a lower pKa than the primary amine. An advantage of this approach is that the acyl-histidine bond is not stable meaning that the protein is slowly released (i.e., the conjugate behaves as a slow release formulation or a pro-drug).

Another approach for PEGylation is to take advantage of a N-terminal serine or threonine, which can be converted to periodate as discussed above. Using this approach, PEG has been conjugated to bioactive proteins (e.g., Gaertner and Offord, 1996).

PEG can also be conjugated to carbohydrate groups.

The present invention also encompasses the use of reversible PEGylation strategies.

Uses

The proteins of the present invention are useful in a variety of applications, including research, diagnostic and therapeutic applications. Depending on the antigen to which the protein binds it may be useful for delivering a compound to a cell, e.g., to kill the cell or prevent growth and/or for imaging and/or for in vitro assays. In one example, the protein is useful for both imaging and delivering a cytotoxic agent to a cell, i.e., it is conjugated to a detectable label and a cytotoxic agent or a composition comprises a mixture of proteins some of which are conjugated to a cytotoxic agent and some of which are conjugated to a detectable label.

The proteins described herein can also act as inhibitors to inhibit (which can be reducing or preventing) (a) binding (e.g., of a ligand, an inhibitor) to a receptor, (b) a receptor signaling function, and/or (c) a stimulatory function. Proteins which act as inhibitors of receptor function can block ligand binding directly or indirectly (e.g., by causing a conformational change).

Antigens

The present invention contemplates a protein comprising at least one variable region comprising at least two cysteine residues in FR2 and/or FR3 capable of specifically binding to any antigen(s), i.e., an example of the invention is generic as opposed to requiring a specific antigen.

Examples of the present invention contemplate a protein that specifically binds to an antigen associated with a disease or disorder (i.e., a condition) e.g., associated with or expressed by a cancer or cancerous/transformed cell and/or associated with an autoimmune disease and/or associated with an inflammatory disease or condition and/or associated with a neurodegenerative disease and/or associated with an immune-deficiency disorder.

Exemplary antigens against which a protein of the invention can be produced include BMPRIB (bone morphogenetic protein receptor-type IB, Dijke. et al 1994, WO2004063362); E16 (LAT1, SLC7A5, Gaugitsch et al 1992; WO2004048938); STEAP1 (six transmembrane epithelial antigen of prostate, Hubert, et al, 1999)); WO2004065577); CA125 (MUC16, WO2004045553); MPF (MSLN, SMR, megakaryocyte potentiating factor, mesothelin, Yamaguchi et al, 1994, WO2003101283); Napi3b (NAPI-3B, NPTIIb, SLC34A2, solute carrier family 34; Feild et al, 1999; WO2004022778); Sema 5b (FLJ10372, KIAA1445, SEMA5B, SEMAG, Semaphorin 5b, sema domain, seven thrombospondin repeats (type 1 and type Hike), transmembrane domain (TM) and short cytoplasmic domain, (semaphorin) 5B, Nagase et al, 2000; WO2004000997); PSCA (Ross et al, 2002; US2003129192); ETBR (Endothelin type B receptor, Nakamuta., et al, 34-39, 1991; WO2004045516); MSG783 (RNF124, WO2003104275); STEAP2 (HGNC_8639, IPCA-I, PCANAP1, STAMP1, STEAP2, STMP, prostate cancer associated gene 1, prostate cancer associated protein 1, six transmembrane epithelial antigen of prostate 2, six transmembrane prostate protein, WO2003087306); TrpM4 (BR22450, FLJ20041, TRPM4, TRPM4B, transient receptor potential cation channel, subfamily M, member 4, Xu et al, 2001, US2003143557); CRIPTO (CR, CR1, CRGF, CRIPTO, TDGF1, teratocarcinoma-derived growth factor, Ciccodicola, et al, 1989; US2003224411); CD21 (CR2 (Complement receptor T) or C3DR (C3d/Epstein Barr virus receptor) Fujisaku et al, 1989; WO2004045520); CD79b (CD79B, CD79β, IGb (immunoglobulin-associated beta), B29, Muller, 1992; WO2004016225); FcRH2 (DFGP4, IRTA4, SPAP1A (SH2 domain containing phosphatase anchor protein Ia), SPAP1B, SPAP1C, Xu, et al, 2001; WO2004016225); HER2 (ErbB2, Coussens et al, 1985; WO2004048938); NCA (CEACAM6, Barnett et al, 1988; WO2004063709); MDP (DPEP1, WO2003016475); IL20Rα (IL20Ra, ZCYTOR7, Clark, et al, 2003; EP1394274); Brevican (BCAN, BEHAB, Gary et al, 2000; US2003186372); EphB2R (DRT, ERK, Hek5, EPHT3, Tyro5, Chan and Watt, 1991; WO2003042661); ASLG659 (B7h, US20040101899); PSCA (Prostate stem cell antigen precursor, Reiter et al, 1735-1740, 1998; WO2004022709); GEDA (lipoma HMGIC fusion-partner-like protein WO2003054152); BAFF-R (B cell-activating factor receptor, BLyS receptor 3, BR3, Thompson, et al, 2001; WO2004058309); CD22 (B-cell receptor CD22-B isoform, BL-CAM, Lyb-8, Lyb8, SIGLEC-2, FLJ22814, Wilson et al, 1991; WO2003072036); CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation; WO2003088808); CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia WO2004040000); HLA-DOB (Beta subunit of MHC class II molecule (Ia antigen) that binds peptides and presents them to CD4+ T lymphocytes; Tonnelle et al, 1985; WO9958658); P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability; Lee et al, 1998; WO2004047749); CD72 (B-cell differentiation antigen CD72, Lyb-2; WO2004042346); LY64 (Lymphocyte antigen 64 (RP 105), type I membrane protein of the leucine rich repeat (LRR) family, regulates B-cell activation and apoptosis, loss of function is associated with increased disease activity in patients with systemic lupus erythematosis; US2002193567); FcRH1 (Fc receptor-like protein 1, a putative receptor for the immunoglobulin Fc domain that contains C2 type Ig-like and ITAM domains, may have a role in B-lymphocyte differentiation WO2003077836); IRTA2 (Immunoglobulin superfamily receptor translocation associated 2, a putative immunoreceptor with possible roles in B cell development and lymphomagenesis; deregulation of the gene by translocation occurs in some B cell malignancies; Nakayama et al, 2000; WO2003077836); TENB2 (TMEFF2, tomoregulin, TPEF, HPP1, TR, putative transmembrane proteoglycan, related to the EGF/heregulin family of growth factors and follistatin; WO2004074320); CD20 (WO94/11026); VEGF-A (Presta et al., 1997); p53; EGFR; progesterone receptor; cathepsin D; Bcl-2; E cadherin; CEA; Lewis X; Ki67; PCNA; CD3; CD4; CD5; CD7; CD11c; CD11d; c-Myc; tau; PrPSC; or Aβ.

Preferably, the protein of the invention specifically binds to HER2 (e.g., comprising a sequence set forth in SEQ ID NO: 150), MUC1 (e.g., comprising a sequence set forth in SEQ ID NO: 152 or 153), TAG72 (a high molecular weight mucin like protein e.g., as described in Johnson et al., 1986) or PSMA (e.g., comprising a sequence set forth in SEQ ID NO: 151). For example, the protein of the invention specifically binds to Her2. For example, the protein of the invention specifically binds to MUC1. For example, the protein of the invention specifically binds to TAG72. For example, the protein of the invention specifically binds to PSMA.

Other exemplary antibodies from which a protein of the invention can be derived will be apparent to the skilled artisan and include, for example, rituximab (C2B8; WO94/11026); or bevacizumab (humanized A.4.6.1; Presta et al., 1997)).

Exemplary bispecific proteins may bind to two different epitopes of the antigen of interest. Other such proteins may combine one antigen binding site with a binding site for another protein. Alternatively, an anti-antigen of interest region may be combined with a region which binds to a triggering molecule on a leukocyte such as a T-cell receptor molecule (e.g., CD3), or Fc receptors for IgG (FcγR), such as FcγRI (CD64), FcγRII (CD32) and/or FcγRIII (CD16), so as to focus and localize cellular defence mechanisms to the cells expressing the antigen of interest. Bispecific proteins may also be used to localize cytotoxic agents to cells which express the antigen of interest. These proteins possess a region that binds the antigen of interest and a region which binds the cytotoxic agent (e.g., saporin, anti-interferon-α, vinca alkaloid, ricin A chain, methotrexate or radioactive isotope hapten). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Pharmaceutical Compositions and Methods of Treatment

The proteins of the present invention (syn. active ingredients) are useful for parenteral, topical, oral, or local administration, aerosol administration, or transdermal administration for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges or by parenteral administration. It is recognized that the pharmaceutical compositions of this invention, when administered orally, should be protected from digestion. This is typically accomplished either by complexing the proteins with a composition to render it resistant to acidic and enzymatic hydrolysis or by packaging the compound in an appropriately resistant carrier such as a liposome. Means of protecting proteins from digestion are known in the art.

Typically, a therapeutically effective amount of the protein will be formulated into a composition for administration to a subject. The phrase "a therapeutically effective amount" refers to an amount sufficient to promote, induce, and/or enhance treatment or other therapeutic effect in a subject. As will be apparent, the concentration of proteins of the present invention in these formulations can vary widely, and will be selected primarily based on fluid volumes, viscosities, body weight and the like in accordance with the particular mode of administration selected and the patient's needs. Depending on the type and severity of the disease, a therapeutically effective amount may be about 1 μg/kg to 15 mg/kg (e.g. 0.1-20 mg/kg) of molecule, whether, for example, by one or more separate administrations, or by continuous infusion. A typical daily dosage might range from about 1 μg/kg to 100 mg/kg or more. An exemplary dosage of the protein to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the protein. Other dosage regimens may be useful. The progress of this therapy is easily monitored by conventional techniques and assays.

Alternatively, the protein of the invention is formulated at a concentrated does that is diluted to a therapeutically effective dose prior to administration to a subject.

The pharmaceutical compositions of this invention are particularly useful for parenteral administration, e.g., formulated for injection via the intravenous, intramuscular, sub-cutaneous, transdermal, or other such routes, including peristaltic administration and direct instillation into a tumour or disease site (intracavity administration). The compositions for administration will commonly comprise a solution of the proteins of the present invention dissolved in a pharmaceutically acceptable carrier, preferably an aqueous carrier. A variety of aqueous carriers can be used, e.g., buffered saline and the like. Other exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Techniques for preparing pharmaceutical compositions are generally known in the art as exemplified by Remington's Pharmaceutical Sciences, 16th Ed. Mack Publishing Company, 1980.

WO2002/080967 describes compositions and methods for administering aerosolized compositions comprising proteins for the treatment of, e.g., asthma, which are also suitable for administration of protein of the present invention.

Suitable dosages of compounds of the present invention will vary depending on the specific protein, the condition to be diagnosed/treated/prevented and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from cell culture assays or animal studies are used, wherein a suitable dose is within a range of circulating concentrations that include the ED50 of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the IC50 (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

A protein of the invention may be combined in a pharmaceutical combination formulation, or dosing regimen as combination therapy, with a second compound. The second compound of the pharmaceutical combination formulation or dosing regimen preferably has complementary activities to the protein of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing a protein of the invention may also have a therapeutically effective amount of a chemotherapeutic agent such as a tubulin-forming inhibitor, a topoisomerase inhibitor, or a DNA binder.

Pharmaceutical "slow release" capsules or compositions may also be used. Slow release formulations are generally designed to give a constant drug level over an extended period and may be used to deliver compounds of the present invention.

The present invention also provides a method of treating or preventing a condition in a subject, the method comprising administering a therapeutically effective amount of a protein of the invention to a subject in need thereof.

As used herein, the terms "preventing", "prevent" or "prevention" in the context of preventing a condition include administering an amount of a protein described herein sufficient to stop or hinder the development of at least one symptom of a specified disease or condition.

As used herein, the terms "treating", "treat" or "treatment" include administering a therapeutically effective amount of an inhibitor(s) and/or agent(s) described herein sufficient to reduce or eliminate at least one symptom of a specified disease or condition.

As used herein, the term "subject" shall be taken to mean any animal including humans, preferably a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). Preferably the mammal is a human or primate. More preferably the mammal is a human.

As used herein, a "condition" is a disruption of or interference with normal function, and is not to be limited to any specific condition, and will include diseases or disorders. In an example, the condition is a cancer or an immunopathological disorder.

Exemplary cancers include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Preferably a cancer is breast cancer or ovarian cancer or prostate cancer.

In one example of the invention, the cancer expresses Her2. Exemplary cancers include breast cancer, ovarian cancer, stomach cancer or uterine cancer, preferably breast cancer. Such a cancer can be treated, for example, with a protein of the invention that binds to Her2.

In another example of the invention, the cancer expresses PSMA. Exemplary cancers include prostate cancer. Such a cancer can be treated, for example, with a protein of the invention that binds to PSMA.

In a further example of the invention, the cancer expresses Tag72. Exemplary cancers include carcinomas, such as colorectal cancer, gastric cancer, pancreatic cancer, ovarian cancer, endometrial cancer, breast cancer, non-small cell lung cancer, and prostate cancer. Such a cancer can be treated, for example, with a protein of the invention that binds to Tag72.

In a further example of the invention, the cancer expresses MUC1, preferably a glycoform of MUC1 associated with cancer. Exemplary cancers include carcinomas, such as colorectal cancer, gastric cancer, pancreatic cancer, breast cancer, lung cancer, and bladder cancer. Such a cancer can be treated, for example, with a protein of the invention that binds to MUC1.

Immunopathology is the study of disease having an immunological cause and immunologic disease is any condition caused by the reactions of immunoglobulins to antigens. Thus, an "immunopathological disorder" can be defined as a disorder arising from reaction of a subject's immune system to antigens. Immunopathological disorders include autoimmune diseases and hypersensitivity responses (e.g. Type I: anaphylaxis, hives, food allergies, asthma; Type II: autoimmune haemolytic anaemia, blood transfusion reactions; Type III: serum sickness, necrotizing vasculitis, glomerulonephritis, rheumatoid arthritis, lupus; Type IV: contact dermatitis, graft rejection). Autoimmune diseases include rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteritis), autoimmune neurological disorders (such as, for example, multiple sclerosis, opsoclonus myoclonus syndrome, myasthenia gravis, neuromyelitis optica, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjogren's syndrome, Graves' disease, IDDM, pernicious anemia, thyroiditis, and glomerulonephritis.

In another embodiment, the disorder is an inflammatory disease. Inflammation is a protective response of body tissues to irritation or injury- and can be acute or chronic. Thus, inflammatory disorders include diseases involving neutrophils, monocytes, mast cells, basophils, eosinophils, macrophages where cytokine release, histamine release, oxidative burst, phagocytosis, release of other granule enzymes and chemotaxis occur. Hypersensitivity responses (defined above under immunopathological disorders) can also be regarded as inflammatory diseases (acute or chronic) since they often involve complement activation and recruitment/infiltration of various leukocytes such as neutrophils, mast cells, basophils, etc.

The compositions of the present invention will be administered in a manner compatible with the dosage formulation and in such amount as is therapeutically/prophylactically effective. Formulations are easily administered in a variety of manners, e.g., by ingestion or injection or inhalation.

Other therapeutic regimens may be combined with the administration of a protein of the invention. The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Prior to therapeutic use, a protein of the invention is preferably tested in vitro and/or in vivo, e.g., as described below.

In Vitro Testing

In one example, a protein of the invention binds to an antigen, even if conjugated to a compound. The protein may bind to the antigen at least as well as the protein from which it is derived. Alternatively, the protein or conjugate comprising same binds to the antigen with at least about 10% or 20% or 30% or 40% or 50% or 60% or 70% or 80% or 90% of the affinity or avidity of the protein from which it is derived or a form of the protein lacking the cysteine residues and/or not conjugated to the compound.

Exemplary methods for determining binding affinity of a protein include a simple immunoassay showing the ability of the protein to block the binding of the unmodified protein or unconjugated protein to a target antigen, e.g., a competitive binding assay. Competitive binding is determined in an assay in which the protein under test inhibits specific binding of a reference protein to a common antigen. Numerous types of competitive binding assays are known, for example, solid phase direct or indirect radioimmunoassay (RIA), solid phase direct or indirect enzyme immunoassay (EIA), sandwich competition assay (see Stahli et al., 1983; Kim, et al., 1989); solid phase direct biotin-avidin EIA (see Kirkland et al., 1986); solid phase direct labelled assay, solid phase direct labelled sandwich assay (see Harlow and Lane, 1988); solid phase direct label RIA using $^{125}$I label (see Morel et al., 1988); solid phase direct biotin-avidin EIA (Cheung et al., 1990); or direct labelled RIA (Moldenhauer et al., 1990). see, for example, Harlow and Lane, 1988). Typically, such an assay involves the use of purified antigen bound to a solid surface or cells bearing either of these, an unlabeled test protein and a labelled reference protein. Competitive inhibition is measured by determining the amount of label bound to the solid surface or cells in the presence of the test protein The present invention also encompasses methods for testing the activity of a protein of the invention. Various assays are available to assess the activity of a protein of the present invention in vitro. For example, a protein of the present invention is administered to a cell or population thereof to determine whether or not it can bind to said cell and/or be internalized by said cell. Such an assay is facilitated by labelling the protein of the present invention with a detectable label (i.e., producing a conjugate), however this is not essential since the protein of the present invention can also be detected with a labelled protein. Such an assay is useful for assessing the ability of a protein of the present invention to deliver a compound (i.e., a payload) to a cell and/or its utility in imaging. Preferably the cell expresses an antigen to which the protein of the present invention binds and more preferably is a cell line or primary cell culture of a cell type that it desired to be detected or treated.

Generally, the cytotoxic or cytostatic activity of a protein of the present invention, e.g. conjugated to a cytotoxic molecule is measured by: exposing cells expressing an antigen to which the protein of the present invention binds to the protein of the present invention; culturing the cells for a suitable period for the protein to exert a biological effect, e.g., from about 6 hours to about 5 days; and measuring cell viability, cytotoxicity and/or cell death. Cell-based in vitro assays useful for measure viability (proliferation), cytotoxicity, and cell death are known in the art.

For example, the CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present in a cell, an indicator of metabolically active cells (Crouch et al 1993; U.S. Pat. No. 6,602,677). Alternatively, cell viability is assayed using non-fluorescent resazurin, which is added to cells cultured in the presence of a protein of the present invention. Viable cells reduce resazurin to red-fluorescent resorufin, easily detectable, using, for example microscopy or a fluorescent plate reader. Kits for analysis of cell viability are available, for example, from Molecular Probes, Eugene, Oreg., USA. Other assays for cell viability include determining incorporation of $^{3}$H-thymidine or $^{14}$C-thymidine into DNA as it is synthesized is an assay for DNA synthesis associated with cell division. In such an assay, a cell is incubated in the presence of labeled thymidine for a time sufficient for cell division to occur. Following washing to remove any unincorporated thymidine, the label (e.g. the radioactive label) is detected, e.g., using a scintillation counter. Alternative assays for determining cellular proliferation, include, for example, measurement of DNA synthesis by BrdU incorporation (by ELISA or immunohistochemistry, kits available from Amersham Pharmacia Biotech). Exemplary assays for detecting cell death include APOPTEST (available from Immunotech) stains cells early in apoptosis, and does not require fixation of the cell sample. This method utilizes an annexin V antibody to detect cell membrane re-configuration that is characteristic of cells undergoing apoptosis. Apoptotic cells stained in this manner can then be sorted either by fluorescence activated cell sorting (FACS), ELISA or by adhesion and panning using immobilized annexin V antibodies. Alternatively, a terminal deoxynucleotidyl transferase-mediated biotinylated UTP nick end-labeling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y.

Stability of a protein of the present invention can also be assessed by exposing a protein of the present invention to serum and/or cells and subsequently isolating the protein of the present invention using, for example, immunoaffinity purification. A reduced amount of recovered protein of the present invention indicates that the protein of the present invention is degraded in serum or when exposed to cells.

In another example, the ability of the protein of the present invention to block binding of a ligand to a receptor is assessed using a standard radio-immunoassay or fluorescent-immunoassay.

In Vivo Testing

A protein of the present invention can also be tested for its stability and/or efficacy in vivo. For example, the protein of the present invention is administered to a subject and the serum levels of the protein is detected over time, e.g., using an ELISA or by detecting a detectable label conjugated to the protein. This permits determination of the in vivo stability of the protein of the present invention.

A protein of the present invention can also be administered to an animal model of a human disease. The skilled artisan will be readily able to determine a suitable model based on the antigen to which the protein of the present invention binds. Exemplary models of, for example, human cancer are known in the art. For example, mouse models of breast cancer include mice overexpressing fibroblast growth factor 3 (Muller et al., 1990); TGF-alpha (Matsui et al, 1990); erbB2 (Guy, et al., 1992); RET-1 (Iwamoto et al., 1990) or transplantation of human breast cancer cells into SCID mice. Models of ovarian cancer include transplantation of ovarian cancer cells into mice (e.g., as described in Roby et al., 2000); transgenic mice chronically secreting luteinising hormone (Risma et al., 1995); or Wx/Wv mice. Mouse models of prostate cancer are also known in the art and include, for example, models resulting from enforced expression of SV40 early genes (e.g., the TRAMP model that utilizes the minimal rat probasin promoter to express the SV40 early genes or transgenic mice using the long probasin promoter to express large T antigen, collectively termed the 'LADY' model or mice expressing c-myc or Bcl-2 or Fgf8b or expressing dominant negative TGFβ (see, Matusik et al., 2001, for a review of transgenic models of prostate cancer).

A protein of the present invention can also be administered to an animal model of a disease other than cancer, e.g., NOD mice to test their ability to suppress, prevent, treat or delay diabetes (e.g., as described in Tang et al. (2004)) and/or to a mouse model of GVHD (e.g., as described in Trenado (2002)) and/or to a mouse model of psoriasis (e.g., Wang et al. 2008) and/or to a model of rheumatoid arthritis e.g., a SKG strain of mouse (Sakaguchi et al.), rat type II collagen arthritis model, mouse type II collagen arthritis model or antigen induced arthritis models in several species (Bendele, 2001)) and/or a model of multiple sclerosis (for example, experimental autoimmune encephalomyelitis (EAE; Bradl and Linington, 1996)) and/or inflammatory airway disease (for example, OVA challenge or cockroach antigen challenge (Chen et al. 2007; Lukacs et al. 2001) and/or models of inflammatory bowel disease (e.g., dextran sodium sulphate (DSS)-induced colitis or Muc2 deficient mouse model of colitis (Van der Sluis et al. 2006).

Diagnostic/Prognostic Methods

In one example, the present invention provides methods for diagnosing or prognosing a condition.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence.

In one example, the method comprises determining the amount of an antigen in a sample. Thus, the proteins of the invention have utility in applications such as cell sorting (e.g., flow cytometry, fluorescence activated cell sorting), for diagnostic or research purposes. For example, a sample is contacted with a protein of the invention for a time and under conditions sufficient for it to bind to an antigen and form a complex and the complex is then detected or the level of complex is determined. For these purposes, the proteins can be labelled or unlabeled. The proteins can be directly labelled, e.g., using a method described herein. When unlabeled, the proteins can be detected using suitable means, as in agglutination assays, for example. Unlabeled antibodies or fragments can also be used in combination with another (i.e., one or more) suitable reagent which can be used to detect a protein, such as a labelled antibody (e.g., a second antibody) reactive with the protein or other suitable reagent (e.g., labelled protein A).

Preferably, a protein of the invention is used in an immunoassay. Preferably, using an assay selected from the group consisting of, immunohistochemistry, immunofluorescence, enzyme linked immunosorbent assay (ELISA), fluorescence linked immunosorbent assay (FLISA) Western blotting, RIA, a biosensor assay, a protein chip assay and an immunostaining assay (e.g. immunofluorescence).

Standard solid-phase ELISA or FLISA formats are particularly useful in determining the concentration of a protein from a variety of samples.

In one form such an assay involves immobilizing a biological sample onto a solid matrix, such as, for example a polystyrene or polycarbonate microwell or dipstick, a membrane, or a glass support (e.g. a glass slide). A protein of the invention that specifically binds to an antigen of interest is brought into direct contact with the immobilized sample, and forms a direct bond with any of its target antigen present in said sample. This protein of the invention is generally labelled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or β-galactosidase) in the case of an ELISA, or alternatively a labelled antibody can be used that binds to the protein of the invention. Following washing to remove any unbound protein the label is detected either directly, in the case of a fluorescent label, or through the addition of a substrate, such as for example hydrogen peroxide, TMB, or toluidine, or 5-bromo-4-chloro-3-indol-beta-D-galactopyranoside (x-gal) in the case of an enzymatic label. Such ELISA or FLISA based systems are particularly suitable for quantification of the amount of a protein in a sample, by calibrating the detection system against known amounts of a protein standard to which the protein binds, such as for example, an isolated and/or recombinant protein or immunogenic fragment thereof or epitope thereof.

In another form, an ELISA or FLISA comprises of immobilizing a protein of the invention or an antibody that binds to an antigen of interest on a solid matrix, such as, for example, a membrane, a polystyrene or polycarbonate microwell, a polystyrene or polycarbonate dipstick or a glass support. A sample is then brought into physical relation with said protein of the invention, and the protein to which said compound binds is bound or 'captured'. The bound protein is then detected using a labelled protein of the invention that binds to a different protein or a different site in the same protein. Alternatively, a third labelled antibody can be used that binds the second (detecting) antibody.

Imaging Methods

As will be apparent to the skilled artisan from the foregoing, the present invention also contemplates imaging methods using a protein of the invention. For imaging, protein of the invention is conjugated to a detectable label, which can be any molecule or agent that can emit a signal that is detectable by imaging. For example, the detectable label may be a protein, a radioisotope, a fluorophore, a visible light emitting fluorophore, infrared light emitting fluorophore, a metal, a ferromagnetic substance, an electromagnetic emitting substance a substance with a specific MR spectroscopic signature, an X-ray absorbing or reflecting substance, or a sound altering substance.

The protein of the present invention can be administered either systemically or locally to the tumour, organ, or tissue to be imaged, prior to the imaging procedure. Generally, the protein is administered in doses effective to achieve the desired optical image of a tumour, tissue, or organ. Such doses may vary widely, depending upon the particular protein employed, the tumour, tissue, or organ subjected to the imaging procedure, the imaging equipment being used, and the like.

In some embodiments of the invention, the protein of the invention is used as in vivo optical imaging agents of tissues and organs in various biomedical applications including, but not limited to, imaging of tumours, tomographic imaging of organs, monitoring of organ functions, coronary angiography, fluorescence endoscopy, laser guided surgery, photoacoustic and sonofluorescence methods, and the like. Exemplary diseases, e.g., cancers, in which a protein of the invention is useful for imaging are described herein and shall be taken to apply mutatis mutandis to the present embodiment of the invention. In one example, the protein conjugates of the invention are useful for the detection of the presence of tumours and other abnormalities by monitoring where a particular protein of the invention is concentrated in a subject. In another embodiment, the protein of the invention is useful for laser-assisted guided surgery for the detection of micro-metastases of tumours upon laparoscopy. In yet another embodiment, the protein of the invention is useful in the diagnosis of atherosclerotic plaques and blood clots.

Examples of imaging methods include magnetic resonance imaging (MRI), MR spectroscopy, radiography, CT, ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

Certain examples of the methods of the present invention further include imaging a tissue during a surgical procedure on a subject.

A variety of techniques for imaging are known to those of ordinary skill in the art. Any of these techniques can be applied in the context of the imaging methods of the present invention to measure a signal from the detectable label. For example, optical imaging is one imaging modality that has gained widespread acceptance in particular areas of medicine. Examples include optical labeling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erytlirosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

Gamma camera imaging is contemplated as a method of imaging that can be utilized for measuring a signal derived from the detectable label. One of ordinary skill in the art would be familiar with techniques for application of gamma camera imaging. In one embodiment, measuring a signal can involve use of gamma-camera imaging of an $^{111}$In or $^{99m}$Tc conjugate, in particular $^{111}$In-octreotide or $^{99m}$Tc-somatostatin analogue.

Computerized tomography (CT) is contemplated as an imaging modality in the context of the present invention. By taking a series of X-rays from various angles and then combining them with a computer, CT made it possible to build up a three-dimensional image of any part of the body. A computer is programmed to display two-dimensional slices from any angle and at any depth. The slices may be combined to build three-dimensional representations.

In CT, intravenous injection of a radiopaque contrast agent conjugated to a protein of the invention, which binds to an antigen of interest can assist in the identification and delineation of soft tissue masses when initial CT scans are not diagnostic. Similarly, contrast agents aid in assessing the vascularity of a soft tissue lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent, for example, gadopentate.

Magnetic resonance imaging (MRI) is an imaging modality that uses a high-strength magnet and radio-frequency signals to produce images. In MRI, the sample to be imaged is placed in a strong static magnetic field and excited with a pulse of radio frequency (RF) radiation to produce a net magnetization in the sample. Various magnetic field gradients and other RF pulses then act to code spatial information into the recorded signals. By collecting and analyzing these signals, it is possible to compute a three-dimensional image which, like a CT image, is normally displayed in two-dimensional slices. The slices may be combined to build three-dimensional representations.

Contrast agents used in MRI or MR spectroscopy imaging differ from those used in other imaging techniques. Examples of MRI contrast agents include gadolinium chelates, manganese chelates, chromium chelates, and iron particles. For example, a protein of the invention is conjugated to a compound comprising a chelate of a paramagnetic metal selected from the group consisting of scandium, titanium, vanadium, chromium, manganese, iron, cobalt, nickel, copper, molybdenum, ruthenium, cerium, indium, praseodymium, neodymium, promethium, samarium, europium, gadolinium, terbium, dysprosium, holmium, erbium, thulium, and ytterbium. A further example of imaging agents useful for the present invention is halocarbon-based nanoparticle such as PFOB or other fluorine-based MRI agents. Both CT and MRI provide anatomical information that aid in distinguishing tissue boundaries and vascular structure.

Imaging modalities that provide information pertaining to information at the cellular level, such as cellular viability, include positron emission tomography (PET) and single-photon emission computed tomography (SPECT). In PET, a patient ingests or is injected with a radioactive substance that emits positrons, which can be monitored as the substance moves through the body.

Closely related to PET is single-photon emission computed tomography, or SPECT. The major difference between the two is that instead of a positron-emitting substance, SPECT uses a radioactive tracer that emits high-energy photons. SPECT is valuable for diagnosing multiple illnesses including coronary artery disease, and already some 2.5 million SPECT heart studies are done in the United States each year.

For PET, a protein of the invention is commonly labeled with positron-emitters such as $^{11}C$, $^{13}N$, $^{15}O$, $^{18}F$, $^{82}Rb$, $^{62}Cu$, and $^{68}Ga$. Proteins of the invention are labelled with positron emitters such as 99mTc, $^{201}Tl$, and $^{67}Ga$, $^{111}In$ for SPECT.

Non-invasive fluorescence imaging of animals and humans can also provide in vivo diagnostic information and be used in a wide variety of clinical specialties. For instance, techniques have been developed over the years including simple observations following UV excitation of fluorophores up to sophisticated spectroscopic imaging using advanced equipment (see, e.g., Andersson-Engels et al, 1997). Specific devices or methods known in the art for the in vivo detection of fluorescence, e.g., from fluorophores or fluorescent proteins, include, but are not limited to, in vivo near-infrared fluorescence (see, e.g., Frangioni, 2003), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, 2001), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

In some examples, an imaging agent is tested using an in vitro or in vivo assay prior to use in humans, e.g., using a model described herein.

Articles of Manufacture

The present invention also provides an article of manufacture, or "kit", containing a protein of the invention. The article of manufacture optionally comprises a container and a label or package insert on or associated with the container, e.g., providing instructions to use the protein of the invention in a method described herein according to any embodiment. Suitable containers include, for example, bottles, vials, syringes, blister pack, etc. The containers may be formed from a variety of materials such as glass or plastic. The container holds a protein of the invention composition and may have a sterile access port (for example the container may be an intravenous solution bag or a vial having a stopper pierceable by a hypodermic injection needle). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The present invention is described further in the following non-limiting examples.

EXAMPLES

In the following examples, Examples 1-8 describe production of proteins comprising an antibody variable region, comprising two or more cysteine residues within FR1 and conjugation of compounds thereto. These experiments are used as a model to demonstrate that the inventors have produced methods for predicting positions of cysteine residues that can form disulphide bonds or provide positions for conjugation without preventing binding of the protein to an antigen. Using these methods, the inventors also identified positions within FR2 and/or a region comprising FR3 and CDR2 in which cysteine residues can be introduced. Examples 9-15 describe experiments in relation to positioning cysteine residues within FR2 and/or FR3 and conjugating compounds thereto.

Example 1

Materials and Methods

1.1 Molecular Modeling and Identification of Framework 1 as Positions to Engineer Cysteine Replacement Mutations The $V_H/V_L$ interfaces of numerous diabody sequences were modeled and residues meeting the following criteria were identified:

- Not involved in the structural integrity of the domains and the domain-domain interfaces;
- Not involved in hydrophobic interactions with other amino acids;
- Not in the CDRs;
- May be in random coils, so their backbones are not involved in secondary structure motifs; and
- Preferably, though not necessarily, surrounded on each side by random coil residues at the surface (e.g., in the middle of unstructured loops outside the CDRs).

From this subset of residues, a disulphide bond, through the replacement of two native residues with cysteines, was engineered.

1.2 Sequence Numbering

Antibody residues are numbered according to Kabat (1987 and/or 1991).

1.3 Synthesis of Antibody $V_L$ and $V_H$ Domain Encoding DNA

DNA constructs encoding diabodies comprising the V regions of a mouse mAb specific for TAG72 (SEQ ID NO: 58) and a human mAb specific for HER2 (SEQ ID NO: 60) were synthesised with the appropriate restriction sites and cloned into pUC57 by GenScript. V regions were arranged as $V_H$-$Gly_4$Ser-$V_L$ or $V_L$-$Gly_4$Ser-$V_H$.

1.4 General Cloning Procedures

All DNA manipulations were carried out according to standard protocols with reagents purchased from New England Biolabs. Diabody encoding DNA constructs were excised from pUC57 with the appropriate restriction enzymes, resolved on a 1% (w/v) agarose gel and purified from the gel using the Qiaquick gel extraction kit (Qiagen). Constructs were ligated into similarly prepared pET22b expression vectors and the ligation mixtures transformed by the electroporation method into *E. coli* XL1-Blue cells. Miniprep DNA was extracted from transformants using the Qiagen miniprep spin kit and recombinant clones identified by sequencing with T7 promoter and terminator primers using Dye Terminator Cycle Sequencing kits with AmpliTaq. The clone containing the V regions of the anti-TAG72 mAb in the $V_H$-$Gly_4$Ser-$V_L$ orientation was designated AVP04-07 (SEQ ID NO: 58). The clone containing the V regions of the anti-HER2 mAb in the $V_H$-$Gly_4Ser$-$V_L$ orientation was designated AVP07-17 (SEQ ID NO: 60). This method of cloning allowed for the insertion of a carboxy terminal 6×HIS tag. This tag was routinely used to streamline downstream purification processes and is known to be neutral in activity.

1.5 Introduction of Cysteine Residues and N-Terminal Serine by Mutagenesis

Cysteine residues were introduced at amino acid positions 8 and 11 of AVP04-07 and at amino acid positions 8 and 12 of AVP07-86 of the FR1 region of the $V_L$ domain of each by altering the nucleotide sequences which encode residues 8 and 11 or 8 and 12. As an illustration, the amino acid sequence $Pro_8Ser_9Ser_{10}Leu_{11}$ is found in the FR1 sequence of the $V_L$ region of the AVP04-07. The Proline residue at position 8 is encoded by the sequence CCG and the Leucine residue at position 11 is encoded by the sequence CTG. Mutagenesis technique was used to alter these nucleotide sequences to TGC, which encodes Cysteine.

Similar techniques were used to replace the native N-terminal residue of the protein with a Serine residue. This was done either before or after introduction of the cysteine residues.

The QuikChange® site-directed mutagenesis method (Stratagene) was used to introduce the cysteine residues and modify the N-terminus. This PCR-based method uses two complementary synthetic oligonucleotides that contain the desired mutations as primers and plasmid DNA as the template to synthesise the double-stranded mutant PCR product. DpnI digestion is then applied to remove the template plasmid to increase the mutagenesis efficiency. Briefly, a PCR is performed using a 50 μl reaction mixture containing 15 ng of template and 125 ng each of the forward and reverse mutagenic primers, according to the manufacturer's instructions.

As an example, to substitute the native N-terminal Glutamine residue with a Serine residue, AVP04-07 (SEQ ID NO: 58) was used as the template, with 5'-CC CAG CCG GCC ATG GCG AGC GTG CAG CTG CAG CAG AGC G-3' (SEQ ID NO: 66) as the forward primer and 5'-C GCT CTG CTG CAG CTG CAC GCT CGC CAT GGC CGG CTG GG-3' (SEQ ID NO: 67) (Geneworks, Adelaide, SA) as the reverse primer. The resulting construct, was used as the template to introduce Cysteine residues at positions 8 and 11 of the FR1 region of the $V_L$ chain using site directed mutagenesis. Amplification was performed using the following conditions in sequence: 95° C. for 30 sec; 18 cycles consisting of 95° C. for 30 sec, 55° C. for 30 sec and 68° C. for 13 min; a final extension of 68° C. for 7 min. The template was digested with DpnI at 37° C. for 1 hour. Transformants were obtained using the protocol supplied by Stratagene, miniprep DNA extracted and the DNA sequence confirmed as above. Similar mutagenesis approaches were utilized to generate all the diabodies exemplified here.

The anti-TAG72 diabody comprising cysteine replacement mutations in the $V_L$ FR1 and an engineered N-terminal serine residue was designated AVP04-50. The anti-HER2 diabody comprising cysteine replacement mutations in the $V_L$ FR1 and an engineered N-terminal serine residue was designated AVP07-63.

1.6 Expression of Diabodies Using Large Scale Bacterial Culture

Diabody encoding DNA were transformed into chemically competent *E. coli* BL21 cells using the standard protocol. A single transformant was inoculated into 500 ml 2×YT containing 1% D-glucose and 100 μg/ml ampicillin and incubated at 37° C. overnight, shaking at 220 rpm. 18 L of the same media was seeded with the overnight culture to a final $OD_{600}$ of 0.1 and incubated at 30° C. until the $OD_{600}$ was between about 0.6-0.8. The cultures were transferred to 12° C. and shaking continued until the induction temperature was reached. Protein expression was induced with the addition of 0.2 mM IPTG and the cultures incubated at 12° C. for 15 hours. Bacterial pellets were prepared by centrifugation at 10,000 g, harvested, weighed and stored at −20° C. overnight.

1.7 Purification of Diabodies Expressed in *E. Coli*

Bacterial pellets (of approximately 150-300 g) were lysed, protein extracted and subsequently purified. 5 mL of His-Tag affinity chromatography extraction buffer (20 mM phosphate, 500 mM NaCl, 20 mM Imidazole, 0.025% Lysozyme (w/v), 1 mM PMSF, 250 U/μL Benzonase, pH 7.4) for every gram of bacterial pellet was employed in the lysis protocol. Bacterial pellets were resuspended in lysis buffer by mechanical homogenisation then sonicated (6×30 second pulses on ice). Bacterial lysate was subsequently incubated at 37° C. for 30 minutes prior to centrifugation (10,000 g, 30 min) and filtration (0.45 μm filter membrane).

His-Tag affinity chromatography purification using the AKTA Purifier 10 (GE LifeSciences) was then used to purify diabodies from filtered bacterial lysate. Between two and four 5 mL HisTrap™ (GE LifeSciences) Crude FF columns were employed in series for purification. Lysate was passed through the nickel column via an external P960 pump. HisTrap™ columns were washed with 10 column volumes of His-Tag affinity chromatography extraction buffer (20 mM phosphate, 500 mM NaCl, 20 mM Imidazole). Purified protein was eluted in 50% His-Tag affinity chromatography elution buffer (500 mM phosphate, 500 mM NaCl, 20 mM Imidazole) and 50% His-Tag affinity chromatography extraction buffer (260 mM Imidazole final concentration). Fractions containing eluted proteins (as determined by 280 mM absorbance on AKTA Unicorn program) were collected, pooled, protein concentration determined and dialysed in the appropriate ion exchange buffer.

Proteins were dialysed in a buffer 1.0-1.5 pH units higher than the pI of the protein (for cation exchange) or 1.0-1.5 pH units lower that the pI of the protein (for anion exchange). Typically, diabodies with a pI of 7.0-8.0 are dialysed in MES buffer (50 mM MES, pH 6.0 for cation exchange), those with a pI of 8.0-9.0 are dialysed in phosphate buffer (50 mM phosphate, pH 7.0 for cation exchange) and those with a pI of 5.0-6.5 are dialysed in Tris buffer (20 mM, pH 7.5 for anion exchange). Most diabody pIs fall within the aforementioned ranges. Diabodies were dialysed into 200× volume of buffer with three identical buffer exchanges no less than 4 hours apart. Dialysis was performed using 10K cut-off dialysis tubing at 4° C.

Following dialysis, the protein sample was centrifuged at 3220×g for 10 minutes to pellet denatured insoluble material prior to ion exchange. Ion exchange was performed using the AKTA purifier 10, employing 2×5 mL HiTrap™ SP HP column run in series, passing the cleared dialysed material through the column via the P960 external pump. Following this step, the column was washed with 10 column volumes of ion-exchange buffer prior to commencement of a linear buffer gradient (salt gradient) for elution of the protein from the column. In this process, the ion exchange buffer was replaced over a linear gradient with the identical buffer with the addition of NaCl to 1M final concentration. The elution gradient was performed over 300 mL with a final concentration of 600 mM NaCl.

Fractions corresponding to the eluted diabody (as determined by the 280 nm absorbance profile on Unicorn) were pooled and quantified. The major protein species eluted from the ion exchange column is typically the dimeric form of the diabody. Following ion exchange, eluted protein material was placed in dialysis membrane (10K cut off) and concentrated to approximately 3 mg/mL at 4° C. by exposing the membrane to a polyethylene glycol product (Aquacide II, Calbiochem). Concentrated protein was subsequently dialysed once in phosphate buffered saline (PBS) (200× volume at 4° C. for 4 hrs minimum) prior to size exclusion chromatography (gel filtration). Size exclusion chromatography was performed using the Pharmacia Amersham (GE LifeSciences) Superdex® 75 26/60 prep-grade column in PBS on the AKTA Purifier 10. Eluted diabodies corresponding to a single peak in the 280 nm chromatograph were quantified and further concentrated to approximately 3 mg/mL and dialysed in PBS as outlined previously, prior to storage at −20° C. Diabodies were routinely monitored by SDS-PAGE (10% Bis-Tris) (Invitrogen, Carlsbad, Calif., USA). Protein (0.5-50 μg) was electrophoresed either in the presence or absence of 100 mM DTT at 150V for 90 min and visualised by Coomassie Brilliant Blue R-250 staining.

1.8 Assays to Determine Diabody Immunoreactivity

Binding activity to soluble antigen was established by a column shift. Soluble antigen for the AVP04-07 and AVP04-50 diabodies is TAG72, available in soluble form from bovine submaxillary mucin (BSM) (Sigma). For the AVP07-17 and AVP07-63 diabodies, the soluble antigen is recombinant HER2 ectodomain. In the column shift assay, at least two times mole excess of soluble antigen to diabody was incubated for 1 hr at ambient temperature. Binding activity was determined by comparing the resulting diabody/antigen complex peak to the free diabody peak. The elution profiles of the diabody or diabody/antigen complex was monitored either directly though absorbance at 280 nm or, in cases where the diabody was Europium labelled, elution fractions were measured in a Victor time-resolved fluorometer using the Europium mode in the Victor multilabel program wizard.

1.9 Europium Labelling to Random Surface Lysines

Diabody at approximately 3 mg/mL was labelled with Europium (DELFIA Eu-N1 ITC Chelate, Perkin Elmer) to free amino groups for dissociation-enhanced time-resolved fluorometric assays. Diabody was labelled with the Europium reagent at a ratio of 20 nmol Europium to 1 nmol protein. This was achieved by adding 100 μg of protein to 40 nmol Europium reagent in the presence of 100 mM sodium bicarbonate buffer pH 9.0-9.3, in a final volume of 48.5 μL. The reaction was performed in a Reacti Vial (Pierce) containing a small magnetic stirring flea. The reaction was performed at 4° C. overnight in the dark. Tris-buffered saline (TBS, 50 mmol/L Tris-HCl, pH 7.8) was added to the reaction after incubation (2004) to quench excess Europium reagent by means of introducing an abundance of free amino groups. The Europium reaction was purified by gel filtration using a Superdex® 200 10/300 column (GE Healthcare Life Sciences) and collecting 0.5 ml fractions that correspond to the purified diabody. The Eu concentration of the fractions was measured by making a 1:100 dilution in DELFIA enhancement solution on a LumiTrac 600 96 well plate. Fractions were measured in a Victor time-resolved fluorometer using the Europium mode in the Victor multilabel program wizard. The fluorescence profile was plotted against the gel filtration 280 nm chromatogram and fractions that correlate to the diabody elution profile (as determined by 280 nm absorbance) and a peak in fluorescence were collected and pooled. Protein was quantified and the $Eu^{3+}$ concentration in the labelled protein was calculated using the Europium standards provided with the kit according to the manufacturer's instructions, whereby the molar absorptivity of reacted Eu-N1 ITC chelate is 8000 at 280 nm (1 μmol/L reacted chelate gives an absorbance of 0.008 at 280 nm). Prior to storage, 7.5% BSA in Tris-HCl (highly pure, supplied with the DELFIA Europium labelling kit) was added to the Europium labelled diabody to a final concentration of 0.1% (w/v).

1.10 Reduction of Thiolated Diabodies

Thiolated Diabodies (a term used herein to identify diabodies comprising cysteine replacement mutations within FR1) were incubated with 3.8 mM of TCEP (Tris(2-carboxyethyl)phosphine hydrochloride) (Pierce, Rockford, Ill.) in PBS for 25 min at RT. Following reduction, TCEP was removed with a PD10 desalting column pre-equilibrated with 100 mM phosphate buffer+1 mM EDTA, 0.5 mL fractions were collected, pooling peak protein fractions.

1.11 Thiol-Specific Europium Labelling

In order to determine free thiol availability to conjugation, thiolated diabodies were reduced and labelled with $Eu^{3-}$ chelate of 1-(p-iodoacetamidobenzyl)diethylenetriamine-$N^1$-$N^1$,$N^2$,$N^3$,$N^3$-pentacetic acid (DTPA) (PerkinElmer, Turku, Finland). The iodoacetamido group reacts with free sulphydryl groups on the diabody forming stable covalent thioether bonds. Labelling was performed according to manufacturer's instructions. Briefly, protein was concentrated to 3 mg/ml in 50-100 mM sodium hydrogen carbonate buffer+4 mM EDTA, pH 8.5. Eu-DTPA was added at 30 times (Eu-DTPA: protein) molar excess to reduced AVP04-50. The reaction was completed following 3-16 hrs at 4° C. Unreacted Eu-DTPA was separated from the protein by gel filtration on a Superdex® 200 10/300 column, pre-equilibrated with Tris-buffered saline, pH 7.4. Each resulting fraction was diluted in Enhancement Solution (PerkinElmer, Turku, Finland) and assayed for Europium counts using a Victor time resolved fluorometer. Peak Europium counts corresponding with peak protein fractions were pooled and stabilised with 0.1% of highly pure BSA, and stored at 4° C., protected from light. Concentration of incorporated Eu-DTPA was determined by calculating Eu counts of the sample relative to a 100 nM Eu standard supplied with the kit.

1.12 Quantification of Free Sulphydryls

Reduced thiolated diabodies were concentrated to at least 2 mg/ml using Microcon centrifugal concentrator (Millipore, Mass.). To test reactive thiols, 25 μl of reduced protein was mixed with 250 μl of 100 mM phosphate buffer+1 mM EDTA, pH 8.0 and 5 μl of 4 mg/mL Ellman's reagent (DTNB) (Pierce, Rockford, Ill.). The reaction was allowed to proceed at ambient temperature for 15 min. Free sulphydryl concentration was quantified by molar absorptivity, assuming the molar extinction coefficient of TNB in this buffer system, at 412 nm, is 14,150 $M^{-1}$ $cm^{-1}$. Estimation of sulphydryl groups per diabody was obtained by dividing the molar concentration of sulphydryls by the molar concentration of diabody.

1.13 Thiol-Site Specific PEGylation of Diabodies

Heterobifunctional, monodispersed Maleimide-PEG2000-NH2 was purchased from JenKem Technology, USA (polydispersity Q-values<1.04). Prior to use, a small amount of PEG was reconstituted in water, and added to reduced thiolated diabody at 20-fold mole excess in 100 mM phosphate buffer+1 mM EDTA pH 7.0. The reaction was allowed to proceed for 3-16 hrs at 4° C. with constant stirring. Following incubation, the entire sample was applied to a Superdex® 200 10/300 column.

Example 2

Figure 1B:
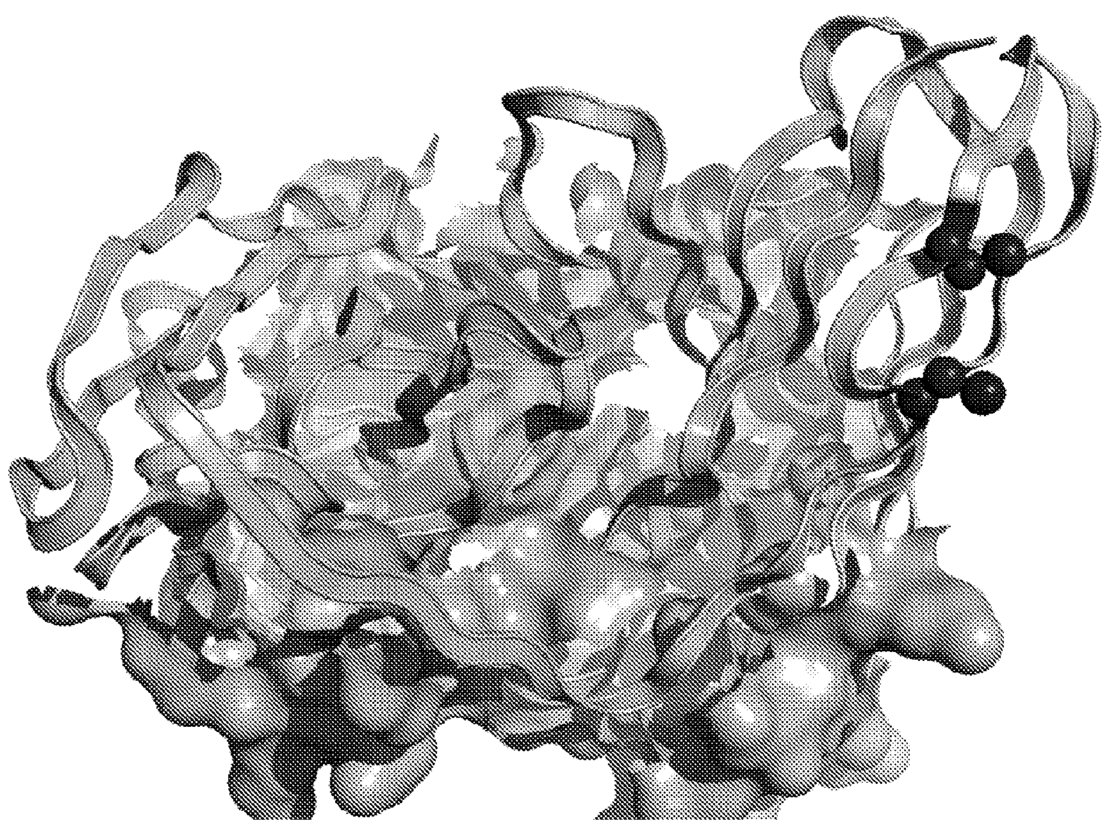
FIG. 1B is a diagrammatic representation showing the antigen binding domains (shaded) and the cysteine replacement mutations in $V_L$ framework 1 Kabat residues 8 and 11 (black space fill) of the diabody AVP04-50 are distant from each other in space.

Molecular Modelling and Identification of Framework 1 as a Suitable Position to Engineer Cysteine Replacement Mutations In silico molecular modelling of variable chains consistently revealed residues in Framework 1 (FR1) which met the criteria outlined in Example 1. In the context of the murine kappa variable light chain containing AVP04-07 (SEQ ID NO: 59), $V_L$ residues between 8 and 11 were indicated as the most structurally suitable for cysteine replacement mutations (FIG. 1A). Furthermore, in silico molecular modelling also indicated that the introduced cysteine replacement mutations in $V_L$ framework 1 were distant in three dimensional space from the known antigen binding site of the diabody (FIG. 1B).

Similar results from molecular modelling were observed when cysteine replacement mutations in residues 8 and 12 were included in silico in the human lambda variable chain containing HER2-specific AVP07-17 diabody (SEQ ID NO: 61).

Example 3

Generation of the Thiolated Diabody Genetic Constructs

Prior to introducing the in silico defined cysteine replacement mutations in the context of AVP04-07 (SEQ ID NO: 58) and AVP07-17 (SEQ ID NO: 60), the codon encoding the native N-terminal residue was replaced in each case with a codon encoding a serine residue, forming new genetic constructs. From these new genetic constructs, the cysteine replacement mutations were introduced into AVP04-07, forming the genetic construct set forth in SEQ ID NO: 154. In the case of AVP07-17, a further modification was made (SEQ ID NO: 64) prior to inserting the cysteine replacement mutations to form the construct comprising the sequence set forth in SEQ ID NO: 156. The genetic sequences of all constructs were validated as outlined in Example 1 prior to subcloning into the BL21 expression bacterial strain for downstream processing, e.g., expression and/or purification and/or analysis.

Example 4

Purification of Diabodies

All diabodies were purified following core techniques outlined in Example 1. A typical purification strategy, exemplified by the TAG72-specific AVP04-50 (SEQ ID NO: 155) diabody is reported here.

Figure 2A:
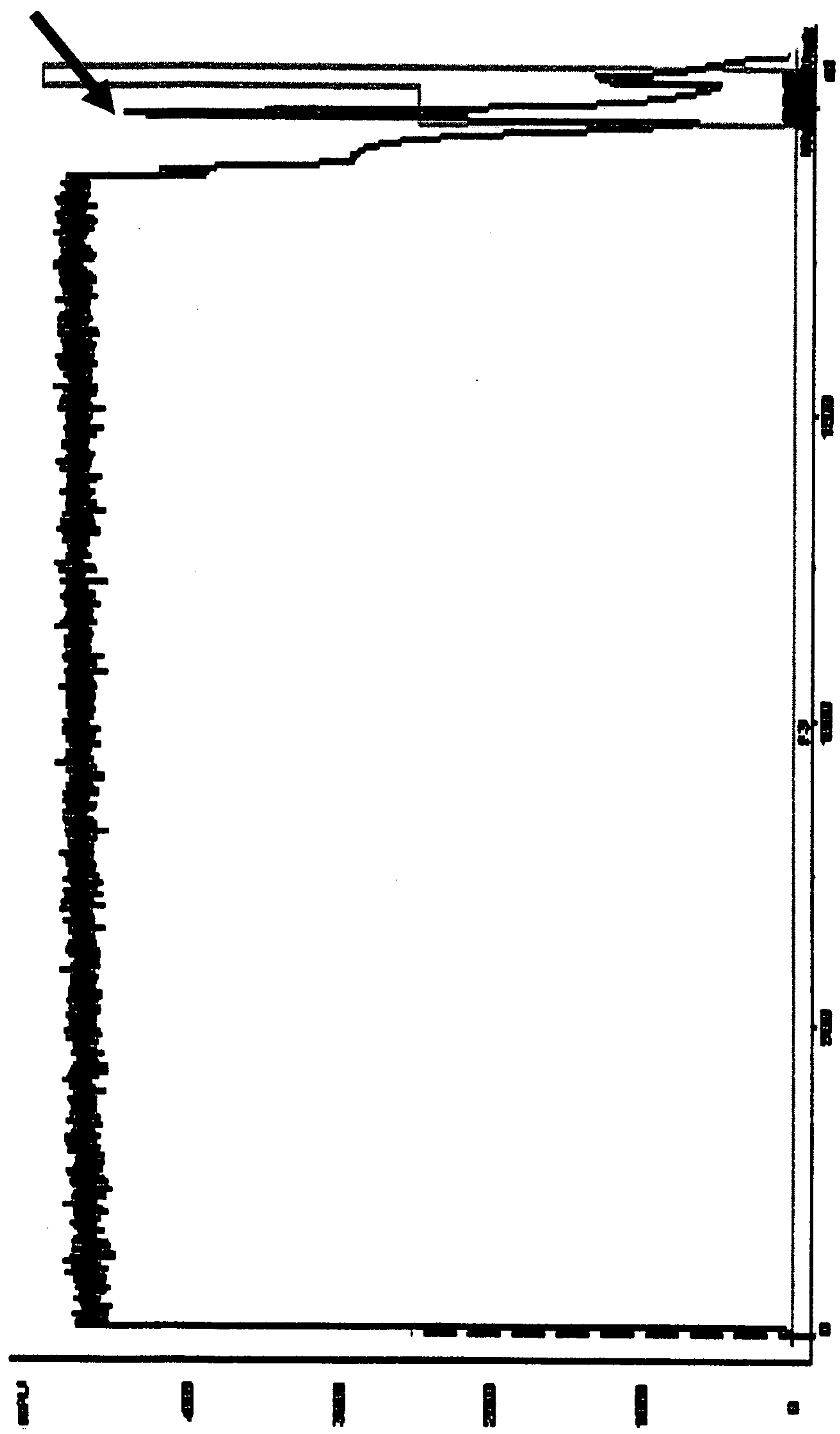
FIG. 2A is a graphical representation showing the 280 nm chromatograph of AVP04-50 His-Tag affinity chromatography purification. Arrow indicates elution peak of interest.
Figure 2B:
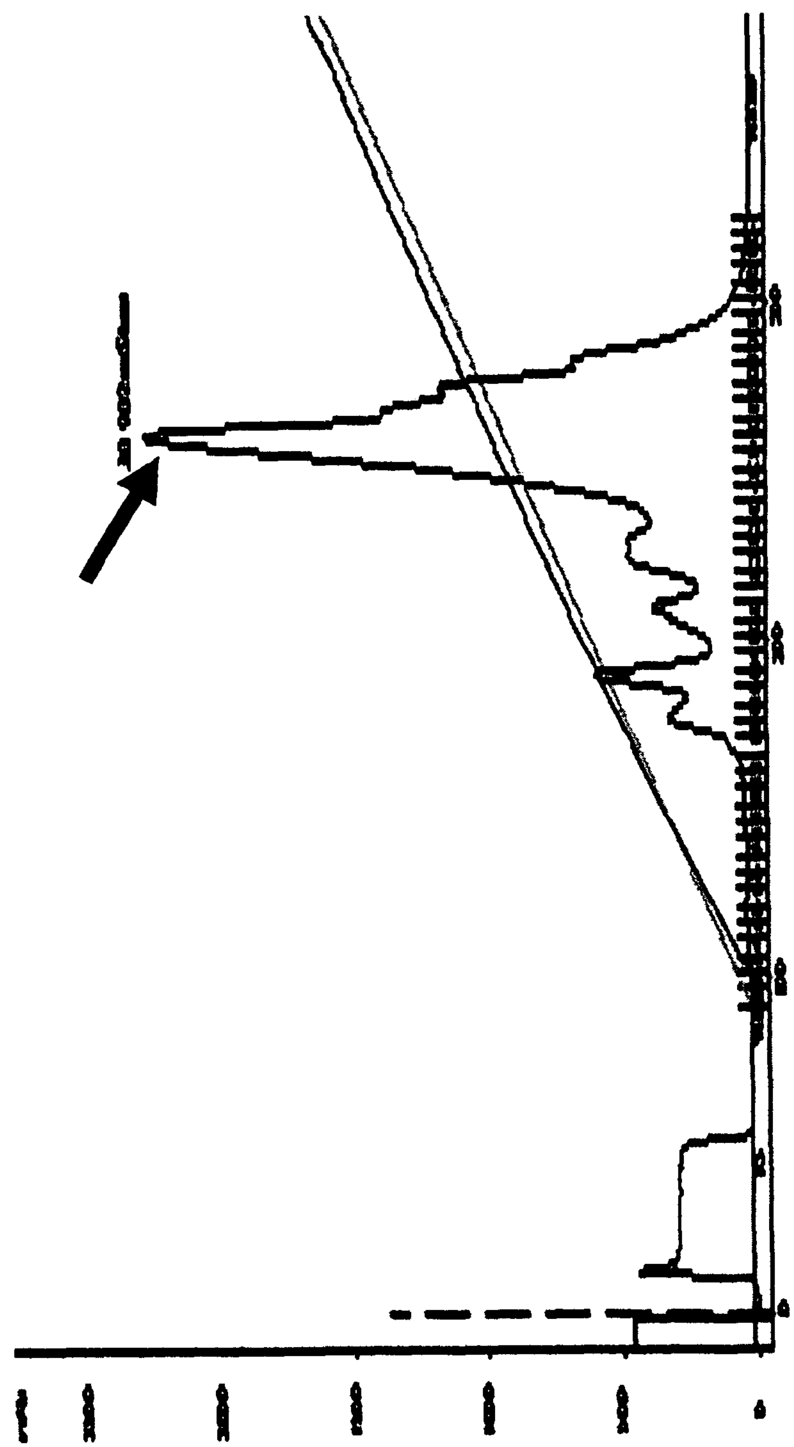
FIG. 2B is a graphical representation showing results of cation purification of AVP04-50. Arrow indicates elution peak of interest.

First step purification of AVP04-50 from bacterial pellets made use of His-Tag affinity chromatography. Processed material was eluted from multiple 5 mL HisTrap™ Crude FF columns set in series and the resulting 280 nm chromatograph elution profile is represented in FIG. 2A. The fractions eluted at 260 mM Imidazole containing the highest absorbance at 280 nm (arrow in FIG. 2A) were pooled and dialysed in 50 mM MES, pH 6.0 (3 buffer changes of 200× volume) prior to cation exchange. Cation exchange was performed on 2× HiTrap™ SP HP columns in series as outlined previously. Under a linear salt gradient ranging in conductance from 1 mS/cm to approximately 80 mS/cm, the AVP04-50 diabody routinely eluted at approximately 30 mS/cm. FIG. 2B represents a typical cationic exchange elution profile tracing absorbance at 280 nm in which the major dimeric isoform (arrow) of AVP04-50 could be easily separated from other unwanted AVP04-50 isoforms or proteins. The elution fractions containing the major isoform of interest (defined with an arrow in FIG. 2B) were pooled for downstream purification.

Figure 2C:
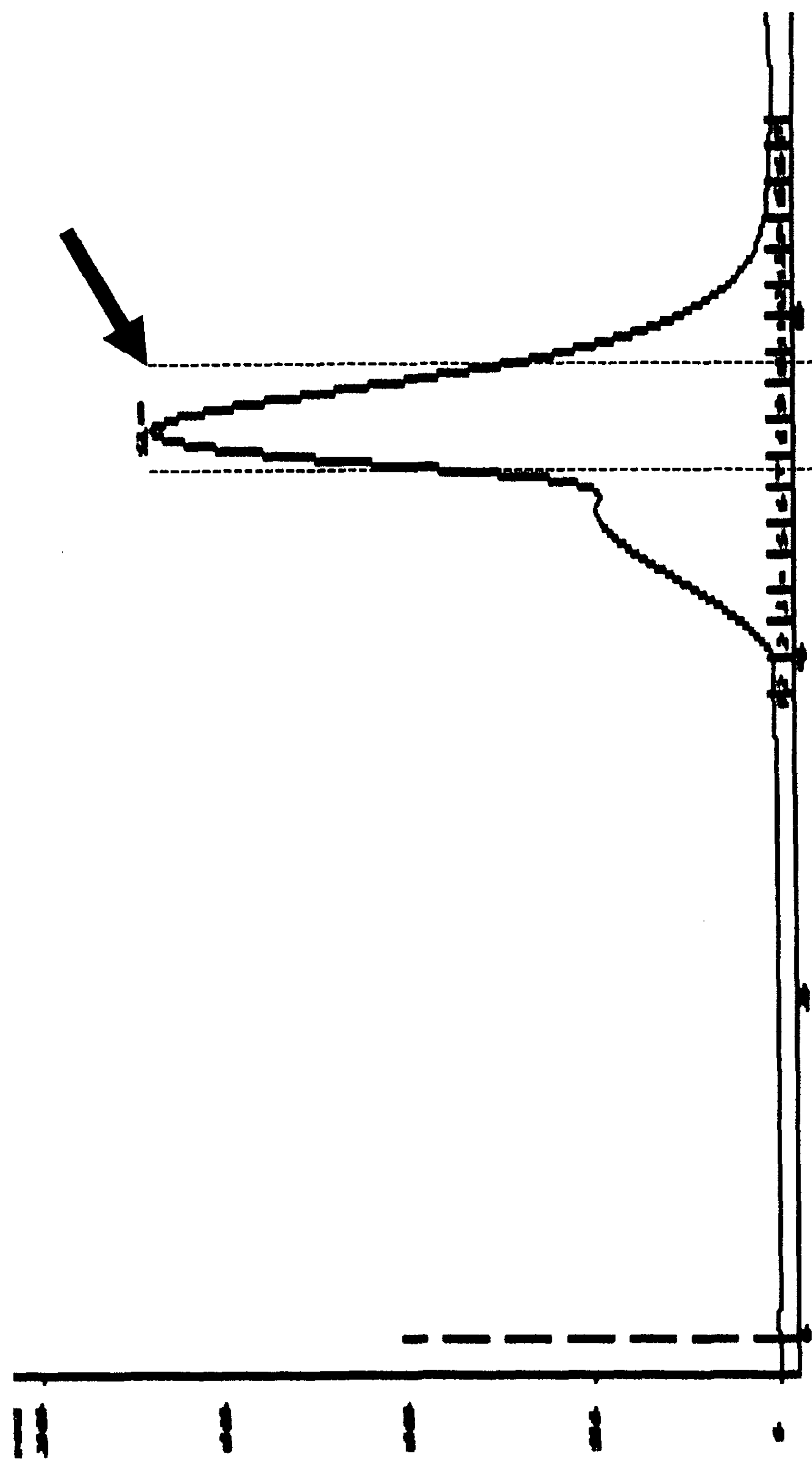
FIG. 2C is a graphical representation showing results of size exclusion chromatography of AVP04-50. Arrow indicates elution peak of interest. Dotted lines outline fractions of interest.
Figure 2D:
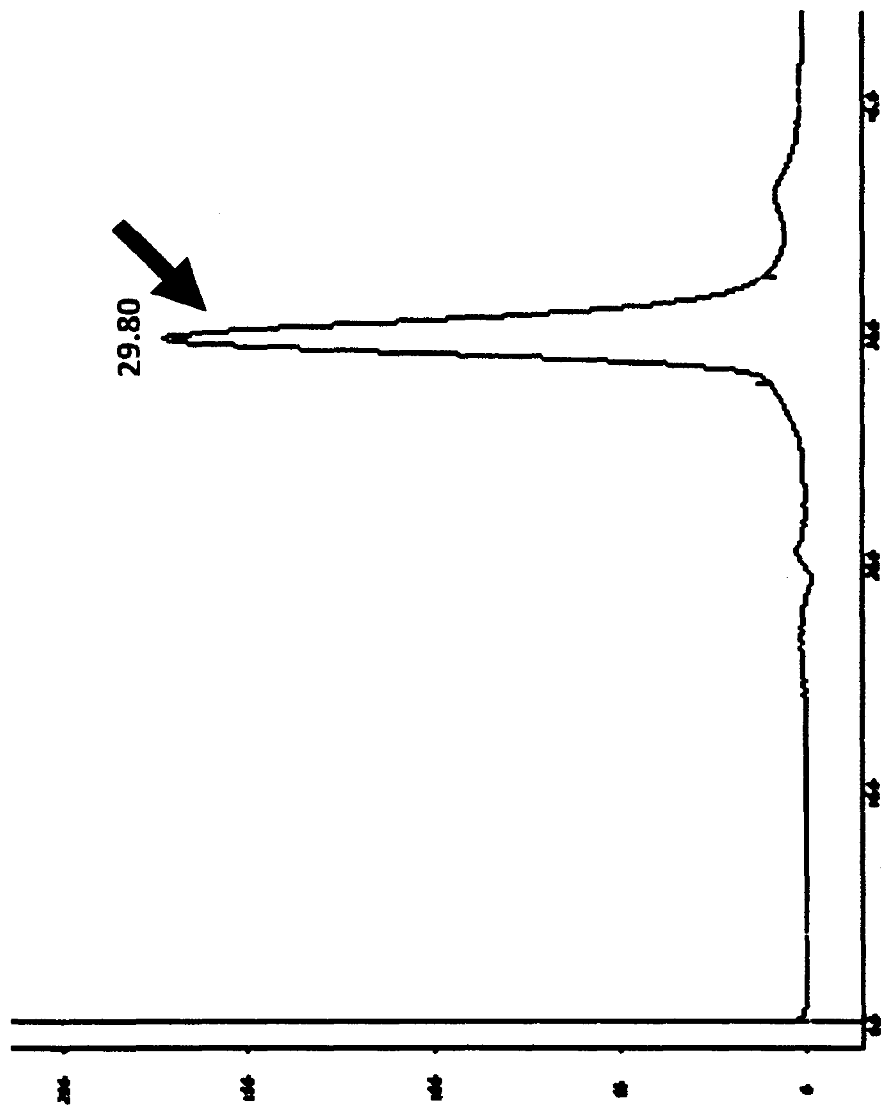
FIG. 2D is a graphical representation showing results of post purification size exclusion chromatography of AVP04-50. Arrow indicates elution peak of interest.
Figure 2E:
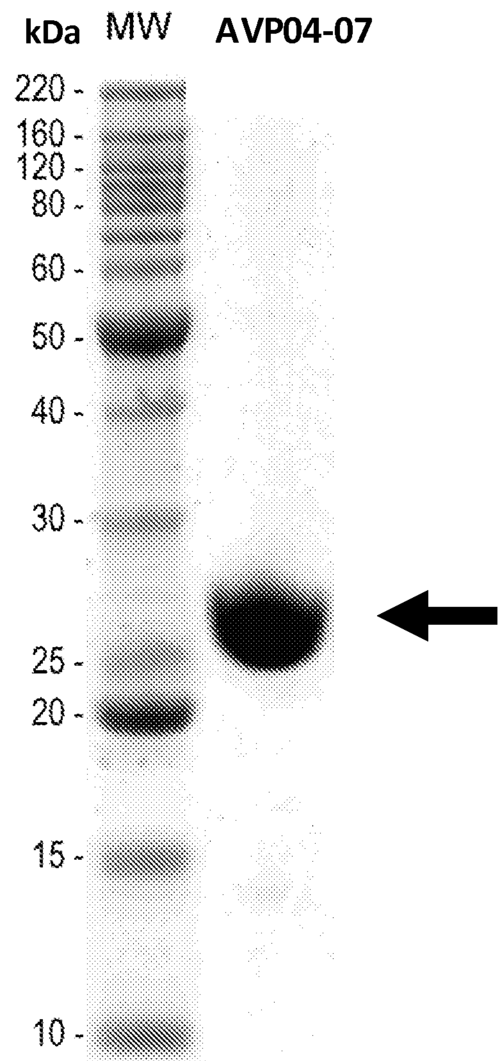
FIG. 2E is a copy of a photographic representation showing results of a reducing SDS-PAGE showing the purity of AVP04-50 post purification. MW. Marker. Arrow indicates AVP04-07 protein band.

Following cation exchange, AVP04-50 dimer was concentrated and passed through a Superdex® 75 26/60 prep-grade column. Under the elution settings outlined in Example 1, the AVP04-50 diabody eluted at approximately 53.5 minutes post injection (FIG. 2C). Fractions within the margins outlined in FIG. 2C, corresponding to the eluted AVP04-50 dimer, were pooled and concentrated to between 1.5-3 mg/ml. The final purity of the purified product was assessed by gel filtration chromatography on a Superdex® 200 10/300 column and SDS-PAGE electrophoresis. The purification regime adopted routinely returned product purities resulting in a single clean elution peak on gel filtration (FIG. 2D) and a single defined species on SDS-PAGE electrophoresis (FIG. 2E). The purification and resultant purity profiles did not differ significantly between any of the diabodies tested, including AVP04-07, AVP04-50, AVP07-17 and AVP07-63. Furthermore, no significant changes to yields were observed between any of the diabodies (AVP04-07 and AVP07-17) and their respective diabody containing an engineered N-terminal serine residue and the cysteine replacement mutations (AVP04-50 and AVP07-63).

Example 5

In Vitro Immunoreactive Assessment of Diabodies

Figure 3A:
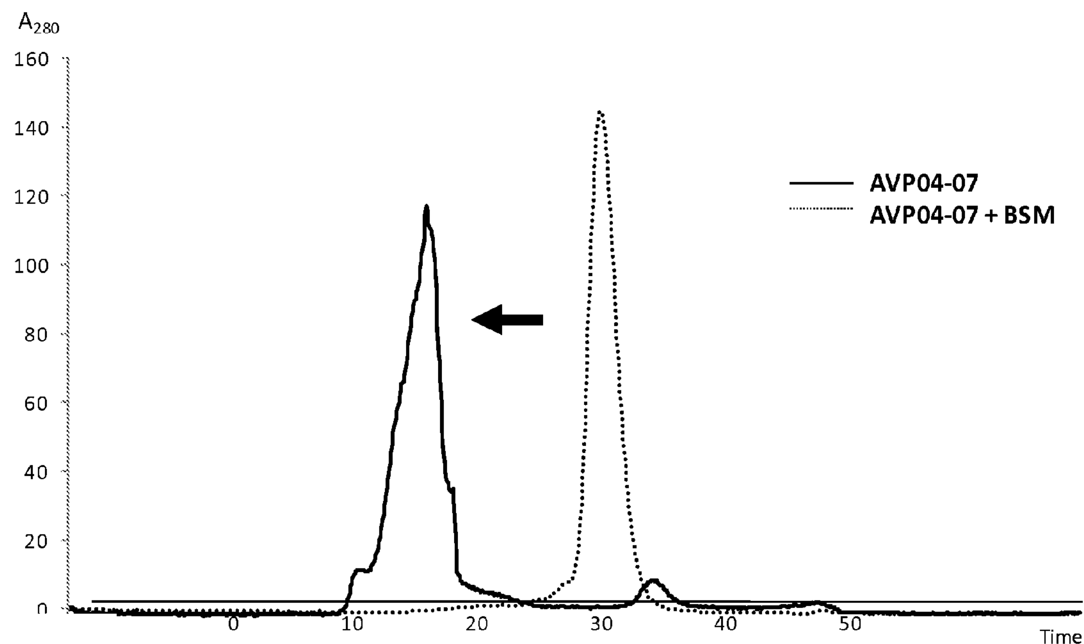
FIG. 3A is a graphical representation showing results of a column shift assay of AVP04-07 (dotted line) and AVP04-07 complexed with its antigen bovine submaxillary mucin (BSM) (containing TAG72) (Black line).
Figure 3B:
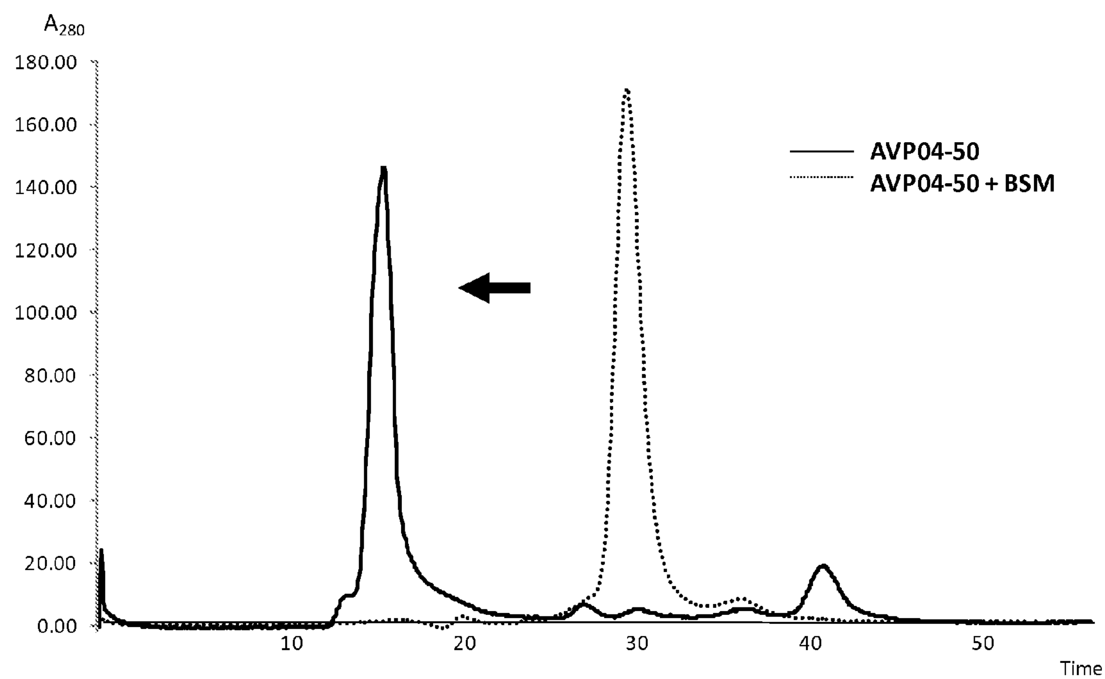
FIG. 3B is a graphical representation showing results of a column shift assay of AVP04-50 (dotted line) and AVP04-50 complexed with its antigen BSM (containing TAG72) (Black line).
Figure 3C:
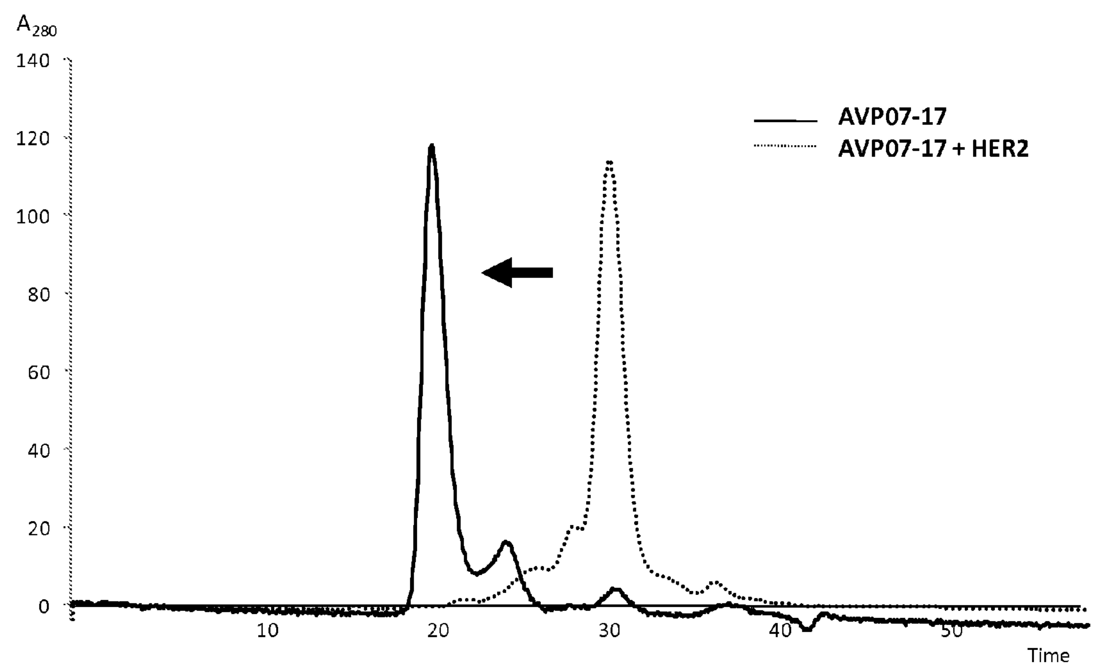
FIG. 3C is a graphical representation showing results of a column shift assay of AVP07-17 (dotted line) and AVP07-17 complexed with its antigen HER2 (Recombinant HER2 ectodomain) (Black line).
Figure 3D:
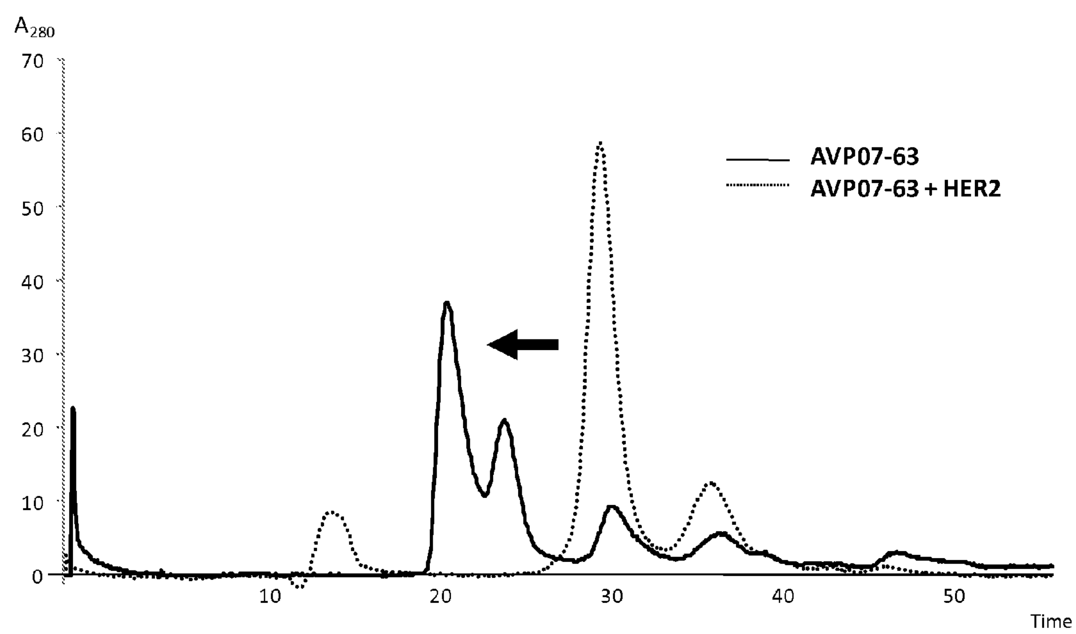
FIG. 3D is a graphical representation showing results of a column shift assay of AVP07-63 (dotted line) and AVP07-63 complexed with its antigen HER2 (Recombinant HER2 ectodomain) (Black line).

The immunoreactivity of purified diabodies (AVP04-07, AVP04-50, AVP07-17 and AVP07-63) was tested in vitro by column shift assay following core methods outlined in Example 1. When AVP04-07 and AVP04-50 were allowed to pre-complex with their antigen BSM (containing TAG72) prior to gel filtration, a significant shortening of elution times were observed when compared to diabody alone (FIGS. 3A, 3B). Similarly, AVP07-17 and AVP07-63 also showed complex formation with their antigen as evidenced by a significant shortening of elution times in gel filtration (FIGS. 3C, 3D). Complex formation was not observed when diabodies were incubated with an irrelevent antigen or when a non-correlated antigen was incubated with diabodies. These results suggest that the cysteine replacement mutations do not abrogate binding of the diabody to its antigen.

Example 6

Quantification of Free Sulphhydryls in Diabodies with Cysteine Replacement Mutations To determine whether or not the cysteine replacement mutations in $V_L$ framework 1 were available for selective reduction, thiolated diabody (AVP04-50) was reduced with TCEP and reactive thiols quantified using Ellman's reagent. Intact IgG and a diabody not containing cysteine replacement mutations in $V_L$ framework 1 (e.g., either AVP04-07) were used as standardizing controls. Under reduction conditions outlined in Example 1, native and intact IgG have 8 reactive thiols available for reduction and diabodies such as AVP04-07 have no free reactive thiols. It is important to note that under these conditions, the conserved cysteines forming a disulphide bond between invariant kabat positions 23 and 88 in variable light chains and kabat positions 22 and 92 in variable heavy chains are not reactive and are not available for conjugation.

Free sulphhydryl quantification indicated that the correct number of cysteines in intact IgG and diabody-controls not containing cysteine replacement mutations, respectively 8 and zero, were reactive (Table 2). In AVP04-50, a diabody consisting of two identical monomeric chains, each with 2 cysteine replacement mutations in $V_L$ framework 1, an average of 4 cysteines were freely accessable to reduction by TCEP, forming at least 4 free and reactive thiols (Table 2). The data shown is representative of three individual experiments.

TABLE 2

Quantification of reactive thiols on AVP04-50 by molar absorptivity.

| Diabody | Protein [mg/mL] | Protein [mol/L] | OD412 nm (cm) | [S—H] mol/L | [S—H]/[Protein] |
|---|---|---|---|---|---|
| IgG | 1.9 | 1.32E−05 | 0.16 +/− 0.01 | 1.3E−04 | 8 |
| AVP04-50 | 2.5 | 4.5E−05 | 0.28 +/− 0.01 | 2.2E−04 | 4 |
| Control Diabody | 3.24 | 5.9E−05 | 0.03 +/− 0.01 | 2.4E−04 | 0 |

Example 7

In Vitro Immunoreactive Assessment of Diabodies Post Conjugation to Reactive Thiols It was important to demonstrate that attaching small payloads to the cysteine replacement mutations in $V_L$ framework 1 did not abrogate binding activity of the diabody. To this end, the diabody was subjected to reducing conditions and then used in thiol-specific europium labelling as outlined in Example 1. Immunoreactivity was assessed post conjugation by column shift.

Figure 4:
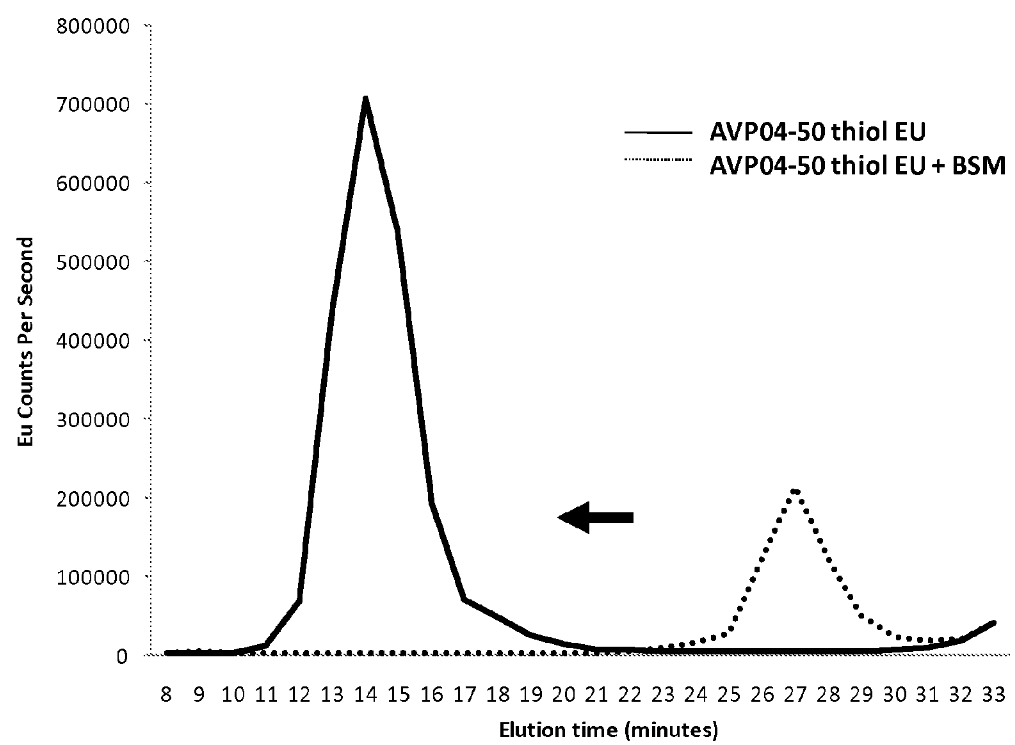
FIG. 4 is a graphical representation showing results of a column shift assay of site-specifically europium labelled AVP04-50 and AVP04-50 complexed with its antigen BSM (containing TAG72). Europium was tracked in each fraction to determine peak shifts, where Eu-AVP04-50/TAG72 complexes elute at 14 min.

The cysteine replacement mutations in $V_L$ framework 1 of AVP04-50 were labelled with a Europium loaded DTPA chelate followed by immunoreactivity assays as outlined in Example 1. Europium-AVP04-50 was shown able to form complexes with its antigen BSM (which contains TAG72), evidenced by a shortening of protein elution times in gel filtration chromatography on a Superdex® 200 10/300 column. The elution times were shortened from an approximate 27 minutes (Eu-AVP04-50) (FIG. 4) to an approximate 14 minutes (Eu-AVP04-50-TAG72 complex) (FIG. 4).

These results indicate that small payloads can be conjugated to a diabody through cysteine replacement mutations without abrogating binding activity and specificity to its antigen.

Example 8

Figure 5A:
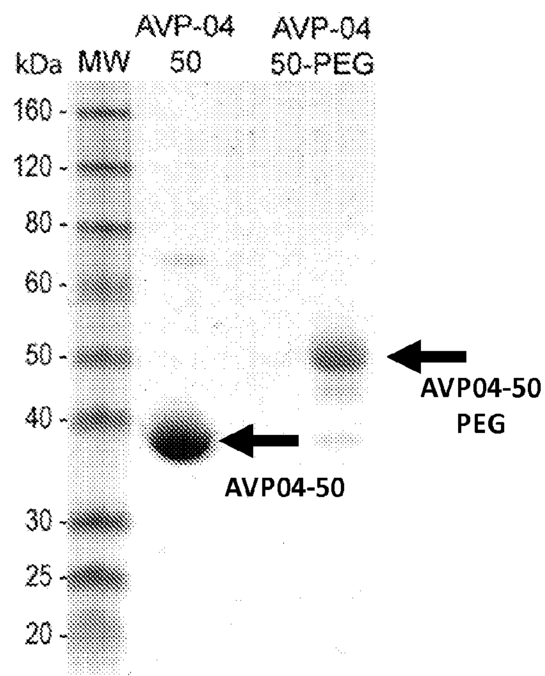
FIG. 5A is a copy of a photographic representation showing PEGylated AVP04-50 resolved using SDS-PAGE. MW. marker, 1. naked AVP04-50, 2. AVP04-50-PEG2000-NH2.
Figure 5B:
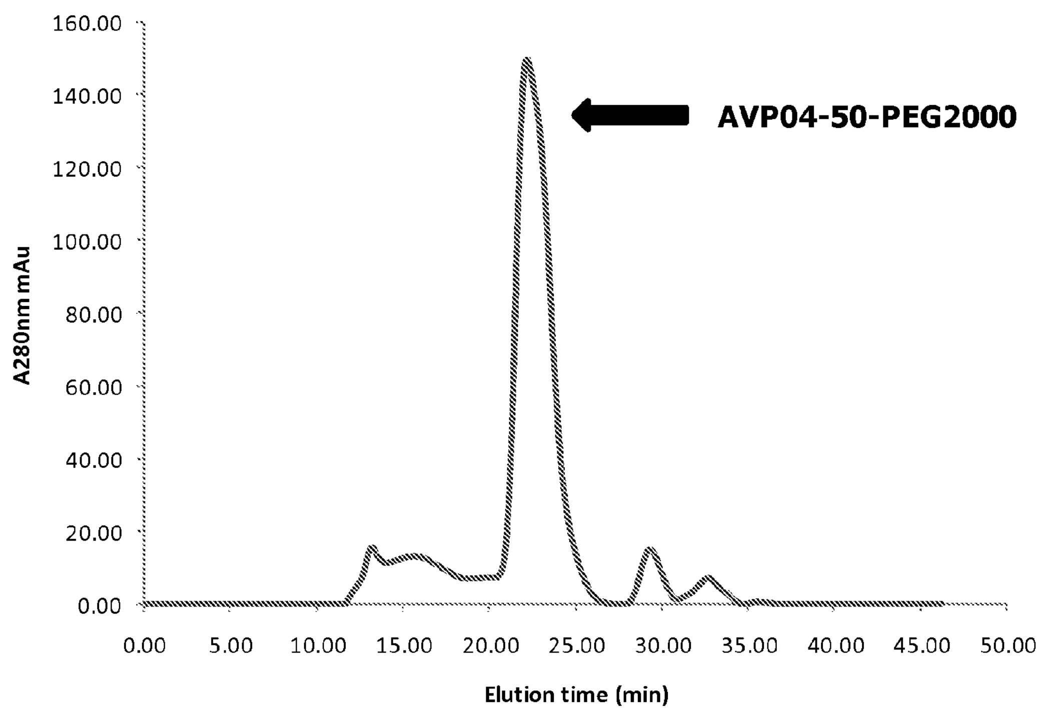
FIG. 5B is a graphical representation showing results of a gel filtration elution of AVP04-50-PEG2000 (Black line).

In Vitro Immunoreactive Assessment of Diabodies Post Conjugation of PEG to Reactive Thiols Having shown that diabodies containing cysteine replacement mutations could be expressed, purified, and shown to be immunoreactive in their native state or when the cysteine replacement mutations were selectively reduced and conjugated to a small payload, it was important to show that in vivo half-life extenders such as PEG could also be specifically conjugated to the reactive cysteine replacement mutations without abrogating immunoreactivity. To this end, a hetero-bifunctional, monodispersed PEG was site specifically conjugated to AVP04-50 (SEQ ID NO: 155) through the cysteine replacement mutations as outlined above and in Example 1. PEGylated protein (AVP04-50-PEG2000) was resolved on a non-reducing SDS-PAGE (FIG. 5A) and an average shift in molecular weight of 10 kDa was observed per AVP04-50 monomeric chain. This shift in molecular weight was also confirmed by a change in protein elution times in gel filtration chromatography on a Superdex® 200 10/300 column. Under gel filtration conditions outlined in Example 1, AVP04-50 in its native state eluted from this column at approximately 30 minutes. When PEG was site specifically conjugated to AVP04-50, elution times of the major isoform were shortened significantly to approximately 24 minutes (FIG. 5B), indicating an increase in apparent molecular weight and hence the diabody had been successfully pegylated.

Figure 5C:
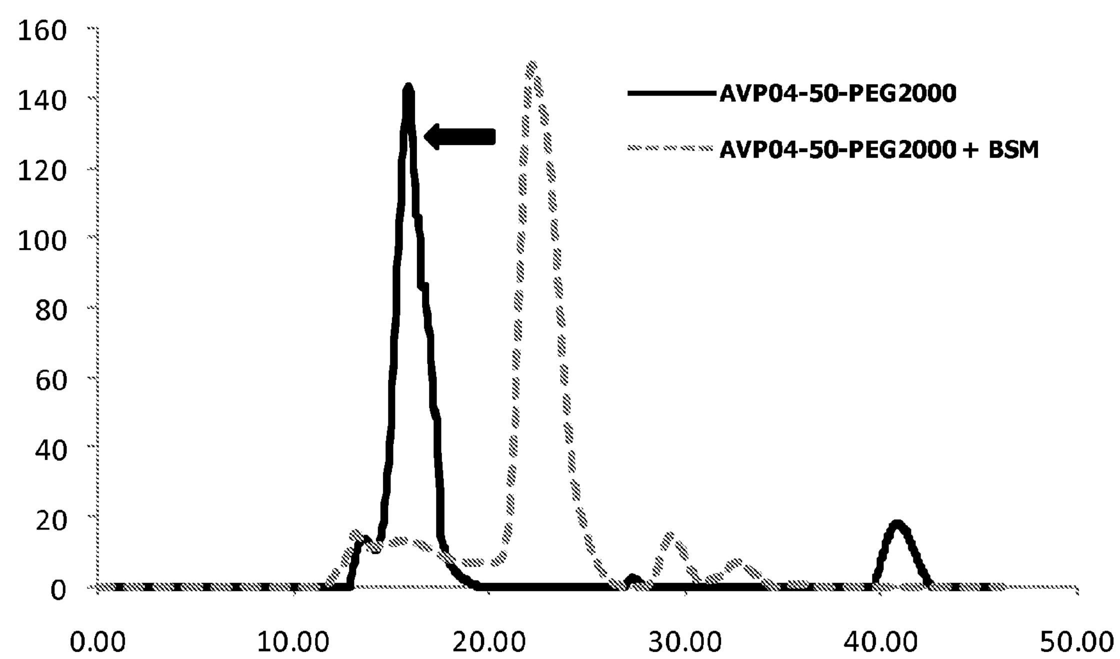
FIG. 5C is a graphical representation showing results of a column shift assay of AVP04-50-PEG2000 (dotted line) and AVP04-50-PEG2000 complexed with its antigen BSM (containing TAG72) (Black line).

To confirm that AVP04-50-PEG2000 was still able to bind antigen, a column shift binding assay was performed as outlined in Example 1. Under standard conditions, AVP04-50-PEG2000 eluted from the Superdex® 200 10/300 column at approximately 24 min (FIG. 5C dotted line). When AVP04-50-PEG2000 was allowed to complex with it's antigen BSM (containing TAG72), a shortening of elution time to 15 min was observed by tracing the absorbance at 280 nm, clearly indicating an AVP04-50-PEG2000/TAG72 complex formation (FIG. 5C).

Taken together, these data suggest that it is possible to site specifically PEGylate AVP04-50 to the cysteine replacement mutations without abrogating binding to antigen. These data also indicate that it is possible to conjugate large compounds to thiolated diabodies without abrogating binding to antigen.

Example 9

Molecular Modeling 9.1 Generation of Molecular Models for Avibodies

Avibodies are recombinant proteins comprising variable domains of antibodies. Avibodies utilize the variable domains of monoclonal antibodies by fusing them into a single polypeptide chain interspersed by a short linker region in either $V_H$-to-$V_L$ or $V_L$-to-$V_H$ orientation. Depending on the linker length, these Avibodies are designed to form stable, biologically active monobodies (scFv), diabodies, triabodies or tetrabodies containing one, two, three or four functional binding sites respectively.

The $V_H$ and $V_L$ domain sequences of the Avibodies modeled were used to search the RCSB PDB Data bank (www-.pdb.org) using both BLAST and/or FASTA searches. The structure hits with the highest sequence identity, resolution and completeness were selected for use as templates for the Fv domains of the modeled Avibodies. If the asymmetric unit in a pdb file contained more than one template model all templates were used and treated identically.

For Avibody diabodies and triabodies, quaternary templates were used to set the arrangement of the template Fvs in space and allow modeling of these Avibodies. For the diabodies 1LMK (Perisic et. al., 1994) or 1MOE (Carmichael et. al., 2003) were variously used and for the triabodies 1NQB (Pei et. al., 1997) was used to arrange the templates in quaternary space for modeling.

For quaternary arrangement, copies of the core coordinate set generated by Israel Gelfand for the Fv domain (Gelfand et. al., 1998a) were least squares aligned to the quaternary template to form a “core” homo-dimer or homo-trimer. The selected Fv templates for each Avibody were then least squares aligned to each Fv in this “core” homo-dimer or homo-trimer to form template homo-dimers or homo-trimers. These files were subsequently edited to reflect the connectivity required for modeling the various Avibodies.

In all cases, the “core” quaternary models were not used for the Fv domain modeling in the final modeling runs and the linking residues were modeled “ab initio” as loops.

Molecular models of Avibodies were generated using Discovery Studio (DS) Software (v2.5, Accelrys, Calif., USA) using the MODELLER algorithm (Sali and Blundell, 1993) embedded in the software and evaluated using the scoring functions contained in the software. The best model was selected on the basis of the presence of a high ranking score in each of the MODELLER generated Probability Density Function (PDF) for total and physical energy and the Discrete Optimized Protein Energy (DOPE) score, (Shen et. al., 2006). The selected model was written out to a pdb file for further analysis. Images of the resulting models were also generated using DS.

Further analysis of each selected model included visual inspection on a graphics workstation and calculation of the solvent accessible surface area (ASA) of mutated residues.

The ASA was used here as an assessment of the modeled disulphide mutant’s ability to be available for conjugation. For each construct 10 models were generated and the average ASA determined for each mutated residue in each modeled V domain, then a standard deviation calculated. In this analysis, a large standard deviation indicates that the surface exposure of a particular residue varies depending on the model indicating variability in the modeled disulphide and hence potentially less accessible for reduction and/or conjugation.

Further analysis of each selected model also included, for each V domain in each construct, an average RMSD (in Yasara) was calculated between the Kabat designated Framework residues in the V domains of the best native model as described above and the Kabat designated Framework residues in the V domains of all the other V domains modeled, both un-mutated and mutated. Again, for each construct a standard deviation was calculated and here indicates the structural variability between firstly; the native V domain framework regions and secondly; between the native V domain framework regions and the mutated V domain framework regions. This analysis gives an indication of the structural impact of the thiol mutations when mutant RMSD values are compared with un-mutated RMSD values for a particular construct.

9.2 Generation of a $V_H$ to $V_L$ Linked Molecular Model for the AVP04-07 Diabody The AVP04-07 Avibody (SEQ ID NO. 59) is a recombinant diabody with a theoretical pI/Mw: 8.0/51 kDa, a $V_L\kappa$ light chain and a subgroup I $V_H$ chain. AVP04-07 recognizes the tumor associated antigen TAG72. Modified versions of this Avibody are referred to herein as AVP04-xx, in which “xx” is a number designating different forms of the Avibody.

This Avibody utilizes the variable regions of the murine monoclonal antibody CC49, fusing them in sequence to form a stable, biologically active diabody containing two functional binding sites. The variable domains of CC49 have been modified (Roberge, et al, 2006) in amino acid sequence in order to achieve a high-expressing and highly stable recombinant molecule with exceptional in vitro and in vivo properties.

Searching the PDB with the $V_H$ and $V_L$ domain sequences of the AVP04-07 highlighted one antibody in the PDB, 1ZA6 (Larson et al., 2005), which had an 82% identity match with AVP04-07 in both $V_H$ and $V_L$ domains in an un-gapped alignment.

The 1ZA6 template encodes the structure of an anti-tumor CH2-domain-deleted humanized antibody. This recombinant humanized antibody also recognizes the TAG72 antigen.

Figure 7:
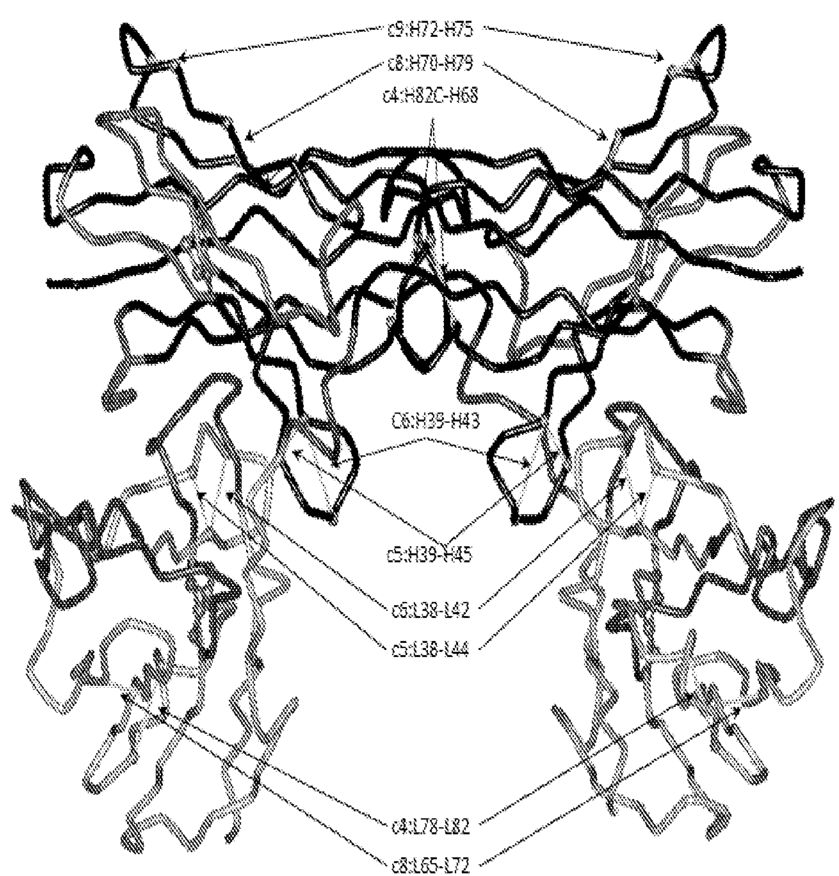
FIG. 7 is a diagrammatic representation showing the in silico homology modelled, un-mutated AVP04-07 diabody (comprising a polypeptide comprising a sequence set forth in SEQ ID NO: 59). Potential disulphide insertion residues identified for mutation are indicated with an arrow.

The Fv structure in the 1ZA6 pdb file was used to model the Fv domains of the AVP04-07 diabody. The 1LMK described above was used for the quaternary spatial alignment of the templates to form an AVP04-07 diabody in the method described above. The selected highest scoring model of the AVP04-07 diabody is shown in FIG. 7 with the positions targeted for thiol mutations (section 9.6) and represents the “un-mutated” configuration of this Avibody dimer.

9.3 Generation of a $V_H$ to $V_L$ Linked Molecular Model for the AVP07-17 Diabody The AVP07-17 Avibody (SEQ ID NO: 61) is a recombinant diabody with a theoretical pI/Mw: 6.4/55 kDa, an exceptionally long CDRH3 loop a $V_L\lambda$ light chain and a subgroup I $V_H$ chain. AVP07-17 recognizes the tumor associated antigen HER2. Modified versions of this Avibody are referred to herein as AVP07-xx, in which “xx” is a number designating different forms of the Avibody.

AVP07-17 has lower identity with the structures available in the RCSB pdb when using standard FASTA and BLAST searches compared to the AVP04-07. No Fv pair of $V_L$ and $V_H$ showed as high an identity with AVP07-17 when compared with the results obtained for AVP04-07.

Alternative methods of searching the PDB were tested to improve template selection for entire Fv domains. The MATRAS server (Kawabata 2003, Kawabata, et. al. 2000) uses a standard sequence homology search against the current PDB using the BLAST program with a graphical representation of the aligned regions to assist in template selection. This method revealed two good templates, both with greater than 64% sequence identity in both the $V_L$ and $V_H$ domains.

The selected Fv templates were contained in the pdb files of a) 2B1H (Stanfield et. al., 2006) which had 80.6% identity to AVP07-17 excluding the linker residues and CDRH3 and b) 3G04 (Sanders et. al., 2007) which had 73.5% identity to AVP07-17 excluding the linker residues and CDRH3.

The 1LMK diabody described above was used for the quaternary spatial alignment of the template Fvs to form an AVP07-17 (“un-mutated”) diabody in the method described above. The long CDRH3 loop length of AVP07-17 was also problematic for modeling as no homologous structures could be found for use as templates. These were modeled as loops with no template constraints (essentially ab initio) and assessed for structural violations after modeling. In all cases presented here, the CDR3 loops are modeled with low confidence levels and are not included in some analyses as they were not considered to affect the overall structure or framework regions of the Avibodies.

Figure 8:
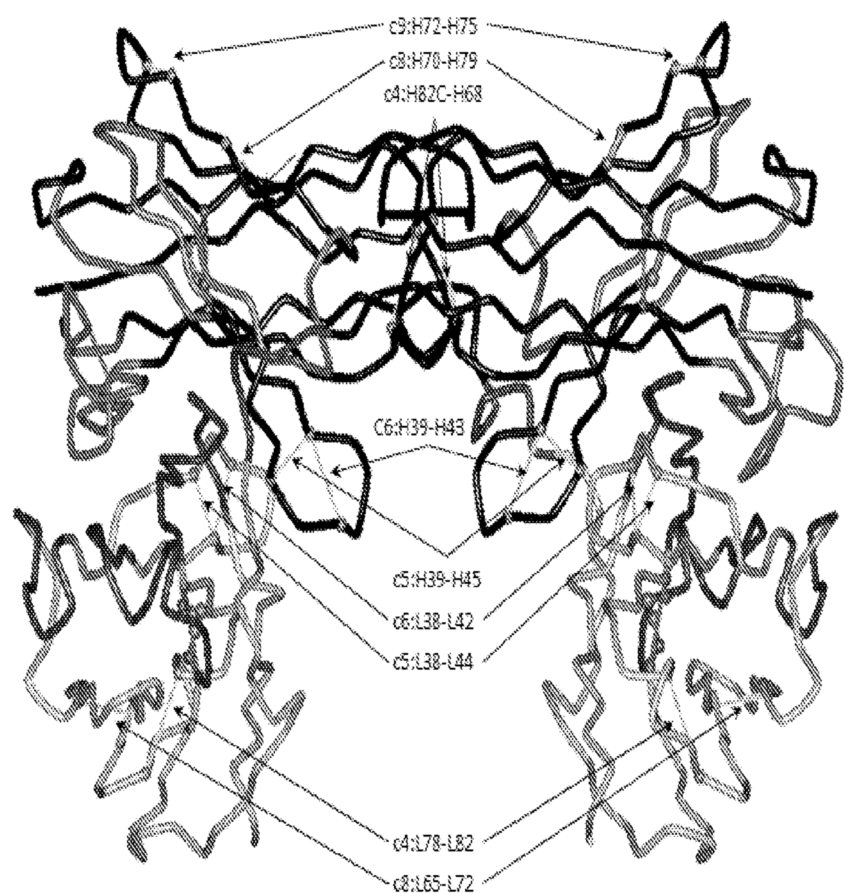
FIG. 8 is a diagrammatic representation showing the in silico homology modelled, un-mutated AVP07-17 diabody (comprising a polypeptide comprising a sequence set forth in SEQ ID NO: 61). Potential disulphide insertion residues identified for mutation are indicated with an arrow.

The selected highest scoring model of the AVP07-17 diabody is shown in FIG. 8 with the positions targeted for thiol mutations (section 9.6) and represents the "un-mutated" configuration for this Avibody dimer.

9.4 Generation of a Molecular Model for the AVP02-60 Diabody

The AVP02-60 Avibody (SEQ ID NO: 63) is a recombinant diabody with a theoretical pI/Mw: 8.47/50.1 kDa, a $V_L$ chain kappa and a subgroup III $V_H$ chain. It is based on the primary mouse monoclonal C595 antibody that recognizes a breast cancer associated mucin encoded by the MUC1 gene, CD227 (Gendler et. al., 1990). It recognizes the epitope RPAP within the protein core of the mucin, a motif repeated some 40 times in the sequence. Modified versions of this Avibody are referred to herein as AVP02-xx, in which "xx" is a number designating different forms of the Avibody.

BLAST and FASTA searching with the $V_L$ or $V_H$ revealed several templates with high identity scores that contained both the $V_L$ and $V_H$ domains. However, only one template had a $V_H$ with sufficient identity in sequence and length to model the CDRH3. Hence two templates were selected for $V_H$ and $V_L$ modeling while one extra template was selected for $V_H$ only modeling. The templates selected were: a) 1MHP $V_H$ and $V_L$ (86.9% identity, 89.6% homology; Karpusas, et. al., 2003), b) 2B2X $V_H$ and $V_L$ (85.7% identity, 88.3% homology; Clark, et. al., 2006) and c) 2ADG $V_H$: (86.8% identity, 96.5% homology; Zhou et. al., 2005) which was the only template with an un-gapped alignment for CDRH3, the $V_L$ domain of this Fv was not used in the modeling.

Overall, the templates and AVP02-60 have 88.4% and identity and 91.1% homology. The 1LMK diabody described above was used for the quaternary spatial alignment of the template Fvs to form an AVP02-60 ("un-mutated") diabody in the method described above.

Figure 9:
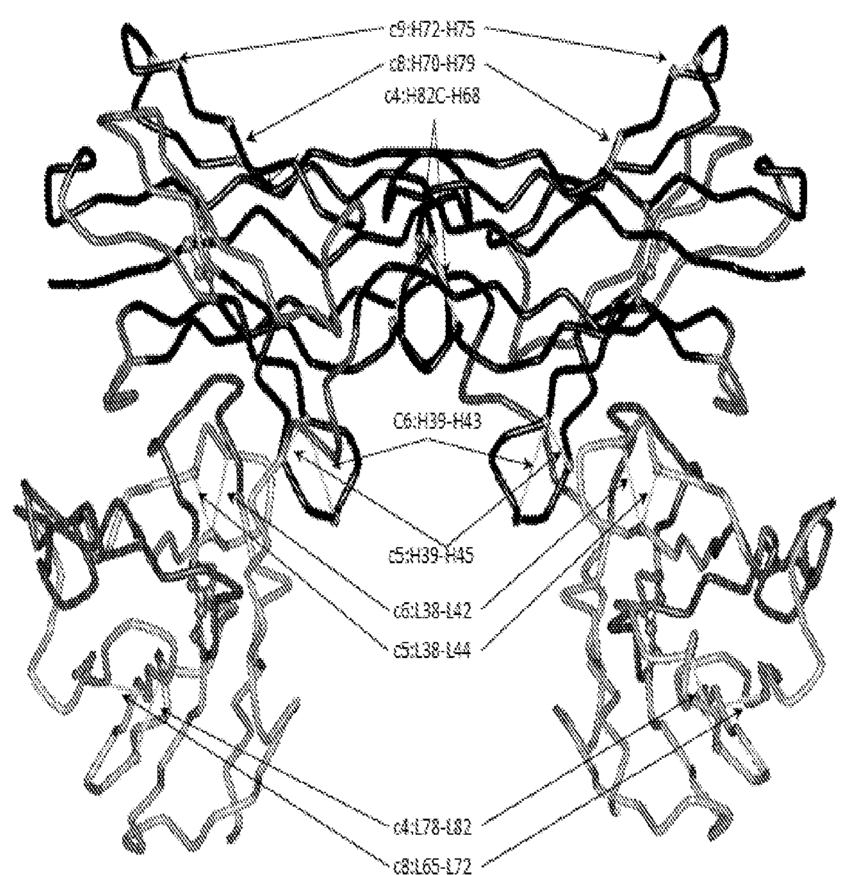
FIG. 9 is a diagrammatic representation showing the in silico homology modelled, un-mutated AVP02-60 diabody (comprising a polypeptide comprising a sequence set forth in SEQ ID NO: 63). Potential disulphide insertion residues identified for mutation are indicated with an arrow.

The selected highest scoring model of the AVP02-60 diabody is shown in FIG. 9 with the positions targeted for thiol mutations (section 9.6) and represents the "un-mutated" configuration of this Avibody dimer.

9.5 Identification of Framework 2 and 3 Disulphide Insertion Positions for Engineering Replacement Cysteine Mutations and Molecular Modeling of the Same The $V_L$ and $V_H$ domains of antibodies are firstly members of the Immunoglobulin superfamily classically containing 7-10β strands in two sheets with a typical topology and connectivity. These domains are secondly members of the V-type immunoglobulins showing symmetry of the β-sheets within the domain axis (Halaby, et. al., 1999). The antibody V-type or V-set domains are divided into $V_H$ (type 1-4), $V_L$κ and $V_L$λ domains in online databases such as SCOP (http://scop.mrc-lmb.cam.ac.uk/scop/data/scop.b.c.b.b.b.html, Murzin, et. al., 1995), InterPro (http://www.ebi.ac.uk/interpro/IEntry?ac=IPR013106, Hunter et. al., 2009) and Pfam (http://pfam.sbc.su.se/family/PF07686, Bateman, et. al., 2004).

Well defined structural similarities exist between $V_H$ (type 1-4), $V_L$κ and $V_L$λ domains. Due to these known and accepted structural similarities, it is reasonable to assume that the majority of intra-framework cysteine replacement mutations identified in any $V_L$ domain should also be transferable to the same structural position in any other $V_H$ domain. This assumption is shown to be true below, with one notable exception in the FR3 $V_H$ that could not be structurally matched with high confidence to the same position in the $V_L$ (see modeling mutation c9 below).

Preferred residues for engineered cysteine replacement were selected by visual inspection of the $V_L$ domain of the AVP04-07 diabody. Preferred residues were identified if they met specific structural requirements including having side chains generally angled towards each other, side chains atoms generally exposed to solvent and distances between Ca carbon atoms of approximately 6-7 Å. Engineered cysteine replacements meeting such criteria were considered good candidates for mutation to form intra-framework disulphide bridges replacements which could be selectively broken on controlled reduction and used to conjugate a payload. These positions in silico were then transferred by least squares alignment to the $V_H$ domain of the same Fv and this domain inspected for any further potential sites.

All identified sites in the AVP04-07 $V_L$ and $V_H$ domains could then be transferred to the AVP02-xx and AVP07-xx family Fvs by least squares alignment and modeling of the same.

Framework 2 (FR2) in the architecture of an immunoglobulin V domain is a candidate for engineering cysteine replacements. FR2 is defined by Kabat as $V_L$ residues 35 to 49 inclusive and $V_H$ residues 36 to 49 inclusive. It comprises C and C' strands of the immunoglobulin β-sheet which extends from CDR1 to a loop/turn then back to CDR2. The C strand is part of the CDC'FG sheet and has interactions with both the C' and the F strand. The C' strand is on the edge of the sheet and is partly involved in the interface between the $V_H$ and $V_L$ domains of the Fv via interaction with opposing domain buried C-terminal section of Kabat CDR3 and FR4.

Two positions were identified as candidates for engineering cysteine replacements in the $V_L$ domain. These positions were Kabat residues L38-L44 (labeled as modeling mutation c5) and L38-L42 (labeled as modeling mutation c6).

Since the structural similarity between $V_H$ and $V_L$ domains of antibodies is known and accepted, the candidates for engineering cysteine replacements in the $V_L$ could be easily mapped to the same structural position in the $V_H$ domain. The structural homologues of modeling mutation c5 and modeling mutation c6 in the $V_H$ were Kabat residues H39-H45 (modeling mutation c5) and H39-H43 (modeling mutation c6).

Framework 3 (FR3) in the architecture of an immunoglobulin V domain is also a good candidate for engineering cysteine replacements. FR3 is defined by Kabat as $V_L$ residues 57 to 88 inclusive and $V_H$ residues 66 to 94 inclusive. It comprises C'', D, E and F strands and their connecting loops/turns. Within FR3, regions between Kabat positions 63-74 of VL and between Kabat positions 68-81 VH were identified as good regions for engineering cysteine replacements. Two positions within each region were identified as good candidates for engineering cysteine replacements. These candidates were $V_H$ Kabat residues H70-L79 (labeled as modeling mutation c8) and H72-H75 (labeled as modeling mutation c9). As outlined above, due to the structural similarity between $V_H$ and $V_L$ domains of antibodies, modeling mutation c8 in FR3 region could be easily mapped to the same structural position in the $V_L$ domain at residues L65-L72. In contrast, no structural homologue for modeling mutation c9 (i.e. Kabat residues $V_H$ H72-H75) exist in the $V_L$ domain because, although this loop is highly conserved within $V_H$ domains, the $V_L$ domain loop is two residues shorter and thus modeling mutation c9 is a poor target for the introduction of disulphides into $V_L$ domains.

In assessing candidates for engineering cysteine replacements, a specific site of interest was FR3 Kabat residues H82C-H86/L78-L82 (labeled as modeling mutation c4). These residues met all the structural requirements for engineering cysteine replacements, except for relatively low solvent exposure. The modeled mutated residues displayed even lower accessible surface areas. Mutants containing modeling mutation c4 (Kabat L78-L82, AVP04-83, SEQ ID NO: 105 and Kabat H82C-H86, AVP04-114, SEQ ID NO: 111) were designed, expressed, tested and used to demonstrate that the introduction of engineering cysteine replacements did not abrogate stability and/or immunoreactivity, but subsequent controlled disulphide-bond reduction and payload conjugation relied on high accessible surface areas.

All Avibodies which contain engineered cysteine replacements are herein referred to as "Thiolated" Avibodies.

9.6 Framework 2 and Framework 3 Cysteine Insertion Positions Identified for Engineering Cysteine Replacement Mutations and Molecular Modeling in AVP04-xx Avibody Diabodies The un-mutated AVP04-07 model was the starting point for mapping the framework 2 (FR2) and framework 3 (FR3) engineered cysteine replacements described above that are capable of forming intra-framework disulphide bonds. The identified positions are indicated in FIG. 7 on the native AVP04-07 diabody model.

Exemplary positions for framework 2 engineered cysteine replacements were identified as:

- AVP04-79 Diabody nucleic acid sequence (SEQ ID NO: 100), forming the Avibody mutated in Kabat residues L38 and L42 (SEQ ID NO: 101) and also referred to herein as modeling mutation number c6.
- AVP04-80 Diabody nucleic acid sequence (SEQ ID NO: 102), forming the Avibody mutated in Kabat residues L38 and L44 (SEQ ID NO: 103) and also referred to herein as modeling mutation number c5.
- AVP04-111 Diabody nucleic acid sequence (SEQ ID NO: 106), forming the Avibody mutated in Kabat residues H39 and H43 (SEQ ID NO: 107) and also referred to herein as modeling mutation number c6.
- AVP04-112 Diabody nucleic acid sequence (SEQ ID NO: 108), forming the Avibody mutated in Kabat residues H39 and H45 (SEQ ID NO: 109) and also referred to herein as modeling mutation number c5.
- AVP04-124 scFv nucleic acid sequence (SEQ ID NO: 118), forming the Avibody mutated in Kabat residues L38 and L42 (SEQ ID NO: 119) and also referred to herein as modeling mutation number c6.
- AVP04-125 Triabody nucleic acid sequence (SEQ ID NO: 120), forming the Avibody mutated in Kabat residues L38 and L42 (SEQ ID NO: 121) and also referred to herein as modeling mutation number c6.

Exemplary positions for framework 3 engineered cysteine replacements were identified as:

- AVP04-120 Diabody nucleic acid sequence (SEQ ID NO: 112), forming the Avibody mutated in Kabat residues H70 and H79 (SEQ ID NO: 113) and also referred to herein as modeling mutation number c8.
- AVP04-123 Diabody nucleic acid sequence (SEQ ID NO: 116), forming the Avibody mutated in Kabat residues L65 and L72 (SEQ ID NO: 117) and also referred to herein as modeling mutation number c8.
- AVP04-121 Diabody nucleic acid sequence (SEQ ID NO: 114), forming the Avibody mutated in Kabat residues H72 and H75 (SEQ ID NO: 115) and also referred to herein as modeling mutation number c9.

As outlined above, the H72-H75 candidate for engineered cysteine replacement (modeling mutation c9) occurs in the loop/turn between the D and E strands. Although this loop is highly conserved within $V_H$ domains, the $V_L$ domain loop is two residues shorter and thus the same structural position in $V_L$ domains appears a poor target for engineered cysteine replacement. This is the only identified exception to the statement herein that mapping engineered cysteine replacements within the $V_L$ domain could be easily mapped to identical structural positions within the $V_H$ domain.

Figure 10A:
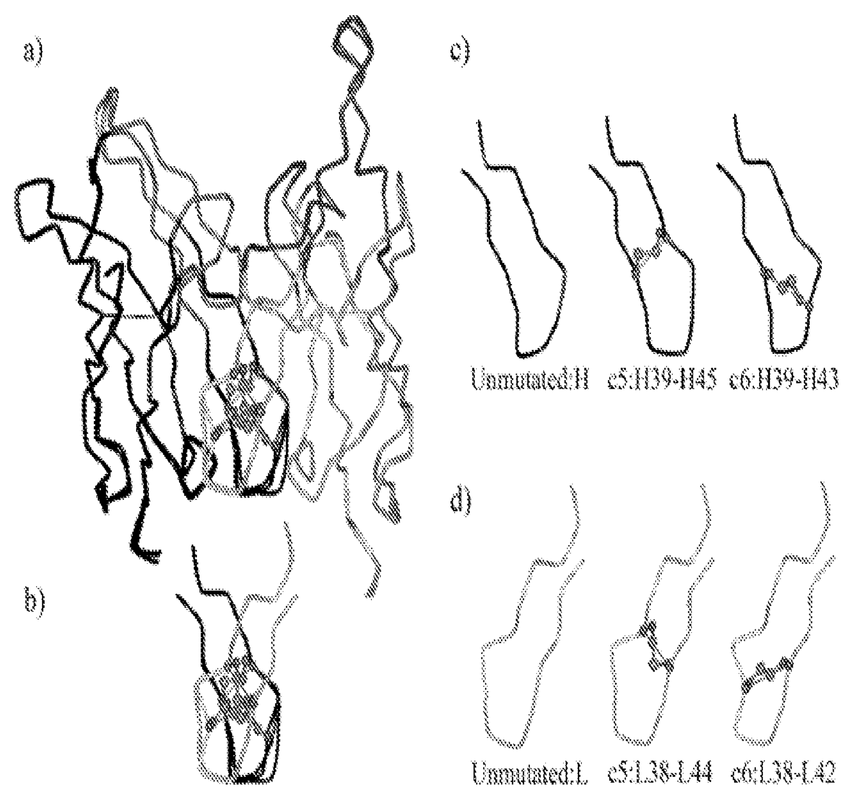
FIG. 10A is a series of diagrammatic representations showing a) an Fv from each of the AVP04-xx diabody models (AVP04-07, AVP04-xx with modelling mutation c5 and AVP04-xx with modelling mutation c6), shown least squares aligned by the framework regions. All the FR2 cysteine mutant side chains are shown as ball and stick. b) represents only the FR2 regions for the Avibodies modelled in A. c) represents the $V_H$ FR2 regions and their mutations side by side for comparison. d) represents the $V_L$ FR2 regions and their mutations side by side for comparison. c) and d) are also labelled with the Kabat residue numbers and modelling mutation numbers (c5, c6) for reference purposes.
Figure 10B:
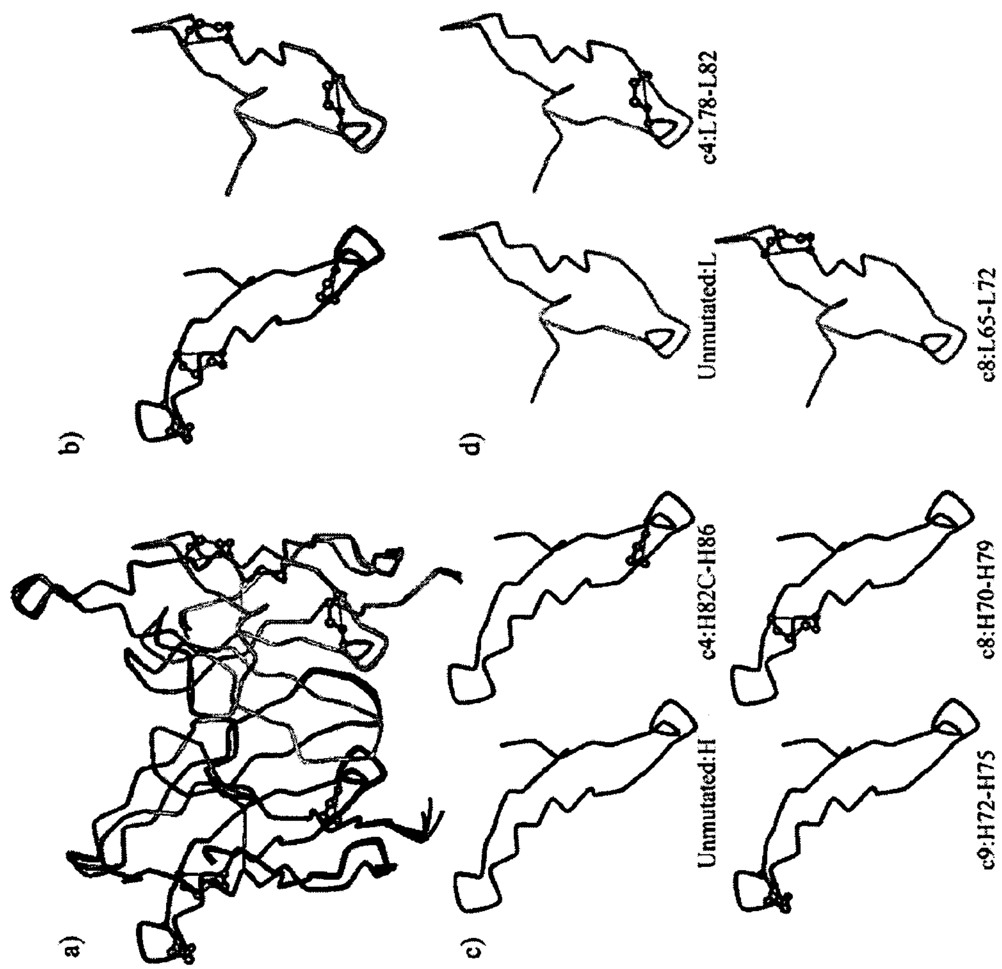
FIG. 10B is a series of diagrammatic representations showing an Fv from each of the AVP04-xx diabody models (AVP04-07, AVP04-xx with modelling mutation c4, AVP04-xx with modelling mutation c8 and AVP04-xx with modelling mutation c9), shown least squares aligned by the framework regions and cysteine mutant side chains shown as ball and stick. b) represents the FR3 regions only for the Avibodies modelled in a. c) represents the $V_H$ FR3 regions and their mutations side by side for comparison. d) represents the $V_L$ FR3 regions and their mutations side by side for comparison. c) and d) are also labelled with the Kabat residue numbers and modelling mutation numbers (c4, c8, c9) for reference purposes.

Modeling of the above mutants was repeated using the method outlined for the AVP04-07 model (Example 9.2) using the same input parameters except for the sequence input and designation of disulphide linkages which reflected the desired mutations above. Model assessment was also carried out as for the AVP04-07 models. Each candidate engineered cysteine replacement was subjected to modeling with one $V_L$ cysteine pair mutant and its analogous $V_H$ cysteine pair mutant included in each modeling run. The results of cysteine replacement modeling onto the AVP04-07 FR2/FR3 structure are shown in FIGS. 10A-B. FIG. 10A-B shows that there was little structural change in the vicinity of the engineered FR2/FR3 cysteine mutations, even when an intra-framework disulphide bond between the cysteine replacements was prescribed in silico.

Figure 11:
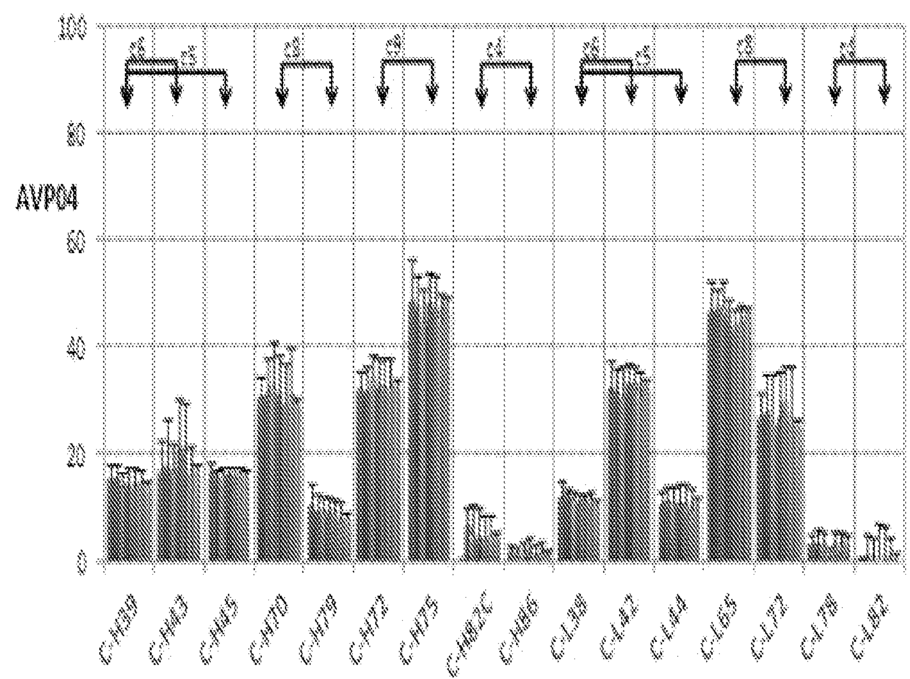
FIG. 11 is a graphical representation of the Accessible Surface Areas (ASA) values for each individual candidate cysteine replacement has been plotted in the context of models of an AVP04-xx diabody in the $V_H$-$V_L$ orientation (first column in each series), an AVP04-xx triabody in the $V_H$-$V_L$ orientation with a −1 residue linker (second column in each series), an AVP04-xx triabody in the $V_H$-$V_L$ orientation with a zero-residue linker (third column in each series), an AVP04-xx diabody in the $V_L$-$V_H$ orientation with Fv spatial orientation modeled on the 1 LMK diabody (fourth column in each series), an AVP04-xx diabody in the $V_L$-$V_H$ orientation with Fv spatial orientation modeled on the 1MOE diabody (fifth column in each series), an AVP04-xx triabody in the $V_L$-$V_H$ orientation with a 1 residue linker (sixth column in each series) and an AVP04-xx triabody in the $V_L$-$V_H$ orientation with a 2 residue linker (seventh and last column in each series). The modeling mutation designated by c6 contain the H39-H43 and L38-L42 disulphide mutations and similarly for c5 H39-H45/L38-L44, c8 H70-H79/L65-L72, c9 H72-H75 and c4 H82C-H86/L78-L82. The error bars show the standard deviation in ASA values with n=20 for the diabodies and n=30 for the triabodies.

With the aim of defining mutatable residue pairs that would be available for controlled reduction and subsequent conjugation to payloads, it was assumed that the candidate cysteine replacement pairs must be "surface exposed" and thus exposed to solvent. The solvent accessible surface area (ASA) values for candidate cysteine replacements was calculated from the models generated above (FIG. 11). In FIG. 11, the ASA values for each individual candidate cysteine replacement has been plotted in the context of models of an AVP04-xx (where -xx represents the clone no. in question) diabody in the $V_H$-$V_L$ orientation (first column in each series), an AVP04-xx triabody in the $V_H$-$V_L$ orientation with a −1 residue linker (second column in each series), an AVP04-xx triabody in the $V_H$-$V_L$ orientation with a zero-residue linker (third column in each series), an AVP04-xx diabody in the $V_L$-$V_H$ orientation with Fv spatial orientation modeled on the 1LMK diabody (fourth column in each series), an AVP04-xx diabody in the $V_L$-$V_H$ orientation with Fv spatial orientation modeled on the 1MOE diabody (fifth column in each series), an AVP04-xx triabody in the $V_L$-$V_H$ orientation with a 1 residue linker (sixth column in each series) and an AVP04-xx triabody in the $V_L$-$V_H$ orientation with a 2 residue linker (seventh and last column in each series). The modeling mutation designated by c6 contain the H39-H43 and L38-L42 disulphide mutations and similarly for c5 H39-H45/L38-L44, c8 H70-H79/L65-L72, c9 H72-H75 and c4 H82C-H86/L78-L82. The error bars show the standard deviation in ASA values with n=20 for the diabodies and n=30 for the triabodies.

In all cases, the ASA values for candidate cysteine replacement pairs was significantly higher than the ASA values of the highly conserved, yet structurally buried, cysteine pairs H22-H92 and L23-L88, which averaged an ASA value of 0.025. In fact, the ASA values of candidate cysteine replacement pairs were more similar to the ASA values of the structurally exposed CDR residues.

In order to demonstrate the preferability of structural positioning and "surface" exposure to solvent in the context of controlled disulphide bond reduction and payload conjugation, it was decided to include an extra FR3 candidate cysteine replacement insertion. This candidate was:

- AVP04-83 Diabody nucleic acid sequence (SEQ ID NO: 104), forming the Avibody mutated in Kabat residues L78 and L82 (SEQ ID NO: 105) and also referred to herein as modeling mutation number c4.

AVP04-114 Diabody nucleic acid sequence (SEQ ID NO: 110), forming the Avibody mutated in Kabat residues H82C and H86 (SEQ ID NO: 111) and also referred to herein as modeling mutation number c4.

Mutants containing modeling mutation c4 met all the structural requirements for engineering cysteine replacements, however, the mutated residues displayed very low accessible surface areas (refer to FIG. 11). Mutants containing modeling mutation c4 were used to clearly demonstrate that the introduction of engineered cysteine replacements does not abrogate stability and immunoreactivity, but it is preferable for subsequent controlled disulphide-bond reduction and payload conjugation that the residues are "surface exposure" to solvent; a characteristic lacking in the mutants of modeling mutation c4.

9.7 Framework 2 and 3 Cysteine Insertion Positions Identified for Engineering Cysteine Replacement Mutations and Molecular Modeling in AVP02-xx and AVP07-xx Avibody Diabodies Structural similarity between the $V_H$ (type 1-4), $V_L\kappa$, $V_L\lambda$ domains across the antibody families is known and accepted. Because of this structural similarity, the cysteine insertion positions identified in silico from the model of AVP04-07 were structurally transferred to the AVP02-xx and AVP07-xx cysteine insertion Avibody models by least squares alignment of the framework regions of these antibodies.

In all cases and as discussed above, the preferred positions identified as being compatible with FR2 and FR3 engineered cysteine insertions all met the key modeling constraints outlined in Example 9.5.

The preferred positions for AVP02-xx Framework 2 or Framework 3 cysteine insertions were identified as:

AVP02-115 Diabody nucleic acid sequence (SEQ ID NO: 122), forming the Avibody mutated in Kabat residues L38 and L42 (SEQ ID NO: 123) and also referred to herein as modeling mutation number c6.

AVP02-116 Diabody nucleic acid sequence (SEQ ID NO: 124), forming the Avibody mutated in Kabat residues H39 and H43 (SEQ ID NO: 125) and also referred to herein as modeling mutation number c6.

AVP02-126 Diabody nucleic acid sequence (SEQ ID NO: 130), forming the Avibody mutated in Kabat residues L38 and L44 (SEQ ID NO: 131) and also referred to herein as modeling mutation number c5.

AVP02-127 Diabody nucleic acid sequence (SEQ ID NO: 132), forming the Avibody mutated in Kabat residues H39 and H45 (SEQ ID NO: 133) and also referred to herein as modeling mutation number c5.

AVP02-128 Diabody nucleic acid sequence (SEQ ID NO: 134), forming the Avibody mutated in Kabat residues L65 and L72 (SEQ ID NO: 135) and also referred to herein as modeling mutation number c8.

AVP02-129 Diabody nucleic acid sequence (SEQ ID NO: 136), forming the Avibody mutated in Kabat residues H70 and H79 (SEQ ID NO: 137) and also referred to herein as modeling mutation number c8.

AVP02-130 Diabody nucleic acid sequence (SEQ ID NO: 138), forming the Avibody mutated in Kabat residues H72 and H75 (SEQ ID NO: 139) and also referred to herein as modeling mutation number c9.

The preferred positions for AVP07-xx framework 2 or framework 3 cysteine insertions were identified as:

AVP07-117 Diabody nucleic acid sequence (SEQ ID NO: 126), forming the Avibody mutated in Kabat residues L38 and L42 (SEQ ID NO: 127) and also referred to herein as modeling mutation number c6.

AVP07-118 Diabody nucleic acid sequence (SEQ ID NO: 128), forming the Avibody mutated in Kabat residues H39 and H43 (SEQ ID NO: 129) and also referred to herein as modeling mutation number c6.

AVP07-131 Diabody nucleic acid sequence (SEQ ID NO: 140), forming the Avibody mutated in Kabat residues L38 and L44 (SEQ ID NO: 141) and also referred to herein as modeling mutation number c5.

AVP07-132 Diabody nucleic acid sequence (SEQ ID NO: 142), forming the Avibody mutated in Kabat residues H39 and H45 (SEQ ID NO: 143) and also referred to herein as modeling mutation number c5.

AVP07-133 Diabody nucleic acid sequence (SEQ ID NO: 144), forming the Avibody mutated in Kabat residues L65 and L72 (SEQ ID NO: 145) and also referred to herein as modeling mutation number c8.

AVP07-134 Diabody nucleic acid sequence (SEQ ID NO: 146), forming the Avibody mutated in Kabat residues H70 and H79 (SEQ ID NO: 147) and also referred to herein as modeling mutation number c8.

AVP07-135 Diabody nucleic acid sequence (SEQ ID NO: 148), forming the Avibody mutated in Kabat residues H72 and H75 (SEQ ID NO: 149) and also referred to herein as modeling mutation number c9.

Figure 12A:
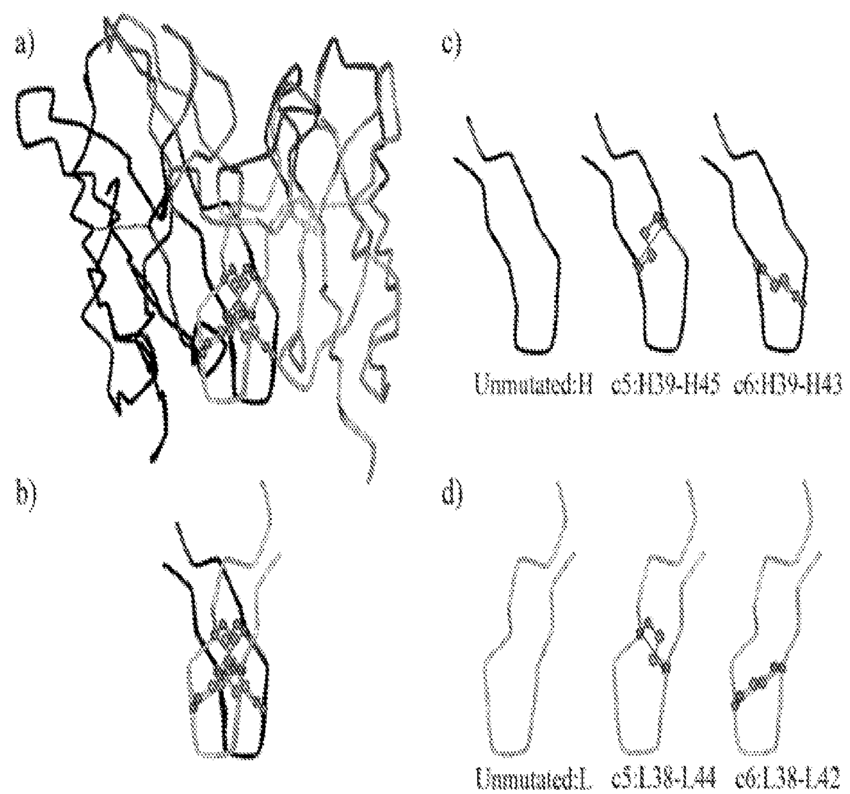
FIG. 12A is a series of diagrammatic representations showing A) an Fv from each of the AVP02-xx diabody models (AVP02-60, AVP02-xx with modeling mutation c5 and AVP02-xx with modeling mutation c6), shown least squares aligned by the framework regions. All the FR2 cysteine mutant side chains are shown as ball and stick. B) represents only the FR2 regions for the Avibodies modeled in A. C) represents the $V_H$ FR2 regions and their mutations side by side for comparison. D) represents the $V_L$ FR2 regions and their mutations side by side for comparison. C) and D) are also labeled with the Kabat residue numbers and modeling mutation numbers (c5, c6) for reference purposes.
Figure 12B:
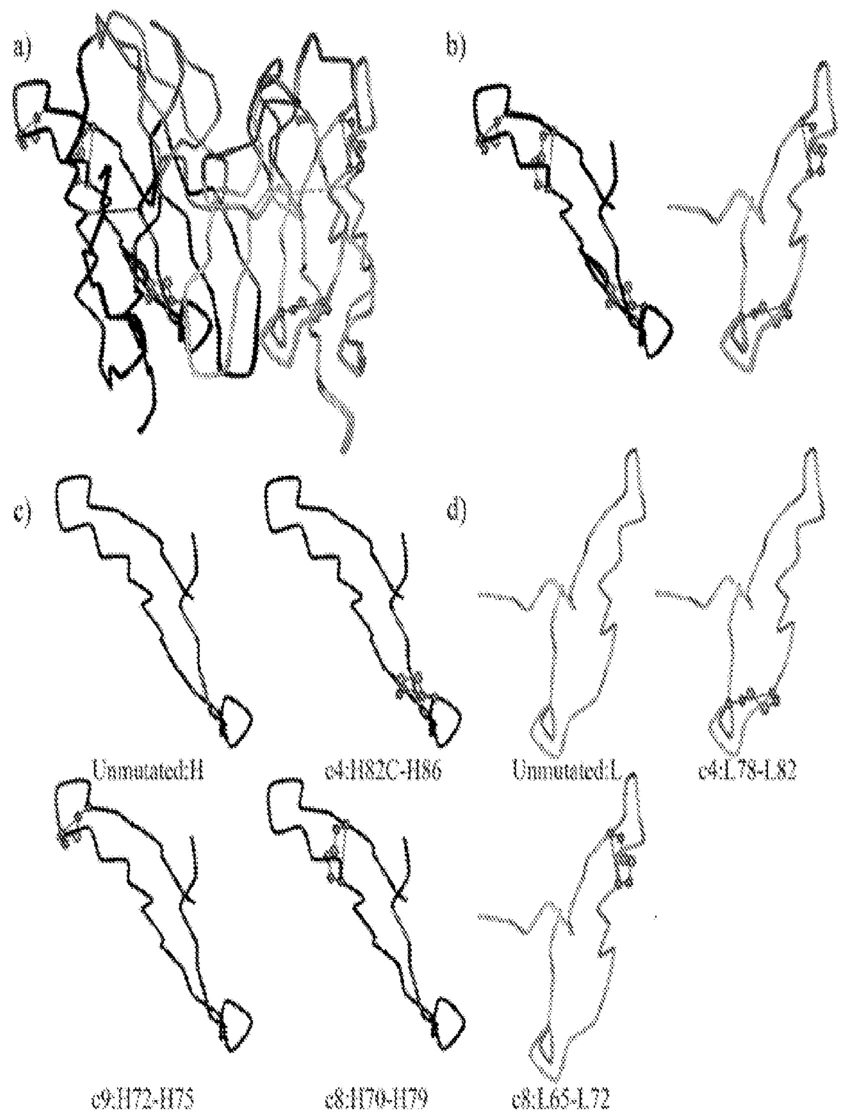
FIG. 12B is a series of diagrammatic representations showing an Fv from each of the AVP02-xx diabody models (AVP02-60, AVP02-xx with modeling mutation c4, AVP02-xx with modeling mutation c8 and AVP02-xx with modeling mutation c9), shown least squares aligned by the framework regions and cysteine mutant side chains shown as ball and stick. B) represents the FR3 regions only for the Avibodies modeled in A. C) represents the $V_H$ FR3 regions and their mutations side by side for comparison. D) represents the $V_L$ FR3 regions and their mutations side by side for comparison. C) and D) are also labeled with the Kabat residue numbers and modeling mutation numbers (c4, c8, c9) for reference purposes.
Figure 13A:
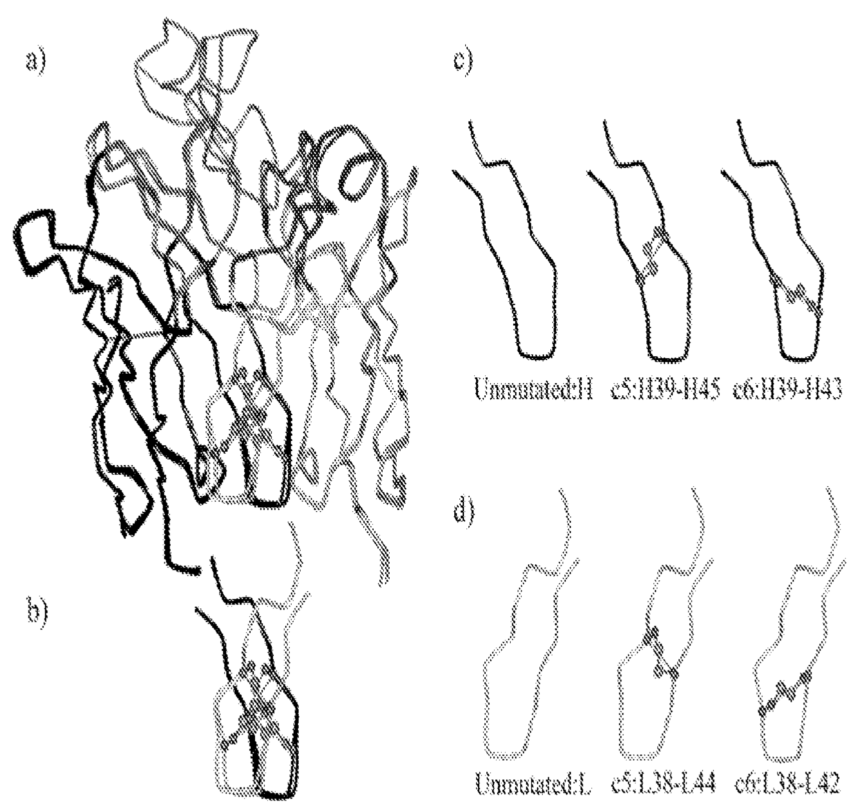
FIG. 13A is a series of diagrammatic representations showing A) an Fv from each of the AVP07-xx diabody models (AVP07-17, AVP07-xx with modeling mutation c5 and AVP07-xx with modeling mutation c6), shown least squares aligned by the framework regions. All the FR2 cysteine mutant side chains are shown as ball and stick. B) represents only the FR2 regions for the Avibodies modeled in A. C) represents the $V_H$ FR2 regions and their mutations side by side for comparison. D) represents the $V_L$ FR2 regions and their mutations side by side for comparison. C) and D) are also labeled with the Kabat residue numbers and modeling mutation numbers (c5, c6) for reference purposes.
Figure 13B:
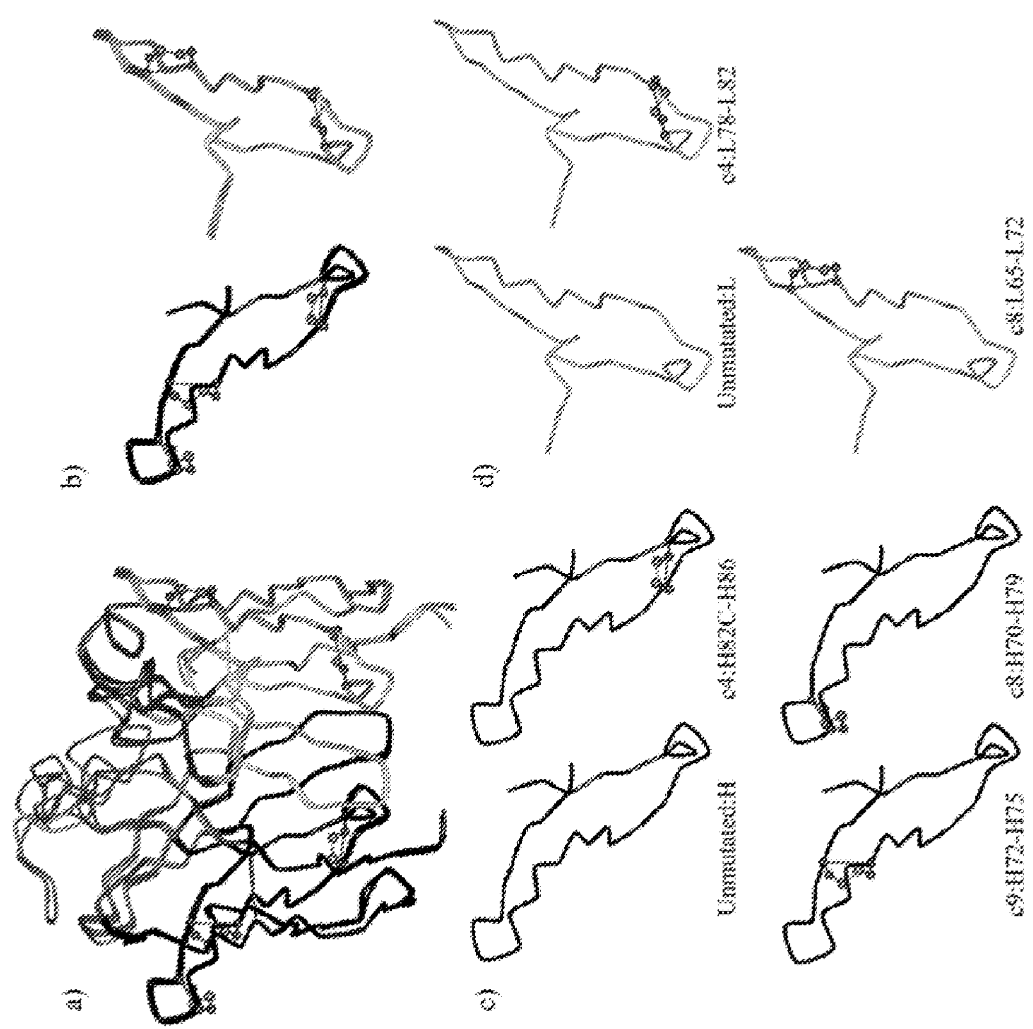
FIG. 13B is a series of diagrammatic representations showing an Fv from each of the AVP07-xx diabody models (AVP07-17, AVP07-xx with modeling mutation c4, AVP07-xx with modeling mutation c8 and AVP07-xx with modeling mutation c9), shown least squares aligned by the framework regions and cysteine mutant side chains shown as ball and stick. B) represents the FR3 regions only for the Avibodies modeled in A. C) represents the $V_H$ FR3 regions and their mutations side by side for comparison. D) represents the $V_L$ FR3 regions and their mutations side by side for comparison. C) and D) are also labeled with the Kabat residue numbers and modeling mutation numbers (c4, c8, c9) for reference purposes.

The results of the cysteine insertion modeling onto the AVP02-xx structure are shown in FIGS. 12A-B and onto the AVP07-xx structure shown FIGS. 13A-B.

Figure 14:
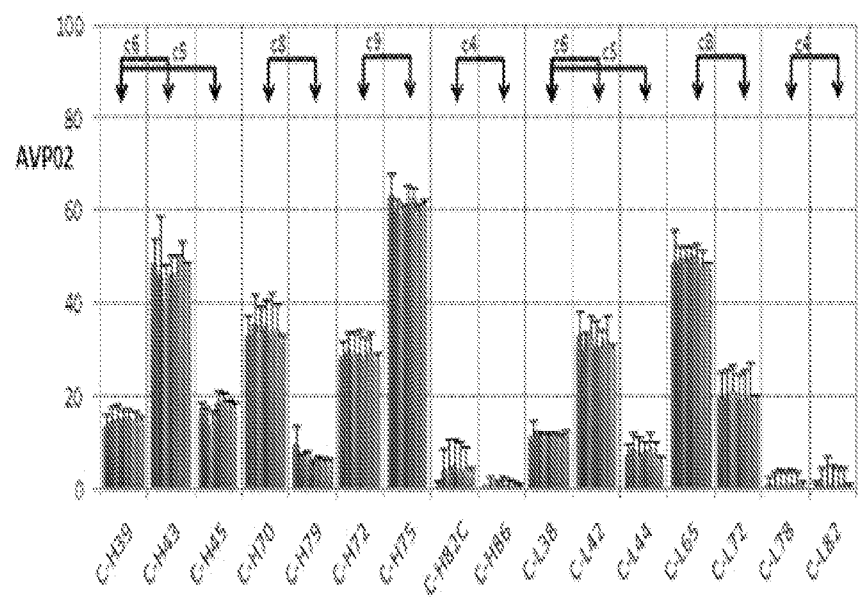
FIG. 14 is a graphical representation showing the Accessible Surface Areas (ASA) values for each individual candidate cysteine replacement has been plotted in the context of models of an AVP02-xx diabody in the $V_H$-$V_L$ orientation (first column in each series), an AVP02-xx triabody in the $V_H$-$V_L$ orientation with a −1 residue linker (second column in each series), an AVP02-xx triabody in the $V_H$-$V_L$ orientation with a zero-residue linker (third column in each series), an AVP02-xx diabody in the $V_L$-$V_H$ orientation with Fv spatial orientation modeled on the 1LMK diabody (fourth column in each series), an AVP02-xx diabody in the $V_L$-$V_H$ orientation with Fv spatial orientation modeled on the 1MOE diabody (fifth column in each series), an AVP02-xx triabody in the $V_L$-$V_H$ orientation with a 1 residue linker (sixth column in each series) and an AVP02-xx triabody in the $V_L$-$V_H$ orientation with a 2 residue linker (seventh and last column in each series). The modeling mutation designated by c6 contain the H39-H43 and L38-L42 disulphide mutations and similarly for c5 H39-H45/L38-L44, c8 H70-H79/L65-L72, c9 H72-H75 and c4 H82C-H86/L78-L82. The error bars show the standard deviation in ASA values with n=20 for the diabodies and n=30 for the triabodies.

As completed for the candidate engineered cysteine positions outlined for AVP04, the solvent accessible surface area (ASA) values for candidate cysteine replacements in AVP02-xx and AVP07-xx was calculated from the models generated above. FIG. 14 outlines the calculated ASA values for AVP02-xx models, FIG. 15 outlines the calculated ASA values for AVP07-xx model. In both FIG. 14 and FIG. 15, the ASA values for each individual candidate cysteine replacement has been plotted in the context of models of an AVP02-xx or AVP07-xx diabody in the $V_H$-$V_L$ orientation (first column in each series), an AVP02-xx or AVP07-xx triabody in the $V_H$-$V_L$ orientation with a −1 residue linker (second column in each series), an AVP02-xx or AVP07-xx triabody in the $V_H$-$V_L$ orientation with a zero-residue linker (third column in each series), an AVP02-xx or AVP07-xx diabody in the $V_L$-$V_H$ orientation with Fv spatial orientation modeled on the 1LMK diabody (fourth column in each series), an AVP02-xx or AVP07-xx diabody in the $V_L$-$V_H$ orientation with Fv spatial orientation modeled on the 1MOE diabody (fifth column in each series), an AVP02-xx or AVP07-xx triabody in the $V_L$-$V_H$ orientation with a 1 residue linker (sixth column in each series) and an AVP02-xx or AVP07-xx triabody in the $V_L$-$V_H$ orientation with a 2 residue linker (seventh and last column in each series). The model mutations designated by c6 contain the H39-H43 and L38-L42 disulphide mutations and similarly for c5 H39-H45/L38-L44, c8 H70-H79/L65-L72, c9 H72-H75 and c4H82C-H86/L78-L82. The error bars show the standard deviation in ASA values with n=20 for the diabodies and n=30 for the triabodies. As for the AVP04 models, an exception was modeling mutation c4 (H82C-H86/L78-L82) which again showed low ASA values in both the AVP02-xx and AVP07-xx.

Figure 15:
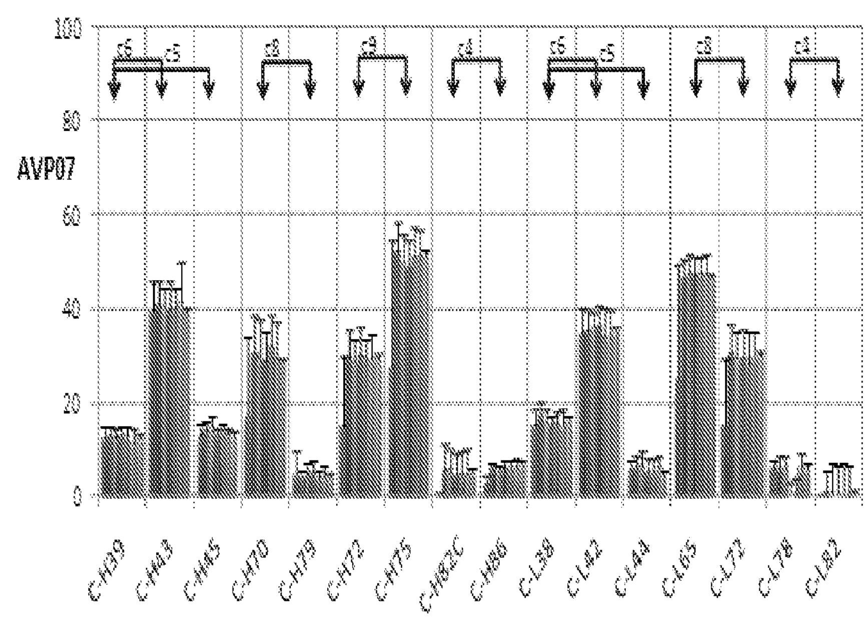
FIG. 15 is a graphical representation showing the Accessible Surface Areas (ASA) values for each individual candidate cysteine replacement has been plotted in the context of models of an AVP07-xx diabody in the $V_H$-$V_L$ orientation (first column in each series), an AVP07-xx triabody in the $V_H$-$V_L$ orientation with a −1 residue linker (second column in each series), an AVP07-xx triabody in the $V_H$-$V_L$ orientation with a zero-residue linker (third column in each series), an AVP07-xx diabody in the $V_L$-$V_H$ orientation with Fv spatial orientation modeled on the 1 LMK diabody (fourth column in each series), an AVP07-xx diabody in the $V_L$-$V_H$ orientation with Fv spatial orientation modeled on the 1MOE diabody (fifth column in each series), an AVP07-xx triabody in the $V_L$-$V_H$ orientation with a 1 residue linker (sixth column in each series) and an AVP07-xx triabody in the $V_L$-$V_H$ orientation with a 2 residue linker (seventh and last column in each series). The modeling mutation designated by c6 contain the H39-H43 and L38-L42 disulphide mutations and similarly for c5 H39-H45/L38-L44, c8 H70-H79/L65-L72, c9 H72-H75 and c4 H82C-H86/L78-L82. The error bars show the standard deviation in ASA values with n=20 for the diabodies and n=30 for the triabodies.

The similarity in ASA values of candidate engineered cysteine positions across models of AVP02-xx, AVP04-xx and AVP07-xx, as reported in FIGS. 11, 14, and 15 supports the known and accepted structural similarities in framework regions of $V_H$ types I-IV, $V_L\kappa$ and $V_L\lambda$ of antibodies of different sequences and specificities. This accepted structural similarity in turn suggests that each candidate engineered cysteine position is likely to show a similar ASA regardless of the V domain type it is present in. This further suggests candidate engineered cysteine positions can be readily transferred to the same structural positions in antibodies of different sequences and specificities. Because of this known and accepted similarities, herein we use a subset of thiolated Avibodies as a model to demonstrate generally that in vitro engineered cysteine positions will form solvent exposed disulphide bridges which can be selectively reduced and conjugated with payloads.

9.8 The Effects of Engineering Cysteine Replacement Mutations on Structural Perturbation The modeling of candidate engineered cysteine mutations onto AVP02-xx, AVP04-xx and AVP07-xx Fvs took into account a defined set of structural requirements including having side chains generally angled towards each other, side chains atoms generally exposed to solvent and distances between Ca carbon atoms of approximately 6-7 Å. An unexpected finding from generating and evaluating these models was the fact that when candidate engineered cysteine mutations were inserted into in silico models as surface exposed disulphide bridges, little or no structural perturbation with respect to wild type (non-thiolated) Avibody structure was detected.

Figure 16:
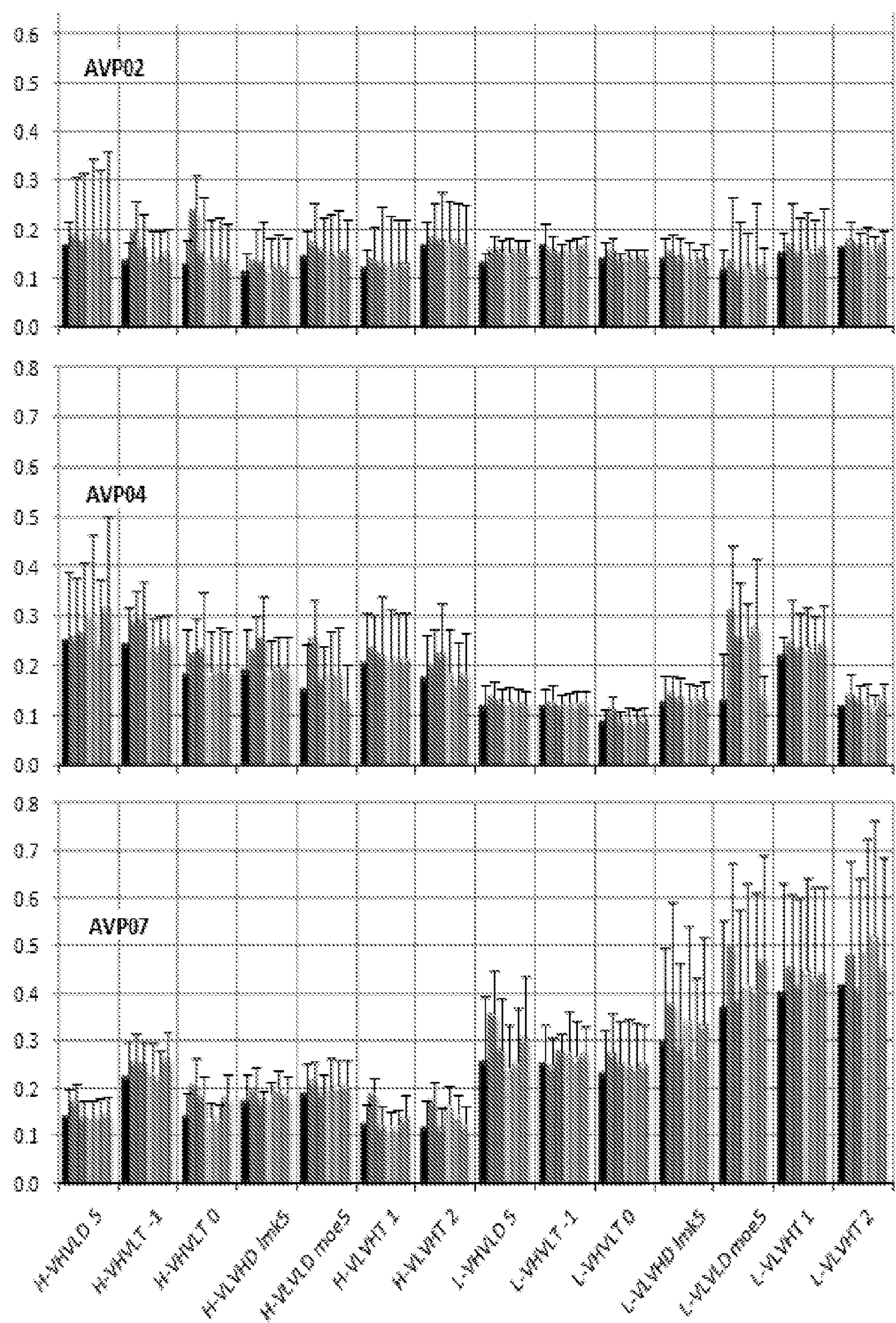
FIG. 16 is a graphical representation of the Root Mean Squared Deviations (RMSDs) for the native and cysteine mutated V domains from Avibody models, where H or L-VH- VLD 5, H or L-VHVLT-1, H or L-VHVLT 0, H or L-VLVHD lmk5, H or L-VLVHD moe5, H or L-VLVHT 1 and H or L-VLVHT 2 are the VH or VL domains from the construct group models defined described in Example 9.8. All Avibody models were compared to all other native (non-thiolated) Avibody models (first column in each construct group) and subsequently compared to all models generated of modeling mutation c6 (H39-H43/L38-L42, second bar in each construct group), modeling mutation c5 (H39-H45/L38-L44, third bar in each construct group), modeling mutation c8 (H70-H79/L65-L72, fourth bar in each construct group), modeling mutation c9 (H72-H75, fifth bar in each construct group) and modeling mutation c4 (H82C-H86/L78-L82, sixth and final bar in each construct group). The error bars show the standard deviation for the RMSD values with n=40 for the diabodies and n=90 for the triabodies.

FIG. 16 shows the Root Mean Squared Deviations (RMSDs) for the native and cysteine-mutated V domains from Avibody construct models. The RMSD values were used to gauge the perturbation of the V domain caused by the in silico insertion of engineered cysteine disulphide mutations. The RMSDs were obtained by alignment of the mutated modeled V domains against the best scoring modeled native structure for the respective construct group. FIG. 16 shows fourteen construct groups which have been labeled as:

- H-VHVLD 5: $V_H$ domains from diabodies in the $V_H$-$V_L$ orientation with a 5 residue linker containing a $V_H$ engineered cysteine replacement pair prescribed to form a disulphide-bond in silico.
- H-VHVLT −1: $V_H$ domains from triabodies in the $V_H$-$V_L$ orientation with a −1 residue linker containing a $V_H$ engineered cysteine replacement pair prescribed to form a disulphide-bond in silico.
- H-VHVLT 0: $V_H$ domains from triabodies in the $V_H$-$V_L$ orientation with a zero residue linker containing a $V_H$ engineered cysteine replacement pair prescribed to form a disulphide-bond in silico.
- H-VLVHD lmk5: $V_H$ domains from diabodies in the $V_L$-$V_H$ orientation with Fv spatial orientation modeled on the 1LMK diabody and with a 5 residue linker containing a $V_H$ engineered cysteine replacement pair prescribed to form a disulphide-bond in silico.
- H-VLVHD moe5: $V_H$ domains from diabodies in the $V_L$-$V_H$ orientation with Fv spatial orientation modeled on the 1MOE diabody and with a 5 residue linker containing a $V_H$ engineered cysteine replacement pair prescribed to form a disulphide-bond in silico.
- H-VLVHT 1: $V_H$ domains from triabodies in the $V_L$-$V_H$ orientation with a one residue linker containing a $V_H$ engineered cysteine replacement pair prescribed to form a disulphide-bond in silico.
- H-VLVHT 2: $V_H$ domains from diabodies triabodies in the $V_L$-$V_H$ orientation with a two residue linker containing a $V_H$ engineered cysteine replacement pair prescribed to form a disulphide-bond in silico.

- L-VHVLD 5: $V_L$ domains from diabodies in the $V_H$-$V_L$ orientation with a 5 residue linker containing a $V_L$ engineered cysteine replacement pair prescribed to form a disulphide-bond in silico.
- L-VHVLT −1: $V_L$ domains from triabodies in the $V_H$-$V_L$ orientation with a −1 residue linker containing a $V_L$ engineered cysteine replacement pair prescribed to form a disulphide-bond in silico.
- L-VHVLT 0: $V_L$ domains from triabodies in the $V_H$-$V_L$ orientation with a zero residue linker containing a $V_L$ engineered cysteine replacement pair prescribed to form a disulphide-bond in silico.
- L-VLVHD lmk5: $V_L$ domains from diabodies in the $V_L$-$V_H$ orientation with Fv spatial orientation modeled on the 1LMK diabody and with a 5 residue linker containing a $V_L$ engineered cysteine replacement pair prescribed to form a disulphide-bond in silico.
- L-VLVHD moe5: $V_L$ domains from diabodies in the $V_L$-$V_H$ orientation with Fv spatial orientation modeled on the 1MOE diabody and with a 5 residue linker containing a $V_L$ engineered cysteine replacement pair prescribed to form a disulphide-bond in silico.
- L-VLVHT 1: $V_L$ domains from triabodies in the $V_L$-$V_H$ orientation with a one residue linker containing a $V_L$ engineered cysteine replacement pair prescribed to form a disulphide-bond in silico.
- L-VLVHT 2: $V_L$ domains from triabodies in the $V_L$-$V_H$ orientation with a two residue linker containing a $V_L$ engineered cysteine replacement pair prescribed to form a disulphide-bond in silico.

The above construct groups were modeled in order to cover all possible Fv permutations of orientation, Fv number and spatial orientation. For each construct group, the best native (non-thiolated) Avibody model was compared to all other native (non-thiolated) Avibody models (first column in each construct group) and subsequently compared to all models generated of modeling mutation c6 (H39-H43/L38-L42, second bar in each construct group), modeling mutation c5 (H39-H45/L38-L44, third bar in each construct group), modeling mutation c8 (H70-H79/L65-L72, fourth bar in each construct group), modeling mutation c9 (H72-H75, fifth bar in each construct group) and modeling mutation c4 (H82C-H86/L78-L82, sixth and final bar in each construct group). The error bars show the standard deviation for the RMSD values with n=40 for the diabodies and n=90 for the triabodies.

In every case, little relevant structural variation was observed between native (non-thiolated) models (first column in each construct group) and any of the thiolated Avibody formats (columns 2-6 in each construct group). The unexpected low RMSD values for all construct permutations across all the antibody sequences modeled suggests that FR2 and FR3 regions in the context of any $V_H$ types I-IV, $V_L\kappa$ and $V_L\lambda$ are A) not generally perturbed by the insertion of engineered cysteine mutations for the formation of surface-exposed disulphides and B) engineered cysteine mutations within these regions can be readily transferred to the same structural positions in antibodies of different sequences, species and specificities.

Because of the generally low RMSD values for all construct permutations across all the antibody sequences modeled, herein we use a subset of all thiolated Avibodies as a model to demonstrate generally that in vitro engineered cysteine positions will form solvent exposed disulphide bridges which can be selectively reduced and conjugated with payloads.

Example 10

Synthesis of Avibody Constructs 10.1 Synthesis of "Un-Mutated" Avibodies without Engineered Intra-Framework Disulphide Insertions DNA constructs encoding the $V_H$ and $V_L$ regions of a mouse mAb specific for TAG72 (SEQ ID NO: 58), a human mAb specific for HER2 (SEQ ID NO: 60) and a murine mAb specific for MUC1 (SEQ ID NO: 62) were synthesized with the appropriate restriction sites and cloned into pUC57 by GenScript (Piscataway, N.J., USA). Although Avibodies have been isolated in either orientation of V region i.e. $V_H$-Linker-$V_L$ and $V_L$-Linker-$V_H$ (Carmichael et al., 2003), all constructs described herein were arranged as $V_H$-Linker-$V_L$.

All DNA manipulations were carried out according to standard protocols with reagents purchased from New England Biolabs (Ipswich, Mass., USA). Diabody encoding DNA constructs were excised from pUC57 with the appropriate restriction enzymes, resolved on a 1% (w/v) agarose gel and purified from the gel using the Qiaquick gel extraction kit (Qiagen). Constructs were ligated into similarly prepared pET22b expression vectors and the ligation mixtures transformed by the electroporation method into *E. coli* XL1-Blue cells. Miniprep DNA was extracted from transformants using the Qiagen miniprep spin kit and recombinant clones identified by sequencing with T7 promoter and terminator primers using Dye Terminator Cycle Sequencing kits with AmpliTaq. The clone containing the V regions of the anti-TAG72 mAb in the $V_H$-$Gly_4$Ser-$V_L$ orientation was designated AVP04-07 (SEQ ID NO: 58). The clone containing the V regions of the anti-HER2 mAb in the $V_H$-$Gly_4$Ser-$V_L$ orientation was designated AVP07-17 (SEQ ID NO: 60). The clone containing the V regions of the anti-MUC1 mAb in the $V_H$-$Gly_4$Ser-$V_L$ orientation was designated AVP02-60 (SEQ ID NO: 62). These three clones formed the base parental sequences from which all other Avibody mutants and thiolated Avibodies were derived.

This method of cloning allowed for the insertion of an amino-terminal pelB leader sequence for periplasmic expression of the target protein and either a carboxy-terminal $(His)_6$ tag or a carboxy-terminal Myc+$(His)_6$ tag. The addition of an affinity tags, such as $(His)_6$, was routinely used to streamline downstream purification processes and is known to be neutral in biological activity.

10.2 Sequence Modification of Avibody Constructs

Standard molecular biology techniques known to those skilled in the art were employed for all modifications to DNA sequences described. Where an Avibody sequence contained 'native' cysteine residues in hypervariable CDR regions, positions that were likely to be surface exposed as suggested by modeling data, these residues were mutated to alternative, non-thiol-containing amino acids by site-directed mutagenesis essentially as described above. As an example, the parental clone for the AVP07-xx family; AVP07-17, contained two such Cysteine residues; Cys104 (Kabat numbering H100) and Cys109 (H100E) within the $V_H$ CDR3 region. These residues were substituted to Alanine using standard Quikchange® site-directed mutagenesis using mutagenic primers SEQ ID NO: 90 and SEQ ID NO: 91, forming AVP07-86 (SEQ ID NO: 64). All AVP07-xx Thiolated Avibodies contain this extra modification of $V_H$ CDR3, rendering the AVP07-xx family compatible with the intra-framework 2 or intra-framework 3 engineered cysteine replacement strategy.

Thiolated Avibodies were also generated with modified linker lengths in order to generate thiolated versions of scFv or Triabodies. It is well known from published literature in the antibody field that modification of linker composition and length can affect formation of Avibody multimers (Kortt et al. 1997). Promotion of scFv formation was engineered by modifying the linker length of the diabody parent from five residues, typically GGGGS (SEQ ID NO: 57) to fifteen, GGGGSGGGGSGGGGS or twenty, GGGGSGGGGSGGGGSGGGGS using a mutagenic primer encoding the extra residues and sequencing the DNA resultant clones for the correct sequence. For example, the nucleic acid encoding the AVP04-124 Avibody (SEQ ID NO: 118), encodes an scFv.

Similarly, triabody formation was encouraged by removal of the linker residues and, in some cases, even removal of up to two residues of the preceding variable domain. For example, the nucleic acid encoding the AVP04-125 Avibody (SEQ ID NO: 120), encodes a triabody with the residues 'VTVS-DIVM' instead of the linker region. This clone was engineered from the parent AVP04-07 by deletion mutagenesis using mutagenic primers encoding the desired sequence above.

2.3 Introduction of Intra-Framework 2 or Intra-Framework 3 Engineered Cysteines and N-Terminal Serine Substitution by Site-Directed Mutagenesis Based on modeling data generated, the intra-framework 2 or intra-framework 3 engineered cysteine insertion mutations were introduced into the Avibody sequences of AVP04-xx, AVP07-xx and AVP02-xx families to form the following thiolated Avibodies:

AVP04-xx Family Template Sequences (TAG72-Specific):

- AVP04-79 Diabody nucleic acid sequence (SEQ ID NO: 100), forming the Avibody mutated in Kabat residues L38 and L42 (SEQ ID NO: 101) and also referred to herein as modeling mutation number c6.
- AVP04-80 Diabody nucleic acid sequence (SEQ ID NO: 102), forming the Avibody mutated in Kabat residues L38 and L44 (SEQ ID NO: 103) and also referred to herein as modeling mutation number c5.
- AVP04-83 Diabody nucleic acid sequence (SEQ ID NO: 104), forming the Avibody mutated in Kabat residues L78 and L82 (SEQ ID NO: 105) and also referred to herein as modeling mutation number c4.
- AVP04-111 Diabody nucleic acid sequence (SEQ ID NO: 106), forming the Avibody mutated in Kabat residues H39 and H43 (SEQ ID NO: 107) and also referred to herein as modeling mutation number c6.
- AVP04-112 Diabody nucleic acid sequence (SEQ ID NO: 108), forming the Avibody mutated in Kabat residues H39 and H45 (SEQ ID NO: 109) and also referred to herein as modeling mutation number c5.
- AVP04-114 Diabody nucleic acid sequence (SEQ ID NO: 110), forming the Avibody mutated in Kabat residues H82C and H86 (SEQ ID NO: 111) and also referred to herein as modeling mutation number c4.
- AVP04-120 Diabody nucleic acid sequence (SEQ ID NO: 112), forming the Avibody mutated in Kabat residues H70 and H79 (SEQ ID NO: 113) and also referred to herein as modeling mutation number c8.

AVP04-121 Diabody nucleic acid sequence (SEQ ID NO: 114), forming the Avibody mutated in Kabat residues H72 and H75 (SEQ ID NO: 115) and also referred to herein as modeling mutation number c9.

AVP04-123 Diabody nucleic acid sequence (SEQ ID NO: 116), forming the Avibody mutated in Kabat residues L65 and L72 (SEQ ID NO: 117) and also referred to herein as modeling mutation number c8.

AVP04-124 scFv nucleic acid sequence (SEQ ID NO: 118), forming the Avibody mutated in Kabat residues L38 and L42 (SEQ ID NO: 119) and also referred to herein as modeling mutation number c6.

AVP04-125 Triabody nucleic acid sequence (SEQ ID NO: 120), forming the Avibody mutated in Kabat residues L38 and L42 (SEQ ID NO: 121) and also referred to herein as modeling mutation number c6.

AVP02-xx Family Template Sequences (MUC1-Specific):

AVP02-115 Diabody nucleic acid sequence (SEQ ID NO: 122), forming the Avibody mutated in Kabat residues L38 and L42 (SEQ ID NO: 123) and also referred to herein as modeling mutation number c6.

AVP02-116 Diabody nucleic acid sequence (SEQ ID NO: 124), forming the Avibody mutated in Kabat residues H39 and H43 (SEQ ID NO: 125) and also referred to herein as modeling mutation number c6.

AVP02-126 Diabody nucleic acid sequence (SEQ ID NO: 130), forming the Avibody mutated in Kabat residues L38 and L44 (SEQ ID NO: 131) and also referred to herein as modeling mutation number c5.

AVP02-127 Diabody nucleic acid sequence (SEQ ID NO: 132), forming the Avibody mutated in Kabat residues H39 and H45 (SEQ ID NO: 133) and also referred to herein as modeling mutation number c5.

AVP07-xx Family Template Sequences (HER2-Specific):

AVP07-117 Diabody nucleic acid sequence (SEQ ID NO: 126), forming the Avibody mutated in Kabat residues L38 and L42 (SEQ ID NO: 127) and also referred to herein as modeling mutation number c6.

AVP07-118 Diabody nucleic acid sequence (SEQ ID NO: 128), forming the Avibody mutated in Kabat residues H39 and H43 (SEQ ID NO: 129) and also referred to herein as modeling mutation number c6.

AVP07-131 Diabody nucleic acid sequence (SEQ ID NO: 140), forming the Avibody mutated in Kabat residues L38 and L44 (SEQ ID NO: 141) and also referred to herein as modeling mutation number c5.

AVP07-132 Diabody nucleic acid sequence (SEQ ID NO: 142), forming the Avibody mutated in Kabat residues H39 and H45 (SEQ ID NO: 143) and also referred to herein as modeling mutation number c5.

These thiolated Avibodies were exemplified herein (either in silico or in vitro) to demonstrate that the preferred framework 2 or framework 3 engineered cysteine insertion mutations were a) functionally transferable between $V_L$ and $V_H$ domains and different subtypes thereof, and b) compatible with proteins (e.g., Avibodies) containing a single (scFv) or multiple (diabody/triabody) Fv domains.

In all cases, cysteine residues were introduced by altering the nucleotide sequences encoding for the specific amino acid of interest using a QuikChange® site-directed mutagenesis method (Stratagene) as per instructions. Using the AVP04-07 Avibody as an illustration, the glutamine residues at Kabat positions L38 and L42 (FR2 $V_L$ region) are both encoded by the nucleotide sequence CAG. The QuikChange® site-directed mutagenesis technique, in context of DNA primers described in SEQ ID NO: 68 and SEQ ID NO: 69, was used to alter both of these nucleotide sequence codons to TGC, which encodes Cysteine. These modifications formed the nucleic acid sequence of the thiolated Avibody AVP04-79 (SEQ ID NO: 100).

The QuikChange® site-directed mutagenesis PCR-based method uses two complementary synthetic oligonucleotides that contain the desired mutations as primers and plasmid DNA as the template to synthesise the double-stranded mutant PCR product. Using the example above, to introduce cysteine residues at Kabat positions L38 and L42 of the FR2 region of the $V_L$ chain in AVP04-07, the following sequence 5'-CAG AAA AAC TAT CTG GCG TGG TAT CAG TGC AAA CCG GGT TGC AGC CCG AAA CTG CTG ATT TAT TGG-3' (SEQ ID NO: 68) was used as the forward primer and 5'-CCA ATA AAT CAG CAG TTT CGG GCT GCA ACC CGG TTT GCA CTG ATA CCA CGC CAG ATA GTT TTT CTG-3' (SEQ ID NO: 69) was used as the reverse primer. Amplification was performed using the following conditions in sequence: 95° C. for 30 sec; 18 cycles consisting of 95° C. for 30 sec, 55° C. for 30 sec and 68° C. for 13 min; a final extension of 68° C. for 7 min. The template was digested with DpnI at 37° C. for 1 hour. Transformants were obtained following the manufacturer's instructions and identified by DNA sequencing as described above.

All other examples of thiolated Avibodies containing intra-framework 2 or intra-framework 3 cysteines residues were generated using the same technique in context of the nucleotide primers outlined in SEQ ID NO: 70-85, 92-99.

Similar mutagenesis approaches were utilized to replace the native N-terminal residue of the protein with a Serine residue. N-terminal Serine substitution was carried out either before or after introduction of the intra-framework disulphide mutations.

Example 11

Expression and Purification of "Un-Mutated" and Thiolated Avibodies Using Bacterial Expression The DNA of individual Avibody constructs was transformed into chemically competent *E. coli* BL21 cells using the manufacturer's standard protocol (Stratagene). The *E. coli* BL21 expression strain served as the major expression strain for all Avibodies exemplified. Expression was by means of two interchangeable approaches depending on expected yield requirements; either bacterial shake-flask expression or bacterial fed-batch fermentation. Quality assessment on Avibody protein from either method indicated that the two methods were interchangeable and protein quality and properties were comparable.

11.1 Bacterial Shake-Flask Expression

A single transformant colony was inoculated into 500 ml 2×YT containing 1% D-glucose and 100 μg/ml ampicillin and incubated at 37° C. overnight, shaking at 220 rpm. 9 L of the same media was seeded with the overnight culture to a final $OD_{600}$ of 0.1 and incubated at 30° C. until the $OD_{600}$ was between about 0.6-0.8. The cultures were transferred to 12° C. and shaking continued until the induction temperature was reached. Protein expression was induced with the addition of 0.2 mM IPTG and the cultures incubated at 12° C. for 15 hours. Bacterial pellets were prepared by centrifugation at 10,000×g, harvested, weighed and stored at −20° C.

Bacterial pellets containing expressed protein from this expression system averaged approximately 6 g/L of culture media.

11.2 Bacterial Fed-Batch Fermentation

Seed cultures were grown in 2 L baffled Erlenmeyer flasks containing 500 mL of a complex medium and incubated at 37° C. shaking at 200 rpm for 16 h; the complex medium contained (per L): Tryptone, 16 g; Yeast Extract, 5 g; NaCl, 5 g; ampicillin, 200 mg. Defined medium was used for protein expression and contained (per L): $KH_2PO_4$, 10.64 g; $(NH_4)_2HPO_4$, 4.0 g; and citric acid monohydrate, 1.7 g; glucose 25 g; $MgSO_4.7H_2O$, 1.25 g; PTM4 trace salts, 5 mL; ampicillin, 200 mg; thiamine-HCl, 4.4 mg. PTM4 trace salts contained (per L): $CuSO_4.5H_2O$, 2.0 g; NaI, 0.08 g; $MnSO_4.H_2O$, 3.0 g; $NaMoO_4.2H_2O$, 0.2 g; $H_3BO_3$, 0.02 g; $CoCl_2.6H_2O$, 0.5 g; $ZnCl_2$, 7.0 g; $FeSO_4.7H_2O$, 22.0 g; $CaSO_4.2H_2O$, 0.5 g; $H_2SO_4$, 1 mL. All media and additives were sterilized by autoclaving at 121° C. for 30 minutes except PTM4 trace salts, thiamine hydrochloride and ampicillin which were filter sterilized.

Protein expression was completed in 2 L glass Biostat B bioreactors (Sartorius Stedim Biotech, Germany) containing 1.6 L of defined medium. The dissolved oxygen concentration was maintained at 20% by automatically varying the agitation rate between 500 and 1,200 rpm and the aeration rate (air supplemented with 5% oxygen) between 0.3 and 1.5 L $min^{-1}$. Oxygen supplementation of the air flow was manually increased as required. The pH of the culture was controlled at 7.0 via automatic addition of 10% (v/v) $H_3PO_4$ or 10% (v/v) $NH_3$ solution and foam was controlled by the automatic addition of antifoaming agent [10% (v/v) polypropylene 2025)]. Unless specified otherwise, the vessel temperature was maintained at 37° C. Bioreactors were inoculated with seed culture to attain a starting optical density (measured at 600 nm) of 0.25.

After complete utilization of the glucose added to the medium, nutrient solution (feed) containing (per L): glucose, 600 g; and $MgSO_4.7H_2O$ 22.4 g, was pumped into the bioreactor at a flow rate of 40 mL $h^{-1}$. Two hours after initiation of the feed the vessel temperature was slowly reduced to 20° C. over a 2.5 hour period (6.8° C. $h^{-1}$) after which protein expression was induced by the addition of 0.2 mM IPTG and the feed rate was decreased to 6 mL $h^{-1}$. Cultures were harvested 12 hours after induction and typically optical densities (measured at 600 nm) reached 110 and approximately 330 g of wet cell paste was recovered from each 2 L culture.

11.3 Purification of Avibodies Expressed in *E. coli*

Irrespective of the expression approach that was implemented, all Avibody proteins were purified essentially as outlined below.

Bacterial pellets harvested from expression culture (approximately 50-400 g depending on expression method) were lysed, protein extracted and subsequently purified by standard chromatographic techniques. 5 mL of His-Tag affinity chromatography lysis buffer (20 mM phosphate, 500 mM NaCl, 20 mM Imidazole, 0.25 mg/ml Lysozyme, 1 mM PMSF, 50 ug/ml DNAseI, pH 7.4) for every gram of bacterial pellet was used to resuspend the cell pellet prior to lysis by mechanical homogenisation then either sonicated (6×30 second pulses on ice) or by three passages through an Emulsiflex-05 cell disruptor (AVESTIN Inc., Canada). The bacterial lysate was subsequently incubated at room temperature for 1 hour prior to centrifugation (16,000×g, 30 min) and filtration (0.45 μm filter membrane).

Figure 17A:
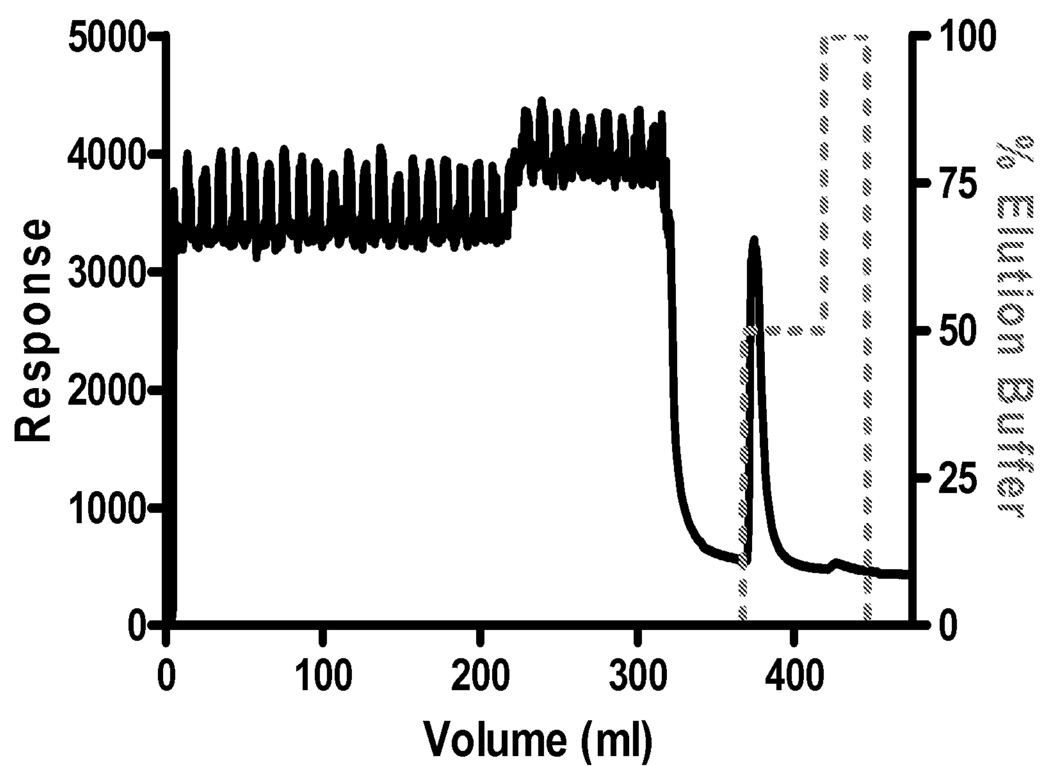
FIG. 17A is a graphical representation showing the 280 nm chromatograph of the His-tag immobilized metal affinity chromatography purification of AVP04-111 (SEQ ID NO: 107). Arrow indicates elution peak of interest. Dotted line indicates proportion of elution buffer.
Figure 17B:
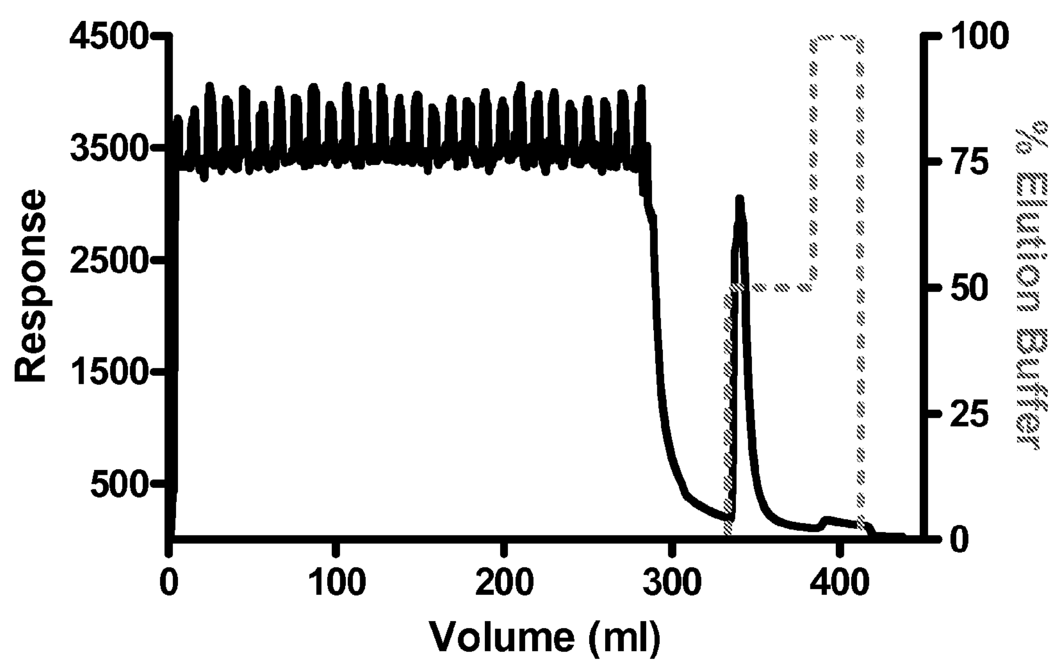
FIG. 17B is a graphical representation showing the 280 nm chromatograph of the His-tag immobilized metal affinity chromatography purification of AVP04-120 (SEQ ID NO: 113). Arrow indicates elution peak of interest. Dotted line indicates proportion of elution buffer.
Figure 17C:
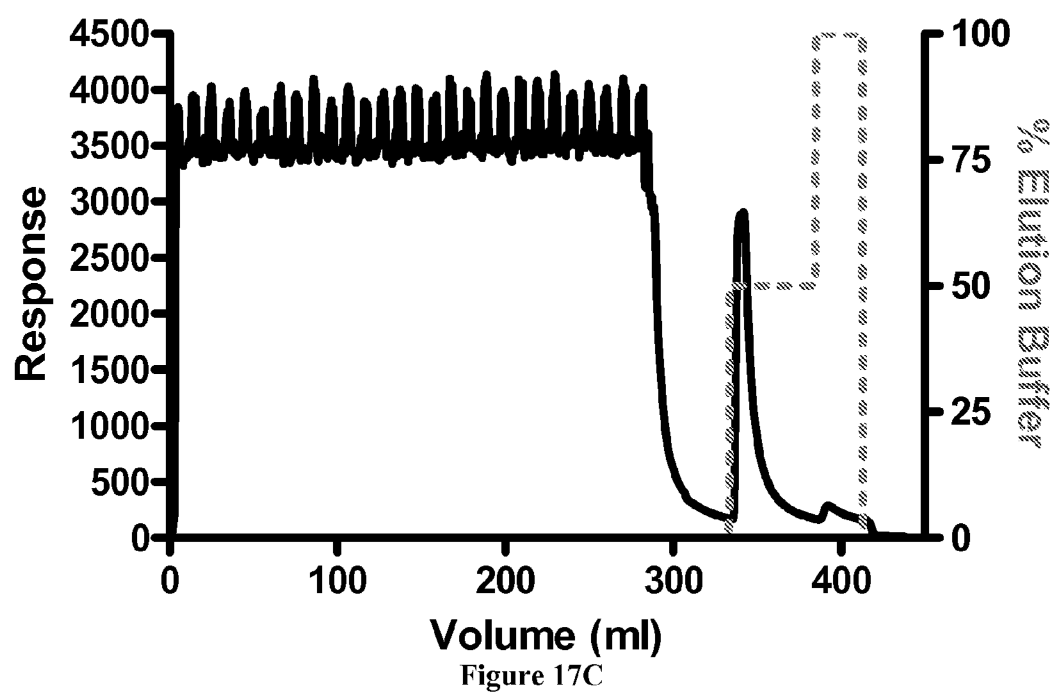
FIG. 17C is a graphical representation showing the 280 nm chromatograph of the His-tag immobilized metal affinity chromatography purification of AVP04-121 (SEQ ID NO: 115). Arrow indicates elution peak of interest. Dotted line indicates proportion of elution buffer.

His-Tag affinity chromatography purification using the AKTA Purifier 10 (GE LifeSciences) was then used to purify diabodies from filtered bacterial lysate. Between one and four 5 mL HisTrap™ (GE LifeSciences) crude FF columns were employed in series for purification depending on the scale of purification. Lysate was passed through the HisTrap™ column via an external P960 pump. HisTrap™ columns were washed with 10 column volumes of His-Tag affinity chromatography extraction buffer (20 mM sodium phosphate, 500 mM NaCl, 20 mM Imidazole, pH7.4). Purified protein was eluted in 50% His-Tag affinity chromatography elution buffer (20 mM sodium phosphate, 500 mM NaCl, 500 mM Imidazole, pH7.4) and 50% His-Tag affinity chromatography extraction buffer (a final concentration of 260 mM Imidazole). Fractions containing eluted proteins (as determined by 280 mM absorbance on AKTA Unicorn software) were collected, pooled, protein concentration determined and dialyzed in the appropriate ion exchange buffer. A typical His-Tag affinity chromatography elution profile, using TAG72-specific AVP04-111 (SEQ ID NO: 107), AVP04-120 (SEQ ID NO: 113) and AVP04-121 (SEQ ID NO: 115) is shown in FIG. 17A-C. All Avibodies described herein showed similar elution profiles.

Partially purified Avibodies were subsequently dialyzed in a buffer 1.0-1.5 pH units lower than the calculated pI of the protein (for cation exchange) or 1.0-1.5 pH units higher than the pI of the protein (for anion exchange). Typically, Avibodies with a pI of 7.0-8.0 were dialyzed in MES buffer (50 mM MES, pH 6.0 for cation exchange), those with a pI of 8.0-9.0 were dialyzed in phosphate buffer (50 mM phosphate, pH 7.0 for cation exchange) and those with a pI of 5.0-6.5 were dialyzed in Tris buffer (20 mM Tris-HCl, pH 8 for anion exchange). All Avibody pI values fell within these ranges. Avibodies were dialyzed into more than 200× volume of buffer with three buffer exchanges no less than 2 hours apart. Dialysis was performed using Spectrapor 6-8000 Da MW cut-off dialysis tubing at 4° C.

Following dialysis, the protein sample was centrifuged at 3220×g for 10 minutes to pellet denatured insoluble material prior to ion exchange. Ion exchange was performed using the AKTA purifier 10, employing up to two 5 mL HiTrap™ SP HP columns in series, passing the cleared dialyzed material through the column via a P960 external pump. Following this step, the column was washed with 10 column volumes of ion-exchange buffer prior to commencement of a linear buffer gradient (salt gradient) for elution of the protein from the column. In this process, the ion exchange buffer was replaced over a linear gradient with the identical buffer with the addition of NaCl to 1M final concentration. The elution gradient was performed over 300 mL with a final concentration of 600 mM NaCl.

Figure 18A:
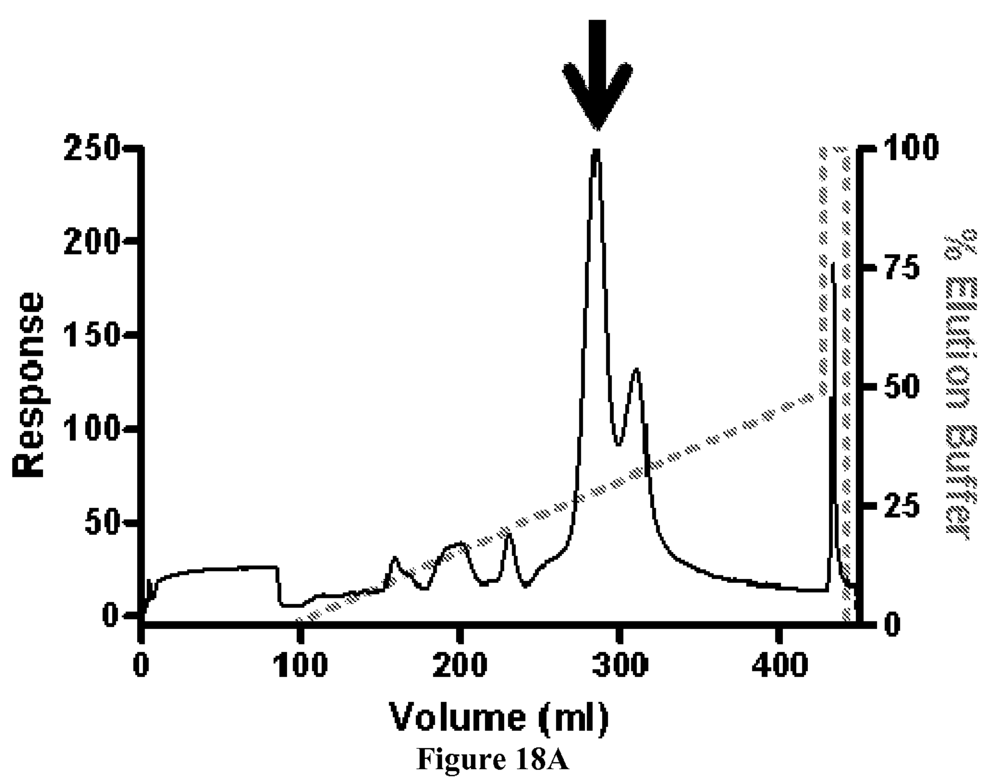
FIG. 18A is a graphical representation showing the 280 nm chromatograph of the anion exchange chromatography purification of AVP04-111 (SEQ ID NO: 107). Arrow indicates elution peak of interest. Dotted line indicates proportion of elution buffer.
Figure 18B:
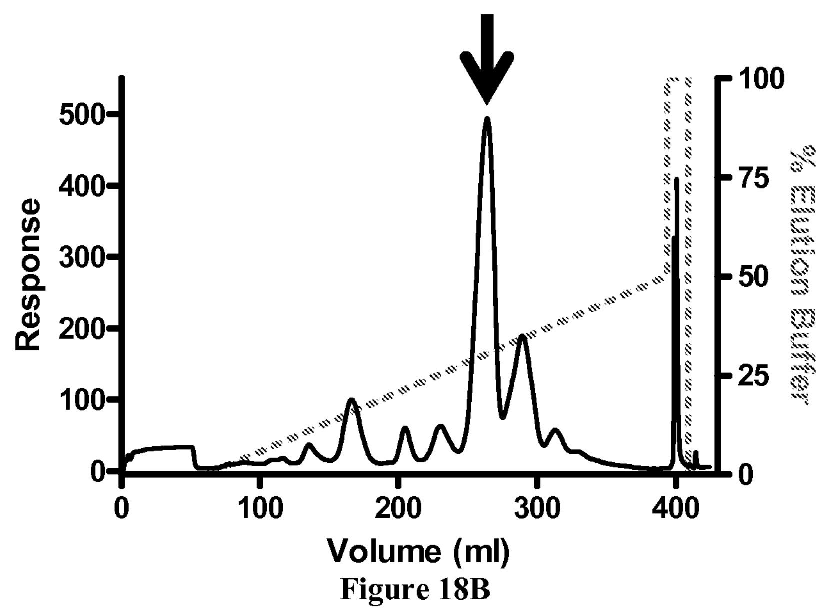
FIG. 18B is a graphical representation showing the 280 nm chromatograph of the anion exchange chromatography purification of AVP04-120 (SEQ ID NO: 113). Arrow indicates elution peak of interest. Dotted line indicates proportion of elution buffer.
Figure 18C:
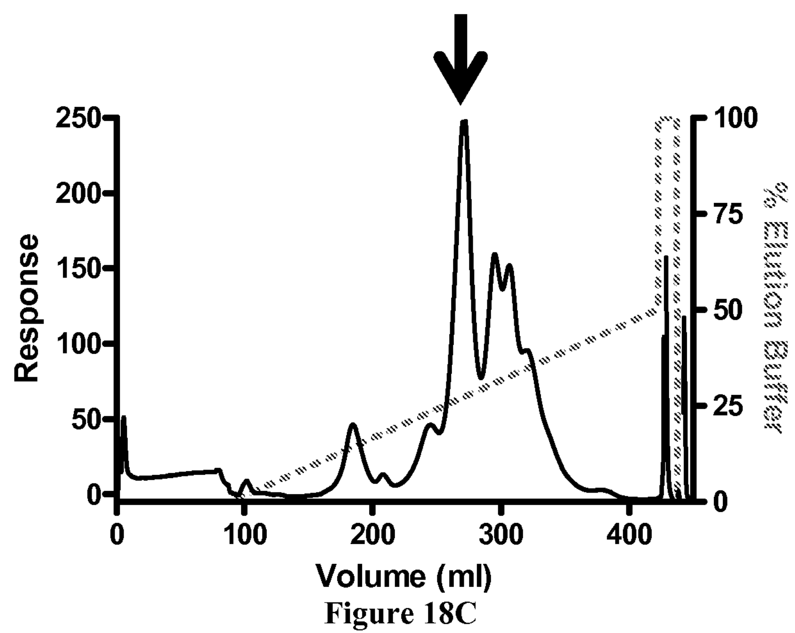
FIG. 18C is a graphical representation showing the 280 nm chromatograph of the anion exchange chromatography purification of AVP04-121 (SEQ ID NO: 115). Arrow indicates elution peak of interest. Dotted line indicates proportion of elution buffer.

Fractions corresponding to the eluted diabody (as determined by the 280 nm absorbance profile on Unicorn software) were pooled and quantified. A typical ion exchange elution profile using TAG72-specific AVP04-111 (SEQ ID NO: 107), AVP04-120 (SEQ ID NO: 113) and AVP04-121 (SEQ ID NO: 115) is presented in FIGS. 18A-C. All diabodies routinely eluted at a salt concentration of approximately 37 mS/cm or 32% B in which the major dimeric isoform (designated by the arrow) could be easily separated from other charge and size variants. The diabody clones, even those from different families, routinely eluted at similar point in the salt gradient. In some cases, analytical size exclusion using a calibrated Superdex 200 10/300 column (GE LifeSciences) in 1×PBS buffer (137 mM NaCl, 2.7 mM KCl, 8.1 mM $Na_2HPO_4$, 1.47 mM $KH_2PO_4$, pH7.4,) was carried out to confirm peak identity of the desired species or composition of specific fractions before pooling. The elution fractions containing the major isoform of interest were pooled for downstream purification.

Figure 19A:
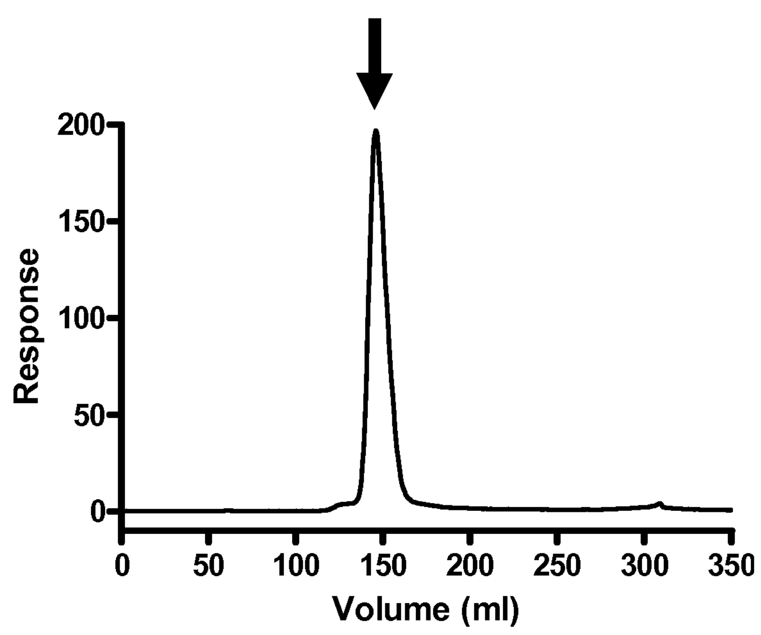
FIG. 19A is a graphical representation showing the 280 nm chromatograph of the Gel filtration chromatography purification of AVP04-111 (SEQ ID NO: 107). Arrow indicates elution peak of interest.
Figure 19B:
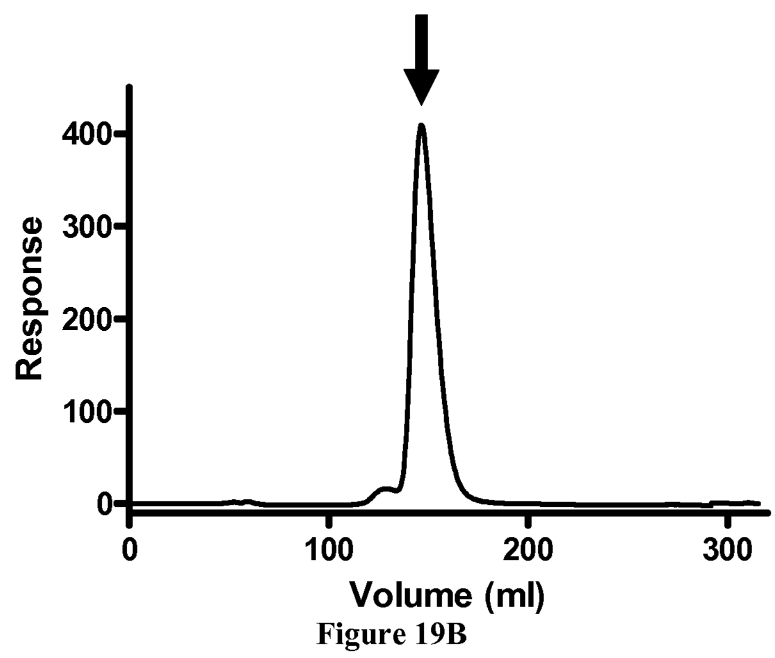
FIG. 19B is a graphical representation showing the 280 nm chromatograph of the Gel filtration chromatography purification of AVP04-120 (SEQ ID NO: 113). Arrow indicates elution peak of interest.
Figure 19C:
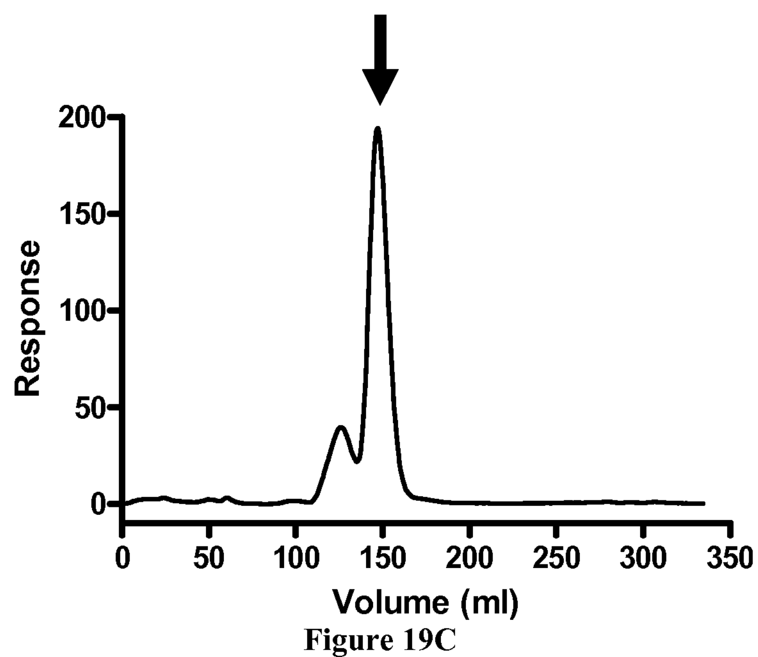
FIG. 19C is a graphical representation showing the 280 nm chromatograph of the Gel filtration chromatography purification of AVP04-121 (SEQ ID NO: 115). Arrow indicates elution peak of interest.

Following ion exchange, eluted protein material was concentrated to approximately 3 mg/mL at 4° C. prior to gel filtration. Gel filtration was performed using the Pharmacia Amersham (GE LifeSciences) Superdex® 75 26/60 prep-grade column in PBS on the AKTA Purifier 10. Using TAG72-specific AVP04-111 (SEQ ID NO: 107), AVP04-120 (SEQ ID NO: 113) and AVP04-121 (SEQ ID NO: 115) diabodies as examples, the proteins eluted at approximately 150 ml post injection (FIGS. 19A-C). Diabody variants, both within the AVP04 family and others, routinely eluted at similar elution volumes as expected of any globular protein with a molecular weight of approximately 54 kDa. Fractions corresponding to the dimer (indicated with an arrow in FIGS. 19A-C) were pooled and concentrated to between 0.5-3 mg/ml using Amicon Ultrafree spin concentrators with a 10K MWCO (Millipore, USA) at 3200×g, 4° C.

Figure 20A:
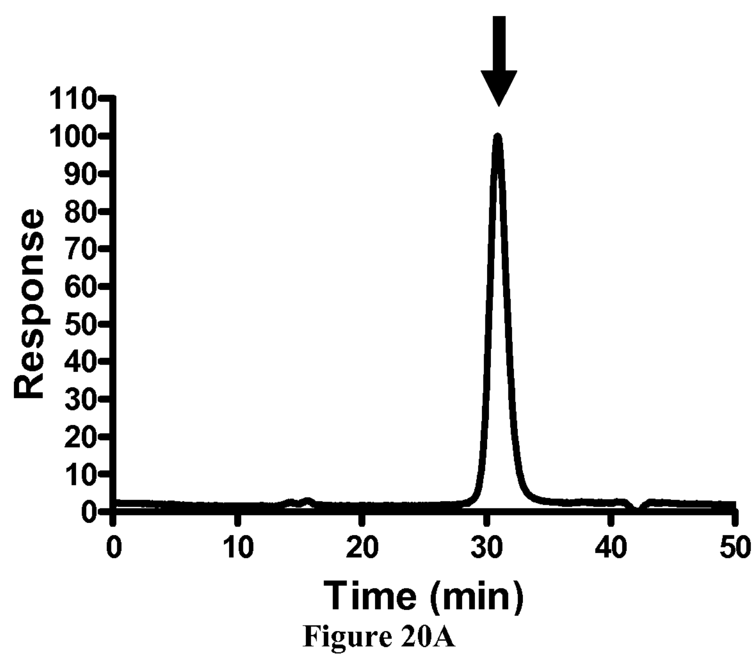
FIG. 20A is a graphical representation showing the 280 nm chromatograph of the size exclusion chromatography analysis of AVP04-111 (SEQ ID NO: 107). Arrow indicates elution peak of interest.
Figure 20B:
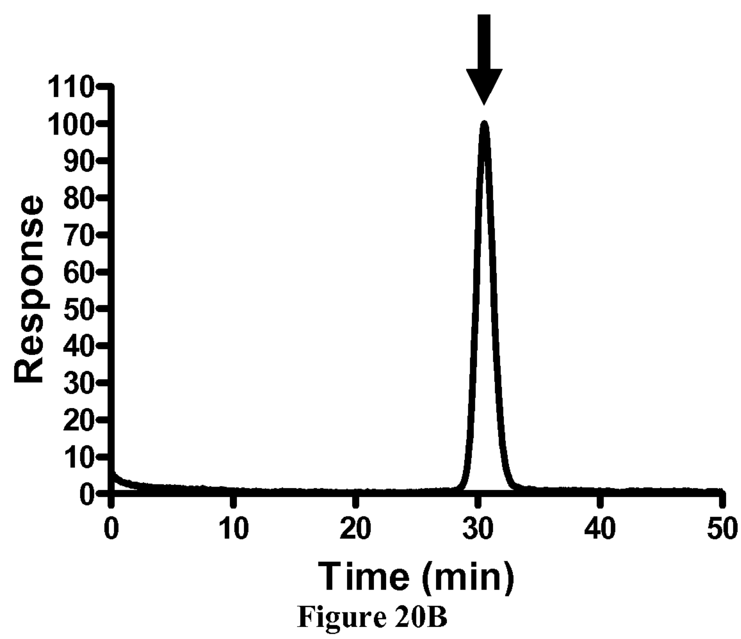
FIG. 20B is a graphical representation showing the 280 nm chromatograph of the size exclusion chromatography analysis of AVP04-120 (SEQ ID NO: 113). Arrow indicates elution peak of interest.
Figure 20C:
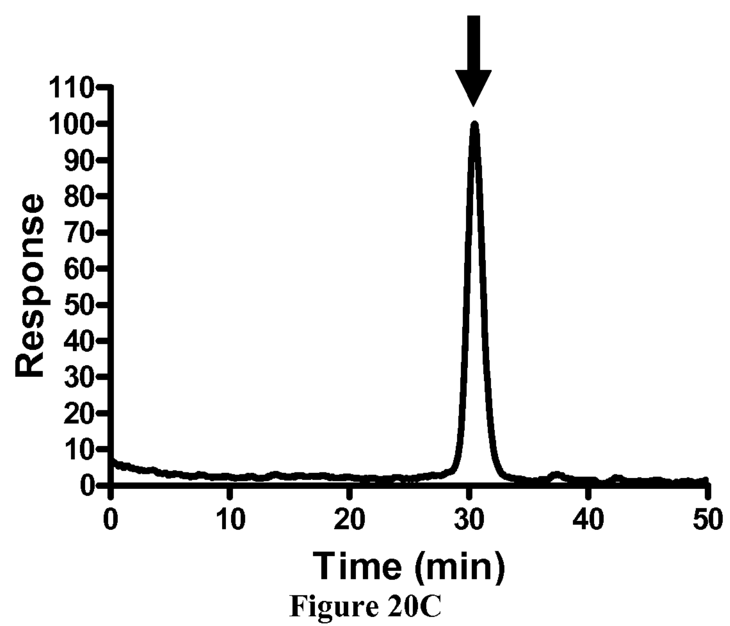
FIG. 20C is a graphical representation showing the 280 nm chromatograph of the size exclusion chromatography analysis of AVP04-121 (SEQ ID NO: 115). Arrow indicates elution peak of interest.

The final purity of the purified product was routinely assessed by size exclusion chromatography on a Superdex® 200 10/300 column and SDS-PAGE electrophoresis. As example, the purification method using TAG72-specific AVP04-111 (SEQ ID NO: 107), AVP04-120 (SEQ ID NO: 113) and AVP04-121 (SEQ ID NO: 115) routinely returned protein with purities resulting in a single clean elution peak on size exclusion chromatography (FIGS. 20A-C).

Figure 21A:
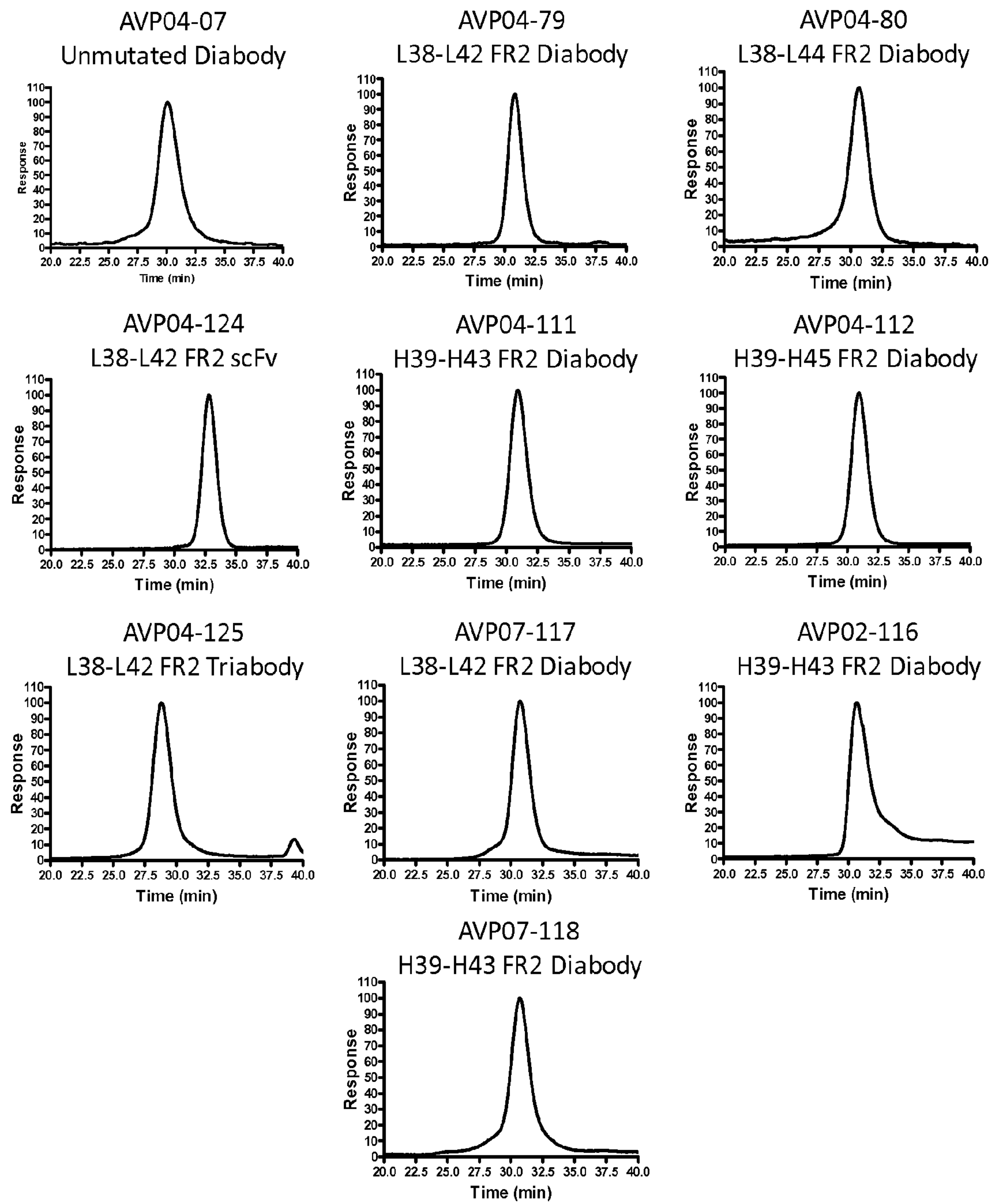
FIGS. 21A and B include a series of graphical representations of the purified Avibodies mentioned herein (as indicated, nomenclature corresponds to that used throughout the text and in the sequence listing) following size exclusion chromatography.
Figure 21B:
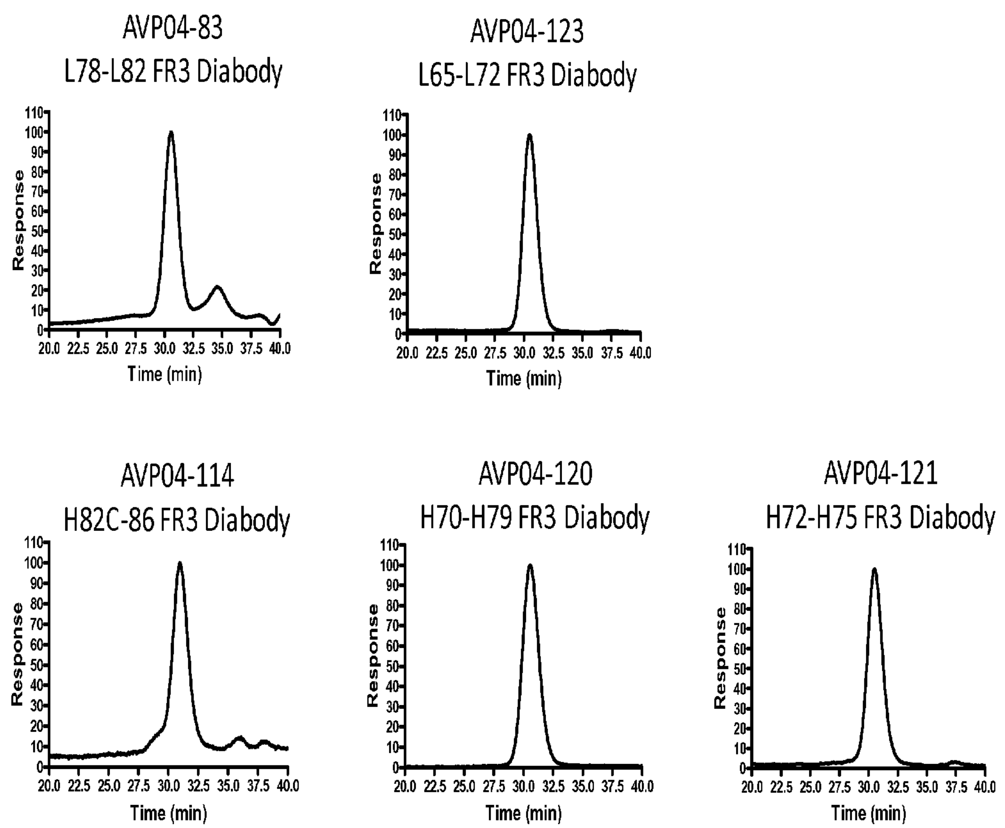

The purification strategy and resultant purity profiles did not differ significantly between any of the Avibodies tested. FIGS. 21A-B highlight the final size exclusion chromatography profiles of Avibodies described herein and as indicated in the Figures. As expected, aside from a small degree of variance both within and between different Avibody families, the elution times of the Avibodies corresponded well to the expected molecular size; triabodies (AVP04-125, SEQ ID NO: 121) eluted earlier than diabodies which eluted later than scFvs (AVP04-124, SEQ ID NO: 119).

All Avibodies described herein could be functionally expressed and purified to substantial homogeneity. The presence of intra-Framework 2 or intra-framework 3 cysteine replacement mutations did not have any effect on the ability to functionally express and purify the Avibody to substantial uniformity, partially confirming modeling data (refer to FIG. 16) suggesting the placement of engineered cysteines within Framework 2 or Framework 3 of Thiolated Avibodies did not cause detrimental structural conformational changes leading to Avibody destabilization.

Example 12

In Vitro Immunoreactive Assessment of Diabodies

Binding activity to soluble antigen was established by a column shift assay using size exclusion chromatography. The antigen for the AVP04-xx Avibodies is TAG72, available in soluble form from bovine submaxillary mucin (BSM) (Sigma). For the AVP07-xx Avibodies, the soluble antigen is recombinant HER2 ectodomain. For the AVP02-xx Avibodies, the soluble antigen is recombinant full length MUC1. Irrespective of Avibody or antigen, the column shift assay was performed essentially as described below.

At least two times molar excess of soluble antigen to diabody was incubated for 1 hr in PBS buffer at ambient temperature. Binding activity was determined by comparing the resulting Avibody-antigen complex peak to the free diabody peak. A positive binding result was regarded as the depletion of the peak corresponding to free Avibody and/or increased size of the peak corresponding to an Avibody-antigen complex following incubation. The elution profiles of the Avibody or Avibody-antigen complex was monitored though absorbance at 280 nm. Herein we report the column shift immunoreactivity assay for AVP04-xx thiolated Avibodies using the BSM antigen.

In all cases, Avibody alone eluted between 28-33 minutes, with triabodies (AVP04-125, SEQ ID NO: 121) eluting earlier than diabodies which eluted later than scFvs (AVP04-124, SEQ ID NO: 119). In all cases, Avibody-Antigen complexes eluted at 10-25 minutes. Complex formation was not observed when Avibodies were incubated with an irrelevant antigen indicating a specific binding interaction occurred.

Figure 22A:
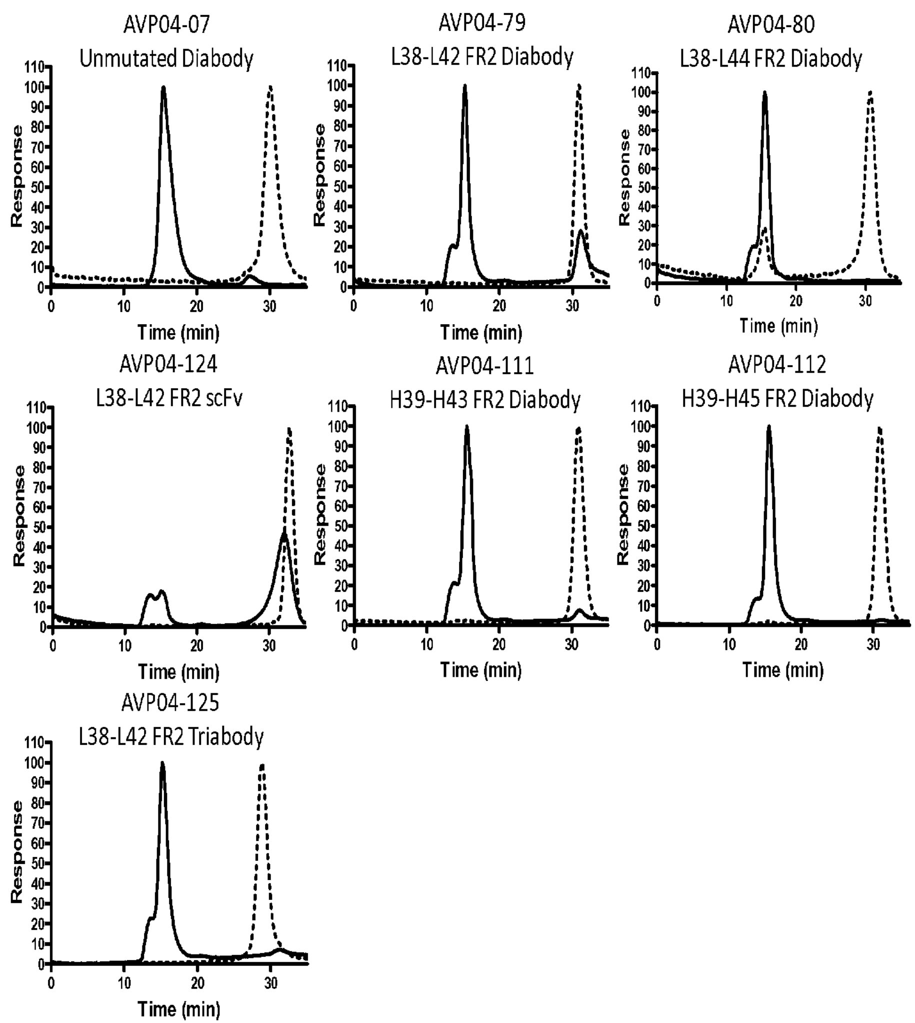
FIGS. 22A and B include a series of graphical representations of a column shift assay used to determine immunoreactivity of Avibodies mentioned herein (as indicated, nomenclature corresponds to that used throughout the text and in the sequence listing). Each graph comprises two overlaid size exclusion chromatography profiles; of the Avibody incubated either in the presence (solid line) or absence (dotted line) of antigen.
Figure 22B:
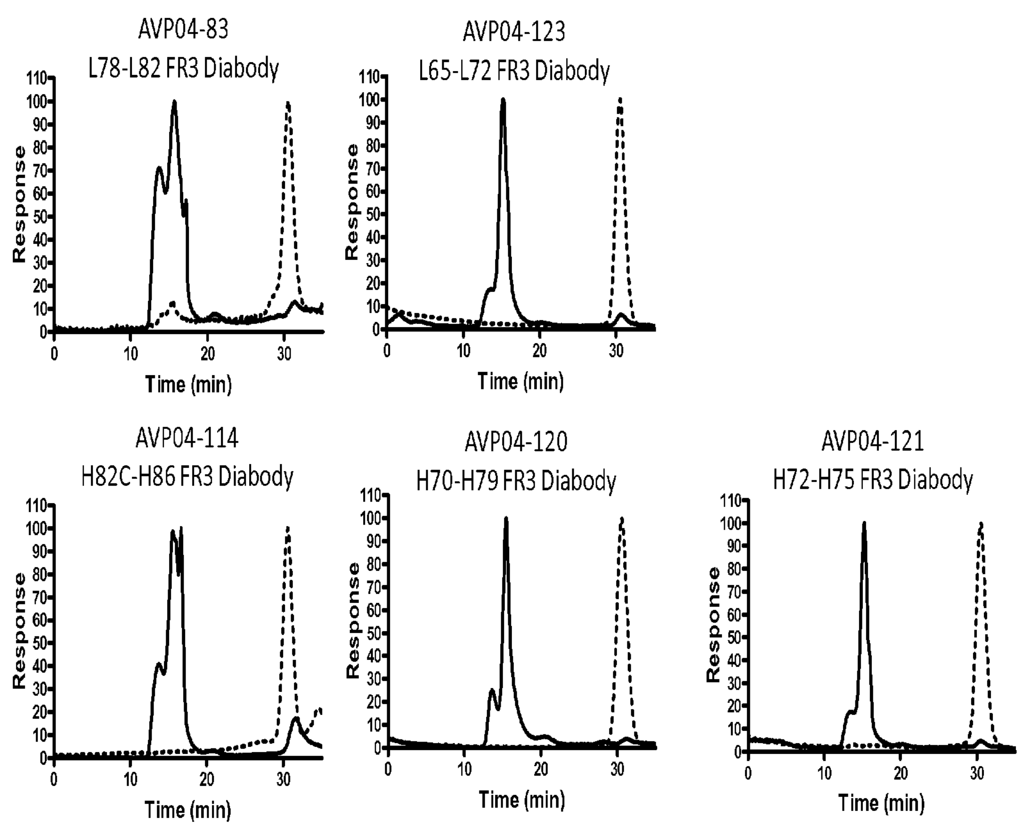

The immunoreactivity of all Avibodies described herein was assessed using the protocol described above and the results depicted in FIGS. 22A-B. In all cases, the formation of an Avibody-antigen complex, evidenced by a significant shortening of elution times in gel filtration, and/or reduced amount of unbound Avibody was observed; indicating Avibodies are immunoreactive. Immunoreactivity was observed for thiolated Avibodies with engineered cysteine replacements interchangeably in $V_H$ or $V_L$ domains, in the diabody, triabody and scFv formats.

The presence or absence of framework 2 or framework 3 cysteine replacement mutations in thiolated Avibodies did not abrogate binding, further indicating that the framework 2 or framework 3 cysteine replacement mutations sites were engineered in positions which had little or no effect on the binding properties of the Avibody.

Example 13

Detection of Free Sulphydryls in Thiolated Avibodies after Controlled-Reduction Thiolated Avibodies could be routinely expressed and purified to substantial homogeneity and were shown to be functionally active. A simple colorimetric assay was devised to demonstrate that framework cysteine replacements formed disulphide bonds which could be selectively broken to release free sulphydryls compatible with payload conjugation.

Thiolated Avibodies were incubated with up to 3.8 mM of TCEP (Tris(2-carboxyethyl)phosphine hydrochloride) (Pierce, Rockford, Ill., USA) in PBS for 25 min at RT. Following reduction, TCEP was removed with a PD10 desalting column pre-equilibrated with 100 mM phosphate buffer +1 mM EDTA pH 6.5, collecting 0.5 mL fractions. Peak protein fractions were identified by UV spectroscopy at 280 nm and pooled.

To test reactive thiols, 50-75 μg of reduced protein was diluted in 100 mM sodium phosphate buffer, 1 mM EDTA, pH 8.0 with 5 μl of 4 mg/mL Ellman's reagent (5,5'-Dithiobis(2-nitrobenzoic acid); DTNB) (Pierce, Rockford, Ill.). The reaction was allowed to proceed at ambient temperature for 15 min. Available thiols react with DTNB, cleaving the disulfide bond to give 2-nitro-5-thiobenzoate ($NTB^-$), which ionizes to the $NTB^{2-}$ dianion (yellow in color) in neutral or alkaline buffers. The resulting yellow coloration was quantified by spectroscopy, assuming the molar extinction coefficient of the $NTB^{2-}$ dianion in this buffer system at 412 nm, is 14,150 $M^{-1}$ $cm^{-1}$. Reactive and available sulphydryl groups were determined by comparing the amount of reactivity with DTNB before and after controlled reduction with TCEP. Thiol reactivity was plotted as a post-reduction to pre-reduction thiol reactivity ratio, where a value of 1 unit indicated there was no difference in reactivity to DTNB between reduced and non-reduced samples, thus indicating no surface-exposed disulphide bridges were broken on reduction, subsequently generating free sulphydryl groups. Thiol reactivity ratios greater than 1 unit indicated that controlled reduction with TCEP increased the number of surface exposed free sulphydryl groups able to react with the DTNB substrate. Increases in thiol reactivity ratio indicated the more free sulphydryl groups made available upon reduction and/or the higher their availability to react with DTNB during the course of the assay.

Figure 23A:
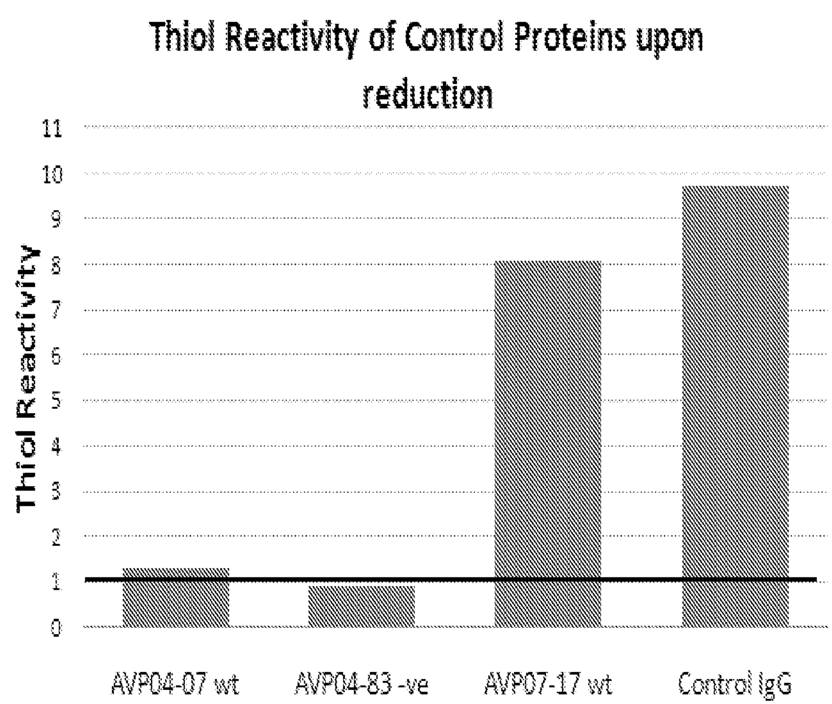
FIGS. 23A and B are a series of graphical representations of thiol reactivity of proteins by Ellman's assay for A) control Avibody proteins and intact IgG and B) Avibody proteins carrying engineered cysteine replacement mutations. The black horizontal line represents 1:1 ratio of thiol reactivity before and after reduction with TCEP.
Figure 23B:
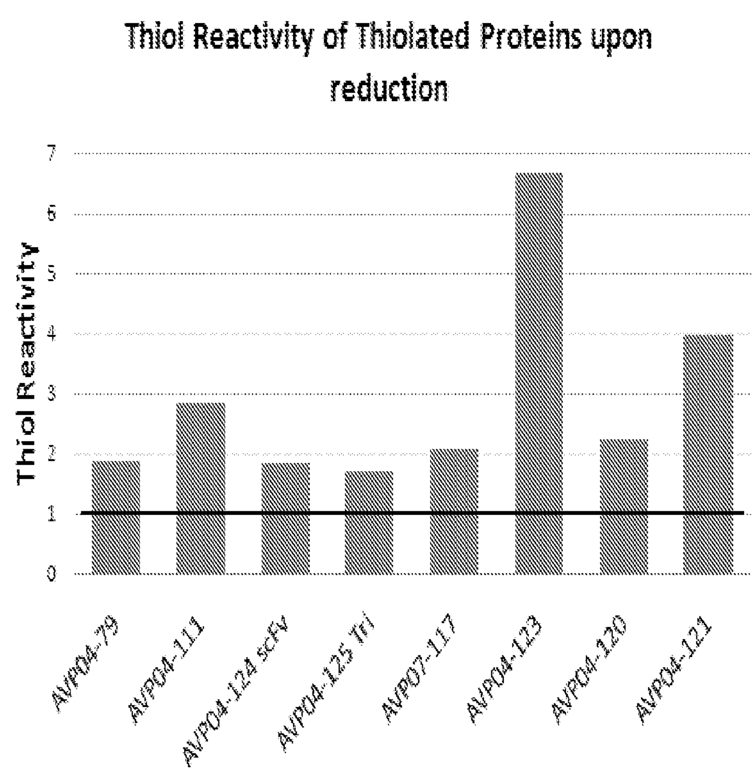

In order to demonstrate that the above detection method was sensitive enough to show that framework cysteine replacements formed disulphide bonds which could be selectively broken to form free sulphydryls, whole IgG (containing 8 surface-exposed cysteines in four disulphide bonds) and AVP07-17 (SEQ ID NO: 61; containing two native cysteine residues forming a surface-exposed disulphide bond within the $V_H$ hypervariable CDR3 region) were used as positive controls (FIG. 23A). In both these positive controls, thiol reactivity ratios were high; above 8 units. This result indicated that these disulphide-exposed proteins are sensitive to treatment with TCEP. The reducing agent has reduced the surface exposed disulphide bond(s) present resulting in free thiols and allowing their free sulphydryl groups to react with DTNB. Conversely, the non-thiolated ("wild-type") AVP04-07 Avibody (SEQ ID NO: 59), that lacks any surface-exposed thiols was used as a negative control in this assay, returned a thiol reactivity ratio of just above 1 unit indicating little change upon treatment with TCEP. The negligible increase in absorbance at 412 nm after controlled reduction with TCEP (FIG. 23A) i.e. the lack of reactivity to DTNB post-reduction indicates that the conserved, structural disulphide bonds between invariant Kabat positions L23 and L88 and invariant Kabat positions H22 and H92, known to be buried within the core structure of the protein and not exposed to the surface, are not available for reduction under the conditions utilized herein.

Similar to the AVP04-07 negative control, AVP04-83, the construct containing modeling mutation c4 (Cysteines inserted in Kabat residues L78 and L82, SEQ ID NO: 105) was also used as a negative control. Although the engineered cysteines inserted to form AVP04-83 met all the structural requirements for engineering cysteine replacements (refer to Example 9.5 and FIG. 10B), the engineered cysteines were shown by modeling to have very low solvent accessible surface areas (refer to FIG. 11) and thus were not expected to be available for reduction and hence would not form thiols that would react with DTNB. No significant difference was observed in absorbance at 412 nm before and after reduction with TCEP, indicating that the engineered cysteines in AVP04-83 were indeed buried within the core of the structure as indicated by modeling. This demonstrated that although cysteine mutations can be inserted into conserved framework residues without abrogating stability or immunoreactivity, compatibility with disulphide bridge reduction and subsequent payload conjugation are preferably determined by structural assessment/surface positioning. This result further demonstrated that molecular modeling was a good predictor of in vitro functionality.

Since modeling and initial in vitro assessment suggested that FR2 or FR3 engineered cysteine replacements generally did not perturb core protein structure and that these engineered cysteine replacements could be readily transferred to the same structural position in Fvs of different sequence, species and specificity, a representative subset of thiolated Avibody proteins were tested in order to demonstrate that a disulphide bridge could be formed between intra-framework engineered cysteine pairs, that this disulphide bridge could be broken on selective reduction to release free sulphydryl groups. The representative Avibodies exemplified in FIG. 17B includes:

Thiolated Avibodies containing modeling mutation c6 in $V_L$ FR2 of a diabody format Avibody (AVP04-79, SEQ ID NO: 101), modeling mutation c6 in $V_H$ FR2 of a diabody format Avibody (AVP04-111, SEQ ID NO: 107), modeling mutation c6 in $V_L$ FR2 of a scFv format Avibody (AVP04-124, SEQ ID NO: 119), modeling mutation c6 in $V_L$ FR2 of a triabody format Avibody (AVP04-125, SEQ ID NO: 121), modeling mutation c6 in $V_L$ FR2 of a diabody format Avibody in another antibody-class/family/species (AVP07-117, SEQ ID NO: 127).

Thiolated Avibodies containing modeling mutation c8 in both $V_L$ FR3 (AVP04-123, SEQ ID NO: 117) and $V_H$ CD3 (AVP04-120, SEQ ID NO: 113).

Thiolated Avibodies containing modeling mutation c9 in only $V_H$ FR3 (AVP04-121, SEQ ID NO: 115) since no structural homologue exists in $V_L$ FR3.

In every case, thiol reactivity ratio was greater than 1 unit, indicating that reduction with TCEP broke disulphide bond(s) present in the native (un-reduced) state, allowing the free sulphydryl groups to react with DTNB. The variance in thiol reactivity after controlled reduction is a measure of the bioavailability of the sulphydryl groups to reaction with DTNB within the time frame of the experiment.

These results indicate that preferred engineered cysteine replacement mutations could be designed to form surface-exposed disulphide bridges which could be selectively reduced. The engineered cysteine replacement mutations could be readily transferred to the same structural position in both $V_H$ and $V_L$ domains in Fvs of different sequence, species and specificity.

Example 14

Payload Conjugation to Reduced Engineered Disulphides in Thiolated Avibodies The availability of engineered FR2 or FR3 disulphide bridges in thiolated Avibodies to controlled reduction indicated that any of a number of thiol-reactive payloads could be conjugated to the exposed and reduced cysteines.

To demonstrate this ability, a maleimide-$PEG_{24}$-methoxy payload was conjugated to the reduced engineered FR2 or FR3 cysteines essentially as described herein.

Following the reduction of Thiolated Avibodies and removal of reducing agent, an excess of maleimide-$PEG_{24}$-methoxy (mal-$PEG_{24}$-OMe) (Quanta Biodesign, OH, USA) was added at 20 equivalents per Avibody and allowed to react overnight at 4° C. Following PEGylation, unreacted PEG was removed by extensive dialysis and assessment of PEG loading was determined by mass spectroscopy.

For mass spectroscopy analysis, an Agilent esiTOF mass spectrometer with a MassPREP on-line desalting cartridge (Waters Corporation, USA) was used to record mass spectra of PEGylated Avibodies. The system was equilibrated for 1 min with 5% $CH_3CN$, followed by an elution gradient from 5-95% acetonitrile over 9 min. PEGylated Avibodies typically eluted at 7 min. MassHunter software was used to determine average mass of the sample by deconvolution of the relevant m/z charge peaks produced. Data is reported in Table 3 and summarizes the average monomeric-chain Avibody mass obtained following deconvolution of mass spectra. The formula mass of $PEG_{24}$ is reported as 1239.44 g/mol, therefore an increase of at least 2478.88 mass units indicates full conjugation to engineered cysteines.

All Avibodies shown to have free sulphydryl groups after controlled reduction with TCEP (refer to Example 5) were used in thiol-mediated conjugation to payload, in this case a maleimide-$PEG_{24}$-methoxy. As shown in Table 3, the following Avibodies allowed at least one payload to be site specifically conjugated to engineered framework cysteines after reduction to free sulphydryls with TCEP:

- Thiolated Avibodies containing modeling mutation c6 in $V_L$ FR2 of a diabody format Avibody (AVP04-79, SEQ ID NO: 101), modeling mutation c6 in $V_H$ FR2 of a diabody format Avibody (AVP04-111, SEQ ID NO: 107), modeling mutation c6 in $V_L$ FR2 of a scFv format Avibody (AVP04-124, SEQ ID NO: 119) and modeling mutation c6 in $V_L$ FR2 of a diabody format Avibody in another antibody-class/family/species (AVP07-117, SEQ ID NO: 127).
- Thiolated Avibodies containing modeling mutation c8 in both $V_L$ FR3 (AVP04-123, SEQ ID NO: 117) and $V_H$ CD3 (AVP04-120, SEQ ID NO: 113).
- Thiolated Avibodies containing modeling mutation c9 in only $V_H$ FR3 (AVP04-121, SEQ ID NO: 115) since no structural homologue exists in $V_L$ FR3.

TABLE 3

PEG loading on thiolated Avibodies as determined by mass spectroscopy.

| Construct | Average Mass (kDa) | PEGylated Mass (kDa) | Mass Increase (kDa) | PEG loaded |
|---|---|---|---|---|
| FR2 Clones | | | | |
| AVP04-79 | 26775.86 | 28018.53 | 1242.67 | 1 |
| AVP04-111 | 26776.02 | 29256.97 | 2480.95 | 2 |
| AVP04-124 | 27722.12 | 28963.33 | 1241.21 | 1 |
| AVP07-117 | 28506.04 | 30986.40 | 2480.36 | 2 |
| FR3 Clones | | | | |
| AVP04-123 | 26844.40 | 29325.37 | 2480.97 | 2 |
| AVP04-120 | 26768.49 | 29249.40 | 2480.91 | 2 |
| AVP04-121 | 26830.81 | 29311.34 | 2480.53 | 2 |
| AVP04-83 -ve | 26832.10 | Not observed | 0 | 0 |

As previously outlined, AVP04-83, the construct containing modeling mutation c4 (cysteines inserted in Kabat residues L78 and L82, SEQ ID NO: 105) was used as a negative control. In this construct, the engineered cysteines inserted to form AVP04-83 met all the structural requirements for engineering cysteine replacements (refer to Example 9.5 and FIG. 10B), however, engineered cysteines were shown by modeling to have very low solvent accessible surface areas (Refer to FIG. 11), not available for reaction with DTNB after controlled reduction with TCEP (Refer to FIG. 23A) and subsequently no payload could be conjugated to the Avibody (Refer to Table 3). This demonstrated that although cysteine mutations can be inserted into conserved framework residues without abrogating stability or immunoreactivity, compatibility with disulphide bridge reduction and subsequent payload conjugation preferably involves defined structural/surface positioning. This result further demonstrates that molecular modeling is a good predictor of in vitro functionality.

Figure 24:
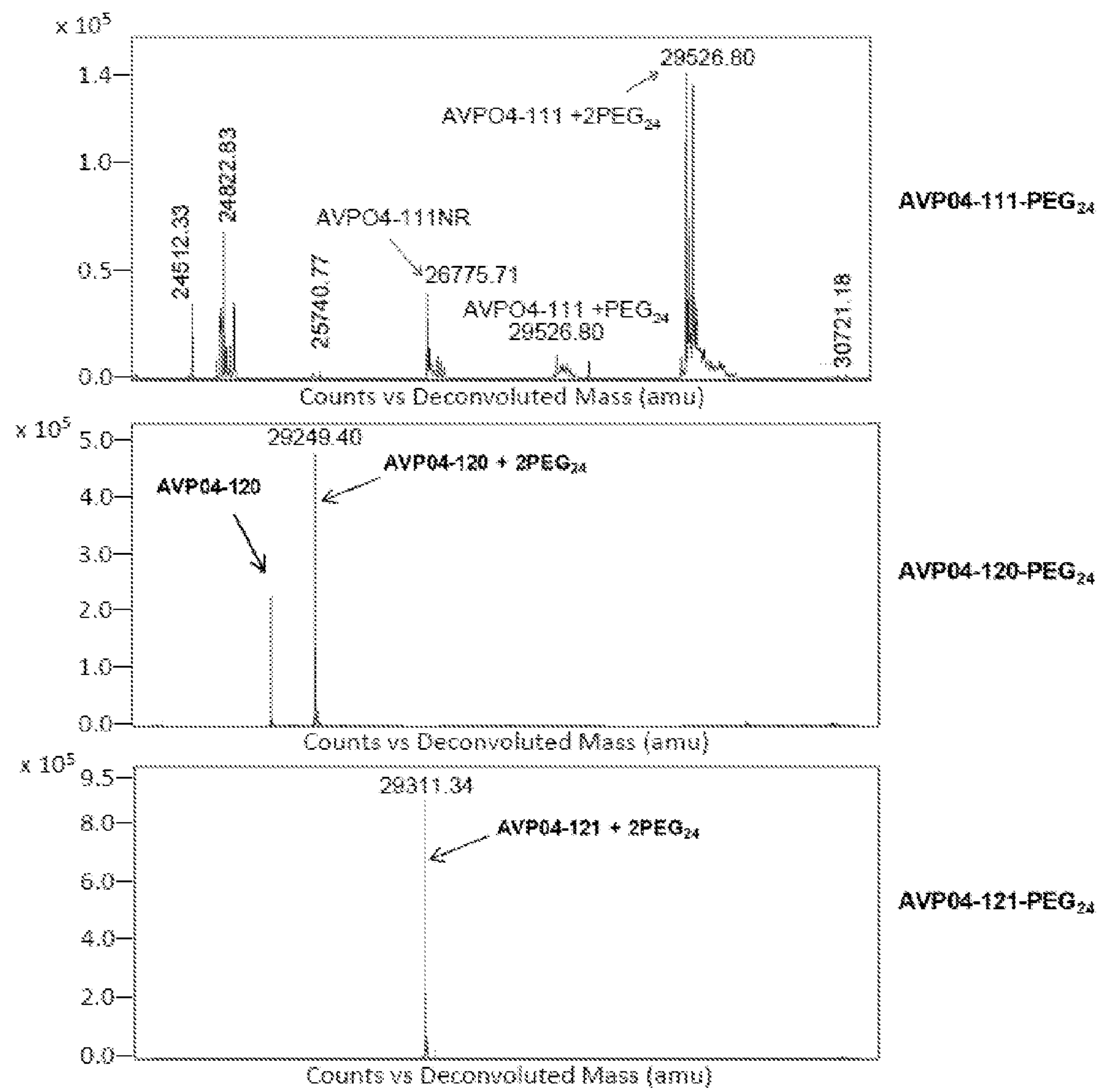
FIG. 24 is a graphical representation of example MS spectra following electrospray ionization mass spectrometry of PEGylated samples (AVP04-111 (SEQ ID NO: 107), AVP04-120 (SEQ ID NO: 113) and AVP04-121 (SEQ ID NO: 115)).

Examples of typical mass spectrum for TAG72-specific AVP04-111 (SEQ ID NO: 107), AVP04-120 (SEQ ID NO: 113) and AVP04-121 (SEQ ID NO: 115) are shown in FIG. 24, indicating that at least one payload could be specifically conjugated to engineered intra-framework cysteines after reduction to free sulphydryls with TCEP.

This result demonstrates the ability to conjugate payloads to thiolated Avibodies, specifically to engineered framework cysteines after reduction to free sulphydryls with TCEP, in a controlled, site-specific manner. This result further demonstrates that the same FR2 or FR3 engineered cysteine insertion mutation was a) functionally transferable between $V_L$ and $V_H$ domains and different subtypes thereof, b) compatible with proteins (e.g., Avibodies) containing a Fv domains in different formats, and c) controlled disulphide-bond reduction and payload conjugation preferably relies on very specific residue "surface exposure" to solvent; a characteristic determined in the modeling phase and exemplified in vitro.

Example 15

In Vitro Immunoreactive Assessment of Payload-Conjugated Thiolated Avibodies

Thiolated Avibodies could be expressed, purified, and were shown to be immunoreactive in their native (un-conjugated) state. Data reported above indicate that stoichiometrically defined conjugation to engineered cysteines was occurring.

To show that immunoreactivity was not abrogated after site specific conjugation to FR2 or FR3 cysteine replacement mutations, the AVP04-xx subset of Avibodies containing engineered cysteine mutations prescribed by modeling mutation c6, c8 and c9 were tested for immunoreactivity by column shift assay using size exclusion chromatography as outlined in Example 12.

Figure 25A:
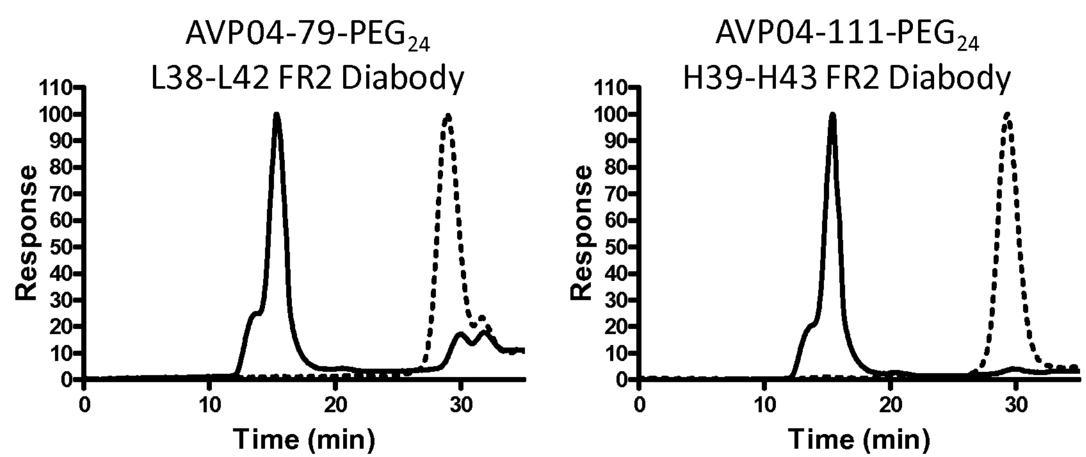
FIGS. 25A and B are a series of a graphical representations showing a column shift assay used to determine immunoreactivity of PEGylated Avibody proteins mentioned herein (as indicated, nomenclature corresponds to that used throughout the text and in the sequence listing). Each graph comprises two overlaid size exclusion chromatography profiles; of the Avibody-PEG conjugate incubated either in the presence (solid line) or absence (dotted line) of antigen.
Figure 25B:
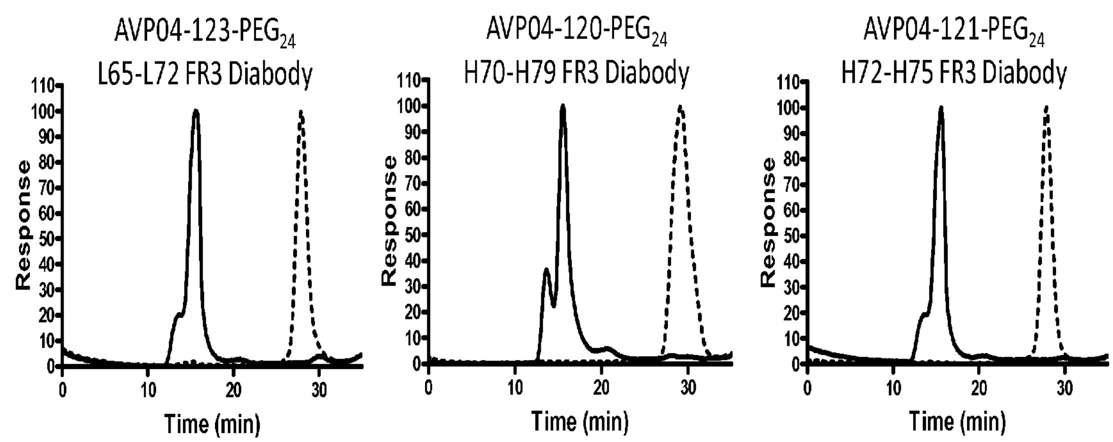

In all cases, Avibody-antigen complex formation, evidenced by a significant shortening of elution times in gel filtration (as described in Example 12), was observed (FIGS. 25A-B). In all cases, Avibody alone eluted between 28-33 minutes, and Avibody-Antigen complexes eluted at 10-25 minutes. As expected, complex formation was not observed when Avibodies were incubated with an irrelevant antigen.

This result indicated that thiolated Avibodies allowed at least one payload to be site specifically conjugated to engineered intra-framework cysteines after reduction to free sulphydryls with TCEP and that controlled, site-specific conjugation event did not abrogate binding.

REFERENCES

Abuchowski et al., *J. Biol. Chem.,* 252: 3582-3586, 1977;

Al-Lazikani et al., *J Mol Biol* 273, 927-948, 1997;

Albrecht et al., *Bioconjug Chem.* 15:16-26, 2004;

Andersson-Engels et al, *Phys. Med. Biol,* 42:815-824, 1997;

F. M. Ausubel et al. (editors), Current Protocols in Molecular Biology, Greene Pub. Associates and Wiley-Interscience, 1988, (including all updates until present);

Axworthy et al *Proc. Natl. Acad. Sci. USA* 97(4): 1802-1807, 2000;

Barnett et al, *Genomics* 3: 59-66, 1988;

Bateman et al *Genomics* 3, 59-66, 1988., *Nucleic Acids Res.* 32: D138-41, 2004;

Bendele *J Musculoskel Neuron Interact;* 1(4):377-385, 2001;

Bernhard et al *Bioconjugate Chem.* 5:126-132, 1994;

Bork et al., *J Mol. Biol.* 242, 309-320, 1994;

Borrebaeck (ed), Antibody Engineering, Oxford University Press, 1995 (ISBN0195091507);

Bowie et al., *Science,* 253:164-70, 1991;

Bradl and Linington *Brain Pathol.,* 6:303-311, 1996

Brennan et al, *Science,* 229: 81-83, 1985;

Brinkmann et al., *Proc. Natl. Acad. Sci. USA,* 90: 7538-7542, 1993;

Brown T. A. (Editor), Essential Molecular Biology: A Practical Approach, Volumes 1 and 2, IRL Press, 1991;

Carmichael et al. *J. Mol. Biol.* 326: 341-351, 2003;

Carpino and Han, *J. Org. Chem.,* 37:3403-3409, 1972;

Carter et al *Nucleic Acids Res.* 13:4431-4443, 1985;
Carter et al. *Bio/Technology* 10: 163-167, 1992;
Chan et al, *Oncogene,* 6: 1057-1061, 1991;
Chari et al *Cancer Research* 52:127-131, 1992;
Chen et al. *Nature,* 446:203-207, 2007;
Cheung et al., *Virology* 176:546, 1990;
Chothia and Lesk *J. Mol Biol.* 196:901-917, 1987;
Chothia et al. *Nature* 342, 877-883, 1989;
Chou et al., *Biochemistry* 13:222-45, 1974;
Chou et al., *Biochemistry* 13:211-22, 1974;
Chou et al., *Adv. Enzymol. Relat. Areas Mol. Biol.* 47:45-48, 1978;
Chou et al., *Ann. Rev. Biochem.* 47:251-276, 1978;
Chou et al., *Biophys. J.* 26:367-84, 1979;
Ciccodicola et al, *EMBO J* 8: 1987-1991, 1989;
Clark, et al *Genome Res.* 13, 2265-2270, 2003;
Clark et al., Protein Sci. 15: 949-960, 2006;
Coligan et al. (Editors), Current Protocols in Immunology, John Wiley & Sons, including all updates until present.
Coussens et al *Science* 230(4730): 1132-1139, 1985;
Crouch et al, *J Immunol Methods,* 160: 81-88, 1993;
Dijke et al., *J Biol Chem,* 269: 16985-16988
Dooley et al., *Dev Comp Immunol,* 30:43-56
Eisen et al., *J. Am. Chem. Soc.,* 75: 4583-4585, 1953;
Feild et al *Biochem. Biophys. Res. Commun.* 258 (3):578-582, 1999;
Frangioni, *Curr. Opin. Chem. Biol,* 7:626-634, 2003;
Froyen et al., *Mol. Immunol.,* 37: 515-521, 1995;
Fujisaku et al, *J Biol Chem* 264: 2118-2125, 1989;
Gaertner and Offord, *Bioconj. Chem.* 264 (4):2118-2125, 1989., 7: 38-44, 1996
Garman, Non-Radioactive Labelling: A Practical Approach, Academic Press, London, 1997;
Gary et al, *Gene* 256: 139-147, 2000;
Gaugitsch et al *J. Biol. Chem.* 267 (16):1 1267-1273, 1992;
Gelfand et al. *Protein Eng.* 11: 1015-1025, 1998a;
Gelfand et al., *Journal of computational biology* 5: 467-477, 1998b;
Gendler et al., *J. Biol. Chem.* 265: 15286-15293, 1990;
Getz et al *Anal. Biochem.* 273:73-80, 1999;
D. M. Glover and B. D. Hames (Editors), DNA Cloning: A Practical Approach, Volumes 1-4, IRL Press, 1995 and 1996;
Goding, Monoclonal Antibodies: Principles and Practice, Academic Press, (1986) pp. 59-103;
Goodman et al., Goodman and Gilman's *The Pharmacological Basis of Therapeutics,* 8th Ed., Macmillan Publishing Co., 1990
Goodson and Katre, *Biotechnology,* 8: 227-231, 1990;
Gribskov et al., *Methods Enzymol.* 183:146-59, 1990;
Gribskov et al., *Proc. Nat. Acad. Sci. U.S.A.* 84:4355-58, 1989;
Grossman et al., *Biochemistry,* 21: 6122-6128, 1981;
Guan et al., *Proc. Natl. Acad. Sci. USA,* 95: 13206-10, 1998;
Guss et al. *EMBO J.* 5: 1567-1575, 1986;
Guy et al., *Mol Cell Biol.* 12(3):954-61, 1992;
Halaby et al., *Protein Engineering* 12: 563-571, 1999;
Harlow and Lane, Antibodies: A Laboratory Manual, Cold Spring Harbor Press, 1988;
Higuchi, in *PCR Protocols*, pp. 177-183, Academic Press, 1990;
Ito et al *Gene* 102:67-70, 1991;
Ho et al *Gene* (*Amst.*) 77:51-59, 1989;
Holliger et alt *Proc. Natl. Acad Sci. USA* 90: 6444-6448, 1993;
Hollinger and Hudson *Nature Biotechnology,* 23: 1126-1136, 2005;
Holm et al., *Nucleic Acids Res.* 27:244-47, 1999;
Hu et al., *Cancer Res.,* 56: 3055-3061, 1996;
Hubert, et al *Proc. Natl. Acad. Sci. U.S.A.* 96: 14523-14528, 1999;
Hudson and Kortt *J. Immunol. Methods,* 231: 177-189, 1999;
Hunter et al., *Nucleic Acids Research* 37: D211-D215, 2009;
Hust et al., *BMC Biotechnology* 7:14, 2007;
Iwamoto et al., *Oncogene.* 5(4):535-42, 1990;
Johnson et al, *Cancer Res,* 46: 850-857, 1986;
Jakobovits et al. *Nature Biotechnology* 25, 1134-1143, 2007;
Jones, *Curr. Opin. Struct. Biol.* 6:210-216, 1996;
Johnson and Wu, *Nucleic acids research* 28: 214-218, 2000;
Junutula et al., *Nature Biotechnology* 26: 925-932, 2008;
Kabat *Sequences of Proteins of Immunological Interest*, National Institutes of Health, Bethesda, Md., 1987 and 1991;
Karpusas et al., *J Mol Biol.* 327:1031-1041, 2003;
Kawabata et al., *Proteins* 41: 108-122, 2000
Kawabata, *Nucleic Acids Res.* 31: 3367-3369, 2003;
Kim. et al., *Mol Cancer Ther.* 7: 2486-2497, 2008;
Kim, et al., *Infect. Immun.* 57:944, 1989;
King et al., *Biochemistry,* 17: 1499-1506, 1978;
Kirkland et al, *J Immunol,* 137: 3614-3619, 1986;
Kohler and Milstein *Nature,* 256:495-497, 1975;
Kortt et al *Protein Eng,* 10: 423-433, 1997;
Kortt et al., *Biomol. Eng.,* 18: 95-108, 2001;
Kostelny et al, *J. Immunol.,* 148(5):1547-1553, 1992;
Kruif and Logtenberg *J. Biol. Chem.,* 271: 7630-7634, 1996;
Kunkel et al *Proc. Natl. Acad. Sci. USA* 82:488, 1987;
Lambert *Curr. Opinion in Pharmacology* 5:543-549, 2005;
Largaespada et al, *Curr. Top. Microbiol. Immunol,* 166, 91-96, 1990;
Larson et al., *J Mol Biol.,* 348:1177-1190, 2005;
Le Gall et al *FEBS Lett,* 453: 164-168, 1999;
Lee et al *FEBS Lett.* 418(1-2):195-199, 1998;
Lewis et al *Bioconj. Chem.* 9:72-86, 1998;
Li et al., *Bioconjug Chem* 17: 68-76, 2006;
Lindmark et al. *J Immunol Meth.* 62: 1-13, 1983;
Lonberg, N. "Transgenic Approaches to Human Monoclonal Antibodies." *Handbook of Experimental Pharmacology* 113: 49-101, 1994;
Lukacs et al. *J. Exp. Med.,* 194: 551-555, 2001;
Marsh et al *Hum. Mol. Genet.* 9, 13-25, 2000;
Matsui et al., *Cell.* 61(6):1147-55, 1990;
Matusik et al., Transgenic mouse models of prostate cancer. In: Transgenics in Endocrinology, ed. by M M Matzuk, C W Brown, and T R Kumar. The Humana Press Inc (Totowa, N.J.) Chapter 19, pp 401-425, 2001
Merrifield, *J. Am. Chem. Soc.,* 85:2149-2154, 1963;
Moldenhauer et al, *Scand J Immunol,* 32: 77-82, 1990;
Morel et al, *Curr Stud Hematol Blood Transfus,* 55: 53-63, 1988;
Moult, *Curr. Opin. Biotechnol.* 7:422-27, 1996;
Muller et al *Eur. J. Immunol.* 22 (6): 1621-1625, 1992;
Muller et al *EMBO J.* 9(3):907-13, 1990;
Murzin et al *J. Mol. Biol.* 247: 536-540, 1995;
Mutsushima et al., *Chem. Lett.,* 773-776, 1980;
Nakamuta., et al *Biochem. Biophys. Res. Commun.* 177, 34-39, 1991;
Nakayama et al *Biochem. Biophys. Res. Commun.* 277(1): 124-127, 2000;
Nagase et al *DNA Res.* 7 (2): 143-150, 2000;
Nguyen et al., *Adv Immunol,* 79:261-296
Panchenko et al. *J. Mol. Biol.* 296: 1319-1331, 2000;
Pei et al. *Proc Natl Acad Sci USA.* 94: 9637-9642, 1997;
Perbal et al. A Practical Guide to Molecular Cloning, John Wiley and Sons, 1984;

Perisic et al., *Structure.* 2:1217-1226, 1994;
Plückthun, *Immunol. Revs.,* 130:151-188, 1992;
Presta et al., *Cancer Res.,* 57: 4593-4599, 1997
Ramseier and Chang *Analyt. Biochem.,* 221: 231-233, 1994;
Ramanujam et al, *IEEE Transactions on Biomedical Engineering,* 48:1034-1041, 2001;
Roberge, et al., *Protein Eng Des Sel* 19: 141-145, 2006;
Ross et al., Cancer Res, 62: 2546-2553, 2002;
Reddy et al., *Synthesis Stutgart:* 999-1002, 1988;
Reiter et al *Proc. Natl. Acad. Sci. U.S.A.* 95, 1735-1740, 1998;
Riechmann et al. *J Immunol Methods,* 231:25-38, 1999;
Risma et al., *Proc Natl Acad Sci USA.;* 92(5):1322-6, 1995;
Roby et al., *Carcinogenesis.* 21(4):585-91, 2000;
Rodwell et al, *Proc. Natl. Acad. Sci. USA* 83: 2632-2636, 1986;
Rost et al. 270: 471-480, 1997;
Roux et al. *J. Immunol.* 161:4083, 1998;
Saha et al., BcePred:Prediction of Continuous B-Cell Epitopes in Antigenic
Sequences Using Physico-chemical Properties. In Nicosia, Cutello, Bentley and Timis (Eds.) ICARIS 2004, LNCS 3239, 197-204, Springer, 2004;
Sakaguchi et al. *Nature,* 426: 454-460;
Sali and Blundell, *J. Mol. Biol.* 234, 779-815, 1993;
Sambrook et al. Molecular Cloning: A Laboratory Manual, Cold Spring Harbour Laboratory Press, 1989;
Sanders et al., *Thyroid* 17: 395-410, 2007;
Schelte et al., *Bioconj. Chem.* 11: 118-123, 2000;
Shalaby et al, *J. Exp. Med.,* 175: 217-225, 1992;
Shao et al., *Mol Immunol,* 44: 656-665
Shen et al., *Protein Sci.* 15: 2507-2524, 2006;
Sirk et al., *Bioconjug Chem.* 19: 2527-2534, 2008;
Skerra et al, *Curr. Opinion in Immunol.,* 5:256-262, 1993;
Stahli et al, *Methods Enzymol,* 92: 242-253, 1983;
Stanfield et al., *J Virol.* 80:6093-6105, 2006;
Tang et al. *J. Exp. Med.,* 199: 1455-1465, 2004;
Thompson et al, *Science,* 293: 2108-2111, 2001;
Todorovska et al., *J. Immunol. Methods,* 248: 47-66, 2001;
Tonnelle et al, *EMBO J,* 4: 2839-2847, 1985;
Trenado et al. *J. Clin. Invest.,* 112: 1688-1696, 2002;
Vallette et al *Nuc. Acids Res.* 17:723-733, 1989;
Van der Sluis et al. *Gastroenterology* 131: 117-129, 2006;
Vitetta et al., Immunol Today, 14: 252-259, 1993;
Wang et al. *J Clin Invest.* 118(7): 2629-2639, 2008;
Weissinger et al. Proc. Natl. Acad. Sci USA, 88, 8735-8739, 1991;
Wells et al *Gene* 34:315-323, 1985;
Wilson et al, *J Exp Med,* 173: 137-146, 1991;
Xu and Xu *Proteins: Structure, Function, and Genetics* 40: 343-354, 2000;
Xu et al, *Proc Natl Acad Sci USA,* 98: 10692-10697, 2001;
Yamaguchi et al *Biol. Chem.* 269 (2), 805-808, 1994;
Yem et al., *J. Biol. Chem.,* 267: 3122-3128, 1992;
Zalipsky et al., *J. Bioact. Compat. Polym.,* 5: 227-231, 1990
Zalipsky et al., *Biotechnol. Appl. Biochem.,* 15: 100-114, 1992;
Zhang and Tam, *Anal. Biochem.* 233: 87-93, 1996;
Zoller et al *Methods Enzymol.* 100:468-500, 1983;
Zoller and Smith. *Nucl. Acids Res.* 10:6487-6500, 1982; and
Zhou et al., Proc Natl Acad Sci USA. 102: 14575-14580, 2005.

The invention claimed is:

1. An isolated protein comprising an immunoglobulin heavy chain variable region ($V_H$) and an immunoglobulin variable region ($V_L$), wherein at least one of the variable regions comprises:

(i) at least two cysteine residues substituted at positions exposed to solvent within a framework region (FR) 2, wherein: the at least two cysteine residues consist of 2, 4, or 6 cysteine residues, and wherein: if the at least two cysteine residues in the FR2, are not conjugated to a compound then an intra-framework region disulphide bond is capable of forming between the at least two cysteine residues in the FR2; or (ii) at least two cysteine residues substituted at positions exposed to solvent within a framework region (FR) 3, wherein the at least two cysteine residues consist of 2, 4, or 6 cysteine residues, and wherein if the at least two cysteine residues in the FR3 are not conjugated to a compound then an intra-framework region disulphide bond is capable of forming between the at least two cysteine residues in FR3.

2. The isolated protein according to claim 1, wherein the at least two cysteine residues are within a $V_L$, and wherein cysteine residues within FR2 are positioned between residues 35 to 49 numbered according to the Kabat numbering system, and cysteine residues within FR3 are positioned between residues 57 to 88 numbered according to the Kabat numbering system.

3. The isolated protein according to claim 2, wherein the cysteine residues within FR2 are positioned between residues 39 to 45 numbered according to the Kabat numbering system, and/or the cysteine residues within FR3 are positioned between residues 68 to 86 numbered according to the Kabat numbering system.

4. The isolated protein according to claim 2, wherein the $V_H$ Kabat positions are selected from the group consisting of: (i) H39 and H43; (ii) H39 and H45; (iii) H70 and H79; or (iv) H72 and H75.

5. The isolated protein according to claim 1 that specifically binds to human epidermal growth factor (Her) 2, tumor associated glycoprotein TAG72, MUC1 or prostate specific membrane antigen (PSMA).

6. The isolated protein according to claim 1, wherein the protein comprises a $V_H$ and a $V_L$ comprising sequences at least about 80% identical to a $V_H$ and a $V_L$ sequence set forth in any one or more of SEQ ID NOs: 59, 61, 63 or 65, modified to include the two or more cysteine residues positioned within FR2 or FR3.

7. The isolated protein according to claim 6 comprising a sequence at least about 80% identical to a sequence set forth in any one or more of SEQ ID NO: 101, 103, 105, 107, 109, 111, 113, 115, 117, 119, 121, 123, 125, 127, 129, 131, 133, 135, 137, 139, 141, 143, 145, 147 or 149, optionally comprising a N-terminal serine residue.

8. The isolated protein according to claim 6, wherein the isolated protein is a diabody, triabody, or tetrabody.

9. The isolated protein according to claim 1 further comprising a compound conjugated to at least one of the cysteine residues, wherein the conjugated compound does not reduce binding of the isolated protein to an antigen.

10. The isolated protein according to claim 1, further comprising an N-terminal threonine or an N-terminal serine residue.

11. The isolated protein according to claim 10 comprising a compound conjugated to the N-terminal threonine or serine residue, wherein the conjugated compound does not reduce binding of the protein to an antigen.

12. The isolated protein according to claim 11 comprising a first compound conjugated to at least one of the cysteine residues in FR2 or FR3 and a second compound conjugated to the N-terminal threonine or serine residue, wherein the second compound is different from the first compound.

13. The isolated protein according to claim 1, wherein the at least two cysteine residues are within a $V_L$, and wherein cysteine residues within FR2 are positioned between residues 35 to 49 numbered according to the Kabat numbering system, and cysteine residues within FR3 are positioned between residues 57 to 88 numbered according to the Kabat numbering system.

14. The isolated protein according to claim 13, wherein the $V_L$ Kabat positions are selected from the group consisting of: (i) L38 and L42; (ii) L38 and L44; or (iii) L65 and L72.

15. The isolated protein according to claim 1, comprising a disulphide bond between the at least two cysteine residues.

16. The isolated protein according to claim 1, wherein the at least two cysteine residues consist of 2 or 4 cysteine residues.

17. The isolated protein according to claim 16, wherein the at least two cysteine residues consist of 2 cysteine residues.

18. The isolated protein according to claim 1, wherein both the immunoglobulin heavy chain variable region ($V_H$) and the immunoglobulin light chain variable region ($V_L$) comprise at least two cysteine residue substitutions.

19. The isolated protein according to claim 1, comprising (i) and (ii).

20. The isolated protein according to claim 1, wherein the isolated protein is an avibody.

21. A composition comprising the isolated protein according to claim 1 and a pharmaceutically acceptable carrier.

22. An isolated protein comprising a Fv comprising at least one isolated protein according to claim 1 in which at least one $V_L$ associates with at least one $V_H$ to form an antigen binding site.

23. The isolated protein according to claim 22, wherein the $V_L$ and the $V_H$ which form the antigen binding site are in a single polypeptide chain.

24. The isolated protein according to claim 23, which is:

(i) a single chain $F_v$ fragment (sc Fv);

(ii) a dimeric scFv (di-scFv); or (iii) at least one of (i) and/or (ii) linked to a Fc or a heavy chain constant domain ($C_H$) 2 or $C_H3$.

25. The isolated protein according to claim 22, wherein the $V_L$ and $V_H$ which form the antigen binding site are in different polypeptide chains.

26. A method for producing an isolated protein comprising a conjugated compound, the method comprising:

(i) obtaining the isolated protein according to claim 1; and (ii) conjugating a compound to at least one of the cysteine residues in the FR2 or FR3 regions of the isolated protein to thereby produce the isolated protein comprising a conjugated compound.

27. The method according to claim 26, wherein the protein comprises at least one N-terminal serine or N-terminal threonine residue and the method additionally comprises conjugating a compound to the N-terminal serine or threonine residue.

28. A method for detecting an antigen in a biological sample, the method comprising contacting the biological sample from the subject with the composition according to claim 1 for a time and under conditions sufficient for the protein to bind to the antigen and form a complex, and detecting the complex.

29. A method for localising or detecting an antigen in a subject, said method comprising:

(i) administering to a subject the protein according to claim 12 for a time and under conditions sufficient for the protein to bind to an antigen, wherein the conjugated compound is a detectable label; and (ii) detecting or localising the detectable label in vivo.

* * * * *

SEQUENCE LISTING

<160> NUMBER OF SEQ ID NOS: 157

<210> SEQ ID NO 1
<211> LENGTH: 14
<212> TYPE: PRT
<213> ORGANISM: artificial sequence
<220> FEATURE:
<223> OTHER INFORMATION: amino acid sequence of FR2 of a human antibody heavy chain

<400> SEQUENCE: 1

Trp Val Arg Gln Ala Pro Gly Lys Gly Leu Glu Trp Val Ser
1 5 10

<210> SEQ ID NO 2
<211> LENGTH: 14
<212> TYPE: PRT
<213> ORGANISM: artificial sequence
<220> FEATURE:
<223> OTHER INFORMATION: amino acid sequence of FR2 of a human antibody heavy chain

<400> SEQUENCE: 2

Trp Val Arg Gln Ala Pro Gly Lys Gly Leu Glu Trp Val Gly
1 5 10

<210> SEQ ID NO 3
<211> LENGTH: 13
<212> TYPE: PRT
<213> ORGANISM: artificial sequence
<220> FEATURE:
<223> OTHER INFORMATION: amino acid sequence of FR2 of a human antibody heavy chain

<400> SEQUENCE: 3

```
Trp Val Arg Gln Ala Pro Gly Gln Leu Glu Trp Met Gly
1               5                   10


<210> SEQ ID NO 4
<211> LENGTH: 14
<212> TYPE: PRT
<213> ORGANISM: artificial sequence
<220> FEATURE:
<223> OTHER INFORMATION: amino acid sequence of FR2 of a human antibody
      heavy chain

<400> SEQUENCE: 4

Trp Val Arg Gln Ala Pro Gly Lys Gly Leu Glu Trp Met Gly
1               5                   10


<210> SEQ ID NO 5
<211> LENGTH: 14
<212> TYPE: PRT
<213> ORGANISM: artificial sequence
<220> FEATURE:
<223> OTHER INFORMATION: amino acid sequence of FR2 of a human antibody
      heavy chain

<400> SEQUENCE: 5

Trp Ile Arg Gln Pro Pro Gly Lys Gly Leu Glu Trp Ile Gly
1               5                   10


<210> SEQ ID NO 6
<211> LENGTH: 14
<212> TYPE: PRT
<213> ORGANISM: artificial sequence
<220> FEATURE:
<223> OTHER INFORMATION: amino acid sequence of FR2 of a human antibody
      heavy chain

<400> SEQUENCE: 6

Trp Ile Arg Gln Pro Pro Gly Lys Ala Leu Glu Trp Leu Gly
1               5                   10


<210> SEQ ID NO 7
<211> LENGTH: 14
<212> TYPE: PRT
<213> ORGANISM: artificial sequence
<220> FEATURE:
<223> OTHER INFORMATION: amino acid sequence of FR2 of a human antibody
      heavy chain

<400> SEQUENCE: 7

Trp Val Arg Gln Met Pro Gly Lys Gly Leu Glu Trp Met Gly
1               5                   10


<210> SEQ ID NO 8
<211> LENGTH: 14
<212> TYPE: PRT
<213> ORGANISM: artificial sequence
<220> FEATURE:
<223> OTHER INFORMATION: amino acid sequence of FR2 of a human antibody
      heavy chain

<400> SEQUENCE: 8

Trp Ile Arg Gln Ser Pro Ser Arg Gly Leu Glu Trp Leu Gly
1               5                   10


<210> SEQ ID NO 9
<211> LENGTH: 15
<212> TYPE: PRT
<213> ORGANISM: artificial sequence
```

```
<220> FEATURE:
<223> OTHER INFORMATION: amino acid sequence of FR2 of a human antibody
      kappa light chain

<400> SEQUENCE: 9

Trp Tyr Gln Gln Lys Pro Gly Lys Ala Pro Lys Leu Leu Ile Tyr
1               5                   10                  15


<210> SEQ ID NO 10
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 10

Trp Tyr Gln Gln Lys Pro Gly Gln Ala Pro Arg Leu Leu Ile Tyr
1               5                   10                  15


<210> SEQ ID NO 11
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 11

Trp Tyr Gln Gln Lys Pro Gly Gln Pro Pro Lys Leu Leu Ile Tyr
1               5                   10                  15


<210> SEQ ID NO 12
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 12

Trp Tyr Leu Gln Lys Pro Gly Gln Ser Pro Gln Leu Leu Ile Tyr
1               5                   10                  15


<210> SEQ ID NO 13
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 13

Trp Tyr Gln Gln Lys Pro Cys Gln Ala Pro Arg Leu Leu Ile Tyr
1               5                   10                  15


<210> SEQ ID NO 14
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 14

Trp Phe Gln Gln Lys Pro Gly Lys Ala Pro Lys Ser Leu Ile Tyr
1               5                   10                  15
```

```
<210> SEQ ID NO 15
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 15

Trp Tyr Gln Gln Lys Pro Ala Lys Ala Pro Lys Leu Phe Ile Tyr
1               5                   10                  15


<210> SEQ ID NO 16
<211> LENGTH: 15
<212> TYPE: PRT
<213> ORGANISM: artificial sequence
<220> FEATURE:
<223> OTHER INFORMATION: amino acid sequence of FR2 of a human antibody
      kappa light chain

<400> SEQUENCE: 16

Trp Tyr Leu Gln Lys Pro Gly Gln Pro Pro Gln Leu Leu Ile Tyr
1               5                   10                  15


<210> SEQ ID NO 17
<211> LENGTH: 15
<212> TYPE: PRT
<213> ORGANISM: artificial sequence
<220> FEATURE:
<223> OTHER INFORMATION: amino acid sequence of FR2 of a human antibody
      lambda light chain

<400> SEQUENCE: 17

Trp Tyr Gln Gln Leu Pro Gly Thr Ala Pro Lys Leu Leu Ile Tyr
1               5                   10                  15


<210> SEQ ID NO 18
<211> LENGTH: 15
<212> TYPE: PRT
<213> ORGANISM: artificial sequence
<220> FEATURE:
<223> OTHER INFORMATION: amino acid sequence of FR2 of a human antibody
      lambda light chain

<400> SEQUENCE: 18

Trp Tyr Gln Gln His Pro Gly Lys Ala Pro Lys Leu Met Ile Tyr
1               5                   10                  15


<210> SEQ ID NO 19
<211> LENGTH: 15
<212> TYPE: PRT
<213> ORGANISM: artificial sequence
<220> FEATURE:
<223> OTHER INFORMATION: amino acid sequence of FR2 of a human antibody
      lambda light chain

<400> SEQUENCE: 19

Trp Tyr Gln Gln Lys Pro Gly Gln Ala Pro Val Leu Val Ile Tyr
1               5                   10                  15


<210> SEQ ID NO 20
<211> LENGTH: 15
<212> TYPE: PRT
<213> ORGANISM: artificial sequence
<220> FEATURE:
<223> OTHER INFORMATION: amino acid sequence of FR2 of a human antibody
      lambda light chain
```

```
<400> SEQUENCE: 20

Trp Tyr Gln Gln Lys Pro Gly Gln Ser Pro Val Leu Val Ile Tyr
1               5                   10                  15


<210> SEQ ID NO 21
<211> LENGTH: 15
<212> TYPE: PRT
<213> ORGANISM: artificial sequence
<220> FEATURE:
<223> OTHER INFORMATION: amino acid sequence of FR2 of a human antibody
      lambda light chain

<400> SEQUENCE: 21

Trp His Gln Gln Gln Pro Glu Lys Gly Pro Arg Tyr Leu Met Tyr
1               5                   10                  15


<210> SEQ ID NO 22
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 22

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30


<210> SEQ ID NO 23
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 23

Arg Phe Thr Ile Ser Arg Asp Asn Ser Lys Asn Thr Leu His Leu Gln
1               5                   10                  15

Met Asn Ser Leu Arg Ala Glu Asp Thr Ala Val Tyr Tyr Cys Lys Arg
            20                  25                  30


<210> SEQ ID NO 24
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 24

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Arg
            20                  25                  30


<210> SEQ ID NO 25
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain
```

<400> SEQUENCE: 25

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 26
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 26

```
Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30
```

<210> SEQ ID NO 27
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 27

```
Arg Phe Val Phe Ser Leu Asp Thr Ser Val Ser Thr Ala Tyr Leu Gln
1               5                   10                  15

Met Ser Ser Leu Lys Ala Glu Asp Thr Ala Val Tyr Tyr Cys Ala Arg
            20                  25                  30
```

<210> SEQ ID NO 28
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 28

```
Arg Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30
```

<210> SEQ ID NO 29
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 29

```
Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 30
<211> LENGTH: 33

<212> TYPE: PRT
<213> ORGANISM: artificial sequence
<220> FEATURE:
<223> OTHER INFORMATION: amino acid sequence of FR3 of a human antibody heavy chain

<400> SEQUENCE: 30

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys Ala Lys
            20                  25                  30

Asp
```

<210> SEQ ID NO 31
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 31

```
Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 32
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 32

```
Arg Val Thr Met Thr Arg Asn Thr Ser Ile Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 33
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 33

```
Arg Phe Thr Ile Ser Arg Asp Asn Ser Lys Asn Thr Leu His Leu Gln
1               5                   10                  15

Met Asn Ser Leu Arg Ala Glu Asp Thr Ala Val Tyr Tyr Cys Lys Lys
            20                  25                  30
```

<210> SEQ ID NO 34
<211> LENGTH: 33
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 34

```
Arg Phe Thr Ile Ser Arg Asp Asn Ser Lys Asn Ser Leu Tyr Leu Gln
```

```
1               5                   10                  15

Met Asn Ser Leu Arg Thr Glu Asp Thr Ala Leu Tyr Tyr Cys Ala Lys
            20                  25                  30

Asp


<210> SEQ ID NO 35
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 35

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30


<210> SEQ ID NO 36
<211> LENGTH: 33
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 36

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

Ile


<210> SEQ ID NO 37
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 37

Arg Phe Val Phe Ser Leu Asp Thr Ser Val Ser Thr Ala Tyr Leu Gln
1               5                   10                  15

Ile Cys Ser Leu Lys Ala Glu Asp Thr Ala Val Tyr Tyr Cys Ala Arg
            20                  25                  30


<210> SEQ ID NO 38
<211> LENGTH: 32
<212> TYPE: PRT
<213> ORGANISM: artificial sequence
<220> FEATURE:
<223> OTHER INFORMATION: amino acid sequence of FR3 of a human antibody
      heavy chain

<400> SEQUENCE: 38

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Tyr Tyr Cys Ala Arg
            20                  25                  30


<210> SEQ ID NO 39
```

<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 39

His Val Thr Ile Ser Ala Asp Lys Ser Ile Ser Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 40
<211> LENGTH: 32
<212> TYPE: PRT
<213> ORGANISM: artificial sequence
<220> FEATURE:
<223> OTHER INFORMATION: amino acid sequence of FR3 of a human antibody heavy chain

<400> SEQUENCE: 40

Arg Val Thr Met Thr Arg Asp Thr Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 41
<211> LENGTH: 32
<212> TYPE: PRT
<213> ORGANISM: artificial sequence
<220> FEATURE:
<223> OTHER INFORMATION: amino acid sequence of FR3 of a human antibody kappa light chain

<400> SEQUENCE: 41

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 42
<211> LENGTH: 32
<212> TYPE: PRT
<213> ORGANISM: artificial sequence
<220> FEATURE:
<223> OTHER INFORMATION: amino acid sequence of FR3 of a human antibody kappa light chain

<400> SEQUENCE: 42

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 43
<211> LENGTH: 32
<212> TYPE: PRT
<213> ORGANISM: artificial sequence
<220> FEATURE:
<223> OTHER INFORMATION: amino acid sequence of FR3 of a human antibody kappa light chain

<400> SEQUENCE: 43

Gly Val Pro Ser Arg Phe Ser Gly Ser Gly Ser Gly Thr Glu Phe Thr
1 5 10 15

```
Leu Thr Ile Ser Ser Leu Gln Pro Asp Asp Phe Ala Thr Tyr Tyr Cys
            20                  25                  30


<210> SEQ ID NO 44
<211> LENGTH: 32
<212> TYPE: PRT
<213> ORGANISM: artificial sequence
<220> FEATURE:
<223> OTHER INFORMATION: amino acid sequence of FR3 of a human antibody
      kappa light chain

<400> SEQUENCE: 44

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30


<210> SEQ ID NO 45
<211> LENGTH: 32
<212> TYPE: PRT
<213> ORGANISM: artificial sequence
<220> FEATURE:
<223> OTHER INFORMATION: amino acid sequence of FR3 of a human antibody
      kappa light chain

<400> SEQUENCE: 45

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30


<210> SEQ ID NO 46
<211> LENGTH: 32
<212> TYPE: PRT
<213> ORGANISM: artificial sequence
<220> FEATURE:
<223> OTHER INFORMATION: amino acid sequence of FR3 of a human antibody
      kappa light chain

<400> SEQUENCE: 46

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30


<210> SEQ ID NO 47
<211> LENGTH: 32
<212> TYPE: PRT
<213> ORGANISM: artificial sequence
<220> FEATURE:
<223> OTHER INFORMATION: amino acid sequence of FR3 of a human antibody
      kappa light chain

<400> SEQUENCE: 47

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30


<210> SEQ ID NO 48
<211> LENGTH: 32
<212> TYPE: PRT
<213> ORGANISM: artificial sequence
<220> FEATURE:
<223> OTHER INFORMATION: amino acid sequence of FR3 of a human antibody
```

kappa light chain

<400> SEQUENCE: 48

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 49
<211> LENGTH: 32
<212> TYPE: PRT
<213> ORGANISM: artificial sequence
<220> FEATURE:
<223> OTHER INFORMATION: amino acid sequence of FR3 of a human antibody lambda light chain

<400> SEQUENCE: 49

Gly Val Pro Ser Arg Phe Ser Gly Ser Gly Ser Gly Thr Asp Phe Thr
1 5 10 15

Leu Thr Ile Ser Cys Leu Gln Ser Glu Asp Phe Ala Thr Tyr Tyr Cys
20 25 30

<210> SEQ ID NO 50
<211> LENGTH: 32
<212> TYPE: PRT
<213> ORGANISM: artificial sequence
<220> FEATURE:
<223> OTHER INFORMATION: amino acid sequence of FR3 of a human antibody lambda light chain

<400> SEQUENCE: 50

Gly Val Pro Ser Arg Phe Ser Gly Ser Gly Ser Gly Thr Glu Phe Thr
1 5 10 15

Leu Thr Ile Ser Ser Leu Gln Pro Glu Asp Phe Ala Thr Tyr Tyr Cys
20 25 30

<210> SEQ ID NO 51
<211> LENGTH: 32
<212> TYPE: PRT
<213> ORGANISM: artificial sequence
<220> FEATURE:
<223> OTHER INFORMATION: amino acid sequence of FR3 of a human antibody lambda light chain

<400> SEQUENCE: 51

Gly Ile Pro Ala Arg Phe Ser Gly Ser Gly Pro Gly Thr Asp Phe Thr
1 5 10 15

Leu Thr Ile Ser Ser Leu Glu Pro Glu Asp Phe Ala Val Tyr Tyr Cys
20 25 30

<210> SEQ ID NO 52
<211> LENGTH: 32
<212> TYPE: PRT
<213> ORGANISM: artificial sequence
<220> FEATURE:
<223> OTHER INFORMATION: amino acid sequence of FR3 of a human antibody lambda light chain

<400> SEQUENCE: 52

Gly Val Pro Ser Arg Phe Ser Gly Ser Gly Ser Gly Thr Asp Phe Thr
1 5 10 15

Leu Thr Ile Asn Ser Leu Glu Ala Glu Asp Ala Ala Thr Tyr Tyr Cys
20 25 30

```
<210> SEQ ID NO 53
<211> LENGTH: 32
<212> TYPE: PRT
<213> ORGANISM: artificial sequence
<220> FEATURE:
<223> OTHER INFORMATION: amino acid sequence of FR3 of a human antibody
      lambda light chain

<400> SEQUENCE: 53

Gly Ile Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30


<210> SEQ ID NO 54
<211> LENGTH: 32
<212> TYPE: PRT
<213> ORGANISM: artificial sequence
<220> FEATURE:
<223> OTHER INFORMATION: amino acid sequence of FR3 of a human antibody
      lambda light chain

<400> SEQUENCE: 54

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30


<210> SEQ ID NO 55
<211> LENGTH: 32
<212> TYPE: PRT
<213> ORGANISM: artificial sequence
<220> FEATURE:
<223> OTHER INFORMATION: amino acid sequence of FR3 of a human antibody
      lambda light chain

<400> SEQUENCE: 55

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30


<210> SEQ ID NO 56
<211> LENGTH: 32
<212> TYPE: PRT
<213> ORGANISM: artificial sequence
<220> FEATURE:
<223> OTHER INFORMATION: amino acid sequence of FR3 of a human antibody
      lambda light chain

<400> SEQUENCE: 56

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30


<210> SEQ ID NO 57
<211> LENGTH: 5
<212> TYPE: PRT
<213> ORGANISM: Artificial
<220> FEATURE:
<223> OTHER INFORMATION: amino acid sequence of a linker

<400> SEQUENCE: 57

Gly Gly Gly Gly Ser
1               5
```

<210> SEQ ID NO 58
<211> LENGTH: 711
<212> TYPE: DNA
<213> ORGANISM: Artificial
<220> FEATURE:
<223> OTHER INFORMATION: nucleotide sequence encoding AVP04-07 anti TAG72 diabody

<400> SEQUENCE: 58

```
caggtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc agcggtagcg gcaccgattt taccctgagc    600

attagcagcg tggaaaccga agatctggcg gtgtattatt gccagcagta ttatagctat    660

ccgctgacct ttggtgcggg caccaaactg gtgctgaaac gtgcggccgc g             711
```

<210> SEQ ID NO 59
<211> LENGTH: 245
<212> TYPE: PRT
<213> ORGANISM: Artificial
<220> FEATURE:
<223> OTHER INFORMATION: amino acid sequence of AVP04-07 anti-TAG72 diabody

<400> SEQUENCE: 59

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175
```

```
Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245


<210> SEQ ID NO 60
<211> LENGTH: 804
<212> TYPE: DNA
<213> ORGANISM: Artificial
<220> FEATURE:
<223> OTHER INFORMATION: nucleotide sequence encoding AVP07-17 anti-Her2
      diabody

<400> SEQUENCE: 60

caggtgcagc tggtgcagtc tggggcagag gtgaaaaagc ccggggagtc tctgaagatc      60

tcctgtaagg gttctggata cagctttacc agctactgga tcgcctgggt gcgccagatg     120

cccgggaaag gcctggagta catggggctc atctatcctg gtgactctga caccaaatac     180

agcccgtcct tccaaggcca ggtcaccatc tcagtcgaca agtccgtcag cactgcctac     240

ttgcaatgga gcagtctgaa gccctcggac agcgccgtgt atttttgtgc gagacatgac     300

gtgggatatt gcagtagttc caactgcgca aagtggcctg aatacttcca gcattggggc     360

cagggcaccc tggtcaccgt ttcctcaggt ggaggcggtt cacagtctgt gttgacgcag     420

ccgccctcag tgtctgcggc cccaggacag aaggtcacca tctcctgctc tggaagcagc     480

tccaacattg ggaataatta tgtatcctgg taccagcagc tcccaggaac agtccccaaa     540

ctcctcatct atggtcacac caatcggccc gcaggggtcc ctgaccgatt ctctggctcc     600

aagtctggca cctcagcctc cctggccatc agtgggttcc ggtccgagga tgaggctgat     660

tattactgtg cagcatggga tgacagcctg agtggttggg tgttcggcgg agggaccaag     720

ctgaccgtcc taggtgcggc cgcagaacaa aaactcatct cagaagagga tctgaatggg     780

gccgcacatc accatcatca ccat                                            804


<210> SEQ ID NO 61
<211> LENGTH: 268
<212> TYPE: PRT
<213> ORGANISM: Artificial
<220> FEATURE:
<223> OTHER INFORMATION: amino acid sequence of AVP07-17 anti-Her2
      diabody

<400> SEQUENCE: 61

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
```

```
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

<210> SEQ ID NO 62
<211> LENGTH: 729
<212> TYPE: DNA
<213> ORGANISM: Artificial
<220> FEATURE:
<223> OTHER INFORMATION: nucleotide sequence encoding AVP02-60 anti-MucI diabody

<400> SEQUENCE: 62

```
gaagtgcagc tggttgaaag cggtggcgga gtggtgcagc caggtggaag cctgcgtctg      60

agctgcgcag caagcggttt tacctttagc agctatggca tgagctgggt gcgtcaggcg     120

ccggataaag gcctggaact ggtggcgacc attaacagca acggtggaag cacctattat     180

ccggatagcg tgaaaggccg ttttaccatt agccgtgata acagcaaaaa caccctgtat     240

ctgcagatga acagcctgcg taccgaagat accgcggtgt attattgcgc gcgtgatcgt     300

gatggctatg atgaaggctt tgattattgg ggccagggca ccctggtgac cgtgagcagc     360

ggtgggggcg gaagccagat tcagctgacc cagagcccga gcagcctgag cgcaagcgtg     420

ggtgatcgtg tgaccattac ctgcagcgcg agcagcagcg tgagctatat gcattggtat     480

cagcagaaac cgggcaaagc gccgaaacgt tggatttatg ataccagcaa actggcgagc     540

ggcgtgccga gccgttttag cggcagcggc agcggcaccg attatacctt taccattagc     600

agcctgcagc cggaagatat tgcgacctat tattgccagc agtggagcag caacccgccg     660

acctttggcc agggcaccaa actgcagatt aaacgtgcgg ccgcactcga gcaccaccac     720

caccaccac                                                             729
```

<210> SEQ ID NO 63
<211> LENGTH: 243
<212> TYPE: PRT

```
<213> ORGANISM: Artificial
<220> FEATURE:
<223> OTHER INFORMATION: amino acid sequence of AVP02-60 anti-MucI
      diabody

<400> SEQUENCE: 63

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His


<210> SEQ ID NO 64
<211> LENGTH: 804
<212> TYPE: DNA
<213> ORGANISM: Artificial
<220> FEATURE:
<223> OTHER INFORMATION: nucleotide sequence encoding a modified
      AVP07-17 anti-HER2 diabody replacing CDR3H Cysteine residues
      Cys104 (Kabat numbering H100) and Cys109 (H100E) with Alanines
      and comprising a N-terminal serine designated AVP07-86

<400> SEQUENCE: 64

agcgtgcagc tggtgcagtc tggggcagag gtgaaaaagc ccggggagtc tctgaagatc     60

tcctgtaagg gttctggata cagctttacc agctactgga tcgcctgggt gcgccagatg    120

cccgggaaag gcctggagta catggggctc atctatcctg gtgactctga caccaaatac    180

agcccgtcct tccaaggcca ggtcaccatc tcagtcgaca agtccgtcag cactgcctac    240

ttgcaatgga gcagtctgaa gccctcggac agcgccgtgt atttttgtgc gagacatgac    300

gtgggatatg cgagtagttc caacgcggca aagtggcctg aatacttcca gcattggggc    360
```

```
cagggcaccc tggtcaccgt ttcctcaggt ggaggcggtt cacagtctgt gttgacgcag    420

ccgccctcag tgtctgcggc cccaggacag aaggtcacca tctcctgctc tggaagcagc    480

tccaacattg ggaataatta tgtatcctgg taccagcagc tcccaggaac agtccccaaa    540

ctcctcatct atggtcacac caatcggccc gcaggggtcc ctgaccgatt ctctggctcc    600

aagtctggca cctcagcctc cctggccatc agtgggttcc ggtccgagga tgaggctgat    660

tattactgtg cagcatggga tgacagcctg agtggttggg tgttcggcgg agggaccaag    720

ctgaccgtcc taggtgcggc cgcagaacaa aaactcatct cagaagagga tctgaatggg    780

gccgcacatc accatcatca ccat                                           804


<210> SEQ ID NO 65
<211> LENGTH: 268
<212> TYPE: PRT
<213> ORGANISM: Artificial
<220> FEATURE:
<223> OTHER INFORMATION: amino acid sequence of modified AVP07-17
      anti-HER2 diabody replacing CDR3H Cysteine residues Cys104
      (Kabat numbering H100) and Cys109 (H100E) with Alanines and
      comprising a N-terminal serine designated AVP07-86

<400> SEQUENCE: 65

Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

```
<210> SEQ ID NO 66
<211> LENGTH: 39
<212> TYPE: DNA
<213> ORGANISM: Artificial
<220> FEATURE:
<223> OTHER INFORMATION: nucleotide sequence of mutagenic primer for
      substituting the N-terminal Gln residue with a Ser residue in
      AVP04-07

<400> SEQUENCE: 66

cccagccggc catggcgagc gtgcagctgc agcagagcg                          39


<210> SEQ ID NO 67
<211> LENGTH: 39
<212> TYPE: DNA
<213> ORGANISM: Artificial
<220> FEATURE:
<223> OTHER INFORMATION: nucleotide sequence of mutagenic primer for
      substituting the N-terminal Gln residue with a Ser residue in
      AVP04-07

<400> SEQUENCE: 67

cgctctgctg cagctgcacg ctcgccatgg ccggctggg                          39


<210> SEQ ID NO 68
<211> LENGTH: 66
<212> TYPE: DNA
<213> ORGANISM: Artificial
<220> FEATURE:
<223> OTHER INFORMATION: nucleotide sequence of mutagenic primer for
      introducing cysteine residue substitutions at positions 38 and 42
      in the VL FR2 of AVP04-07

<400> SEQUENCE: 68

cagaaaaact atctggcgtg gtatcagtgc aaaccgggtt gcagcccgaa actgctgatt    60

tattgg                                                              66


<210> SEQ ID NO 69
<211> LENGTH: 66
<212> TYPE: DNA
<213> ORGANISM: Artificial
<220> FEATURE:
<223> OTHER INFORMATION: nucleotide sequence of mutagenic primer for
      introducing cysteine residue substitutions at positions 38 and 42
      in the VL FR2 of AVP04-07

<400> SEQUENCE: 69

ccaataaatc agcagtttcg ggctgcaacc cggtttgcac tgataccacg ccagatagtt    60

tttctg                                                              66


<210> SEQ ID NO 70
<211> LENGTH: 72
<212> TYPE: DNA
<213> ORGANISM: Artificial
<220> FEATURE:
<223> OTHER INFORMATION: nucleotide sequence of mutagenic primer for
      introducing cysteine residue substitutions at positions 38 and 44
      in the VL FR2 of AVP04-07

<400> SEQUENCE: 70

cagaaaaact atctggcgtg gtatcagtgc aaaccgggtc agagctgcaa actgctgatt    60

tattgggcga gc                                                       72


<210> SEQ ID NO 71
```

<211> LENGTH: 72
<212> TYPE: DNA
<213> ORGANISM: Artificial
<220> FEATURE:
<223> OTHER INFORMATION: nucleotide sequence of mutagenic primer for introducing cysteine residue substitutions at positions 38 and 44 in the VL FR2 of AVP04-07

<400> SEQUENCE: 71
gctcgcccaa taaatcagca gtttgcagct ctgacccggt ttgcactgat accacgccag 60
atagtttttc tg 72

<210> SEQ ID NO 72
<211> LENGTH: 65
<212> TYPE: DNA
<213> ORGANISM: Artificial
<220> FEATURE:
<223> OTHER INFORMATION: nucleotide sequence of mutagenic primer for introducing cysteine residue substitutions at positions 78 and 82 in the VL FR3 of AVP04-07

<400> SEQUENCE: 72
ccgattttac cctgagcatt agcagctgcg aaaccgaatg cctggcggtg tattattgcc 60
agcag 65

<210> SEQ ID NO 73
<211> LENGTH: 65
<212> TYPE: DNA
<213> ORGANISM: Artificial
<220> FEATURE:
<223> OTHER INFORMATION: nucleotide sequence of mutagenic primer for introducing cysteine residue substitutions at positions 78 and 82 in the VL FR3 of AVP04-07

<400> SEQUENCE: 73
ctgctggcaa taatacaccg ccaggcattc ggtttcgcag ctgctaatgc tcagggtaaa 60
atcgg 65

<210> SEQ ID NO 74
<211> LENGTH: 67
<212> TYPE: DNA
<213> ORGANISM: Artificial
<220> FEATURE:
<223> OTHER INFORMATION: nucleotide sequence of mutagenic primer for introducing cysteine residue substitutions at positions 39 and 43 in the VH FR2 of AVP04-07

<400> SEQUENCE: 74
cgatcatgcg attcattggg tgaaatgcaa tccggaatgc ggcctggaat ggattggcta 60
ttttagc 67

<210> SEQ ID NO 75
<211> LENGTH: 67
<212> TYPE: DNA
<213> ORGANISM: Artificial
<220> FEATURE:
<223> OTHER INFORMATION: nucleotide sequence of mutagenic primer for introducing cysteine residue substitutions at positions 39 and 43 in the VH FR2 of AVP04-07

<400> SEQUENCE: 75
gctaaaatag ccaatccatt ccaggccgca ttccggattg catttcaccc aatgaatcgc 60
atgatcg 67

<210> SEQ ID NO 76
<211> LENGTH: 70
<212> TYPE: DNA
<213> ORGANISM: Artificial
<220> FEATURE:
<223> OTHER INFORMATION: nucleotide sequence of mutagenic primer for introducing cysteine residue substitutions at positions 39 and 45 in the VH FR2 of AVP04-07

<400> SEQUENCE: 76
cgatcatgcg attcattggg tgaaatgcaa tccggaacag ggctgcgaat ggattggcta 60
ttttagcccg 70

<210> SEQ ID NO 77
<211> LENGTH: 70
<212> TYPE: DNA
<213> ORGANISM: Artificial
<220> FEATURE:
<223> OTHER INFORMATION: nucleotide sequence of mutagenic primer for introducing cysteine residue substitutions at positions 39 and 45 in the VH FR2 of AVP04-07

<400> SEQUENCE: 77
cgggctaaaa tagccaatcc attcgcagcc ctgttccgga ttgcatttca cccaatgaat 60
cgcatgatcg 70

<210> SEQ ID NO 78
<211> LENGTH: 58
<212> TYPE: DNA
<213> ORGANISM: Artificial
<220> FEATURE:
<223> OTHER INFORMATION: nucleotide sequence of mutagenic primer for introducing cysteine residue substitutions at positions 82C and 86 in the VH FR3 of AVP04-07

<400> SEQUENCE: 78
gcgtatctgc agctgaacag ctgcaccagc gaatgcagcg cggtgtattt ttgcaccc 58

<210> SEQ ID NO 79
<211> LENGTH: 58
<212> TYPE: DNA
<213> ORGANISM: Artificial
<220> FEATURE:
<223> OTHER INFORMATION: nucleotide sequence of mutagenic primer for introducing cysteine residue substitutions at positions 82C and 86 in the VH FR3 of AVP04-07

<400> SEQUENCE: 79
gggtgcaaaa atacaccgcg ctgcattcgc tggtgcagct gttcagctgc agatacgc 58

<210> SEQ ID NO 80
<211> LENGTH: 60
<212> TYPE: DNA
<213> ORGANISM: Artificial
<220> FEATURE:
<223> OTHER INFORMATION: nucleotide sequence of mutagenic primer for introducing cysteine residue substitutions at positions 70 and 79 in the VH FR3 of AVP04-07

<400> SEQUENCE: 80
ggcaaagcga ccctgtgcgc ggataaaagc agcagcaccg cgtgcctgca gctgaacagc 60

<210> SEQ ID NO 81
<211> LENGTH: 56
<212> TYPE: DNA
<213> ORGANISM: Artificial
<220> FEATURE:

<223> OTHER INFORMATION: nucleotide sequence of mutagenic primer for introducing cysteine residue substitutions at positions 70 and 79 in the VH FR3 of AVP04-07

<400> SEQUENCE: 81
cgctgctaat gcacagggta aaatcggtgc cgctaccgct gccgcaaaaa cgatcc 56

<210> SEQ ID NO 82
<211> LENGTH: 54
<212> TYPE: DNA
<213> ORGANISM: Artificial
<220> FEATURE:
<223> OTHER INFORMATION: nucleotide sequence of mutagenic primer for introducing cysteine residue substitutions at positions 72 and 75 in the VH FR3 of AVP04-07

<400> SEQUENCE: 82
ggcaaagcga ccctgaccgc gtgcaaaagc tgcagcaccg cgtatctgca gctg 54

<210> SEQ ID NO 83
<211> LENGTH: 54
<212> TYPE: DNA
<213> ORGANISM: Artificial
<220> FEATURE:
<223> OTHER INFORMATION: nucleotide sequence of mutagenic primer for introducing cysteine residue substitutions at positions 72 and 75 in the VH FR3 of AVP04-07

<400> SEQUENCE: 83
cagctgcaga tacgcggtgc tgcagctttt gcacgcggtc agggtcgctt tgcc 54

<210> SEQ ID NO 84
<211> LENGTH: 48
<212> TYPE: DNA
<213> ORGANISM: Artificial
<220> FEATURE:
<223> OTHER INFORMATION: nucleotide sequence of mutagenic primer for introducing cysteine residue substitutions at positions 65 and 72 in the VL FR3 of AVP04-07

<400> SEQUENCE: 84
cgttttaccg gctgcggtag cggcaccgat ttttgcctga gcattagc 48

<210> SEQ ID NO 85
<211> LENGTH: 48
<212> TYPE: DNA
<213> ORGANISM: Artificial
<220> FEATURE:
<223> OTHER INFORMATION: nucleotide sequence of mutagenic primer for introducing cysteine residue substitutions at positions 65 and 72 in the VL FR3 of AVP04-07

<400> SEQUENCE: 85
gctaatgctc aggcaaaaat cggtgccgct accgcagccg gtaaaacg 48

<210> SEQ ID NO 86
<211> LENGTH: 50
<212> TYPE: DNA
<213> ORGANISM: Artificial
<220> FEATURE:
<223> OTHER INFORMATION: nucleotide sequence of mutagenic primer for modification of linker residues of AVP04-79 for scFv expression

<400> SEQUENCE: 86
ctcggtcacc gtgagcagcg gtggcggcgg cagcggtggc ggcggcagcg 50

<210> SEQ ID NO 87

<211> LENGTH: 50
<212> TYPE: DNA
<213> ORGANISM: Artificial
<220> FEATURE:
<223> OTHER INFORMATION: nucleotide sequence of mutagenic primer for modification of linker residues of AVP04-79 for scFv expression

<400> SEQUENCE: 87
cgctgccgcc gccaccgctg ccgccgccac cgctgctcac ggtgaccgag 50

<210> SEQ ID NO 88
<211> LENGTH: 42
<212> TYPE: DNA
<213> ORGANISM: Artificial
<220> FEATURE:
<223> OTHER INFORMATION: nucleotide sequence of mutagenic primer for modification of linker residues of AVP04-79 for triabody expression

<400> SEQUENCE: 88
ggcacctcgg tcaccgtgag cgatatcgtg atgacccaga gc 42

<210> SEQ ID NO 89
<211> LENGTH: 42
<212> TYPE: DNA
<213> ORGANISM: Artificial
<220> FEATURE:
<223> OTHER INFORMATION: nucleotide sequence of mutagenic primer for modification of linker residues of AVP04-79 for triabody expression

<400> SEQUENCE: 89
gctctgggtc atcacgatat cgctcacggt gaccgaggtg cc 42

<210> SEQ ID NO 90
<211> LENGTH: 39
<212> TYPE: DNA
<213> ORGANISM: Artificial
<220> FEATURE:
<223> OTHER INFORMATION: nucleotide sequence of mutagenic primer for AVP07-17 anti-HER2 diabody replacing CDR3H Cysteine residues with alanines designated AVP07-86

<400> SEQUENCE: 90
cccagccggc catggcgagc gtgcagctgg tgcagtctg 39

<210> SEQ ID NO 91
<211> LENGTH: 39
<212> TYPE: DNA
<213> ORGANISM: Artificial
<220> FEATURE:
<223> OTHER INFORMATION: nucleotide sequence of mutagenic primer for AVP07-17 anti-HER2 diabody replacing CDR3H Cysteine residues with alanines designated AVP07-86

<400> SEQUENCE: 91
cagactgcac cagctgcacg ctcgccatgg ccggctggg 39

<210> SEQ ID NO 92
<211> LENGTH: 66
<212> TYPE: DNA
<213> ORGANISM: Artificial
<220> FEATURE:
<223> OTHER INFORMATION: nucleotide sequence of mutagenic primer for introducing cysteine residue substitutions at positions 38 and 42 in the VL FR2 of AVP02-60

<400> SEQUENCE: 92

```
cgtgagctat atgcattggt atcagtgcaa accgggctgc gcgccgaaac gttggattta     60

tgatac                                                                66


<210> SEQ ID NO 93
<211> LENGTH: 66
<212> TYPE: DNA
<213> ORGANISM: Artificial
<220> FEATURE:
<223> OTHER INFORMATION: nucleotide sequence of mutagenic primer for
      introducing cysteine residue substitutions at positions 38 and 42
      in the VL FR2 of AVP02-60

<400> SEQUENCE: 93

gtatcataaa tccaacgttt cggcgcgcag cccggtttgc actgatacca atgcatatag     60

ctcacg                                                                66


<210> SEQ ID NO 94
<211> LENGTH: 55
<212> TYPE: DNA
<213> ORGANISM: Artificial
<220> FEATURE:
<223> OTHER INFORMATION: nucleotide sequence of mutagenic primer for
      introducing cysteine residue substitutions at positions 39 and 43
      in the VH FR2 of AVP02-60

<400> SEQUENCE: 94

ctatggcatg agctgggtgc gttgcgcgcc ggattgcggc ctggaactgg tggcg          55


<210> SEQ ID NO 95
<211> LENGTH: 55
<212> TYPE: DNA
<213> ORGANISM: Artificial
<220> FEATURE:
<223> OTHER INFORMATION: nucleotide sequence of mutagenic primer for
      introducing cysteine residue substitutions at positions 39 and 43
      in the VH FR2 of AVP02-60

<400> SEQUENCE: 95

cgccaccagt tccaggccgc aatccggcgc gcaacgcacc cagctcatgc catag          55


<210> SEQ ID NO 96
<211> LENGTH: 65
<212> TYPE: DNA
<213> ORGANISM: Artificial
<220> FEATURE:
<223> OTHER INFORMATION: nucleotide sequence of mutagenic primer for
      introducing cysteine residue substitutions at positions 38 and 42
      in the VL FR2 of AVP07-86

<400> SEQUENCE: 96

gggaataatt atgtatcctg gtaccagtgc ctcccaggat gcgtccccaa actcctcatc     60

tatgg                                                                 65


<210> SEQ ID NO 97
<211> LENGTH: 65
<212> TYPE: DNA
<213> ORGANISM: Artificial
<220> FEATURE:
<223> OTHER INFORMATION: nucleotide sequence of mutagenic primer for
      introducing cysteine residue substitutions at positions 38 and 42
      in the VL FR2 of AVP07-86

<400> SEQUENCE: 97

ccatagatga ggagtttggg gacgcatcct gggaggcact ggtaccagga tacataatta     60

ttccc                                                                 65
```

<210> SEQ ID NO 98
<211> LENGTH: 51
<212> TYPE: DNA
<213> ORGANISM: Artificial
<220> FEATURE:
<223> OTHER INFORMATION: nucleotide sequence of mutagenic primer for introducing cysteine residue substitutions at positions 39 and 43 in the VH FR2 of AVP07-86

<400> SEQUENCE: 98
ggatcgcctg ggtgcgctgc atgcccgggt gcggcctgga gtacatgggg c 51

<210> SEQ ID NO 99
<211> LENGTH: 51
<212> TYPE: DNA
<213> ORGANISM: Artificial
<220> FEATURE:
<223> OTHER INFORMATION: nucleotide sequence of mutagenic primer for introducing cysteine residue substitutions at positions 39 and 43 in the VH FR2 of AVP07-86

<400> SEQUENCE: 99
gccccatgta ctccaggccg cacccgggca tgcagcgcac ccaggcgatc c 51

<210> SEQ ID NO 100
<211> LENGTH: 735
<212> TYPE: DNA
<213> ORGANISM: Artificial
<220> FEATURE:
<223> OTHER INFORMATION: nucleotide sequence of an anti-TAG72 diabody comprising cysteine replacement mutations in the VL FR2 Kabat positions 38 and 42 designated AVP04-79.

<400> SEQUENCE: 100
agcgtgcagc tgcagcagag cgatgcggaa ctggtgaaac cgggcgcgag cgtgaaaatt 60
agctgcaaag cgagcggcta tacctttacc gatcatgcga ttcattgggt gaaacagaat 120
ccggaacagg gcctggaatg gattggctat tttagcccgg gcaacgatga ttttaaatat 180
aacgaacgtt ttaaaggcaa agcgaccctg accgcggata aaagcagcag caccgcgtat 240
ctgcagctga acagcctgac cagcgaagat agcgcggtgt atttttgcac ccgtagcctg 300
aatatggcgt attggggtca gggcacctcg gtcaccgtga gcagcggtgg cggcggcagc 360
gatatcgtga tgacccagag cccgagcagc ctgccggtga gcgtgggcga aaaagtgacc 420
ctgagctgca aaagcagcca gagcctgctg tatagcggca atcagaaaaa ctatctggcg 480
tggtatcagt gcaaaccggg ttgcagcccg aaactgctga tttattgggc gagcacccgt 540
gaaagcggcg tgccggatcg ttttaccggc agcggtagcg gcaccgattt taccctgagc 600
attagcagcg tggaaaccga agatctggcg gtgtattatt gccagcagta ttatagctat 660
ccgctgacct ttggtgcggg caccaaactg gtgctgaaac gtgcggccgc actcgagcac 720
caccaccacc accac 735

<210> SEQ ID NO 101
<211> LENGTH: 245
<212> TYPE: PRT
<213> ORGANISM: Artificial
<220> FEATURE:
<223> OTHER INFORMATION: amino acid sequence of an anti-TAG72 diabody comprising cysteine replacement mutations in the VL FR2 Kabat positions 38 and 42 designated AVP04-79.

<400> SEQUENCE: 101

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Cys Lys Pro Gly Cys Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245
```

<210> SEQ ID NO 102
<211> LENGTH: 735
<212> TYPE: DNA
<213> ORGANISM: Artificial
<220> FEATURE:
<223> OTHER INFORMATION: nucleotide sequence of an anti-TAG72 diabody comprising cysteine replacement mutations in the VL FR2 Kabat positions 38 and 44 is designated AVP04-80.

<400> SEQUENCE: 102

```
agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagt gcaaaccggg tcagagctgc aaactgctga tttattgggc gagcacccgt    540

gaaagcggcg tgccggatcg ttttaccggc agcggtagcg gcaccgattt taccctgagc    600
```

```
attagcagcg tggaaaccga agatctggcg gtgtattatt gccagcagta ttatagctat    660

ccgctgacct ttggtgcggg caccaaactg gtgctgaaac gtgcggccgc actcgagcac    720

caccaccacc accac                                                     735


<210> SEQ ID NO 103
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VL FR2 Kabat
      positions 38 and 44 is designated AVP04-80.

<400> SEQUENCE: 103

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Cys Lys Pro Gly Gln Ser Cys Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245


<210> SEQ ID NO 104
<211> LENGTH: 735
<212> TYPE: DNA
<213> ORGANISM: Artificial
<220> FEATURE:
<223> OTHER INFORMATION: nucleotide sequence of an anti-TAG72 diabody
      comprising cysteine replacement mutations in the VL FR3 Kabat
      positions 78 and 82 designated AVP04-83.

<400> SEQUENCE: 104
```

```
agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc agcggtagcg gcaccgattt taccctgagc    600

attagcagct gcgaaaccga atgcctggcg gtgtattatt gccagcagta ttatagctat    660

ccgctgacct ttggtgcggg caccaaactg gtgctgaaac gtgcggccgc actcgagcac    720

caccaccacc accac                                                      735
```

```
<210> SEQ ID NO 105
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VL FR3 Kabat
      positions 78 and 82 designated AVP04-83.

<400> SEQUENCE: 105

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Ala Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Cys Glu Thr Glu Cys
        195                 200                 205

Leu Ala Val Tyr Tyr Cys Gln Gln Tyr Tyr Ser Tyr Pro Leu Thr Phe
    210                 215                 220
```

```
Gly Ala Gly Thr Lys Leu Val Leu Lys Arg Ala Ala Ala Leu Glu His
225                 230                 235                 240

His His His His His
                245


<210> SEQ ID NO 106
<211> LENGTH: 735
<212> TYPE: DNA
<213> ORGANISM: Artificial
<220> FEATURE:
<223> OTHER INFORMATION: nucleotide sequence of an anti-TAG72 diabody
      comprising cysteine replacement mutations in the VH FR2 Kabat
      positions 39 and 43 designated AVP04-111.

<400> SEQUENCE: 106

agcgtgcagc tgcagcagag cgatgcggaa ctggtgaaac cgggcgcgag cgtgaaaatt      60

agctgcaaag cgagcggcta tacctttacc gatcatgcga ttcattgggt gaaatgcaat     120

ccggaatgcg gcctggaatg gattggctat tttagcccgg gcaacgatga ttttaaatat     180

aacgaacgtt ttaaaggcaa agcgaccctg accgcggata aaagcagcag caccgcgtat     240

ctgcagctga acagcctgac cagcgaagat agcgcggtgt atttttgcac ccgtagcctg     300

aatatggcgt attggggtca gggcacctcg gtcaccgtga gcagcggtgg cggcggcagc     360

gatatcgtga tgacccagag cccgagcagc ctgccggtga gcgtgggcga aaaagtgacc     420

ctgagctgca aaagcagcca gagcctgctg tatagcggca atcagaaaaa ctatctggcg     480

tggtatcagc agaaaccggg tcagagcccg aaactgctga tttattgggc gagcacccgt     540

gaaagcggcg tgccggatcg ttttaccggc agcggtagcg gcaccgattt taccctgagc     600

attagcagcg tggaaaccga agatctggcg gtgtattatt gccagcagta ttatagctat     660

ccgctgacct ttggtgcggg caccaaactg gtgctgaaac gtgcggccgc actcgagcac     720

caccaccacc accac                                                      735


<210> SEQ ID NO 107
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VH FR2 Kabat
      positions 39 and 43 designated AVP04-111.

<400> SEQUENCE: 107

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Cys Asn Pro Glu Cys Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
```

```
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245


<210> SEQ ID NO 108
<211> LENGTH: 735
<212> TYPE: DNA
<213> ORGANISM: Artificial
<220> FEATURE:
<223> OTHER INFORMATION: nucleotide sequence of an anti-TAG72 diabody
      comprising cysteine replacement mutations in the VH FR2 Kabat
      positions 39 and 45 designated AVP04-112.

<400> SEQUENCE: 108

agcgtgcagc tgcagcagag cgatgcggaa ctggtgaaac cgggcgcgag cgtgaaaatt      60

agctgcaaag cgagcggcta tacctttacc gatcatgcga ttcattgggt gaaatgcaat     120

ccggaacagg gctgcgaatg gattggctat tttagcccgg gcaacgatga ttttaaatat     180

aacgaacgtt ttaaaggcaa agcgaccctg accgcggata aaagcagcag caccgcgtat     240

ctgcagctga acagcctgac cagcgaagat agcgcggtgt atttttgcac ccgtagcctg     300

aatatggcgt attggggtca gggcacctcg gtcaccgtga gcagcggtgg cggcggcagc     360

gatatcgtga tgacccagag cccgagcagc ctgccggtga gcgtgggcga aaaagtgacc     420

ctgagctgca aaagcagcca gagcctgctg tatagcggca atcagaaaaa ctatctggcg     480

tggtatcagc agaaaccggg tcagagcccg aaactgctga tttattgggc gagcacccgt     540

gaaagcggcg tgccggatcg ttttaccggc agcggtagcg gcaccgattt taccctgagc     600

attagcagcg tggaaaccga agatctggcg gtgtattatt gccagcagta ttatagctat     660

ccgctgacct ttggtgcggg caccaaactg gtgctgaaac gtgcggccgc actcgagcac     720

caccaccacc accac                                                      735


<210> SEQ ID NO 109
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VH FR2 Kabat
      positions 39 and 45 designated AVP04-112.

<400> SEQUENCE: 109

Ser Val Gln Leu Gln Gln Ser Asp Ala Glu Leu Val Lys Pro Gly Ala
1               5                   10                  15
```

```
Ser Val Lys Ile Ser Cys Lys Ala Ser Gly Tyr Thr Phe Thr Asp His
            20                  25                  30

Ala Ile His Trp Val Lys Cys Asn Pro Glu Gln Gly Cys Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245
```

<210> SEQ ID NO 110
<211> LENGTH: 735
<212> TYPE: DNA
<213> ORGANISM: Artificial
<220> FEATURE:
<223> OTHER INFORMATION: nucleotide sequence of an anti-TAG72 diabody comprising cysteine replacement mutations in the VH FR3 Kabat positions 82C and 86 designated AVP04-114

<400> SEQUENCE: 110

```
agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagctgcac cagcgaatgc agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc agcggtagcg gcaccgattt taccctgagc    600

attagcagcg tggaaaccga agatctggcg gtgtattatt gccagcagta ttatagctat    660
```

ccgctgacct ttggtgcggg caccaaactg gtgctgaaac gtgcggccgc actcgagcac 720
caccaccacc accac 735

<210> SEQ ID NO 111
<211> LENGTH: 245
<212> TYPE: PRT
<213> ORGANISM: Artificial
<220> FEATURE:
<223> OTHER INFORMATION: amino acid sequence of an anti-TAG72 diabody comprising cysteine replacement mutations in the VH FR3 Kabat positions 82C and 86 designated AVP04-114.

<400> SEQUENCE: 111

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Cys Thr Ser Glu Cys Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245
```

<210> SEQ ID NO 112
<211> LENGTH: 735
<212> TYPE: DNA
<213> ORGANISM: Artificial
<220> FEATURE:
<223> OTHER INFORMATION: nucleotide sequence of an anti-TAG72 diabody comprising cysteine replacement mutations in the VH FR3 Kabat positions 70 and 79 designated AVP04-120

<400> SEQUENCE: 112
agcgtgcagc tgcagcagag cgatgcggaa ctggtgaaac cgggcgcgag cgtgaaaatt 60
agctgcaaag cgagcggcta tacctttacc gatcatgcga ttcattgggt gaaacagaat 120

```
ccggaacagg gcctggaatg gattggctat tttagcccgg gcaacgatga ttttaaatat    180

aacgaacgtt ttaaaggcaa agcgaccctg tgcgcggata aaagcagcag caccgcgtgc    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc agcggtagcg gcaccgattt taccctgagc    600

attagcagcg tggaaaccga agatctggcg gtgtattatt gccagcagta ttatagctat    660

ccgctgacct ttggtgcggg caccaaactg gtgctgaaac gtgcggccgc actcgagcac    720

caccaccacc accac                                                     735
```

```
<210> SEQ ID NO 113
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VH FR3 Kabat
      positions 70 and 79 designated AVP04-120

<400> SEQUENCE: 113

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Cys Ala Asp Lys Ser Ser Ser Thr Ala Cys
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240
```

```
His His His His His
                245


<210> SEQ ID NO 114
<211> LENGTH: 735
<212> TYPE: DNA
<213> ORGANISM: Artificial
<220> FEATURE:
<223> OTHER INFORMATION: nucleotide sequence of an anti-TAG72 diabody
      comprising cysteine replacement mutations in the VH FR3 Kabat
      positions 72 and 75 designated AVP04-121

<400> SEQUENCE: 114

agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcgtgca aaagctgcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc agcggtagcg gcaccgattt taccctgagc    600

attagcagcg tggaaaccga agatctggcg gtgtattatt gccagcagta ttatagctat    660

ccgctgacct ttggtgcggg caccaaactg gtgctgaaac gtgcggccgc actcgagcac    720

caccaccacc accac                                                     735


<210> SEQ ID NO 115
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VH FR3 Kabat
      positions 72 and 75 designated AVP04-121

<400> SEQUENCE: 115

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Cys Lys Ser Cys Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
```

```
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245


<210> SEQ ID NO 116
<211> LENGTH: 735
<212> TYPE: DNA
<213> ORGANISM: Artificial
<220> FEATURE:
<223> OTHER INFORMATION: nucleotide sequence of an anti-TAG72 diabody
      comprising cysteine replacement mutations in the VL FR3 Kabat
      positions 65 and 72 designated AVP04-123.

<400> SEQUENCE: 116

agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag cccgagcagc ctgccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc tgcggtagcg gcaccgattt ttgcctgagc    600

attagcagcg tggaaaccga agatctggcg gtgtattatt gccagcagta ttatagctat    660

ccgctgacct ttggtgcggg caccaaactg gtgctgaaac gtgcggccgc actcgagcac    720

caccaccacc accac                                                     735


<210> SEQ ID NO 117
<211> LENGTH: 245
<212> TYPE: PRT
<213> ORGANISM: Artificial
<220> FEATURE:
<223> OTHER INFORMATION: amino acid sequence of an anti-TAG72 diabody
      comprising cysteine replacement mutations in the VL FR3 Kabat
      positions 65 and 72 designated AVP04-123.

<400> SEQUENCE: 117

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30
```

```
Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Cys Gly
            180                 185                 190

Ser Gly Thr Asp Phe Cys Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
                245
```

<210> SEQ ID NO 118
<211> LENGTH: 765
<212> TYPE: DNA
<213> ORGANISM: Artificial
<220> FEATURE:
<223> OTHER INFORMATION: nucleotide sequence of an anti-TAG72 scFv comprising cysteine replacement mutations in the VL FR2 Kabat positions 38 and 42 designated AVP04-124

<400> SEQUENCE: 118

```
agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120

ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

ggtggcggcg gcagcggtgg cggcggcagc gatatcgtga tgacccagag cccgagcagc    420

ctgccggtga gcgtgggcga aaaagtgacc ctgagctgca aaagcagcca gagcctgctg    480

tatagcggca atcagaaaaa ctatctggcg tggtatcagt gcaaaccggg ttgcagcccg    540

aaactgctga tttattgggc gagcacccgt gaaagcggcg tgccggatcg ttttaccggc    600

agcggtagcg gcaccgattt taccctgagc attagcagcg tggaaaccga agatctggcg    660

gtgtattatt gccagcagta ttatagctat ccgctgacct ttggtgcggg caccaaactg    720

gtgctgaaac gtgcggccgc actcgagcac caccaccacc accac                    765
```

<210> SEQ ID NO 119
<211> LENGTH: 260
<212> TYPE: PRT
<213> ORGANISM: Artificial
<220> FEATURE:
<223> OTHER INFORMATION: amino acid sequence of an anti-TAG72 scFv comprising cysteine replacement mutations in the VL FR2 Kabat positions 38 and 42 designated AVP04-124.

<400> SEQUENCE: 119

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Pro Val Ser Val Gly Glu Lys Val Thr Leu Ser Cys Lys Ser
145                 150                 155                 160

Ser Gln Ser Leu Leu Tyr Ser Gly Asn Gln Lys Asn Tyr Leu Ala Trp
                165                 170                 175

Tyr Gln Cys Lys Pro Gly Cys Ser Pro Lys Leu Leu Ile Tyr Trp Ala
            180                 185                 190

Ser Thr Arg Glu Ser Gly Val Pro Asp Arg Phe Thr Gly Ser Gly Ser
        195                 200                 205

Gly Thr Asp Phe Thr Leu Ser Ile Ser Ser Val Glu Thr Glu Asp Leu
    210                 215                 220

Ala Val Tyr Tyr Cys Gln Gln Tyr Tyr Ser Tyr Pro Leu Thr Phe Gly
225                 230                 235                 240

Ala Gly Thr Lys Leu Val Leu Lys Arg Ala Ala Ala Leu Glu His His
                245                 250                 255

His His His His
            260
```

<210> SEQ ID NO 120
<211> LENGTH: 717
<212> TYPE: DNA
<213> ORGANISM: Artificial
<220> FEATURE:
<223> OTHER INFORMATION: nucleotide sequence of an anti-TAG72 triabody comprising cysteine replacement mutations in the VL FR2 Kabat positions 38 and 42 designated AVP04-125.

<400> SEQUENCE: 120

```
caggtgcagc tgcagcagag cgatgcggaa ctggtgaaac cgggcgcgag cgtgaaaatt      60

agctgcaaag cgagcggcta tacctttacc gatcatgcga ttcattgggt gaaacagaat     120
```

```
ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcgatatcgt gatgacccag    360

agcccgagca gcctgccggt gagcgtgggc gaaaaagtga ccctgagctg caaaagcagc    420

cagagcctgc tgtatagcgg caatcagaaa aactatctgg cgtggtatca gtgcaaaccg    480

ggttgcagcc cgaaactgct gatttattgg gcgagcaccc gtgaaagcgg cgtgccggat    540

cgttttaccg gcagcggtag cggcaccgat tttaccctga gcattagcag cgtggaaacc    600

gaagatctgg cggtgtatta ttgccagcag tattatagct atccgctgac ctttggtgcg    660

ggcaccaaac tggtgctgaa acgtgcggcc gcactcgagc accaccacca ccaccac       717
```

<210> SEQ ID NO 121
<211> LENGTH: 239
<212> TYPE: PRT
<213> ORGANISM: Artificial
<220> FEATURE:
<223> OTHER INFORMATION: amino acid sequence of an anti-TAG72 triabody comprising cysteine replacement mutations in the VL FR2 Kabat positions 38 and 42 designated AVP04-125

<400> SEQUENCE: 121

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Asp Ile Val Met Thr Gln Ser Pro Ser Ser Leu Pro Val Ser
        115                 120                 125

Val Gly Glu Lys Val Thr Leu Ser Cys Lys Ser Ser Gln Ser Leu Leu
    130                 135                 140

Tyr Ser Gly Asn Gln Lys Asn Tyr Leu Ala Trp Tyr Gln Cys Lys Pro
145                 150                 155                 160

Gly Cys Ser Pro Lys Leu Leu Ile Tyr Trp Ala Ser Thr Arg Glu Ser
                165                 170                 175

Gly Val Pro Asp Arg Phe Thr Gly Ser Gly Ser Gly Thr Asp Phe Thr
            180                 185                 190

Leu Ser Ile Ser Ser Val Glu Thr Glu Asp Leu Ala Val Tyr Tyr Cys
        195                 200                 205

Gln Gln Tyr Tyr Ser Tyr Pro Leu Thr Phe Gly Ala Gly Thr Lys Leu
    210                 215                 220

Val Leu Lys Arg Ala Ala Ala Leu Glu His His His His His His
225                 230                 235
```

```
<210> SEQ ID NO 122
<211> LENGTH: 729
<212> TYPE: DNA
<213> ORGANISM: Artificial
<220> FEATURE:
<223> OTHER INFORMATION: nucleotide sequence of an anti-MucI diabody
      comprising cysteine replacement mutations in the VL FR2 Kabat
      positions 38 and 42 designated AVP02-115

<400> SEQUENCE: 122

agcgtgcagc tggttgaaag cggtggcgga gtggtgcagc caggtggaag cctgcgtctg      60

agctgcgcag caagcggttt tacctttagc agctatggca tgagctgggt gcgtcaggcg     120

ccggataaag gcctggaact ggtggcgacc attaacagca acggtggaag cacctattat     180

ccggatagcg tgaaaggccg ttttaccatt agccgtgata acagcaaaaa caccctgtat     240

ctgcagatga acagcctgcg taccgaagat accgcggtgt attattgcgc gcgtgatcgt     300

gatggctatg atgaaggctt tgattattgg ggccagggca ccctggtgac cgtgagcagc     360

ggtgggggcg gaagccagat tcagctgacc cagagcccga gcagcctgag cgcaagcgtg     420

ggtgatcgtg tgaccattac ctgcagcgcg agcagcagcg tgagctatat gcattggtat     480

cagtgcaaac cgggctgcgc gccgaaacgt tggatttatg ataccagcaa actggcgagc     540

ggcgtgccga gccgttttag cggcagcggc agcggcaccg attatacctt taccattagc     600

agcctgcagc cggaagatat tgcgacctat tattgccagc agtggagcag caacccgccg     660

acctttggcc agggcaccaa actgcagatt aaacgtgcgg ccgcactcga gcaccaccac     720

caccaccac                                                             729


<210> SEQ ID NO 123
<211> LENGTH: 243
<212> TYPE: PRT
<213> ORGANISM: Artificial
<220> FEATURE:
<223> OTHER INFORMATION: amino acid sequence of an anti-MucI diabody
      comprising cysteine replacement mutations in the VL FR2 Kabat
      positions 38 and 42 designated AVP02-115

<400> SEQUENCE: 123

Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160
```

```
Gln Cys Lys Pro Gly Cys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His


<210> SEQ ID NO 124
<211> LENGTH: 729
<212> TYPE: DNA
<213> ORGANISM: Artificial
<220> FEATURE:
<223> OTHER INFORMATION: nucleotide sequence of an anti-MucI diabody
      comprising cysteine replacement mutations in the VH FR2 Kabat
      positions 39 and 43 designated AVP02-116.

<400> SEQUENCE: 124

agcgtgcagc tggttgaaag cggtggcgga gtggtgcagc caggtggaag cctgcgtctg      60

agctgcgcag caagcggttt tacctttagc agctatggca tgagctgggt gcgttgcgcg     120

ccggattgcg gcctggaact ggtggcgacc attaacagca acggtggaag cacctattat     180

ccggatagcg tgaaaggccg ttttaccatt agccgtgata acagcaaaaa caccctgtat     240

ctgcagatga acagcctgcg taccgaagat accgcggtgt attattgcgc gcgtgatcgt     300

gatggctatg atgaaggctt tgattattgg ggccagggca ccctggtgac cgtgagcagc     360

ggtgggggcg gaagccagat tcagctgacc cagagcccga gcagcctgag cgcaagcgtg     420

ggtgatcgtg tgaccattac ctgcagcgcg agcagcagcg tgagctatat gcattggtat     480

cagcagaaac cgggcaaagc gccgaaacgt tggatttatg ataccagcaa actggcgagc     540

ggcgtgccga gccgttttag cggcagcggc agcggcaccg attatacctt taccattagc     600

agcctgcagc cggaagatat tgcgacctat tattgccagc agtggagcag caacccgccg     660

acctttggcc agggcaccaa actgcagatt aaacgtgcgg ccgcactcga gcaccaccac     720

caccaccac                                                              729


<210> SEQ ID NO 125
<211> LENGTH: 243
<212> TYPE: PRT
<213> ORGANISM: Artificial
<220> FEATURE:
<223> OTHER INFORMATION: amino acid sequence of an anti-MucI diabody
      comprising cysteine replacement mutations in the VH FR2 Kabat
      positions 39 and 43 designated AVP02-116.

<400> SEQUENCE: 125

Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Cys Ala Pro Asp Cys Gly Leu Glu Leu Val
        35                  40                  45

Ala Thr Ile Asn Ser Asn Gly Gly Ser Thr Tyr Tyr Pro Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His
```

<210> SEQ ID NO 126
<211> LENGTH: 804
<212> TYPE: DNA
<213> ORGANISM: Artificial
<220> FEATURE:
<223> OTHER INFORMATION: nucleotide sequence of an anti-Her2 diabody comprising cysteine replacement mutations in the VL FR2 Kabat positions 38 and 42 designated AVP07-117.

<400> SEQUENCE: 126

```
agcgtgcagc tggtgcagtc tggggcagag gtgaaaaagc ccggggagtc tctgaagatc     60

tcctgtaagg gttctggata cagctttacc agctactgga tcgcctgggt gcgccagatg    120

cccgggaaag gcctggagta catggggctc atctatcctg gtgactctga caccaaatac    180

agcccgtcct tccaaggcca ggtcaccatc tcagtcgaca agtccgtcag cactgcctac    240

ttgcaatgga gcagtctgaa ggcctcggac agcgccgtgt atttttgtgc gagacatgac    300

gtgggatatg cgagtagttc caacgcggca aagtggcctg aatacttcca gcattggggc    360

cagggcaccc tggtcaccgt ttcctcaggt ggaggcggtt cacagtctgt gttgacgcag    420

ccgccctcag tgtctgcggc cccaggacag aaggtcacca tctcctgctc tggaagcagc    480

tccaacattg ggaataatta tgtatcctgg taccagtgcc tcccaggatg cgtccccaaa    540

ctcctcatct atggtcacac caatcggccc gcaggggtcc ctgaccgatt ctctggctcc    600

aagtctggca cctcagcctc cctggccatc agtgggttcc ggtccgagga tgaggctgat    660

tattactgtg cagcatggga tgacagcctg agtggttggg tgttcggcgg agggaccaag    720

ctgaccgtcc taggtgcggc cgcagaacaa aaactcatct cagaagagga tctgaatggg    780

gccgcacatc accatcatca ccat                                           804
```

<210> SEQ ID NO 127
<211> LENGTH: 268
<212> TYPE: PRT

<213> ORGANISM: Artificial
<220> FEATURE:
<223> OTHER INFORMATION: amino acid sequence of an anti-Her2 diabody comprising cysteine replacement mutations in the VL FR2 Kabat positions 38 and 42 designated AVP07-117.

<400> SEQUENCE: 127

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Cys Leu Pro Gly
                165                 170                 175

Cys Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

<210> SEQ ID NO 128
<211> LENGTH: 804
<212> TYPE: DNA
<213> ORGANISM: Artificial
<220> FEATURE:
<223> OTHER INFORMATION: nucleotide sequence of an anti-Her2 diabody comprising cysteine replacement mutations in the VH FR2 Kabat positions 39 and 43 designated AVP07-118.

<400> SEQUENCE: 128

```
agcgtgcagc tggtgcagtc tggggcagag gtgaaaaagc ccggggagtc tctgaagatc     60

tcctgtaagg gttctggata cagctttacc agctactgga tcgcctgggt gcgctgcatg    120

cccgggtgcg gcctggagta catggggctc atctatcctg gtgactctga caccaaatac    180

agcccgtcct tccaaggcca ggtcaccatc tcagtcgaca agtccgtcag cactgcctac    240
```

```
ttgcaatgga gcagtctgaa gccctcggac agcgccgtgt atttttgtgc gagacatgac    300

gtgggatatg cgagtagttc caacgcggca aagtggcctg aatacttcca gcattggggc    360

cagggcaccc tggtcaccgt ttcctcaggt ggaggcggtt cacagtctgt gttgacgcag    420

ccgccctcag tgtctgcggc cccaggacag aaggtcacca tctcctgctc tggaagcagc    480

tccaacattg ggaataatta tgtatcctgg taccagcagc tcccaggaac agtccccaaa    540

ctcctcatct atggtcacac caatcggccc gcaggggtcc ctgaccgatt ctctggctcc    600

aagtctggca cctcagcctc cctggccatc agtgggttcc ggtccgagga tgaggctgat    660

tattactgtg cagcatggga tgacagcctg agtggttggg tgttcggcgg agggaccaag    720

ctgaccgtcc taggtgcggc cgcagaacaa aaactcatct cagaagagga tctgaatggg    780

gccgcacatc accatcatca ccat                                           804
```

<210> SEQ ID NO 129
<211> LENGTH: 268
<212> TYPE: PRT
<213> ORGANISM: Artificial
<220> FEATURE:
<223> OTHER INFORMATION: amino acid sequence of an anti-Her2 diabody comprising cysteine replacement mutations in the VH FR2 Kabat positions 39 and 43 designated AVP07-118.

<400> SEQUENCE: 129

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Cys Met Pro Gly Cys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255
```

```
Asp Leu Asn Gly Ala Ala His His His His His His
            260                 265


<210> SEQ ID NO 130
<211> LENGTH: 729
<212> TYPE: DNA
<213> ORGANISM: Artificial
<220> FEATURE:
<223> OTHER INFORMATION: nucleotide sequence of an anti-MucI diabody
      comprising cysteine replacement mutations in the VL FR2 Kabat
      positions 38 and 44 designated AVP02-126

<400> SEQUENCE: 130

agcgtgcagc tggttgaaag cggtggcgga gtggtgcagc caggtggaag cctgcgtctg     60

agctgcgcag caagcggttt tacctttagc agctatggca tgagctgggt gcgtcaggcg    120

ccggataaag gcctggaact ggtggcgacc attaacagca acggtggaag cacctattat    180

ccggatagcg tgaaaggccg ttttaccatt agccgtgata acagcaaaaa caccctgtat    240

ctgcagatga acagcctgcg taccgaagat accgcggtgt attattgcgc gcgtgatcgt    300

gatggctatg atgaaggctt tgattattgg ggccagggca ccctggtgac cgtgagcagc    360

ggtgggggcg gaagccagat tcagctgacc cagagcccga gcagcctgag cgcaagcgtg    420

ggtgatcgtg tgaccattac ctgcagcgcg agcagcagcg tgagctatat gcattggtat    480

cagtgcaaac cgggcaaagc gtgcaaacgt tggatttatg ataccagcaa actggcgagc    540

ggcgtgccga gccgttttag cggcagcggc agcggcaccg attatacctt taccattagc    600

agcctgcagc cggaagatat tgcgacctat tattgccagc agtggagcag caacccgccg    660

acctttggcc agggcaccaa actgcagatt aaacgtgcgg ccgcactcga gcaccaccac    720

caccaccac                                                            729


<210> SEQ ID NO 131
<211> LENGTH: 243
<212> TYPE: PRT
<213> ORGANISM: Artificial
<220> FEATURE:
<223> OTHER INFORMATION: amino acid sequence of an anti-MucI diabody
      comprising cysteine replacement mutations in the VL FR2 Kabat
      positions 38 and 44 designated AVP02-126.

<400> SEQUENCE: 131

Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
```

```
    130                 135                 140

Thr Ile Thr Cys Ser Ala Ser Ser Ser Val Ser Tyr Met His Trp Tyr
145                 150                 155                 160

Gln Cys Lys Pro Gly Lys Ala Cys Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His
```

<210> SEQ ID NO 132
<211> LENGTH: 729
<212> TYPE: DNA
<213> ORGANISM: Artificial
<220> FEATURE:
<223> OTHER INFORMATION: nucleotide sequence of an anti-MucI diabody comprising cysteine replacement mutations in the VH FR2 Kabat positions 39 and 45 designated AVP02-127

<400> SEQUENCE: 132

```
agcgtgcagc tggttgaaag cggtggcgga gtggtgcagc caggtggaag cctgcgtctg     60

agctgcgcag caagcggttt tacctttagc agctatggca tgagctgggt gcgttgcgcg    120

ccggataaag gctgcgaact ggtggcgacc attaacagca acggtggaag cacctattat    180

ccggatagcg tgaaaggccg ttttaccatt agccgtgata acagcaaaaa caccctgtat    240

ctgcagatga acagcctgcg taccgaagat accgcggtgt attattgcgc gcgtgatcgt    300

gatggctatg atgaaggctt tgattattgg ggccagggca ccctggtgac cgtgagcagc    360

ggtgggggcg gaagccagat tcagctgacc cagagcccga gcagcctgag cgcaagcgtg    420

ggtgatcgtg tgaccattac ctgcagcgcg agcagcagcg tgagctatat gcattggtat    480

cagcagaaac cgggcaaagc gccgaaacgt tggatttatg ataccagcaa actggcgagc    540

ggcgtgccga gccgttttag cggcagcggc agcggcaccg attatacctt taccattagc    600

agcctgcagc cggaagatat tgcgacctat tattgccagc agtggagcag caacccgccg    660

acctttggcc agggcaccaa actgcagatt aaacgtgcgg ccgcactcga gcaccaccac    720

caccaccac                                                            729
```

<210> SEQ ID NO 133
<211> LENGTH: 243
<212> TYPE: PRT
<213> ORGANISM: Artificial
<220> FEATURE:
<223> OTHER INFORMATION: amino acid sequence of an anti-MucI diabody comprising cysteine replacement mutations in the VH FR2 Kabat positions 39 and 45 designated AVP02-127.

<400> SEQUENCE: 133

```
Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Cys Ala Pro Asp Lys Gly Cys Glu Leu Val
```

```
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His
```

<210> SEQ ID NO 134
<211> LENGTH: 729
<212> TYPE: DNA
<213> ORGANISM: Artificial
<220> FEATURE:
<223> OTHER INFORMATION: nucleotide sequence of an anti-MucI diabody comprising cysteine replacement mutations in the VL FR3 Kabat positions 65 and 72 designated AVP02-128

<400> SEQUENCE: 134

```
agcgtgcagc tggttgaaag cggtggcgga gtggtgcagc caggtggaag cctgcgtctg     60

agctgcgcag caagcggttt tacctttagc agctatggca tgagctgggt gcgtcaggcg    120

ccggataaag gcctggaact ggtggcgacc attaacagca acggtggaag cacctattat    180

ccggatagcg tgaaaggccg ttttaccatt agccgtgata acagcaaaaa caccctgtat    240

ctgcagatga acagcctgcg taccgaagat accgcggtgt attattgcgc gcgtgatcgt    300

gatggctatg atgaaggctt tgattattgg ggccagggca ccctggtgac cgtgagcagc    360

ggtgggggcg gaagccagat tcagctgacc cagagcccga gcagcctgag cgcaagcgtg    420

ggtgatcgtg tgaccattac ctgcagcgcg agcagcagcg tgagctatat gcattggtat    480

cagcagaaac cgggcaaagc gccgaaacgt tggatttatg ataccagcaa actggcgagc    540

ggcgtgccga gccgttttag cggctgcggc agcggcaccg attattgctt taccattagc    600

agcctgcagc cggaagatat tgcgacctat tattgccagc agtggagcag caacccgccg    660

acctttggcc agggcaccaa actgcagatt aaacgtgcgg ccgcactcga gcaccaccac    720

caccaccac                                                            729
```

```
<210> SEQ ID NO 135
<211> LENGTH: 243
<212> TYPE: PRT
<213> ORGANISM: Artificial
<220> FEATURE:
<223> OTHER INFORMATION: amino acid sequence of an anti-MucI diabody
      comprising cysteine replacement mutations in the VL FR3 Kabat
      positions 65 and 72 designated AVP02-128.

<400> SEQUENCE: 135

Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Cys Gly Ser Gly
            180                 185                 190

Thr Asp Tyr Cys Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His


<210> SEQ ID NO 136
<211> LENGTH: 729
<212> TYPE: DNA
<213> ORGANISM: Artificial
<220> FEATURE:
<223> OTHER INFORMATION: nucleotide sequence of an anti-MucI diabody
      comprising cysteine replacement mutations in the VH FR3 Kabat
      positions 70 and 79 designated AVP02-129.

<400> SEQUENCE: 136

agcgtgcagc tggttgaaag cggtggcgga gtggtgcagc caggtggaag cctgcgtctg     60

agctgcgcag caagcggttt tacctttagc agctatggca tgagctgggt gcgtcaggcg    120

ccggataaag gcctggaact ggtggcgacc attaacagca acggtggaag cacctattat    180

ccggatagcg tgaaaggccg ttttaccatt tgccgtgata acagcaaaaa caccctgtgc    240

ctgcagatga acagcctgcg taccgaagat accgcggtgt attattgcgc gcgtgatcgt    300
```

```
gatggctatg atgaaggctt tgattattgg ggccagggca ccctggtgac cgtgagcagc    360

ggtgggggcg gaagccagat tcagctgacc cagagcccga gcagcctgag cgcaagcgtg    420

ggtgatcgtg tgaccattac ctgcagcgcg agcagcagcg tgagctatat gcattggtat    480

cagcagaaac cgggcaaagc gccgaaacgt tggatttatg ataccagcaa actggcgagc    540

ggcgtgccga gccgttttag cggcagcggc agcggcaccg attatacctt taccattagc    600

agcctgcagc cggaagatat tgcgacctat tattgccagc agtggagcag caacccgccg    660

acctttggcc agggcaccaa actgcagatt aaacgtgcgg ccgcactcga gcaccaccac    720

caccaccac                                                            729
```

<210> SEQ ID NO 137
<211> LENGTH: 243
<212> TYPE: PRT
<213> ORGANISM: Artificial
<220> FEATURE:
<223> OTHER INFORMATION: amino acid sequence of an anti-MucI diabody comprising cysteine replacement mutations in the VH FR3 Kabat positions 70 and 79 designated AVP02-129

<400> SEQUENCE: 137

```
Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Cys Arg Asp Asn Ser Lys Asn Thr Leu Cys
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His
```

<210> SEQ ID NO 138
<211> LENGTH: 729

```
<212> TYPE: DNA
<213> ORGANISM: Artificial
<220> FEATURE:
<223> OTHER INFORMATION: nucleotide sequence of an anti-MucI diabody
      comprising cysteine replacement mutations in the VH FR3 Kabat
      positions 72 and 75 designated AVP02-130

<400> SEQUENCE: 138

agcgtgcagc tggttgaaag cggtggcgga gtggtgcagc caggtggaag cctgcgtctg     60

agctgcgcag caagcggttt tacctttagc agctatggca tgagctgggt gcgtcaggcg    120

ccggataaag gcctggaact ggtggcgacc attaacagca acggtggaag cacctattat    180

ccggatagcg tgaaaggccg ttttaccatt agccgttgca acagctgcaa caccctgtat    240

ctgcagatga acagcctgcg taccgaagat accgcggtgt attattgcgc gcgtgatcgt    300

gatggctatg atgaaggctt tgattattgg ggccagggca ccctggtgac cgtgagcagc    360

ggtgggggcg gaagccagat tcagctgacc cagagcccga gcagcctgag cgcaagcgtg    420

ggtgatcgtg tgaccattac ctgcagcgcg agcagcagcg tgagctatat gcattggtat    480

cagcagaaac cgggcaaagc gccgaaacgt tggatttatg ataccagcaa actggcgagc    540

ggcgtgccga gccgttttag cggcagcggc agcggcaccg attatacctt taccattagc    600

agcctgcagc cggaagatat tgcgacctat tattgccagc agtggagcag caacccgccg    660

acctttggcc agggcaccaa actgcagatt aaacgtgcgg ccgcactcga gcaccaccac    720

caccaccac                                                            729


<210> SEQ ID NO 139
<211> LENGTH: 243
<212> TYPE: PRT
<213> ORGANISM: Artificial
<220> FEATURE:
<223> OTHER INFORMATION: amino acid sequence of an anti-MucI diabody
      comprising cysteine replacement mutations in the VH FR3 Kabat
      positions 72 and 75 designated AVP02-130.

<400> SEQUENCE: 139

Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Cys Asn Ser Cys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175
```

```
Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg Ala Ala Ala Leu Glu His His His
225                 230                 235                 240

His His His


<210> SEQ ID NO 140
<211> LENGTH: 804
<212> TYPE: DNA
<213> ORGANISM: Artificial
<220> FEATURE:
<223> OTHER INFORMATION: nucleotide sequence of an anti-Her2 diabody
      comprising cysteine replacement mutations in the VL FR2 Kabat
      positions 38 and 44 designated AVP07-131.

<400> SEQUENCE: 140

agcgtgcagc tggtgcagtc tggggcagag gtgaaaaagc ccggggagtc tctgaagatc      60

tcctgtaagg gttctggata cagctttacc agctactgga tcgcctgggt gcgccagatg     120

cccgggaaag gcctggagta catggggctc atctatcctg gtgactctga caccaaatac     180

agcccgtcct tccaaggcca ggtcaccatc tcagtcgaca agtccgtcag cactgcctac     240

ttgcaatgga gcagtctgaa gccctcggac agcgccgtgt atttttgtgc gagacatgac     300

gtgggatatg cgagtagttc caacgcggca aagtggcctg aatacttcca gcattggggc     360

cagggcaccc tggtcaccgt ttcctcaggt ggaggcggtt cacagtctgt gttgacgcag     420

ccgccctcag tgtctgcggc cccaggacag aaggtcacca tctcctgctc tggaagcagc     480

tccaacattg ggaataatta tgtatcctgg taccagtgcc tcccaggaac agtctgcaaa     540

ctcctcatct atggtcacac caatcggccc gcaggggtcc ctgaccgatt ctctggctcc     600

aagtctggca cctcagcctc cctggccatc agtgggttcc ggtccgagga tgaggctgat     660

tattactgtg cagcatggga tgacagcctg agtggttggg tgttcggcgg agggaccaag     720

ctgaccgtcc taggtgcggc cgcagaacaa aaactcatct cagaagagga tctgaatggg     780

gccgcacatc accatcatca ccat                                            804


<210> SEQ ID NO 141
<211> LENGTH: 268
<212> TYPE: PRT
<213> ORGANISM: Artificial
<220> FEATURE:
<223> OTHER INFORMATION: amino acid sequence of an anti-Her2 diabody
      comprising cysteine replacement mutations in the VL FR2 Kabat
      positions 38 and 44 designated AVP07-131.

<400> SEQUENCE: 141

Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60
```

```
Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Cys Leu Pro Gly
                165                 170                 175

Thr Val Cys Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

```
<210> SEQ ID NO 142
<211> LENGTH: 804
<212> TYPE: DNA
<213> ORGANISM: Artificial
<220> FEATURE:
<223> OTHER INFORMATION: nucleotide sequence of an anti-Her2 diabody
      comprising cysteine replacement mutations in the VH FR2 Kabat
      positions 39 and 45 designated AVP07-132.

<400> SEQUENCE: 142

agcgtgcagc tggtgcagtc tggggcagag gtgaaaaagc ccggggagtc tctgaagatc      60

tcctgtaagg gttctggata cagctttacc agctactgga tcgcctgggt gcgctgcatg     120

cccgggaaag gctgcgagta catggggctc atctatcctg gtgactctga caccaaatac     180

agcccgtcct tccaaggcca ggtcaccatc tcagtcgaca agtccgtcag cactgcctac     240

ttgcaatgga gcagtctgaa ggcctcggac agcgccgtgt atttttgtgc gagacatgac     300

gtgggatatg cgagtagttc caacgcggca aagtggcctg aatacttcca gcattggggc     360

cagggcaccc tggtcaccgt ttcctcaggt ggaggcggtt cacagtctgt gttgacgcag     420

ccgccctcag tgtctgcggc cccaggacag aaggtcacca tctcctgctc tggaagcagc     480

tccaacattg ggaataatta tgtatcctgg taccagcagc tcccaggaac agtccccaaa     540

ctcctcatct atggtcacac caatcggccc gcaggggtcc ctgaccgatt ctctggctcc     600

aagtctggca cctcagcctc cctggccatc agtgggttcc ggtccgagga tgaggctgat     660

tattactgtg cagcatggga tgacagcctg agtggttggg tgttcggcgg agggaccaag     720

ctgaccgtcc taggtgcggc cgcagaacaa aaactcatct cagaagagga tctgaatggg     780

gccgcacatc accatcatca ccat                                            804
```

<210> SEQ ID NO 143
<211> LENGTH: 268
<212> TYPE: PRT
<213> ORGANISM: Artificial
<220> FEATURE:
<223> OTHER INFORMATION: amino acid sequence of an anti-Her2 diabody comprising cysteine replacement mutations in the VH FR2 Kabat positions 39 and 45 designated AVP07-132.

<400> SEQUENCE: 143

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Cys Met Pro Gly Lys Gly Cys Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

<210> SEQ ID NO 144
<211> LENGTH: 804
<212> TYPE: DNA
<213> ORGANISM: Artificial
<220> FEATURE:
<223> OTHER INFORMATION: nucleotide sequence of an anti-Her2 diabody comprising cysteine replacement mutations in the VL FR3 Kabat positions 65 and 72 designated AVP07-133.

<400> SEQUENCE: 144

```
agcgtgcagc tggtgcagtc tggggcagag gtgaaaaagc ccggggagtc tctgaagatc     60

tcctgtaagg gttctggata cagctttacc agctactgga tcgcctgggt gcgccagatg    120
```

```
cccgggaaag gcctggagta catggggctc atctatcctg gtgactctga caccaaatac    180

agcccgtcct tccaaggcca ggtcaccatc tcagtcgaca agtccgtcag cactgcctac    240

ttgcaatgga gcagtctgaa gccctcggac agcgccgtgt atttttgtgc gagacatgac    300

gtgggatatg cgagtagttc caacgcggca aagtggcctg aatacttcca gcattggggc    360

cagggcaccc tggtcaccgt ttcctcaggt ggaggcggtt cacagtctgt gttgacgcag    420

ccgccctcag tgtctgcggc cccaggacag aaggtcacca tctcctgctc tggaagcagc    480

tccaacattg ggaataatta tgtatcctgg taccagcagc tcccaggaac agtccccaaa    540

ctcctcatct atggtcacac caatcggccc gcaggggtcc ctgaccgatt ctctggctgc    600

aagtctggca cctcagcctg cctggccatc agtgggttcc ggtccgagga tgaggctgat    660

tattactgtg cagcatggga tgacagcctg agtggttggg tgttcggcgg agggaccaag    720

ctgaccgtcc taggtgcggc cgcagaacaa aaactcatct cagaagagga tctgaatggg    780

gccgcacatc accatcatca ccat                                           804
```

<210> SEQ ID NO 145
<211> LENGTH: 268
<212> TYPE: PRT
<213> ORGANISM: Artificial
<220> FEATURE:
<223> OTHER INFORMATION: amino acid sequence of an anti-Her2 diabody comprising cysteine replacement mutations in the VL FR3 Kabat positions 65 and 72 designated AVP07-133.

<400> SEQUENCE: 145

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Cys Lys Ser Gly Thr Ser Ala Cys Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
```

```
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265


<210> SEQ ID NO 146
<211> LENGTH: 804
<212> TYPE: DNA
<213> ORGANISM: Artificial
<220> FEATURE:
<223> OTHER INFORMATION: nucleotide sequence of an anti-Her2 diabody
      comprising cysteine replacement mutations in the VH FR3 Kabat
      positions 70 and 79 designated AVP07-134.

<400> SEQUENCE: 146

agcgtgcagc tggtgcagtc tggggcagag gtgaaaaagc ccggggagtc tctgaagatc     60

tcctgtaagg gttctggata cagctttacc agctactgga tcgcctgggt gcgccagatg    120

cccgggaaag gcctggagta catggggctc atctatcctg gtgactctga caccaaatac    180

agcccgtcct tccaaggcca ggtcaccatc tgcgtcgaca agtccgtcag cactgcctgc    240

ttgcaatgga gcagtctgaa gccctcggac agcgccgtgt atttttgtgc gagacatgac    300

gtgggatatg cgagtagttc caacgcggca aagtggcctg aatacttcca gcattggggc    360

cagggcaccc tggtcaccgt ttcctcaggt ggaggcggtt cacagtctgt gttgacgcag    420

ccgccctcag tgtctgcggc cccaggacag aaggtcacca tctcctgctc tggaagcagc    480

tccaacattg ggaataatta tgtatcctgg taccagcagc tcccaggaac agtccccaaa    540

ctcctcatct atggtcacac caatcggccc gcaggggtcc ctgaccgatt ctctggctcc    600

aagtctggca cctcagcctc cctggccatc agtgggttcc ggtccgagga tgaggctgat    660

tattactgtg cagcatggga tgacagcctg agtggttggg tgttcggcgg agggaccaag    720

ctgaccgtcc taggtgcggc cgcagaacaa aaactcatct cagaagagga tctgaatggg    780

gccgcacatc accatcatca ccat                                           804


<210> SEQ ID NO 147
<211> LENGTH: 268
<212> TYPE: PRT
<213> ORGANISM: Artificial
<220> FEATURE:
<223> OTHER INFORMATION: amino acid sequence of an anti-Her2 diabody
      comprising cysteine replacement mutations in the VH FR3 Kabat
      positions 70 and 79 designated AVP07-134

<400> SEQUENCE: 147

Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Cys Val Asp Lys Ser Val Ser Thr Ala Cys
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
```

```
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

```
<210> SEQ ID NO 148
<211> LENGTH: 804
<212> TYPE: DNA
<213> ORGANISM: Artificial
<220> FEATURE:
<223> OTHER INFORMATION: SEQ ID NO: 148 - nucleotide sequence of an
      anti-Her2 diabody comprising cysteine replacement mutations in the
      VH FR3 Kabat positions 72 and 75 designated AVP07-135.

<400> SEQUENCE: 148

agcgtgcagc tggtgcagtc tggggcagag gtgaaaaagc ccggggagtc tctgaagatc     60

tcctgtaagg gttctggata cagctttacc agctactgga tcgcctgggt gcgccagatg    120

cccgggaaag gcctggagta catggggctc atctatcctg gtgactctga caccaaatac    180

agcccgtcct tccaaggcca ggtcaccatc tcagtctgca agtcctgcag cactgcctac    240

ttgcaatgga gcagtctgaa ggcctcggac agcgccgtgt atttttgtgc gagacatgac    300

gtgggatatg cgagtagttc caacgcggca aagtggcctg aatacttcca gcattggggc    360

cagggcaccc tggtcaccgt ttcctcaggt ggaggcggtt cacagtctgt gttgacgcag    420

ccgccctcag tgtctgcggc cccaggacag aaggtcacca tctcctgctc tggaagcagc    480

tccaacattg ggaataatta tgtatcctgg taccagcagc tcccaggaac agtccccaaa    540

ctcctcatct atggtcacac caatcggccc gcaggggtcc ctgaccgatt ctctggctcc    600

aagtctggca cctcagcctc cctggccatc agtgggttcc ggtccgagga tgaggctgat    660

tattactgtg cagcatggga tgacagcctg agtggttggg tgttcggcgg agggaccaag    720

ctgaccgtcc taggtgcggc cgcagaacaa aaactcatct cagaagagga tctgaatggg    780

gccgcacatc accatcatca ccat                                           804


<210> SEQ ID NO 149
<211> LENGTH: 268
<212> TYPE: PRT
<213> ORGANISM: Artificial
<220> FEATURE:
<223> OTHER INFORMATION: amino acid sequence of an anti-Her2 diabody
```

comprising cysteine replacement mutations in the VH FR3 Kabat positions 72 and 75 designated AVP07-135.

<400> SEQUENCE: 149

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Cys Lys Ser Cys Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```

<210> SEQ ID NO 150
<211> LENGTH: 1255
<212> TYPE: PRT
<213> ORGANISM: Homo sapiens

<400> SEQUENCE: 150

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80
```

```
Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
```

```
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925
```

```
Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                 1005

Leu Glu  Asp Asp Asp Met Gly  Asp Leu Val Asp Ala  Glu Glu Tyr
    1010                 1015                 1020

Leu Val  Pro Gln Gln Gly Phe  Phe Cys Pro Asp Pro  Ala Pro Gly
    1025                 1030                 1035

Ala Gly  Gly Met Val His His  Arg His Arg Ser Ser  Ser Thr Arg
    1040                 1045                 1050

Ser Gly  Gly Gly Asp Leu Thr  Leu Gly Leu Glu Pro  Ser Glu Glu
    1055                 1060                 1065

Glu Ala  Pro Arg Ser Pro Leu  Ala Pro Ser Glu Gly  Ala Gly Ser
    1070                 1075                 1080

Asp Val  Phe Asp Gly Asp Leu  Gly Met Gly Ala Ala  Lys Gly Leu
    1085                 1090                 1095

Gln Ser  Leu Pro Thr His Asp  Pro Ser Pro Leu Gln  Arg Tyr Ser
    1100                 1105                 1110

Glu Asp  Pro Thr Val Pro Leu  Pro Ser Glu Thr Asp  Gly Tyr Val
    1115                 1120                 1125

Ala Pro  Leu Thr Cys Ser Pro  Gln Pro Glu Tyr Val  Asn Gln Pro
    1130                 1135                 1140

Asp Val  Arg Pro Gln Pro Pro  Ser Pro Arg Glu Gly  Pro Leu Pro
    1145                 1150                 1155

Ala Ala  Arg Pro Ala Gly Ala  Thr Leu Glu Arg Ala  Lys Thr Leu
    1160                 1165                 1170

Ser Pro  Gly Lys Asn Gly Val  Val Lys Asp Val Phe  Ala Phe Gly
    1175                 1180                 1185

Gly Ala  Val Glu Asn Pro Glu  Tyr Leu Thr Pro Gln  Gly Gly Ala
    1190                 1195                 1200

Ala Pro  Gln Pro His Pro Pro  Pro Ala Phe Ser Pro  Ala Phe Asp
    1205                 1210                 1215

Asn Leu  Tyr Tyr Trp Asp Gln  Asp Pro Pro Glu Arg  Gly Ala Pro
    1220                 1225                 1230

Pro Ser  Thr Phe Lys Gly Thr  Pro Thr Ala Glu Asn  Pro Glu Tyr
    1235                 1240                 1245

Leu Gly  Leu Asp Val Pro Val
    1250                 1255


<210> SEQ ID NO 151
<211> LENGTH: 750
<212> TYPE: PRT
<213> ORGANISM: Homo sapiens

<400> SEQUENCE: 151

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
```

```
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445
```

```
Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750


<210> SEQ ID NO 152
<211> LENGTH: 475
<212> TYPE: PRT
<213> ORGANISM: Homo sapiens

<400> SEQUENCE: 152

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
```

```
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
    290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
    370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Thr Tyr His Pro Met Ser Glu Tyr Pro Thr Tyr
            420                 425                 430

His Thr His Gly Arg Tyr Val Pro Pro Ser Ser Thr Asp Arg Ser Pro
        435                 440                 445

Tyr Glu Lys Val Ser Ala Gly Asn Gly Gly Ser Ser Leu Ser Tyr Thr
    450                 455                 460

Asn Pro Ala Val Ala Ala Thr Ser Ala Asn Leu
465                 470                 475

<210> SEQ ID NO 153
```

<211> LENGTH: 307
<212> TYPE: PRT
<213> ORGANISM: Homo sapiens

<400> SEQUENCE: 153

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala Gln Gly Val Thr Ser Ala Pro Glu Thr
    130                 135                 140

Arg Pro Pro Pro Gly Ser Thr Ala Pro Pro Ala His Gly Val Thr Ser
145                 150                 155                 160

Ala Pro Asp Asn Arg Pro Ala Leu Ala Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Val Ser Ile Gly Leu Ser Phe Pro
    290                 295                 300

Met Leu Pro
305
```

<210> SEQ ID NO 154
<211> LENGTH: 735
<212> TYPE: DNA
<213> ORGANISM: artificial
<220> FEATURE:
<223> OTHER INFORMATION: nucleotide sequence encoding AVP04-50 diabody

<400> SEQUENCE: 154

```
agcgtgcagc tgcagcagag cgatgcggaa ctggtgaaac cgggcgcgag cgtgaaaatt     60

agctgcaaag cgagcggcta tacctttacc gatcatgcga ttcattgggt gaaacagaat    120
```

```
ccggaacagg gcctggaatg gattggctat tttagcccgg gcaacgatga ttttaaatat    180

aacgaacgtt ttaaaggcaa agcgaccctg accgcggata aaagcagcag caccgcgtat    240

ctgcagctga acagcctgac cagcgaagat agcgcggtgt atttttgcac ccgtagcctg    300

aatatggcgt attggggtca gggcacctcg gtcaccgtga gcagcggtgg cggcggcagc    360

gatatcgtga tgacccagag ctgcagcagc tgcccggtga gcgtgggcga aaaagtgacc    420

ctgagctgca aaagcagcca gagcctgctg tatagcggca atcagaaaaa ctatctggcg    480

tggtatcagc agaaaccggg tcagagcccg aaactgctga tttattgggc gagcacccgt    540

gaaagcggcg tgccggatcg ttttaccggc agcggtagcg gcaccgattt taccctgagc    600

attagcagcg tggaaaccga agatctggcg gtgtattatt gccagcagta ttatagctat    660

ccgctgacct ttggtgcggg caccaaactg gtgctgaaac gtgcggccgc actcgagcac    720

caccaccacc accac                                                     735


<210> SEQ ID NO 155
<211> LENGTH: 245
<212> TYPE: PRT
<213> ORGANISM: artificial
<220> FEATURE:
<223> OTHER INFORMATION: amino acid sequence of AVP04-50 diabody

<400> SEQUENCE: 155

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Cys
        115                 120                 125

Ser Ser Cys Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg Ala Ala Ala Leu Glu His
225                 230                 235                 240

His His His His His
```

245

<210> SEQ ID NO 156
<211> LENGTH: 804
<212> TYPE: DNA
<213> ORGANISM: artificial
<220> FEATURE:
<223> OTHER INFORMATION: nucleotide sequence encoding AVP07-63 diabody

<400> SEQUENCE: 156
agcgtgcagc tggtgcagtc tggggcagag gtgaaaaagc ccggggagtc tctgaagatc 60
tcctgtaagg gttctggata cagctttacc agctactgga tcgcctgggt gcgccagatg 120
cccgggaaag gcctggagta catggggctc atctatcctg gtgactctga caccaaatac 180
agcccgtcct tccaaggcca ggtcaccatc tcagtcgaca agtccgtcag cactgcctac 240
ttgcaatgga gcagtctgaa gccctcggac agcgccgtgt atttttgtgc gagacatgac 300
gtgggatatg cgagtagttc caacgcggca aagtggcctg aatacttcca gcattggggc 360
cagggcaccc tggtcaccgt ttcctcaggt ggaggcggtt cacagtctgt gttgacgcag 420
ccgtgcagca gctgcgcggc cccaggacag aaggtcacca tctcctgctc tggaagcagc 480
tccaacattg ggaataatta tgtatcctgg taccagcagc tcccaggaac agtccccaaa 540
ctcctcatct atggtcacac caatcggccc gcaggggtcc ctgaccgatt ctctggctcc 600
aagtctggca cctcagcctc cctggccatc agtgggttcc ggtccgagga tgaggctgat 660
tattactgtg cagcatggga tgacagcctg agtggttggg tgttcggcgg agggaccaag 720
ctgaccgtcc taggtgcggc cgcagaacaa aaactcatct cagaagagga tctgaatggg 780
gccgcacatc accatcatca ccat 804

<210> SEQ ID NO 157
<211> LENGTH: 268
<212> TYPE: PRT
<213> ORGANISM: artificial
<220> FEATURE:
<223> OTHER INFORMATION: amino acid sequence of AVP07-63 diabody

<400> SEQUENCE: 157

Ser Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Ala Trp Val Arg Gln Met Pro Gly Lys Gly Leu Glu Tyr Met
35 40 45

Gly Leu Ile Tyr Pro Gly Asp Ser Asp Thr Lys Tyr Ser Pro Ser Phe
50 55 60

Gln Gly Gln Val Thr Ile Ser Val Asp Lys Ser Val Ser Thr Ala Tyr
65 70 75 80

Leu Gln Trp Ser Ser Leu Lys Pro Ser Asp Ser Ala Val Tyr Phe Cys
85 90 95

Ala Arg His Asp Val Gly Tyr Ala Ser Ser Ser Asn Ala Ala Lys Trp
100 105 110

Pro Glu Tyr Phe Gln His Trp Gly Gln Gly Thr Leu Val Thr Val Ser
115 120 125

Ser Gly Gly Gly Gly Ser Gln Ser Val Leu Thr Gln Pro Cys Ser Ser
130 135 140

Cys Ala Ala Pro Gly Gln Lys Val Thr Ile Ser Cys Ser Gly Ser Ser
145 150 155 160

-continued

```
Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly Ala Ala Ala Glu Gln Lys Leu Ile Ser Glu Glu
                245                 250                 255

Asp Leu Asn Gly Ala Ala His His His His His His
            260                 265
```